United States Patent
Liang et al.

(10) Patent No.: US 12,060,333 B2
(45) Date of Patent: Aug. 13, 2024

(54) AMINOCARBAMOYL COMPOUNDS FOR THE TREATMENT OF VIRAL INFECTIONS

(71) Applicant: Hoffmann-La Roche Inc., Little Falls, NJ (US)

(72) Inventors: Chungen Liang, Shanghai (CN); Hongying Yun, Shanghai (CN); Weixing Zhang, Shanghai (CN); Kun Miao, Shanghai (CN); Jianguo Chen, Shanghai (CN); Yao Wu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/445,989

(22) Filed: Aug. 26, 2021

(65) Prior Publication Data
US 2022/0064128 A1   Mar. 3, 2022

(51) Int. Cl.
| | |
|---|---|
| *C07D 241/24* | (2006.01) |
| *C07C 243/34* | (2006.01) |
| *C07C 311/35* | (2006.01) |
| *C07D 207/26* | (2006.01) |
| *C07D 209/42* | (2006.01) |
| *C07D 211/76* | (2006.01) |
| *C07D 231/12* | (2006.01) |
| *C07D 233/64* | (2006.01) |
| *C07D 235/24* | (2006.01) |
| *C07D 261/18* | (2006.01) |
| *C07D 401/04* | (2006.01) |
| *C07D 403/12* | (2006.01) |
| *C07D 413/12* | (2006.01) |

(52) U.S. Cl.
CPC .......... *C07D 241/24* (2013.01); *C07C 243/34* (2013.01); *C07C 311/35* (2013.01); *C07D 207/26* (2013.01); *C07D 209/42* (2013.01); *C07D 211/76* (2013.01); *C07D 231/12* (2013.01); *C07D 233/64* (2013.01); *C07D 235/24* (2013.01); *C07D 261/18* (2013.01); *C07D 401/04* (2013.01); *C07D 403/12* (2013.01); *C07D 413/12* (2013.01)

(58) Field of Classification Search
CPC .. C07D 241/24; C07D 207/26; C07D 209/42; C07D 211/76; C07D 231/12; C07D 233/64; C07D 235/24; C07D 261/18; C07D 401/04; C07D 403/12; C07D 413/12; C07C 243/34; C07C 311/35
See application file for complete search history.

(56) References Cited

U.S. PATENT DOCUMENTS

2022/0324800 A1* 10/2022 Webber .............. C07D 207/267

FOREIGN PATENT DOCUMENTS

| WO | 96/30395 A2 | 10/1996 | | |
|---|---|---|---|---|
| WO | 03/016335 A2 | 2/2003 | | |
| WO | WO-2022020711 A1 * | 1/2022 | ........... | C07C 271/22 |
| WO | WO-2023006645 A1 * | 2/2023 | | |
| WO | WO-2023104882 A1 * | 6/2023 | | |

OTHER PUBLICATIONS

Graybill; Bioorganic & Medicinal Chemistry Letters 1992, 2, 1375-1380. https://doi.org/10.1016/S0960-894X(00)80516-8 (Year: 1992).*
Hoffman; ChemRxiv, Jul. 22, 2020, 106 pages. https://doi.org/10.26434/chemrxiv.12631496.v1 (Year: 2020).*
Kati; Arch Biochem Biophys 1999, 362, 363-375. https://doi.org/10.1006/abbi.1998.1038 (Year: 1999).*
Konno; Bioorg Med Chem. 2013, 21, 412-24. https://doi.org/10.1016/j.bmc.2012.11.017 (Year: 2013).*
Shanker; New J. Chem., 2020,44, 9202. https://doi.org/10.1039/D0NJ00974A (Year: 2020).*
Shindo; Nat Chem Biol 2019, 15, 250-258. https://doi.org/10.1038/s41589-018-0204-3 (Year: 2019).*
Chauhan; Canadian Journal of Chemistry 2020, 98, 485-494. https://doi.org/10.1139/cjc-2020-0052 (Year: 2020).*
Giordano et al., "Inhibition of Mammalian Legumain by Michael Acceptors and AzaAsn-Halomethylketones" Eur. J. Med. Chem. 28:297-311 ( 1993).
Hoffman et al., "Discovery of Ketone-Based Covalent Inhibitors of Coronavirus 3CL Proteases for the Potential Therapeutic Treatment of COVID-19" J. Med. Chem./Pfizer Research:1-106 ( 2020).
International Preliminary Report on Patentability—PCT/EP2021/073503 issued Feb. 28, 2023, pp. 1-8.
International Search Report for PCT/EP2021/073503 mailed Dec. 23, 2021.

(Continued)

*Primary Examiner* — Daniel R Carcanague
(74) *Attorney, Agent, or Firm* — Robert C. Hall

(57) ABSTRACT

The present invention relates to compounds of formula (I),

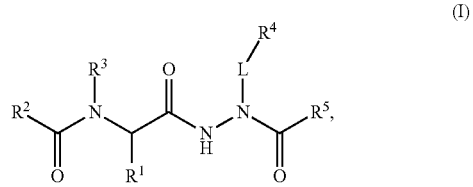

wherein $R^1$-$R^5$ and L are as described herein, and their pharmaceutically acceptable salt thereof, and compositions including the compounds and methods of using the compounds.

15 Claims, No Drawings

Specification includes a Sequence Listing.

(56) References Cited

OTHER PUBLICATIONS

Kati et al., "Inhibition of 3C Protease from Human Rhinovirus Strain 1B by Peptidyl Bromomethylketonehydrazides" Archives of Biochim. Biophys 362(2):363-375 ( 1999).
Konno et al., "Design and synthesis of new tripeptide-type SARS-CoV 3CL protease inhibitors containing an electrophilic arylketone moiety" Bioorg. Med. Chem. 21(2):412-424 ( 2013).
Niestroj et al., "Inhibition of Mammalian Legumain by Michael Acceptors and AzaAsn-Halomethylketones" Biol. Chem. 383:1205-1214 ( 2002).
Wang et al., "Dipeptidyl aspartyl fluoromethylketones as potent caspase-3 inhibitors: SAR of the P2 amino acid" Bioorg. Med. Chem. Lett. 14:1269-1272 ( 2004).
Yang et al., "MX1013, a dipeptide caspase inhibitor with potent in vivo antiapoptotic activity" Br J Pharmacol. 140:402-412 ( 2003).
Zhang et al., "Design and Synthesis of Dipeptidyl Glutaminyl Fluoromethyl Ketones as Potent Severe Acute Respiratory Syndrome Coronavirus (SARS-CoV) Inhibitors" J. Med. Chem. 49:1198-1201 ( 2006).
Zhou, P. et al., "A pneumonia outbreak associated with a new coronavirus of probable bat origin" Nature 579:270-273 ( 2000).

\* cited by examiner

SEQUENCE LISTING

<160> NUMBER OF SEQ ID NOS: 6

<210> SEQ ID NO 1
<211> LENGTH: 306
<212> TYPE: PRT
<213> ORGANISM: SARS-CoV-2

<400> SEQUENCE: 1

```
Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Val Val Tyr Cys Pro Arg His Val Ile Cys Thr Ser Glu Asp
        35                  40                  45

Met Leu Asn Pro Asn Tyr Glu Asp Leu Leu Ile Arg Lys Ser Asn His
    50                  55                  60

Asn Phe Leu Val Gln Ala Gly Asn Val Gln Leu Arg Val Ile Gly His
65                  70                  75                  80

Ser Met Gln Asn Cys Val Leu Lys Leu Lys Val Asp Thr Ala Asn Pro
                85                  90                  95

Lys Thr Pro Lys Tyr Lys Phe Val Arg Ile Gln Pro Gly Gln Thr Phe
            100                 105                 110

Ser Val Leu Ala Cys Tyr Asn Gly Ser Pro Ser Gly Val Tyr Gln Cys
        115                 120                 125

Ala Met Arg Pro Asn Phe Thr Ile Lys Gly Ser Phe Leu Asn Gly Ser
    130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Asn Phe Tyr Gly Pro Phe Val Asp Arg Gln Thr Ala Gln
            180                 185                 190

Ala Ala Gly Thr Asp Thr Thr Ile Thr Val Asn Val Leu Ala Trp Leu
        195                 200                 205

Tyr Ala Ala Val Ile Asn Gly Asp Arg Trp Phe Leu Asn Arg Phe Thr
    210                 215                 220

Thr Thr Leu Asn Asp Phe Asn Leu Val Ala Met Lys Tyr Asn Tyr Glu
225                 230                 235                 240
```

```
Pro Leu Thr Gln Asp His Val Asp Ile Leu Gly Pro Leu Ser Ala Gln
            245                 250                 255

Thr Gly Ile Ala Val Leu Asp Met Cys Ala Ser Leu Lys Glu Leu Leu
        260                 265                 270

Gln Asn Gly Met Asn Gly Arg Thr Ile Leu Gly Ser Ala Leu Leu Glu
        275                 280                 285

Asp Glu Phe Thr Pro Phe Asp Val Val Arg Gln Cys Ser Gly Val Thr
290                 295                 300

Phe Gln
305

<210> SEQ ID NO 2
<211> LENGTH: 306
<212> TYPE: PRT
<213> ORGANISM: SARS-CoV

<400> SEQUENCE: 2

Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Thr Val Tyr Cys Pro Arg His Val Ile Cys Thr Ala Glu Asp
        35                  40                  45

Met Leu Asn Pro Asn Tyr Glu Asp Leu Leu Ile Arg Lys Ser Asn His
    50                  55                  60

Ser Phe Leu Val Gln Ala Gly Asn Val Gln Leu Arg Val Ile Gly His
65                  70                  75                  80

Ser Met Gln Asn Cys Leu Leu Arg Leu Lys Val Asp Thr Ser Asn Pro
                85                  90                  95

Lys Thr Pro Lys Tyr Lys Phe Val Arg Ile Gln Pro Gly Gln Thr Phe
            100                 105                 110

Ser Val Leu Ala Cys Tyr Asn Gly Ser Pro Ser Gly Val Tyr Gln Cys
        115                 120                 125

Ala Met Arg Pro Asn His Thr Ile Lys Gly Ser Phe Leu Asn Gly Ser
    130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Lys Phe Tyr Gly Pro Phe Val Asp Arg Gln Thr Ala Gln
            180                 185                 190

Ala Ala Gly Thr Asp Thr Thr Ile Thr Leu Asn Val Leu Ala Trp Leu
        195                 200                 205

Tyr Ala Ala Val Ile Asn Gly Asp Arg Trp Phe Leu Asn Arg Phe Thr
    210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
                245                 250                 255

Thr Gly Ile Ala Val Leu Asp Met Cys Ala Ala Leu Lys Glu Leu Leu
            260                 265                 270

Gln Asn Gly Met Asn Gly Arg Thr Ile Leu Gly Ser Thr Ile Leu Glu
        275                 280                 285

Asp Glu Phe Thr Pro Phe Asp Val Val Arg Gln Cys Ser Gly Val Thr
```

```
              290                 295                 300

Phe Gln
305

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Lys Thr Ser Ala Val Leu Gln Ser Gly Phe Arg Lys Met Glu Lys
1               5                   10                  15

<210> SEQ ID NO 4
<211> LENGTH: 306
<212> TYPE: PRT
<213> ORGANISM: MERS-CoV

<400> SEQUENCE: 4

Ser Gly Leu Val Lys Met Ser His Pro Ser Gly Asp Val Glu Ala Cys
1               5                   10                  15

Met Val Gln Val Thr Cys Gly Ser Met Thr Leu Asn Gly Leu Trp Leu
                20                  25                  30

Asp Asn Thr Val Trp Cys Pro Arg His Val Met Cys Pro Ala Asp Gln
            35                  40                  45

Leu Ser Asp Pro Asn Tyr Asp Ala Leu Leu Ile Ser Met Thr Asn His
        50                  55                  60

Ser Phe Ser Val Gln Lys His Ile Gly Ala Pro Ala Asn Leu Arg Val
65                  70                  75                  80

Val Gly His Ala Met Gln Gly Thr Leu Leu Lys Leu Thr Val Asp Val
                85                  90                  95

Ala Asn Pro Ser Thr Pro Ala Tyr Thr Phe Thr Thr Val Lys Pro Gly
            100                 105                 110

Ala Ala Phe Ser Val Leu Ala Cys Tyr Asn Gly Arg Pro Thr Gly Thr
        115                 120                 125

Phe Thr Val Val Met Arg Pro Asn Tyr Thr Ile Lys Gly Ser Phe Leu
130                 135                 140

Cys Gly Ser Cys Gly Ser Val Gly Tyr Thr Lys Glu Gly Ser Val Ile
145                 150                 155                 160

Asn Phe Cys Tyr Met His Gln Met Glu Leu Ala Asn Gly Thr His Thr
                165                 170                 175

Gly Ser Ala Phe Asp Gly Thr Met Tyr Gly Ala Phe Met Asp Lys Gln
            180                 185                 190

Val His Gln Val Gln Leu Thr Asp Lys Tyr Cys Ser Val Asn Val Val
        195                 200                 205

Ala Trp Leu Tyr Ala Ala Ile Leu Asn Gly Cys Ala Trp Phe Val Lys
210                 215                 220

Pro Asn Arg Thr Ser Val Val Ser Phe Asn Glu Trp Ala Leu Ala Asn
225                 230                 235                 240

Gln Phe Thr Glu Phe Val Gly Thr Gln Ser Val Asp Met Leu Ala Val
                245                 250                 255

Lys Thr Gly Val Ala Ile Glu Gln Leu Leu Tyr Ala Ile Gln Gln Leu
            260                 265                 270

Tyr Thr Gly Phe Gln Gly Lys Gln Ile Leu Gly Ser Thr Met Leu Glu
        275                 280                 285
```

-continued

Asp Glu Phe Thr Pro Glu Asp Val Asn Met Gln Ile Met Gly Val Val
290                 295                 300

Met Gln
305

<210> SEQ ID NO 5
<211> LENGTH: 302
<212> TYPE: PRT
<213> ORGANISM: HCoV-229E

<400> SEQUENCE: 5

Ala Gly Leu Arg Lys Met Ala Gln Pro Ser Gly Phe Val Glu Lys Cys
1               5                   10                  15

Val Val Arg Val Cys Tyr Gly Asn Thr Val Leu Asn Gly Leu Trp Leu
            20                  25                  30

Gly Asp Ile Val Tyr Cys Pro Arg His Val Ile Ala Ser Asn Thr Thr
        35                  40                  45

Ser Ala Ile Asp Tyr Asp His Glu Tyr Ser Ile Met Arg Leu His Asn
    50                  55                  60

Phe Ser Ile Ile Ser Gly Thr Ala Phe Leu Gly Val Val Gly Ala Thr
65                  70                  75                  80

Met His Gly Val Thr Leu Lys Ile Lys Val Ser Gln Thr Asn Met His
                85                  90                  95

Thr Pro Arg His Ser Phe Arg Thr Leu Lys Ser Gly Glu Gly Phe Asn
            100                 105                 110

Ile Leu Ala Cys Tyr Asp Gly Cys Ala Gln Gly Val Phe Gly Val Asn
        115                 120                 125

Met Arg Thr Asn Trp Thr Ile Arg Gly Ser Phe Ile Asn Gly Ala Cys
    130                 135                 140

Gly Ser Pro Gly Tyr Asn Leu Lys Asn Gly Glu Val Glu Phe Val Tyr
145                 150                 155                 160

Met His Gln Ile Glu Leu Gly Ser Gly Ser His Val Gly Ser Ser Phe
                165                 170                 175

Asp Gly Val Met Tyr Gly Gly Phe Glu Asp Gln Pro Asn Leu Gln Val
            180                 185                 190

Glu Ser Ala Asn Gln Met Leu Thr Val Asn Val Val Ala Phe Leu Tyr
        195                 200                 205

Ala Ala Ile Leu Asn Gly Cys Thr Trp Trp Leu Lys Gly Glu Lys Leu
    210                 215                 220

Phe Val Glu His Tyr Asn Glu Trp Ala Gln Ala Asn Gly Phe Thr Ala
225                 230                 235                 240

Met Asn Gly Glu Asp Ala Phe Ser Ile Leu Ala Ala Lys Thr Gly Val
                245                 250                 255

Cys Val Glu Arg Leu Leu His Ala Ile Gln Val Leu Asn Asn Gly Phe
            260                 265                 270

Gly Gly Lys Gln Ile Leu Gly Tyr Ser Ser Leu Asn Asp Glu Phe Ser
        275                 280                 285

Ile Asn Glu Val Val Lys Gln Met Phe Gly Val Asn Leu Gln
    290                 295                 300

<210> SEQ ID NO 6
<211> LENGTH: 302
<212> TYPE: PRT
<213> ORGANISM: HCoV-OC43

<400> SEQUENCE: 6

```
Ser Gly Ile Val Lys Met Val Asn Pro Thr Ser Lys Val Glu Pro Cys
1               5                   10                  15
Val Val Ser Val Thr Tyr His Asn Met Thr Leu Asn Gly Leu Trp Leu
            20                  25                  30
Asp Asp Lys Val Tyr Cys Pro Arg His Val Ile Cys Ser Ala Ser Asp
        35                  40                  45
Met Thr Asn Pro Asp Tyr Thr Asn Leu Leu Cys Val Thr Ser Ser Asp
    50                  55                  60
Phe Thr Val Leu Phe Asp Arg Leu Ser Leu Thr Val Met Ser Tyr Gln
65                  70                  75                  80
Met Arg Gly Cys Met Leu Val Leu Thr Val Thr Leu Gln Asn Ser Arg
                85                  90                  95
Thr Pro Lys Tyr Thr Phe Gly Val Val Lys Pro Gly Glu Thr Phe Thr
            100                 105                 110
Val Leu Ala Ala Tyr Asn Gly Lys Pro Gln Gly Ala Phe His Val Thr
            115                 120                 125
Met Arg Ser Ser Tyr Thr Ile Lys Gly Ser Phe Leu Cys Gly Ser Cys
    130                 135                 140
Gly Ser Val Gly Tyr Val Ile Met Gly Asp Cys Val Lys Phe Val Tyr
145                 150                 155                 160
Met His Gln Leu Glu Leu Ser Thr Gly Cys His Thr Gly Thr Asp Phe
                165                 170                 175
Asn Gly Asp Phe Tyr Gly Pro Tyr Lys Asp Ala Gln Val Val Gln Leu
            180                 185                 190
Pro Ile Gln Asp Tyr Ile Gln Ser Val Asn Phe Leu Ala Trp Leu Tyr
    195                 200                 205
Ala Ala Ile Leu Asn Asn Cys Asn Trp Phe Ile Gln Ser Asp Lys Cys
210                 215                 220
Ser Val Glu Asp Phe Asn Val Met Ala Leu Ser Asn Gly Phe Ser Gln
225                 230                 235                 240
Val Lys Ser Asp Leu Val Ile Asp Ala Leu Ala Ser Met Thr Gly Val
            245                 250                 255
Ser Leu Glu Thr Leu Leu Ala Ala Ile Lys Arg Leu Lys Asn Gly Phe
            260                 265                 270
Gln Gly Arg Gln Ile Met Gly Ser Cys Ser Phe Glu Asp Glu Leu Thr
            275                 280                 285
Pro Ser Asp Val Tyr Gln Gln Leu Ala Gly Ile Lys Leu Gln
            290                 295                 300
```

AMINOCARBAMOYL COMPOUNDS FOR THE TREATMENT OF VIRAL INFECTIONS

CROSS-REFERENCE TO RELATED APPLICATION

This application is entitled to the priority benefit of International Application No. PCT/CN2020/111852 filed on Aug. 27, 2020 and International Application No. PCT/CN2021/108676 filed on Jul. 27, 2021, the disclosures of which are incorporated herein by reference.

SEQUENCE LISTING

This application contains a Sequence Listing which has been submitted electronically in ASCII format and is hereby incorporated by reference in its entirety. Said ASCII copy, created on Aug. 24, 2021, is named P36352-US sequence listing ST25.txt and is 13,863 bytes in size.

FIELD OF THE INVENTION

The invention relates to peptidomimetic (or peptide-like) compounds, specifically viral protease inhibitors, for the treatment of viral infections, and methods of preparing and using such compounds.

BACKGROUND OF THE INVENTION

In December 2019, a new coronavirus, named severe acute respiratory syndrome coronavirus 2 (SARS-CoV-2), caused an outbreak of the novel coronavirus disease COVID-19, which has spread to more than 200 countries with over 9 million confirmed cases and over 479,133 confirmed deaths worldwide as of Jun. 26, 2020 (WHO COVID-19 situation report—157). The WHO declared the coronavirus outbreak a public health emergency of international concern. Currently, there are no clinically effective vaccine or specific antiviral drug available for the prevention and treatment of SARS-CoV-2 infections.

Coronaviruses (CoVs) are enveloped, positive-sense, single-stranded RNA viruses. Seven human coronaviruses (HCoVs) have been so far identified, namely HCoV-229E, HCoV-OC43, HCoV-NL63, HCoV-HKU1, SARS coronavirus (SARS-CoV), Middle East respiratory syndrome coronavirus (MERS-CoV) and the novel coronavirus (SARS-CoV-2). While SARS-CoV, MERS-CoV, and SARS-CoV-2 are highly pathogenic, the others generally cause mild to moderate upper-respiratory tract illness and contribute to 15%-30% cases of common colds in human adults.

The RNA genome of SARS-CoV-2 is about 30 kilobases in length shares approximately 80% sequence identity with SARS-CoV (Zhou P. et al. "A pneumonia outbreak associated with a new coronavirus of probable bat origin." Nature 579(7798): 270-273, 2020). It consists six major open-reading frames (ORFs). ORF 1a/b, which is about two thirds of the whole genome length, directly translates two polyproteins, pp1a and pp1ab, which encodes 16 nonstructural proteins (nsps) to form the replication transcription complex. Nsp3, which encodes papain-like protease ($PL^{pro}$), and nsp5, which encodes 3-chymotrypsin-like cysteine protease ($3CL^{pro}$, also known as main protease, $M^{pro}$), are essential for processing these polyproteins. $3CL^{pro}$ cleaves the polyprotein at 11 distinct sites to generate various nsps that are important for viral replication. Accordingly, inhibitors that block the cleavage function of $3CL^{pro}$ could inhibit virus replication. In addition, $3CL^{pro}$ is highly conserved between SARS-CoV and SARS-CoV-2 (96% sequence identity), as well as the other human coronaviruses. Furthermore, no human proteases with a similar cleavage specificity is known. These desired properties make $3CL^{pro}$ one of the most attractive targets against coronavirus infections.

SUMMARY OF THE INVENTION

The invention relates to novel compounds of formula (II), as well as to pharmaceutically acceptable salts thereof,

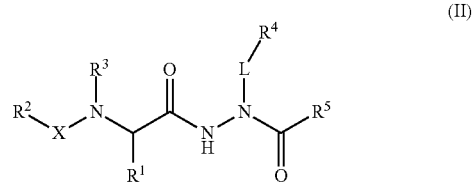

(II)

wherein X, L, $R^1$, $R^2$, $R^3$, $R^4$, and $R^5$ are as defined herein.

Another object of the present invention is related to novel compounds of formula (IIa), as well as to pharmaceutically acceptable salts thereof,

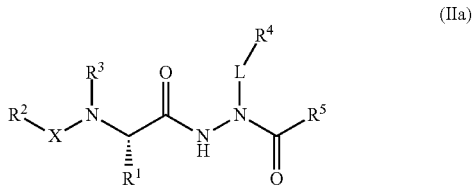

(IIa)

wherein X, L, $R^1$, $R^2$, $R^3$, $R^4$, and $R^5$ are as defined herein.

The invention is also concerned with processes for the manufacture of compounds of formula (II) or (IIa).

The invention also relates to pharmaceutical compositions comprising a compound of formula (II) or (IIa) as described above and a pharmaceutically acceptable carrier and/or adjuvant.

A further aspect of the invention is the use of compounds of formula (II) or (IIa) as therapeutic active substances for the treatment of diseases which are associated with the inhibition of $3CL^{pro}$. The invention thus relates to a method for the treatment of a disease associated with the inhibition of $3CL^{pro}$ activity such as for example coronavirus infections. The compounds of formula (II) or (IIa) show superior $3CL^{pro}$ inhibition activity. In addition, the compounds of formula (II) or (IIa) also show good cytotoxicity, phototoxicity, solubility, hPBMC, human microsome stability and SDPK profiles, as well as low Cytochrome P450 (CYP) inhibition.

DETAILED DESCRIPTION OF THE INVENTION

Definitions

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light. Whenever a chiral center is present in a chemical structure, it is intended that all stereoisomers associated with that chiral center are encompassed by the present invention.

The term "compound(s) of this invention" and "compound(s) of the present invention" refers to compounds of formula (II) or (IIa) and stereoisomers, solvates or salts thereof (e.g., pharmaceutically acceptable salts).

The term "substituent" denotes an atom or a group of atoms replacing a hydrogen atom on the parent molecule.

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "$C_{3-7}$cycloalkyl" denotes a saturated moncyclic hydrocarbon group containing from 3 to 7 carbon atoms, such as cyclopropyl, cyclobutyl, cyclopentyl, cyclohexyl or cycloheptyl, more particularly cyclopropyl. In addition, the term "cycloalkyl" also embraces bicyclic hydrocarbon groups containing from 3 to 10 carbon atoms. Bicyclic means consisting of two saturated carbocycles having one or more carbon atoms in common. Examples for bicyclic cycloalkyl are bicyclo[2.2.1]heptanyl or bicyclo[2.2.2]octanyl.

The term "$C_{2-6}$-alkenyl" denotes an unsaturated, linear or branched chain alkenyl group containing 2 to 6, particularly 2 to 4 carbon atoms, for example vinyl, propenyl, allyl, butenyl and the like. Particular "$C_{2-6}$alkenyl" groups are allyl and vinyl.

The term "$C_{1-6}$alkoxy" denotes $C_{1-6}$alkyl-O—.

The term "$C_xH_{2x}$" alone or in combination signifies a saturated, linear or branched chain alkyl group containing x carbon atoms, wherein x is 1, 2, 3, 4, 5, or 6.

The term "oxy" denotes —O—. Example such as benzyloxy refers to benzyl-O—.

The term "oxo" denotes =O.

The term "halogen" and "halo" are used interchangeably herein and denote fluoro, chloro, bromo, or iodo.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Inhibitors of 3CL$^{pro}$

In a first aspect, the present invention provides a compound of formula (II),

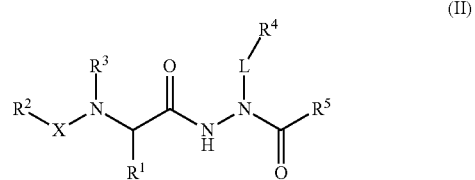

(II)

wherein
X is carbonyl or $SO_2$;
$R^1$ is H, $C_{1-6}$alkyl, $C_{3-7}$cycloalkyl$C_{1-6}$alkyl, or $(C_{1-6}$alkyl$)_3$Si—$C_{1-6}$alkyl, wherein said $C_{3-7}$cycloalkyl is optionally substituted with one to two substituents independently selected from halogen and $C_{1-6}$alkyl;
$R^2$ is $C_{1-6}$alkoxy, phenyl$C_{2-6}$alkenyl, benzyloxy, oxazolyl, isoxazolyl, 1H-pyrrolo[2,3-b]pyridinyl, 1H-pyrrolo[3,2-c]pyridinyl, 6H-pyrrolo[2,3-c]pyridinyl, 1H-indolyl, 1H-benzimidazolyl, benzyl, imidazolyl, pyrazinyl, thiazolyl, imidazo[1,2-a]pyridine, pyrazolo[1,5-a]pyridine, phenyl-NH—$C_{1-6}$alkyl; wherein each of said phenyl$C_{2-6}$alkenyl, phenyl-NH—$C_{1-6}$alkyl, oxazolyl, isoxazolyl, thiazolyl, benzimidazolyl, 6H-pyrrolo[2,3-c]pyridinyl, and 1H-indolyl is unsubstituted or substituted with one to two substituents independently selected from halogen, $C_{1-6}$alkyl, halo-$C_{1-6}$alkyl, and $C_{1-6}$alkoxy;
$R^3$ is H or $C_{1-6}$alkyl;

R⁴ is H, carbamoyl, axopyrrolidinyl, oxopiperidinyl, 1H-pyrazolyl, 1H-imidazolyl, or ($C_{1-6}$ alkylamino)carbonyl;

R⁵ is $C_{1-6}$alkyl substituted with one to two substituents independently selected from halogen and phenyl;

L is —$C_xH_{2x}$—, wherein x is 1, 2, 3, 4, 5, or 6;

or a pharmaceutically acceptable salt thereof.

In one embodiment, the present invention provides a compound of formula (II) as described herein, or a pharmaceutically acceptable salt thereof, wherein the compound of formula (II) is a compound of formula (IIa),

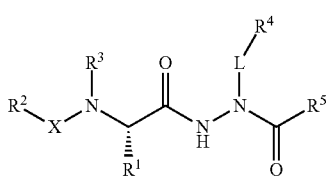

(IIa)

wherein X, L, R¹, R², R³, R⁴, and R⁵ are as defined in claim 1.

In one embodiment, the present invention provides a compound of formula (II) as described herein, or a pharmaceutically acceptable salt thereof, wherein the compound of formula (II) is a compound of formula (I),

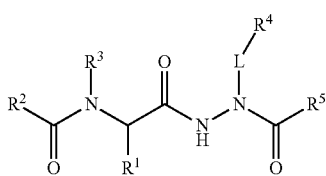

(I)

wherein L, R¹, R², R³, R⁴, and R⁵ are as defined herein.

In a preferred embodiment, the present invention provides a compound of formula (II) as described herein, or a pharmaceutically acceptable salt thereof, wherein R¹ is $C_{1-6}$alkyl, $(C_{1-6}alkyl)_3Si$—$C_{1-6}$alkyl, or $C_{3-7}$cycloalkyl $C_{1-6}$alkyl, wherein said $C_{3-7}$cycloalkyl is optionally substituted with one $C_{1-6}$alkyl substituent.

In a particularly preferred embodiment, the present invention provides a compound of formula (II) as described herein, or a pharmaceutically acceptable salt thereof, wherein R¹ is isobutyl, isopentyl, 2,2, dimethylpropyl, trimethylsilylmethyl, cyclopropylmethyl, (1-methylcyclopropyl)methyl, 1-bicyclo[1.1.1]pentanylmethyl, or cyclohexylmethyl.

In a preferred embodiment, the present invention provides a compound of formula (II) as described herein, or a pharmaceutically acceptable salt thereof, wherein R² is benzyloxy, 1H-indolyl, benzimidazolyl, or isoxazolyl, wherein each of said 1H-indolyl, benzimidazolyl, and isoxazolyl is unsubstituted or substituted with one substituent selected from halogen, $C_{1-6}$alkyl, halo-$C_{1-6}$alkyl, and $C_{1-6}$alkoxy.

In a particularly preferred embodiment, the present invention provides a compound of formula (II) as described herein, or a pharmaceutically acceptable salt thereof, wherein R² is benzyloxy, 1H-indolyl, benzimidazolyl, 5-methylisoxazolyl, 5-(difluoromethyl)isoxazolyl, 5-(trifluoromethyl)isoxazolyl, 5-chloro-1H-benzimidazolyl, 5-chloro-1H-indolyl, or 4-methoxy-1H-indolyl.

In a particularly preferred embodiment, the present invention provides a compound of formula (II) as described herein, or a pharmaceutically acceptable salt thereof, wherein R³ is H.

In a particularly preferred embodiment, the present invention provides a compound of formula (II) as described herein, or a pharmaceutically acceptable salt thereof, wherein R⁴ is carbamoyl or axopyrrolidinyl.

In a particularly preferred embodiment, the present invention provides a compound of formula (II) as described herein, or a pharmaceutically acceptable salt thereof, wherein L is —$CH_2$— or —$CH_2$—$CH_2$—.

In a preferred embodiment, the present invention provides a compound of formula (II) as described herein, or a pharmaceutically acceptable salt thereof, wherein R⁵ is $C_{1-6}$alkyl substituted twice with halogen.

In a particularly preferred embodiment, the present invention provides a compound of formula (II) as described herein, or a pharmaceutically acceptable salt thereof, wherein R⁵ is chlorofluoromethyl.

In a preferred embodiment, the present invention provides a compound of formula (II) as described herein, or a pharmaceutically acceptable salt thereof, wherein R¹ is $C_{1-6}$alkyl, $(C_{1-6}alkyl)_3Si$—$C_{1-6}$alkyl, or $C_{3-7}$cycloalkyl$C_{1-6}$alkyl, wherein said $C_{3-7}$cycloalkyl is optionally substituted with one $C_{1-6}$alkyl substituent;

R² is benzyloxy, 1H-indolyl, benzimidazolyl, or isoxazolyl, wherein each of said 1H-indolyl, benzimidazolyl, and isoxazolyl is unsubstituted or substituted with one substituent selected from halogen, $C_{1-6}$alkyl, halo-$C_{1-6}$alkyl, and $C_{1-6}$alkoxy;

R³ is H;

R⁴ is carbamoyl or axopyrrolidinyl;

R⁵ is $C_{1-6}$alkyl substituted twice with halogen; and

L is —$CH_2$— or —$CH_2$—$CH_2$—.

In a particularly preferred embodiment, the present invention provides a compound of formula (II) as described herein, or a pharmaceutically acceptable salt thereof, wherein R¹ is isobutyl isopentyl, 2,2, dimethylpropyl, trimethylsilylmethyl, cyclopropylmethyl, (1-methylcyclopropyl)methyl, 1-bicyclo[1.1.1]pentanylmethyl, or cyclohexylmethyl;

R² is benzyloxy, 1H-indolyl, benzimidazolyl, 5-methylisoxazolyl, 5-(difluoromethyl)isoxazolyl, 5-(trifluoromethyl)isoxazolyl, 5-chloro-1H-benzimidazolyl, 5-chloro-1H-indolyl, or 4-methoxy-1H-indolyl;

R³ is H;

R⁴ is carbamoyl or axopyrrolidinyl;

R⁵ is chlorofluoromethyl; and

L is —$CH_2$— or —$CH_2$—$CH_2$—.

In one embodiment, the present invention provides a compound of formula (II) as described herein, or a pharmaceutically acceptable salt thereof, wherein said compound of formula (II) is selected from:

Benzyl N-[2-[2-(3-amino-3-oxo-propyl)-2-(2-chloroacetyl)hydrazino]-2-axo-ethyl]carbamate;

Benzyl N-[(1S)-1-[[(3-amino-3-oxo-propyl)-(2-chloroacetyl)amino]carbamoyl]-3-methyl-butyl]carbamate;

Benzyl N-[(1S)-1-[[(3-amino-3-oxo-propyl)-(2-chloro-2-phenyl-acetyl)amino]carbamoyl]-3-methyl-butyl]carbamate;

Benzyl N-[(1S)-1-[[(3-amino-3-oxo-propyl)-(2-chloropropanoyl)amino]carbamoyl]-3-methyl-butyl]carbamate;

Benzyl N-[(1S)-1-[[(3-amino-3-oxo-propyl)-(2-chlorobutanoyl)amino]carbamoyl]-3-methyl-butyl]carbamate;

Benzyl N-[(1S)-1-[[(3-amino-3-oxo-propyl)-(2-bromo-acetyl)amino]carbamoyl]-3-methyl-butyl]carbamate;

Benzyl N-[(1S)-2-[2-(3-amino-3-oxo-propyl)-2-(2-chloro-acetyl)hydrazino]-1-(cyclohexylmethyl)-2-axo-ethyl]carbamate;

Benzyl N-[(1S)-2-[2-(3-amino-3-oxo-propyl)-2-(2-chloro-acetyl)hydrazino]-1-(cyclopentylmethyl)-2-axo-ethyl]carbamate;

Benzyl N-[(1S)-2-[2-(3-amino-3-oxo-propyl)-2-(2-chloro-acetyl)hydrazino]-1-(cyclopropylmethyl)-2-axo-ethyl]carbamate;

Benzyl N-[(1S)-2-[2-(3-amino-3-oxo-propyl)-2-(2-fluoro-acetyl)hydrazino]-1-(cyclohexylmethyl)-2-axo-ethyl]carbamate;

Benzyl N-[(1S)-2-[2-(3-amino-3-oxo-propyl)-2-(2-chloro-2-fluoro-acetyl)hydrazino]-1-(cyclohexylmethyl)-2-axo-ethyl]carbamate;

Benzyl((S)-1-(2-(3-amino-3-oxo-propyl)-2-((S)-2-chloro-2-fluoroacetyl)hydrazinyl)-3-cyclohexyl-1-oxo-propan-2-yl)carbamate;

Benzyl((S)-1-(2-(3-amino-3-oxo-propyl)-2-((R)-2-chloro-2-fluoroacetyl)hydrazinyl)-3-cyclohexyl-1-oxo-propan-2-yl)carbamate Benzyl N-[(1S)-1-[[(3-amino-3-oxo-propyl)-(2-chloro-2-fluoro-acetyl)amino]carbamoyl]-3-methyl-butyl]carbamate;

Benzyl N-[(1 S)-1-[[(3-amino-3-oxo-propyl)-[(2S)-2-chloro-2-fluoro-acetyl]amino]carbamoyl]-3-methyl-butyl]carbamate;

Benzyl N-[(1S)-1-[[(3-amino-3-oxo-propyl)-[(2R)-2-chloro-2-fluoro-acetyl]amino]carbamoyl]-3-methyl-butyl]carbamate;

Benzyl N-[(1S)-1-[[(2-chloroacetyl)-[(2-oxo-pyrrolidin-3-yl)methyl]amino]carbamoyl]-3-methyl-butyl]carbamate;

Benzyl N-[(1S)-1-[[(2-chloroacetyl)-[(2-oxo-3-piperidyl)methyl]amino]carbamoyl]-3-methyl-butyl]carbamate;

Benzyl N-[(1S)-1-[[(2-chloroacetyl)-propyl-amino]carbamoyl]-3-methyl-butyl]carbamate;

Benzyl N-[(1/S)-1-[[(2-chloroacetyl)-(1H-pyrazol-3-ylmethyl)amino]carbamoyl]-3-methyl-butyl]carbamate;

Benzyl N-[(1/S)-1-[[(2-chloroacetyl)-(1H-imidazol-4-ylmethyl)amino]carbamoyl]-3-methyl-butyl]carbamate;

tert-Butyl N-[(1/S)-1-[[(3-amino-3-oxo-propyl)-(2-chloro-acetyl)amino]carbamoyl]-3-methyl-butyl]carbamate;

4-Methoxy-N-[(1S)-1-[[(3-amino-3-oxo-propyl)-(2-chloro-acetyl)amino]carbamoyl]-3-methyl-butyl]-1H-indole-2-carboxamide;

N-[(1S)-1-[[(3-amino-3-oxo-propyl)-(2-chloroacetyl)amino]carbamoyl]-3-methyl-butyl]-1H-indole-2-carboxamide;

N-[(1S)-1-[[(3-amino-3-oxo-propyl)-(2-chloroacetyl)amino]carbamoyl]-3-methyl-butyl]-2-methyl-oxazole-4-carboxamide;

N-[(1S)-1-[[(3-Amino-3-oxo-propyl)-(2-fluoroacetyl)amino]carbamoyl]-3-methyl-butyl]-4-methoxy-1H-indole-2-carboxamide;

N-[(1S)-1-[[(3-Amino-3-oxo-propyl)-(2-fluoroacetyl)amino]carbamoyl]-3-methyl-butyl]-1H-indole-2-carboxamide;

N-[(1S)-2-[2-(3-Amino-3-oxo-propyl)-2-(2-chloroacetyl)hydrazino]-1-(cyclohexylmethyl)-2-axo-ethyl]-4-methoxy-1H-indole-2-carboxamide;

3-[(2-Chloroacetyl)-[[(2S)-2-[[(E)-3-(4-chloro-2-fluoro-phenyl)prop-2-enoyl]amino]-3-cyclohexyl-propanoyl]amino]amino]propanamide;

3-[(2-Chloroacetyl)-[[(2S)-2-[[(E)-3-(4-chloro-2-fluoro-phenyl)prop-2-enoyl]amino]-4-methyl-pentanoyl]amino]amino]propanamide;

N-[(1S)-2-[2-(3-Amino-3-oxo-propyl)-2-(2-chloroacetyl)hydrazino]-1-(cyclohexylmethyl)-2-axo-ethyl]-1H-indole-2-carboxamide;

N-[(1S)-2-[2-(3-Amino-3-oxo-propyl)-2-(2-fluoroacetyl)hydrazino]-1-(cyclohexylmethyl)-2-axo-ethyl]-1H-indole-2-carboxamide;

N-[(1S)-2-[2-(3-Amino-3-oxo-propyl)-2-(2-fluoroacetyl)hydrazino]-1-(cyclohexylmethyl)-2-axo-ethyl]-4-methoxy-1H-indole-2-carboxamide;

N-[(1S)-1-[[(2-fluoroacetyl)-[(2-oxo-pyrrolidin-3-yl)methyl]amino]carbamoyl]-3-methyl-butyl]-1H-indole-2-carboxamide;

N-[(1S)-1-[[(2-Fluoroacetyl)-[[(3S)-2-oxo-pyrrolidin-3-yl]methyl]amino]carbamoyl]-3-methyl-butyl]-1H-indole-2-carboxamide;

N-[(1S)-1-[[(2-fluoroacetyl)-[[(3R)-2-oxo-pyrrolidin-3-yl]methyl]amino]carbamoyl]-3-methyl-butyl]-1H-indole-2-carboxamide;

N-[(1S)-2-[2-(3-Amino-3-oxo-propyl)-2-(2-chloroacetyl)hydrazino]-1-(cyclohexylmethyl)-2-axo-ethyl]-N-methyl-1H-indole-2-carboxamide;

N-[(1S)-1-[[(3-Amino-3-oxo-propyl)-(2-chloroacetyl)amino]carbamoyl]-3-methyl-butyl]-N-methyl-1H-indole-2-carboxamide;

N-[(1S)-1-[[(3-Amino-3-oxo-propyl)-(2-chloro-2-fluoro-acetyl)amino]carbamoyl]-3-methyl-butyl]-1H-indole-2-carboxamide;

N-[(1S)-1-[[(3-amino-3-oxo-propyl)-[(2S)-2-chloro-2-fluoro-acetyl]amino]carbamoyl]-3-methyl-butyl]-1H-indole-2-carboxamide;

N-[(1S)-1-[[(3-amino-3-oxo-propyl)-[(2R)-2-chloro-2-fluoro-acetyl]amino]carbamoyl]-3-methyl-butyl]-1H-indole-2-carboxamide;

N-[(1S)-1-[[(3-Amino-3-oxo-propyl)-(2-chloroacetyl)amino]carbamoyl]-3-methyl-butyl]-1H-benzimidazole-2-carboxamide;

N-[(1S)-1-[[(3-Amino-3-oxo-propyl)-(2-chloroacetyl)amino]carbamoyl]-3-methyl-butyl]isoxazole-3-carboxamide;

N-[(1S)-1-[[(3-Amino-3-oxo-propyl)-(2-chloroacetyl)amino]carbamoyl]-3-methyl-butyl]-1H-pyrrolo[2,3-b]pyridine-2-carboxamide;

N-[(1S)-1-[[(3-Amino-3-oxo-propyl)-(2-chloroacetyl)amino]carbamoyl]-3-methyl-butyl]-2-methyl-oxazole-4-carboxamide;

N-[(1S)-1-[[(3-Amino-3-oxo-propyl)-(2-chloroacetyl)amino]carbamoyl]-3-methyl-butyl]-5-methyl-isoxazole-4-carboxamide;

N-[(1S)-1-[[(3-Amino-3-oxo-propyl)-(2-chloroacetyl)amino]carbamoyl]-3-methyl-butyl]-5-methoxy-6H-pyrrolo[2,3-c]pyridine-2-carboxamide;

N-[(1S)-2-[2-(3-amino-3-oxo-propyl)-2-(2-chloroacetyl)hydrazino]-1-(cyclohexylmethyl)-2-axo-ethyl]-5-methyl-isoxazole-3-carboxamide;

4-Methoxy-N-[(1S)-1-[[(3-amino-3-oxo-propyl)-(2-chloro-2-fluoro-acetyl)amino]carbamoyl]-3-methyl-butyl]-1H-indole-2-carboxamide;

N-[(1S)-1-[[(2-Chloroacetyl)-3-(methylamino)-3-oxo-propyl]amino]carbamoyl]-3-methyl-butyl]-N-methyl-1H-indole-2-carboxamide;

N-[(1S)-1-[[(2-Chloroacetyl)-[(2-oxo-pyrrolidin-3-yl)methyl]amino]carbamoyl]-3-methyl-butyl]-1H-indole-2-carboxamide;

N-[(1S)-1-[[(2-chloroacetyl)-[[(3S)-2-oxo-pyrrolidin-3-yl]methyl]amino]carbamoyl]-3-methyl-butyl]-1H-indole-2-carboxamide;

N-[(1S)-1-[[(2-chloroacetyl)-[[(3R)-2-oxo-pyrrolidin-3-yl]methyl]amino]carbamoyl]-3-methyl-butyl]-1H-indole-2-carboxamide;

N-[(1S)-1-[[(3-amino-3-oxo-propyl)-(2-chloroacetyl)amino]carbamoyl]-3-methyl-butyl]-1H-pyrrolo[3,2-c]pyridine-2-carboxamide;

4-chloro-N-[rac-(1S)-1-[[(3-amino-3-oxo-propyl)-(2-chloro-2-fluoro-acetyl)amino]carbamoyl]-3-methyl-butyl]-1H-indole-2-carboxamide;

N-[(1S)-1-[[(3-amino-3-oxo-propyl)-[(2S)-2-chloro-2-fluoro-acetyl]amino]carbamoyl]-3-methyl-butyl]-4-chloro-1H-indole-2-carboxamide;

N-[(1S)-1-[[(3-amino-3-oxo-propyl)-[(2R)-2-chloro-2-fluoro-acetyl]amino]carbamoyl]-3-methyl-butyl]-4-chloro-1H-indole-2-carboxamide;

N-[(1S)-1-[[(3-amino-3-oxo-propyl)-[(2S)-2-chloro-2-fluoro-acetyl]amino]carbamoyl]-3-methyl-butyl]-4-methoxy-1H-indole-2-carboxamide;

N-[(1S)-1-[[(3-amino-3-oxo-propyl)-[(2R)-2-chloro-2-fluoro-acetyl]amino]carbamoyl]-3-methyl-butyl]-4-methoxy-1H-indole-2-carboxamide;

4-methoxy-N-[rac-(1S)-2-[2-(2-chloro-2-fluoro-acetyl)-2-[(2-axopyrrolidin-3-yl)methyl]hydrazino]-1-(cyclopropylmethyl)-2-axo-ethyl]-1H-indole-2-carboxamide;

N-[(1S)-2-[2-(3-amino-3-oxo-propyl)-2-(2-chloro-2-fluoro-acetyl)hydrazino]-1-(cyclohexylmethyl)-2-axo-ethyl]-4-methoxy-1H-indole-2-carboxamide;

N-[(1S)-2-[2-(3-amino-3-oxo-propyl)-2-[(2R)-2-chloro-2-fluoro-acetyl]hydrazino]-1-(cyclohexylmethyl)-2-axo-ethyl]-4-methoxy-1H-indole-2-carboxamide;

N-[(1S)-2-[2-(3-amino-3-oxo-propyl)-2-[(2S)-2-chloro-2-fluoro-acetyl]hydrazino]-1-(cyclohexylmethyl)-2-axo-ethyl]-4-methoxy-1H-indole-2-carboxamide;

5-fluoro-N-[rac-(1S)-1-[[(3-amino-3-oxo-propyl)-(2-chloro-2-fluoro-acetyl)amino]carbamoyl]-3-methyl-butyl]-1H-indole-2-carboxamide;

N-[(1S)-1-[[(3-amino-3-oxo-propyl)-[(2R)-2-chloro-2-fluoro-acetyl]amino]carbamoyl]-3-methyl-butyl]-5-fluoro-1H-indole-2-carboxamide;

N-[(1S)-1-[[(3-amino-3-oxo-propyl)-[(2S)-2-chloro-2-fluoro-acetyl]amino]carbamoyl]-3-methyl-butyl]-5-fluoro-1H-indole-2-carboxamide;

5-chloro-N-[rac-(1S)-1-[[(3-amino-3-oxo-propyl)-(2-chloro-2-fluoro-acetyl)amino]carbamoyl]-3-methyl-butyl]-1H-indole-2-carboxamide;

N-[(1S)-1-[[(3-amino-3-oxo-propyl)-[(2R)-2-chloro-2-fluoro-acetyl]amino]carbamoyl]-3-methyl-butyl]-5-chloro-1H-indole-2-carboxamide;

N-[(1S)-1-[[(3-amino-3-oxo-propyl)-[(2S)-2-chloro-2-fluoro-acetyl]amino]carbamoyl]-3-methyl-butyl]-5-chloro-1H-indole-2-carboxamide;

N-[(1S)-2-[2-(3-amino-3-oxo-propyl)-2-(2-chloro-2-fluoro-acetyl)hydrazino]-1-(cyclohexylmethyl)-2-axo-ethyl]-1H-indole-2-carboxamide;

N-[(1S)-2-[2-(3-amino-3-oxo-propyl)-2-[(2R)-2-chloro-2-fluoro-acetyl]hydrazino]-1-(cyclohexylmethyl)-2-axo-ethyl]-1H-indole-2-carboxamide;

N-[(1S)-2-[2-(3-amino-3-oxo-propyl)-2-[(2S)-2-chloro-2-fluoro-acetyl]hydrazino]-1-(cyclohexylmethyl)-2-axo-ethyl]-1H-indole-2-carboxamide;

5-chloro-N-[rac-(1S)-1-[[(3-amino-3-oxo-propyl)-(2-chloro-2-fluoro-acetyl)amino]carbamoyl]-3-methyl-butyl]-1H-benzimidazole-2-carboxamide;

N-[(1S)-1-[[(3-amino-3-oxo-propyl)-[(2R)-2-chloro-2-fluoro-acetyl]amino]carbamoyl]-3-methyl-butyl]-5-chloro-1H-benzimidazole-2-carboxamide;

N-[(1S)-1-[[(3-amino-3-oxo-propyl)-[(2S)-2-chloro-2-fluoro-acetyl]amino]carbamoyl]-3-methyl-butyl]-5-chloro-1H-benzimidazole-2-carboxamide;

5-chloro-N-[rac-(1S)-2-[2-(3-amino-3-oxo-propyl)-2-(2-chloro-2-fluoro-acetyl)hydrazino]-1-(1-bicyclo[1.1.1]pentanylmethyl)-2-axo-ethyl]-1H-indole-2-carboxamide;

N-[rac-(1S)-2-[2-(3-amino-3-oxo-propyl)-2-(2-chloro-2-fluoro-acetyl)hydrazino]-1-(cyclopropylmethyl)-2-axo-ethyl]-1H-indole-2-carboxamide;

N-[(1S)-1-[[(3-amino-3-oxo-propyl)-(2-chloro-2-fluoro-acetyl)amino]carbamoyl]-3-methyl-butyl]-1H-benzimidazole-2-carboxamide;

N-[(1S)-1-[[(3-amino-3-oxo-propyl)-[(2R)-2-chloro-2-fluoro-acetyl]amino]carbamoyl]-3-methyl-butyl]-1H-benzimidazole-2-carboxamide;

N-[(1S)-1-[[(3-amino-3-oxo-propyl)-[(2S)-2-chloro-2-fluoro-acetyl]amino]carbamoyl]-3-methyl-butyl]-1H-benzimidazole-2-carboxamide;

N-[(1S)-1-[[(3-amino-3-oxo-propyl)-(2-chloro-2-fluoro-acetyl)amino]carbamoyl]-3-methyl-butyl]pyrazolo[1,5-a]pyridine-2-carboxamide;

N-[(1S)-1-[[(3-amino-3-oxo-propyl)-(2-chloro-2-fluoro-acetyl)amino]carbamoyl]-3,3-dimethyl-butyl]-1H-benzimidazole-2-carboxamide;

N-[(1S)-1-[[(3-amino-3-oxo-propyl)-[(2R)-2-chloro-2-fluoro-acetyl]amino]carbamoyl]-3,3-dimethyl-butyl]-1H-benzimidazole-2-carboxamide;

N-[(1S)-1-[[(3-amino-3-oxo-propyl)-[(2S)-2-chloro-2-fluoro-acetyl]amino]carbamoyl]-3,3-dimethyl-butyl]-1H-benzimidazole-2-carboxamide;

N-[rac-(1S)-2-[2-(3-amino-3-oxo-propyl)-2-(2-chloro-2-fluoro-acetyl)hydrazino]-1-(cyclobutylmethyl)-2-axo-ethyl]-1H-benzimidazole-2-carboxamide;

N-[rac-(1S)-2-[2-(3-amino-3-oxo-propyl)-2-(2-chloro-2-fluoro-acetyl)hydrazino]-1-(1-bicyclo[1.1.1]pentanylmethyl)-2-axo-ethyl]-1H-benzimidazole-2-carboxamide;

N-[(1S)-1-[[(2-chloro-2-fluoro-acetyl)-[(2-axopyrrolidin-3-yl)methyl]amino]carbamoyl]-3-methyl-butyl]-5-methyl-isoxazole-3-carboxamide;

N-[(1S)-1-[[[(2S)-2-chloro-2-fluoro-acetyl]-[[(3S)-2-axopyrrolidin-3-yl]methyl]amino]carbamoyl]-3-methyl-butyl]-5-methyl-isoxazole-3-carboxamide;

N-[(1S)-1-[[[(2R)-2-chloro-2-fluoro-acetyl]-[[(3R)-2-axopyrrolidin-3-yl]methyl]amino]carbamoyl]-3-methyl-butyl]-5-methyl-isoxazole-3-carboxamide;

N-[(1S)-1-[[[(2S)-2-chloro-2-fluoro-acetyl]-[[(3R)-2-axopyrrolidin-3-yl]methyl]amino]carbamoyl]-3-methyl-butyl]-5-methyl-isoxazole-3-carboxamide;

N-[(1R)-2-[2-(2-chloro-2-fluoro-acetyl)-2-[(2-axopyrrolidin-3-yl)methyl]hydrazino]-2-oxo-1-(trimethylsilylmethyl)ethyl]-5-methyl-isoxazole-3-carboxamide;

N-[(1R)-2-[2-[(2R)-2-chloro-2-fluoro-acetyl]-2-[[(3R)-2-axopyrrolidin-3-yl]methyl]hydrazino]-2-oxo-1-(trimethylsilylmethyl)ethyl]-5-methyl-isoxazole-3-carboxamide;

N-[(1R)-2-[2-[(2R)-2-chloro-2-fluoro-acetyl]-2-[[(3S)-2-axopyrrolidin-3-yl]methyl]hydrazino]-2-oxo-1-(trimethylsilylmethyl)ethyl]-5-methyl-isoxazole-3-carboxamide;

N-[(1R)-2-[2-[(2S)-2-chloro-2-fluoro-acetyl]-2-[[(3S)-2-axopyrrolidin-3-yl]methyl]hydrazino]-2-oxo-1-(trimethylsilylmethyl)ethyl]-5-methyl-isoxazole-3-carboxamide;

N-[(1R)-2-[2-[(2S)-2-chloro-2-fluoro-acetyl]-2-[[(3R)-2-axopyrrolidin-3-yl]methyl]hydrazino]-2-oxo-1-(trimethylsilylmethyl)ethyl]-5-methyl-isoxazole-3-carboxamide;

N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-methyl-isoxazole-3-carboxamide;

N-[(1S)-1-(1-bicyclo[1.1.1]pentanylmethyl)-2-[2-[(2R)-2-chloro-2-fluoro-acetyl]-2-[[(3S)-2-axopyrrolidin-3-yl]methyl]hydrazino]-2-axo-ethyl]-5-methyl-isoxazole-3-carboxamide;

N-[(1S)-1-[[[(2R)-2-chloro-2-fluoro-acetyl]-[[(3R)-2-axopyrrolidin-3-yl]methyl]amino]carbamoyl]-3,3-dimethyl-butyl]-5-methyl-isoxazole-3-carboxamide;

N-[(1S)-2-[2-[(2R)-2-chloro-2-fluoro-acetyl]-2-[[(3S)-2-axopyrrolidin-3-yl]methyl]hydrazino]-1-(cyclopropylmethyl)-2-axo-ethyl]-5-methyl-isoxazole-3-carboxamide;

5-methyl-N-[rac-(1S)-2-[2-(3-amino-3-oxo-propyl)-2-(2-chloro-2-fluoro-acetyl)hydrazino]-1-(cyclohexylmethyl)-2-axo-ethyl]isoxazole-3-carboxamide;

5-methyl-N-[rac-(1S)-2-[2-(3-amino-3-oxo-propyl)-2-(2-chloro-2-fluoro-acetyl)hydrazino]-1-(cyclopropylmethyl)-2-axo-ethyl]isoxazole-3-carboxamide;

N-[rac-(1S)-1-(1-bicyclo[1.1.1]pentanylmethyl)-2-[2-(2-chloro-2-fluoro-acetyl)-2-[(2-axopyrrolidin-3-yl)methyl]hydrazino]-2-axo-ethyl]pyrazine-2-carboxamide;

N-[rac-(1S)-1-[[(2-chloro-2-fluoro-acetyl)-[(2-axopyrrolidin-3-yl)methyl]amino]carbamoyl]-3,3-dimethyl-butyl]pyrazine-2-carboxamide;

N-[rac-(1S)-1-[[(3-amino-3-oxo-propyl)-(2-chloro-2-fluoro-acetyl)amino]carbamoyl]-3,3-dimethyl-butyl]pyrazine-2-carboxamide;

N-[rac-(1S)-2-[2-(3-amino-3-oxo-propyl)-2-(2-chloro-2-fluoro-acetyl)hydrazino]-1-(cyclobutylmethyl)-2-axo-ethyl]pyrazine-2-carboxamide;

N-[2-[2-(3-amino-3-oxo-propyl)-2-(2-chloro-2-fluoro-acetyl)hydrazino]-1-[(3,3-difluorocyclobutyl)methyl]-2-axo-ethyl]-2-methyl-oxazole-4-carboxamide;

2-methyl-N-[rac-(1S)-1-[[(2-chloro-2-fluoro-acetyl)-[(2-axopyrrolidin-3-yl)methyl]amino]carbamoyl]-3-methyl-butyl]oxazole-4-carboxamide;

N-[rac-(1S)-2-[2-(3-amino-3-oxo-propyl)-2-(2-chloro-2-fluoro-acetyl)hydrazino]-1-(cyclohexylmethyl)-2-axo-ethyl]imidazo[1,2-a]pyridine-2-carboxamide;

3-[(2-chloro-2-fluoro-acetyl)-[[(2S)-2-[[2-(3-methoxyanilino)acetyl]amino]-4-methyl-pentanoyl]amino]amino]propanamide;

3-[[(2R)-2-chloro-2-fluoro-acetyl]-[[(2S)-2-[[2-(3-methoxyanilino)acetyl]amino]-4-methyl-pentanoyl]amino]amino]propanamide;

3-[[(2S)-2-chloro-2-fluoro-acetyl]-[[(2S)-2-[[2-(3-methoxyanilino)acetyl]amino]-4-methyl-pentanoyl]amino]amino]propanamide;

3-[(2-chloro-2-fluoro-acetyl)-[[rac-(2S)-2-(benzylsulfonylamino)-3-cyclohexyl-propanoyl]amino]amino]propanamide;

3-[(2-chloro-2-fluoro-acetyl)-[[rac-(2S)-2-(benzylsulfonylamino)-3-cyclopropyl-propanoyl]amino]amino]propanamide;

3-[(2-chloro-2-fluoro-acetyl)-[[(2S)-4-methyl-2-[[(E)-3-phenylprop-2-enoyl]amino]pentanoyl]amino]amino]propanamide;

3-[[(2R)-2-chloro-2-fluoro-acetyl]-[[(2S)-4-methyl-2-[[(E)-3-phenylprop-2-enoyl]amino]pentanoyl]amino]amino]propanamide;

3-[[(2S)-2-chloro-2-fluoro-acetyl]-[[(2S)-4-methyl-2-[[(E)-3-phenylprop-2-enoyl]amino]pentanoyl]amino]amino]propanamide;

N-[(1S)-1-[[(3-amino-3-oxo-propyl)-[(2R)-2-chloro-2-fluoro-acetyl]amino]carbamoyl]-3-methyl-butyl]-2-methyl-thiazole-4-carboxamide;

N-[(1S)-1-[[(3-amino-3-oxo-propyl)-(2-chloro-2-fluoro-acetyl)amino]carbamoyl]-3-methyl-butyl]-1H-pyrrolo[2,3-c]pyridine-2-carboxamide;

N-[(1S)-1-[[(3-amino-3-oxo-propyl)-[(2R)-2-chloro-2-fluoro-acetyl]amino]carbamoyl]-3-methyl-butyl]-1H-pyrrolo[2,3-c]pyridine-2-carboxamide;

N-[(1S)-1-[[(3-amino-3-oxo-propyl)-[(2S)-2-chloro-2-fluoro-acetyl]amino]carbamoyl]-3-methyl-butyl]-1H-pyrrolo[2,3-c]pyridine-2-carboxamide;

5-methoxy-N-[rac-(1S)-1-[[(3-amino-3-oxo-propyl)-(2-chloro-2-fluoro-acetyl)amino]carbamoyl]-3-methyl-butyl]-1H-pyrrolo[2,3-c]pyridine-2-carboxamide;

N-[rac-(1S)-1-[[(3-amino-3-oxo-propyl)-(2-chloro-2-fluoro-acetyl)amino]carbamoyl]-3-methyl-butyl]pyrazolo[1,5-a]pyridine-2-carboxamide;

N-[(1S)-1-[[(3-amino-3-oxo-propyl)-[(2R)-2-chloro-2-fluoro-acetyl]amino]carbamoyl]-3-methyl-butyl]pyrazolo[1,5-a]pyridine-2-carboxamide;

N-[(1S)-1-[[(3-amino-3-oxo-propyl)-[(2S)-2-chloro-2-fluoro-acetyl]amino]carbamoyl]-3-methyl-butyl]pyrazolo[1,5-a]pyridine-2-carboxamide;

N-[(1S)-1-[[(3-amino-3-oxo-propyl)-(2-chloro-2-fluoro-acetyl)amino]carbamoyl]-3-methyl-butyl]-1H-pyrrolo[3,2-b]pyridine-2-carboxamide;

N-[(1S)-1-[[(3-amino-3-oxo-propyl)-[(2R)-2-chloro-2-fluoro-acetyl]amino]carbamoyl]-3-methyl-butyl]-1H-pyrrolo[3,2-b]pyridine-2-carboxamide;

N-[(1S)-1-[[(3-amino-3-oxo-propyl)-[(2S)-2-chloro-2-fluoro-acetyl]amino]carbamoyl]-3-methyl-butyl]-1H-pyrrolo[3,2-b]pyridine-2-carboxamide;

N-[rac-(1S)-2-[2-(2-chloro-2-fluoro-acetyl)-2-[(2-axopyrrolidin-3-yl)methyl]hydrazino]-1-(cyclopropylmethyl)-2-axo-ethyl]-1H-indole-2-carboxamide;

N-[rac-(1S)-1-[[(2-chloro-2-fluoro-acetyl)-[(2-axopyrrolidin-3-yl)methyl]amino]carbamoyl]-3-methyl-butyl]-1H-benzimidazole-2-carboxamide;

5-methyl-N-[rac-(1S)-2-[2-(2-chloro-2-fluoro-acetyl)-2-[(2-axopyrrolidin-3-yl)methyl]hydrazino]-1-(cyclohexylmethyl)-2-axo-ethyl]isoxazole-3-carboxamide;

N-[rac-(1S)-1-[[(3-amino-3-oxo-propyl)-(2-chloro-2-fluoro-acetyl)amino]carbamoyl]-3-methyl-butyl]imidazo[1,2-a]pyridine-2-carboxamide;

N-[rac-(1S)-1-[[(3-amino-3-oxo-propyl)-(2-chloro-2-fluoro-acetyl)amino]carbamoyl]-3-methyl-butyl]-1H-imidazole-2-carboxamide;

5-methyl-N-[rac-(1S)-1-[[(3-amino-3-oxo-propyl)-(2-chloro-2-fluoro-acetyl)amino]carbamoyl]-3-methyl-butyl]isoxazole-3-carboxamide;

N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-(trifluoromethyl)isoxazole-3-carboxamide;

N-[(1S)-1-(1-bicyclo[1.1.1]pentanylmethyl)-2-[2-[(2R)-2-chloro-2-fluoro-acetyl]-2-[[(3S)-2-axopyrrolidin-3-yl]methyl]hydrazino]-2-axo-ethyl]-5-(trifluoromethyl)isoxazole-3-carboxamide;

N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-(difluoromethyl)isoxazole-3-carboxamide; and N-[(1S)-1-[[[(2R)-2-chloro-2-fluoro-acetyl]-[[(3S)-2-axopyrrolidin-3-yl]methyl]amino]carbamoyl]-4-methyl-pentyl]-5-methyl-isoxazole-3-carboxamide.

In a preferred embodiment, the present invention provides a compound of formula (II) as described herein, or a pharmaceutically acceptable salt thereof, wherein said compound of formula (II) is selected from:
N-[(1S)-2-[2-(3-amino-3-oxo-propyl)-2-[(2R)-2-chloro-2-fluoro-acetyl]hydrazino]-1-(cyclohexylmethyl)-2-axo-ethyl]-4-methoxy-1H-indole-2-carboxamide;
N-[(1S)-1-[[(3-amino-3-oxo-propyl)-[(2S)-2-chloro-2-fluoro-acetyl]amino]carbamoyl]-3-methyl-butyl]-5-chloro-1H-indole-2-carboxamide;
N-[(1S)-2-[2-(3-amino-3-oxo-propyl)-2-[(2S)-2-chloro-2-fluoro-acetyl]hydrazino]-1-(cyclohexylmethyl)-2-axo-ethyl]-1H-indole-2-carboxamide;
N-[(1S)-1-[[(3-amino-3-oxo-propyl)-[(2R)-2-chloro-2-fluoro-acetyl]amino]carbamoyl]-3-methyl-butyl]-5-chloro-1H-benzimidazole-2-carboxamide;
N-[(1S)-1-[[(3-amino-3-oxo-propyl)-[(2S)-2-chloro-2-fluoro-acetyl]amino]carbamoyl]-3-methyl-butyl]-1H-benzimidazole-2-carboxamide;
N-[(1S)-1-[[(3-amino-3-oxo-propyl)-(2-chloro-2-fluoro-acetyl)amino]carbamoyl]-3,3-dimethyl-butyl]-1H-benzimidazole-2-carboxamide;
N-[(1S)-1-[[[(2R)-2-chloro-2-fluoro-acetyl]-[[(3R)-2-axopyrrolidin-3-yl]methyl]amino]carbamoyl]-3-methyl-butyl]-5-methyl-isoxazole-3-carboxamide;
N-[(1R)-2-[2-[(2R)-2-chloro-2-fluoro-acetyl]-2-[[(3S)-2-axopyrrolidin-3-yl]methyl]hydrazino]-2-oxo-1-(trimethylsilylmethyl)ethyl]-5-methyl-isoxazole-3-carboxamide;
N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-methyl-isoxazole-3-carboxamide;
N-[(1S)-1-(1-bicyclo[1.1.1]pentanylmethyl)-2-[2-[(2R)-2-chloro-2-fluoro-acetyl]-2-[[(3S)-2-axopyrrolidin-3-yl]methyl]hydrazino]-2-axo-ethyl]-5-methyl-isoxazole-3-carboxamide;
N-[(1S)-1-[[[(2R)-2-chloro-2-fluoro-acetyl]-[[(3R)-2-axopyrrolidin-3-yl]methyl]amino]carbamoyl]-3,3-dimethyl-butyl]-5-methyl-isoxazole-3-carboxamide;
N-[(1S)-2-[2-[(2R)-2-chloro-2-fluoro-acetyl]-2-[[(3S)-2-axopyrrolidin-3-yl]methyl]hydrazino]-1-(cyclopropylmethyl)-2-axo-ethyl]-5-methyl-isoxazole-3-carboxamide;
5-methyl-N-[rac-(1S)-2-[2-(2-chloro-2-fluoro-acetyl)-2-[(2-axopyrrolidin-3-yl)methyl]hydrazino]-1-(cyclohexylmethyl)-2-axo-ethyl]isoxazole-3-carboxamide;
N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-(trifluoromethyl)isoxazole-3-carboxamide;
N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-(difluoromethyl)isoxazole-3-carboxamide; and
N-[(1S)-1-[[[(2R)-2-chloro-2-fluoro-acetyl]-[[(3S)-2-axopyrrolidin-3-yl]methyl]amino]carbamoyl]-4-methyl-pentyl]-5-methyl-isoxazole-3-carboxamide.

The present invention also relates to the following enumerated embodiments. Thus, in one aspect, the present invention relates to (i) a compound of formula (I),

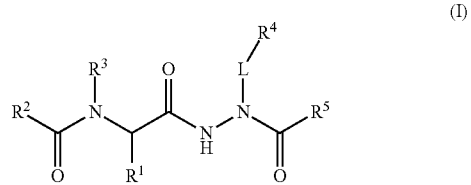

(I)

wherein
R$^1$ is H, C$_{1-6}$alkyl, or C$_{3-7}$cycloalkylC$_{1-6}$alkyl;
R$^2$ is C$_{1-6}$alkoxy, phenylC$_{2-6}$alkenyl, benzyloxy, oxazolyl, isoxazolyl, 1H-pyrrolo[2,3-b]pyridinyl, 1H-pyrrolo[3,2-c]pyridinyl, 6H-pyrrolo[2,3-c]pyridinyl, 1H-indolyl, or 1H-benzimidazolyl; wherein each of said phenylC$_2$-alkenyl, oxazolyl, isoxazolyl, 6H-pyrrolo[2,3-c]pyridinyl, and 1H-indolyl is unsubstituted or substituted with one to two substituents independently selected from halogen, C$_{1-6}$alkyl, and C$_{1-6}$alkoxy;
R$^3$ is H or C$_{1-6}$alkyl;
R$^4$ is H, carbamoyl, axopyrrolidinyl, oxopiperidinyl, 1H-pyrazolyl, 1H-imidazolyl, or (C$_{1-6}$ alkylamino)carbonyl;
R$^5$ is C$_{1-6}$alkyl substituted with one to two substituents independently selected from halogen and phenyl;
L is —C$_x$H$_{2x}$—, wherein x is 1, 2, 3, 4, 5, or 6;
or a pharmaceutically acceptable salt thereof.

Another embodiment of present invention is (ii) a compound of formula (Ia),

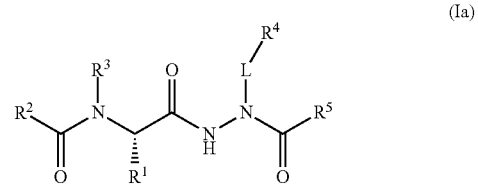

(Ia)

wherein
R$^1$ is H, C$_{1-6}$alkyl, or C$_{3-7}$cycloalkylC$_{1-6}$alkyl;
R$^2$ is C$_{1-6}$alkoxy, phenylC$_{2-6}$alkenyl, benzyloxy, oxazolyl, isoxazolyl, 1H-pyrrolo[2,3-b]pyridinyl, 1H-pyrrolo[3,2-c]pyridinyl, 6H-pyrrolo[2,3-c]pyridinyl, 1H-indolyl, or 1H-benzimidazolyl; wherein each of said phenylC$_{2-6}$alkenyl, oxazolyl, isoxazolyl, 6H-pyrrolo[2,3-c]pyridinyl, and 1H-indolyl is unsubstituted or substituted with one to two substituents independently selected from halogen, C$_{1-6}$alkyl, and C$_{1-6}$alkoxy;
R$^3$ is H or C$_{1-6}$alkyl;
R$^4$ is H, carbamoyl, axopyrrolidinyl, oxopiperidinyl, 1H-pyrazolyl, 1H-imidazolyl, or (C$_{1-6}$ alkylamino)carbonyl;
R$^5$ is C$_{1-6}$alkyl substituted with one to two substituents independently selected from halogen and phenyl;
L is —C$_x$H$_{2x}$—, wherein x is 1, 2, 3, 4, 5, or 6;
or a pharmaceutically acceptable salt thereof.

A further embodiment of present invention is (iii) a compound of formula (I) or (Ia), or a pharmaceutically acceptable salt thereof, according to (i) or (ii), wherein R$^1$ is C$_{1-6}$alkyl or C$_{3-7}$cycloalkylC$_{1-6}$alkyl.

A further embodiment of present invention is (iv) a compound of formula (I) or (Ia), or a pharmaceutically acceptable salt thereof, according to (iii), wherein R$^1$ is isobutyl or cyclohexylmethyl.

A further embodiment of present invention is (v) a compound of formula (I) or (Ia), or a pharmaceutically acceptable salt thereof, according to any one of (i) to (iv), wherein R$^2$ is benzyloxy, 1H-indolyl, or C$_{1-6}$alkoxy-1H-indolyl.

A further embodiment of present invention is (vi) a compound of formula (I) or (Ta), or a pharmaceutically acceptable salt thereof, according to (v), wherein R$^2$ is benzyloxy, 1H-indolyl, or 4-methoxy-1H-indolyl.

A further embodiment of present invention is (vii) a compound of formula (I) or (Ta), or a pharmaceutically acceptable salt thereof, according to any one of (i) to (vi), wherein R³ is H.

A further embodiment of present invention is (viii) a compound of formula (I) or (Ta), or a pharmaceutically acceptable salt thereof, according to any one of (i) to (vii), wherein R⁴ is carbamoyl.

A further embodiment of present invention is (ix) a compound of formula (I) or (Ta), or a pharmaceutically acceptable salt thereof, according to any one of (i) to (viii), wherein L is —C$_x$H$_{2x}$—, and wherein x is 2.

A further embodiment of present invention is (x) a compound of formula (I) or (Ta), or a pharmaceutically acceptable salt thereof, according to (ix), wherein L is —CH$_2$—CH$_2$—.

A further embodiment of present invention is (xi) a compound of formula (I) or (Ta), or a pharmaceutically acceptable salt thereof, according to any one of (i) to (x), R⁵ is C$_{1-6}$alkyl substituted twice with halogen.

A further embodiment of present invention is (xii) a compound of formula (I) or (Ta), or a pharmaceutically acceptable salt thereof, according to (xi), wherein R⁵ is chlorofluoromethyl.

A further embodiment of present invention is (xiii) a compound of formula (I) or (Ia), or a pharmaceutically acceptable salt thereof, according to any one of (i) to (xii), wherein
- R¹ is C$_{1-6}$alkyl or C$_{3-7}$cycloalkylC$_{1-6}$alkyl;
- R² is benzyloxy, 1H-indolyl, or C$_{1-6}$alkoxy-1H-indolyl;
- R³ is H;
- R⁴ is carbamoyl;
- R⁵ is C$_{1-6}$alkyl substituted twice with halogen;
- L is —C$_x$H$_{2x}$—, and wherein x is 2.

A further embodiment of present invention is (xiv) a compound of formula (I) or (Ia), or a pharmaceutically acceptable salt thereof, according to (xiii), wherein
- R¹ is isobutyl or cyclohexylmethyl;
- R² is benzyloxy, 1H-indolyl, or 4-methoxy-1H-indolyl;
- R³ is H;
- R⁴ is carbamoyl;
- R⁵ is chlorofluoromethyl;
- L is —CH$_2$—CH$_2$—.

A further embodiment of present invention is (xv) a compound selected from:

Benzyl N-[2-[2-(3-amino-3-oxo-propyl)-2-(2-chloroacetyl)hydrazino]-2-axo-ethyl]carbamate;
Benzyl N-[(1S)-1-[[(3-amino-3-oxo-propyl)-(2-chloroacetyl)amino]carbamoyl]-3-methyl-butyl]carbamate;
Benzyl N-[(1S)-1-[[(3-amino-3-oxo-propyl)-(2-chloro-2-phenyl-acetyl)amino]carbamoyl]-3-methyl-butyl]carbamate;
Benzyl N-[(1S)-1-[[(3-amino-3-oxo-propyl)-(2-chloropropanoyl)amino]carbamoyl]-3-methyl-butyl]carbamate;
Benzyl N-[(1S)-1-[[(3-amino-3-oxo-propyl)-(2-chlorobutanoyl)amino]carbamoyl]-3-methyl-butyl]carbamate;
Benzyl N-[(1S)-1-[[(3-amino-3-oxo-propyl)-(2-bromoacetyl)amino]carbamoyl]-3-methyl-butyl]carbamate;
Benzyl N-[(1S)-2-[2-(3-amino-3-oxo-propyl)-2-(2-chloroacetyl)hydrazino]-1-(cyclohexylmethyl)-2-axo-ethyl]carbamate;
Benzyl N-[(1S)-2-[2-(3-amino-3-oxo-propyl)-2-(2-chloroacetyl)hydrazino]-1-(cyclopentylmethyl)-2-axo-ethyl]carbamate;
Benzyl N-[(1S)-2-[2-(3-amino-3-oxo-propyl)-2-(2-chloroacetyl)hydrazino]-1-(cyclopropylmethyl)-2-axo-ethyl]carbamate;
Benzyl N-[(1S)-2-[2-(3-amino-3-oxo-propyl)-2-(2-fluoroacetyl)hydrazino]-1-(cyclohexylmethyl)-2-axo-ethyl]carbamate;
Benzyl N-[(1S)-2-[2-(3-amino-3-oxo-propyl)-2-(2-chloro-2-fluoro-acetyl)hydrazino]-1-(cyclohexylmethyl)-2-axo-ethyl]carbamate;
Benzyl((S)-1-(2-(3-amino-3-oxo-propyl)-2-((S)-2-chloro-2-fluoroacetyl)hydrazinyl)-3-cyclohexyl-1-oxo-propan-2-yl)carbamate;
Benzyl((S)-1-(2-(3-amino-3-oxo-propyl)-2-((R)-2-chloro-2-fluoroacetyl)hydrazinyl)-3-cyclohexyl-1-oxo-propan-2-yl)carbamate
Benzyl N-[(1S)-1-[[(3-amino-3-oxo-propyl)-(2-chloro-2-fluoro-acetyl)amino]carbamoyl]-3-methyl-butyl]carbamate;
Benzyl N-[(1 S)-1-[[(3-amino-3-oxo-propyl)-[(2S)-2-chloro-2-fluoro-acetyl]amino]carbamoyl]-3-methyl-butyl]carbamate;
Benzyl N-[(1 S)-1-[[(3-amino-3-oxo-propyl)-[(2R)-2-chloro-2-fluoro-acetyl]amino]carbamoyl]-3-methyl-butyl]carbamate;
Benzyl N-[(1S)-1-[[(2-chloroacetyl)-[(2-oxo-pyrrolidin-3-yl)methyl]amino]carbamoyl]-3-methyl-butyl]carbamate;
Benzyl N-[(1S)-1-[[(2-chloroacetyl)-[(2-oxo-3-piperidyl)methyl]amino]carbamoyl]-3-methyl-butyl]carbamate;
Benzyl N-[(1S)-1-[[(2-chloroacetyl)-propyl-amino]carbamoyl]-3-methyl-butyl]carbamate;
Benzyl N-[(1/S)-1-[[(2-chloroacetyl)-(1H-pyrazol-3-ylmethyl)amino]carbamoyl]-3-methyl-butyl]carbamate;
Benzyl N-[(1/S)-1-[[(2-chloroacetyl)-(1H-imidazol-4-ylmethyl)amino]carbamoyl]-3-methyl-butyl]carbamate;
tert-Butyl N-[(1S)-1-[[(3-amino-3-oxo-propyl)-(2-chloroacetyl)amino]carbamoyl]-3-methyl-butyl]carbamate;
4-Methoxy-N-[(1S)-1-[[(3-amino-3-oxo-propyl)-(2-chloroacetyl)amino]carbamoyl]-3-methyl-butyl]-1H-indole-2-carboxamide;
N-[(1S)-1-[[(3-amino-3-oxo-propyl)-(2-chloroacetyl)amino]carbamoyl]-3-methyl-butyl]-1H-indole-2-carboxamide;
N-[(1S)-1-[[(3-amino-3-oxo-propyl)-(2-chloroacetyl)amino]carbamoyl]-3-methyl-butyl]-2-methyl-oxazole-4-carboxamide;
N-[(1S)-1-[[(3-Amino-3-oxo-propyl)-(2-fluoroacetyl)amino]carbamoyl]-3-methyl-butyl]-4-methoxy-1H-indole-2-carboxamide;
N-[(1S)-1-[[(3-Amino-3-oxo-propyl)-(2-fluoroacetyl)amino]carbamoyl]-3-methyl-butyl]-1H-indole-2-carboxamide;
N-[(1S)-2-[2-(3-Amino-3-oxo-propyl)-2-(2-chloroacetyl)hydrazino]-1-(cyclohexylmethyl)-2-axo-ethyl]-4-methoxy-1H-indole-2-carboxamide;
3-[(2-Chloroacetyl)-[[(2S)-2-[[(E)-3-(4-chloro-2-fluorophenyl)prop-2-enoyl]amino]-3-cyclohexyl-propanoyl]amino]amino]propanamide;
3-[(2-Chloroacetyl)-[[(2S)-2-[[(E)-3-(4-chloro-2-fluorophenyl)prop-2-enoyl]amino]-4-methyl-pentanoyl]amino]amino]propanamide;
N-[(1S)-2-[2-(3-Amino-3-oxo-propyl)-2-(2-chloroacetyl)hydrazino]-1-(cyclohexylmethyl)-2-axo-ethyl]-1H-indole-2-carboxamide;
N-[(1S)-2-[2-(3-Amino-3-oxo-propyl)-2-(2-fluoroacetyl)hydrazino]-1-(cyclohexylmethyl)-2-axo-ethyl]-1H-indole-2-carboxamide;
N-[(1S)-2-[2-(3-Amino-3-oxo-propyl)-2-(2-fluoroacetyl)hydrazino]-1-(cyclohexylmethyl)-2-axo-ethyl]-4-methoxy-1H-indole-2-carboxamide;

N-[(1S)-1-[[(2-fluoroacetyl)-[(2-oxo-pyrrolidin-3-yl)methyl]amino]carbamoyl]-3-methyl-butyl]-1H-indole-2-carboxamide;

N-[(1S)-1-[[(2-Fluoroacetyl)-[[(3S)-2-oxo-pyrrolidin-3-yl]methyl]amino]carbamoyl]-3-methyl-butyl]-1H-indole-2-carboxamide;

N-[(1S)-1-[[(2-fluoroacetyl)-[[(3R)-2-oxo-pyrrolidin-3-yl]methyl]amino]carbamoyl]-3-methyl-butyl]-1H-indole-2-carboxamide;

N-[(1S)-2-[2-(3-Amino-3-oxo-propyl)-2-(2-chloroacetyl)hydrazino]-1-(cyclohexylmethyl)-2-axo-ethyl]-N-methyl-1H-indole-2-carboxamide;

N-[(1S)-1-[[(3-Amino-3-oxo-propyl)-(2-chloroacetyl)amino]carbamoyl]-3-methyl-butyl]-N-methyl-1H-indole-2-carboxamide;

N-[(1S)-1-[[(3-Amino-3-oxo-propyl)-(2-chloro-2-fluoro-acetyl)amino]carbamoyl]-3-methyl-butyl]-1H-indole-2-carboxamide;

N-[(1S)-1-[[(3-amino-3-oxo-propyl)-[(2S)-2-chloro-2-fluoro-acetyl]amino]carbamoyl]-3-methyl-butyl]-1H-indole-2-carboxamide;

N-[(1S)-1-[[(3-amino-3-oxo-propyl)-[(2R)-2-chloro-2-fluoro-acetyl]amino]carbamoyl]-3-methyl-butyl]-1H-indole-2-carboxamide;

N-[(1S)-1-[[(3-Amino-3-oxo-propyl)-(2-chloroacetyl)amino]carbamoyl]-3-methyl-butyl]-1H-benzimidazole-2-carboxamide;

N-[(1S)-1-[[(3-Amino-3-oxo-propyl)-(2-chloroacetyl)amino]carbamoyl]-3-methyl-butyl]isoxazole-3-carboxamide;

N-[(1S)-1-[[(3-Amino-3-oxo-propyl)-(2-chloroacetyl)amino]carbamoyl]-3-methyl-butyl]-1H-pyrrolo[2,3-b]pyridine-2-carboxamide;

N-[(1S)-1-[[(3-Amino-3-oxo-propyl)-(2-chloroacetyl)amino]carbamoyl]-3-methyl-butyl]-2-methyl-oxazole-4-carboxamide;

N-[(1S)-1-[[(3-Amino-3-oxo-propyl)-(2-chloroacetyl)amino]carbamoyl]-3-methyl-butyl]-5-methyl-isoxazole-4-carboxamide;

N-[(1S)-1-[[(3-Amino-3-oxo-propyl)-(2-chloroacetyl)amino]carbamoyl]-3-methyl-butyl]-5-methoxy-6H-pyrrolo[2,3-c]pyridine-2-carboxamide;

N-[(1S)-2-[2-(3-amino-3-oxo-propyl)-2-(2-chloroacetyl)hydrazino]-1-(cyclohexylmethyl)-2-axo-ethyl]-5-methyl-isoxazole-3-carboxamide;

4-Methoxy-N-[(1S)-1-[[(3-amino-3-oxo-propyl)-(2-chloro-2-fluoro-acetyl)amino]carbamoyl]-3-methyl-butyl]-1H-indole-2-carboxamide;

N-[(1S)-1-[[(2-Chloroacetyl)-[3-(methylamino)-3-oxo-propyl]amino]carbamoyl]-3-methyl-butyl]-N-methyl-1H-indole-2-carboxamide;

N-[(1S)-1-[[(2-Chloroacetyl)-[(2-oxo-pyrrolidin-3-yl)methyl]amino]carbamoyl]-3-methyl-butyl]-1H-indole-2-carboxamide;

N-[(1S)-1-[[(2-chloroacetyl)-[[(3S)-2-oxo-pyrrolidin-3-yl]methyl]amino]carbamoyl]-3-methyl-butyl]-1H-indole-2-carboxamide;

N-[(1S)-1-[[(2-chloroacetyl)-[[(3R)-2-oxo-pyrrolidin-3-yl]methyl]amino]carbamoyl]-3-methyl-butyl]-1H-indole-2-carboxamide;

N-[(1S)-1-[[(3-amino-3-oxo-propyl)-(2-chloroacetyl)amino]carbamoyl]-3-methyl-butyl]-1H-pyrrolo[3,2-c]pyridine-2-carboxamide;

or a pharmaceutically acceptable salt thereof.

A further embodiment of present invention is (xvi) a compound selected from:

Benzyl N-[2-[2-(3-amino-3-oxo-propyl)-2-(2-chloroacetyl)hydrazino]-2-axo-ethyl]carbamate;

Benzyl N-[1-[[(3-amino-3-oxo-propyl)-(2-chloroacetyl)amino]carbamoyl]-3-methyl-butyl]carbamate;

Benzyl N-[1-[[(3-amino-3-oxo-propyl)-(2-chloro-2-phenyl-acetyl)amino]carbamoyl]-3-methyl-butyl]carbamate;

Benzyl N-[1-[[(3-amino-3-oxo-propyl)-(2-chloropropanoyl)amino]carbamoyl]-3-methyl-butyl]carbamate;

Benzyl N-[1-[[(3-amino-3-oxo-propyl)-(2-chlorobutanoyl)amino]carbamoyl]-3-methyl-butyl]carbamate;

Benzyl N-[1-[[(3-amino-3-oxo-propyl)-(2-bromoacetyl)amino]carbamoyl]-3-methyl-butyl]carbamate;

Benzyl N-[2-[2-(3-amino-3-oxo-propyl)-2-(2-chloroacetyl)hydrazino]-1-(cyclohexylmethyl)-2-axo-ethyl]carbamate;

Benzyl N-[2-[2-(3-amino-3-oxo-propyl)-2-(2-chloroacetyl)hydrazino]-1-(cyclopentylmethyl)-2-axo-ethyl]carbamate;

Benzyl N-[2-[2-(3-amino-3-oxo-propyl)-2-(2-chloroacetyl)hydrazino]-1-(cyclopropylmethyl)-2-axo-ethyl]carbamate;

Benzyl N-[2-[2-(3-amino-3-oxo-propyl)-2-(2-fluoroacetyl)hydrazino]-1-(cyclohexylmethyl)-2-axo-ethyl]carbamate;

Benzyl N-[2-[2-(3-amino-3-oxo-propyl)-2-(2-chloro-2-fluoro-acetyl)hydrazino]-1-(cyclohexylmethyl)-2-axo-ethyl]carbamate;

Benzyl(1-(2-(3-amino-3-oxo-propyl)-2-((S)-2-chloro-2-fluoroacetyl)hydrazinyl)-3-cyclohexyl-1-oxo-propan-2-yl)carbamate;

Benzyl(1-(2-(3-amino-3-oxo-propyl)-2-((R)-2-chloro-2-fluoroacetyl)hydrazinyl)-3-cyclohexyl-1-oxo-propan-2-yl)carbamate Benzyl N-[1-[[(3-amino-3-oxo-propyl)-(2-chloro-2-fluoro-acetyl)amino]carbamoyl]-3-methyl-butyl]carbamate;

Benzyl N-[1-[[(3-amino-3-oxo-propyl)-[(2S)-2-chloro-2-fluoro-acetyl]amino]carbamoyl]-3-methyl-butyl]carbamate;

Benzyl N-[1-[[(3-amino-3-oxo-propyl)-[(2R)-2-chloro-2-fluoro-acetyl]amino]carbamoyl]-3-methyl-butyl]carbamate;

Benzyl N-[1-[[(2-chloroacetyl)-[(2-oxo-pyrrolidin-3-yl)methyl]amino]carbamoyl]-3-methyl-butyl]carbamate;

Benzyl N-[1-[[(2-chloroacetyl)-[(2-oxo-3-piperidyl)methyl]amino]carbamoyl]-3-methyl-butyl]carbamate;

Benzyl N-[1-[[(2-chloroacetyl)-propyl-amino]carbamoyl]-3-methyl-butyl]carbamate;

Benzyl N-[1-[[(2-chloroacetyl)-(1H-pyrazol-3-ylmethyl)amino]carbamoyl]-3-methyl-butyl]carbamate;

Benzyl N-[1-[[(2-chloroacetyl)-(1H-imidazol-4-ylmethyl)amino]carbamoyl]-3-methyl-butyl]carbamate;

tert-Butyl N-[1-[[(3-amino-3-oxo-propyl)-(2-chloroacetyl)amino]carbamoyl]-3-methyl-butyl]carbamate;

4-Methoxy-N-[1-[[(3-amino-3-oxo-propyl)-(2-chloro-acetyl)amino]carbamoyl]-3-methyl-butyl]-1H-indole-2-carboxamide;

N-[1-[[(3-amino-3-oxo-propyl)-(2-chloroacetyl)amino]carbamoyl]-3-methyl-butyl]-1H-indole-2-carboxamide;

N-[1-[[(3-amino-3-oxo-propyl)-(2-chloroacetyl)amino]carbamoyl]-3-methyl-butyl]-2-methyl-oxazole-4-carboxamide;

N-[1-[[(3-Amino-3-oxo-propyl)-(2-fluoroacetyl)amino]carbamoyl]-3-methyl-butyl]-4-methoxy-1H-indole-2-carboxamide;

N-[1-[[(3-Amino-3-oxo-propyl)-(2-fluoroacetyl)amino]carbamoyl]-3-methyl-butyl]-1H-indole-2-carboxamide;

N-[2-[2-(3-Amino-3-oxo-propyl)-2-(2-chloroacetyl)hydrazino]-1-(cyclohexylmethyl)-2-axo-ethyl]-4-methoxy-1H-indole-2-carboxamide;

3-[(2-Chloroacetyl)-[[2-[[(E)-3-(4-chloro-2-fluoro-phenyl) prop-2-enoyl]amino]-3-cyclohexyl-propanoyl]amino] amino]propanamide;

3-[(2-Chloroacetyl)-[[2-[[(E)-3-(4-chloro-2-fluoro-phenyl) prop-2-enoyl]amino]-4-methyl-pentanoyl]amino]amino] propanamide;

N-[2-[2-(3-Amino-3-oxo-propyl)-2-(2-chloroacetyl)hydrazino]-1-(cyclohexylmethyl)-2-axo-ethyl]-1H-indole-2-carboxamide;

N-[2-[2-(3-Amino-3-oxo-propyl)-2-(2-fluoroacetyl)hydrazino]-1-(cyclohexylmethyl)-2-axo-ethyl]-1H-indole-2-carboxamide;

N-[2-[2-(3-Amino-3-oxo-propyl)-2-(2-fluoroacetyl)hydrazino]-1-(cyclohexylmethyl)-2-axo-ethyl]-4-methoxy-1H-indole-2-carboxamide;

N-[1-[[(2-fluoroacetyl)-[(2-oxo-pyrrolidin-3-yl)methyl] amino]carbamoyl]-3-methyl-butyl]-1H-indole-2-carboxamide;

N-[1-[[(2-Fluoroacetyl)-[[(3S)-2-oxo-pyrrolidin-3-yl] methyl]amino]carbamoyl]-3-methyl-butyl]-1H-indole-2-carboxamide;

N-[1-[[(2-fluoroacetyl)-[[(3R)-2-oxo-pyrrolidin-3-yl] methyl]amino]carbamoyl]-3-methyl-butyl]-1H-indole-2-carboxamide;

N-[2-[2-(3-Amino-3-oxo-propyl)-2-(2-chloroacetyl)hydrazino]-1-(cyclohexylmethyl)-2-axo-ethyl]-N-methyl-1H-indole-2-carboxamide;

N-[1-[[(3-Amino-3-oxo-propyl)-(2-chloroacetyl)amino]carbamoyl]-3-methyl-butyl]-N-methyl-1H-indole-2-carboxamide;

N-[1-[[(3-Amino-3-oxo-propyl)-(2-chloro-2-fluoro-acetyl) amino]carbamoyl]-3-methyl-butyl]-1H-indole-2-carboxamide;

N-[1-[[(3-amino-3-oxo-propyl)-[(2S)-2-chloro-2-fluoroacetyl]amino]carbamoyl]-3-methyl-butyl]-1H-indole-2-carboxamide;

N-[1-[[(3-amino-3-oxo-propyl)-[(2R)-2-chloro-2-fluoroacetyl]amino]carbamoyl]-3-methyl-butyl]-1H-indole-2-carboxamide;

N-[1-[[(3-Amino-3-oxo-propyl)-(2-chloroacetyl)amino]carbamoyl]-3-methyl-butyl]-1H-benzimidazole-2-carboxamide;

N-[1-[[(3-Amino-3-oxo-propyl)-(2-chloroacetyl)amino]carbamoyl]-3-methyl-butyl]isoxazole-3-carboxamide;

N-[1-[[(3-Amino-3-oxo-propyl)-(2-chloroacetyl)amino]carbamoyl]-3-methyl-butyl]-1H-pyrrolo[2,3-b]pyridine-2-carboxamide;

N-[1-[[(3-Amino-3-oxo-propyl)-(2-chloroacetyl)amino]carbamoyl]-3-methyl-butyl]-2-methyl-oxazole-4-carboxamide;

N-[1-[[(3-Amino-3-oxo-propyl)-(2-chloroacetyl)amino]carbamoyl]-3-methyl-butyl]-5-methyl-isoxazole-4-carboxamide;

N-[1-[[(3-Amino-3-oxo-propyl)-(2-chloroacetyl)amino]carbamoyl]-3-methyl-butyl]-5-methoxy-6H-pyrrolo[2,3-c] pyridine-2-carboxamide;

N-[2-[2-(3-amino-3-oxo-propyl)-2-(2-chloroacetyl)hydrazino]-1-(cyclohexylmethyl)-2-axo-ethyl]-5-methyl-isoxazole-3-carboxamide;

4-Methoxy-N-[1-[[(3-amino-3-oxo-propyl)-(2-chloro-2-fluoro-acetyl)amino]carbamoyl]-3-methyl-butyl]-1H-indole-2-carboxamide;

N-[1-[[(2-Chloroacetyl)-[3-(methylamino)-3-oxo-propyl] amino]carbamoyl]-3-methyl-butyl]-N-methyl-1H-indole-2-carboxamide;

N-[1-[[(2-Chloroacetyl)-[(2-oxo-pyrrolidin-3-yl)methyl] amino]carbamoyl]-3-methyl-butyl]-1H-indole-2-carboxamide;

N-[1-[[(2-chloroacetyl)-[[(3S)-2-oxo-pyrrolidin-3-yl] methyl]amino]carbamoyl]-3-methyl-butyl]-1H-indole-2-carboxamide;

N-[1-[[(2-chloroacetyl)-[[(3R)-2-oxo-pyrrolidin-3-yl] methyl]amino]carbamoyl]-3-methyl-butyl]-1H-indole-2-carboxamide;

N-[1-[[(3-amino-3-oxo-propyl)-(2-chloroacetyl)amino]carbamoyl]-3-methyl-butyl]-1H-pyrrolo[3,2-c]pyridine-2-carboxamide;

or a pharmaceutically acceptable salt thereof.

A further embodiment of present invention is (xvii) a compound selected from:

Benzyl N-[2-[2-(3-amino-3-oxo-propyl)-2-(2-chloroacetyl) hydrazino]-2-axo-ethyl]carbamate;

Benzyl N-[(1R)-1-[[(3-amino-3-oxo-propyl)-(2-chloroacetyl)amino]carbamoyl]-3-methyl-butyl]carbamate;

Benzyl N-[(1R)-1-[[(3-amino-3-oxo-propyl)-(2-chloro-2-phenyl-acetyl)amino]carbamoyl]-3-methyl-butyl]carbamate;

Benzyl N-[(1R)-1-[[(3-amino-3-oxo-propyl)-(2-chloropropanoyl)amino]carbamoyl]-3-methyl-butyl]carbamate;

Benzyl N-[(1R)-1-[[(3-amino-3-oxo-propyl)-(2-chlorobutanoyl)amino]carbamoyl]-3-methyl-butyl]carbamate;

Benzyl N-[(1R)-1-[[(3-amino-3-oxo-propyl)-(2-bromoacetyl)amino]carbamoyl]-3-methyl-butyl]carbamate;

Benzyl N-[(1R)-2-[2-(3-amino-3-oxo-propyl)-2-(2-chloroacetyl)hydrazino]-1-(cyclohexylmethyl)-2-axo-ethyl]carbamate;

Benzyl N-[(1R)-2-[2-(3-amino-3-oxo-propyl)-2-(2-chloroacetyl)hydrazino]-1-(cyclopentylmethyl)-2-axo-ethyl] carbamate;

Benzyl N-[(1R)-2-[2-(3-amino-3-oxo-propyl)-2-(2-chloroacetyl)hydrazino]-1-(cyclopropylmethyl)-2-axo-ethyl] carbamate;

Benzyl N-[(1R)-2-[2-(3-amino-3-oxo-propyl)-2-(2-fluoroacetyl)hydrazino]-1-(cyclohexylmethyl)-2-axo-ethyl]carbamate;

Benzyl N-[(1R)-2-[2-(3-amino-3-oxo-propyl)-2-(2-chloro-2-fluoro-acetyl)hydrazino]-1-(cyclohexylmethyl)-2-axo-ethyl]carbamate;

Benzyl((R)-1-(2-(3-amino-3-oxo-propyl)-2-((S)-2-chloro-2-fluoroacetyl)hydrazinyl)-3-cyclohexyl-1-oxo-propan-2-yl)carbamate;

Benzyl((R)-1-(2-(3-amino-3-oxo-propyl)-2-((R)-2-chloro-2-fluoroacetyl)hydrazinyl)-3-cyclohexyl-1-oxo-propan-2-yl)carbamate;

Benzyl N-[(1R)-1-[[(3-amino-3-oxo-propyl)-(2-chloro-2-fluoro-acetyl)amino]carbamoyl]-3-methyl-butyl]carbamate;

Benzyl N-[(1R)-1-[[(3-amino-3-oxo-propyl)-[(2S)-2-chloro-2-fluoro-acetyl]amino]carbamoyl]-3-methyl-butyl]carbamate;

Benzyl N-[(1R)-1-[[(3-amino-3-oxo-propyl)-[(2R)-2-chloro-2-fluoro-acetyl]amino]carbamoyl]-3-methyl-butyl]carbamate;

Benzyl N-[(1R)-1-[[(2-chloroacetyl)-[(2-oxo-pyrrolidin-3-yl)methyl]amino]carbamoyl]-3-methyl-butyl]carbamate;

Benzyl N-[(1R)-1-[[(2-chloroacetyl)-[(2-oxo-3-piperidyl) methyl]amino]carbamoyl]-3-methyl-butyl]carbamate;

Benzyl N-[(1R)-1-[[(2-chloroacetyl)-propyl-amino]carbamoyl]-3-methyl-butyl]carbamate;

Benzyl N-[(1R)-1-[[(2-chloroacetyl)-(1H-pyrazol-3-ylmethyl)amino]carbamoyl]-3-methyl-butyl]carbamate;

Benzyl N-[(1R)-1-[[(2-chloroacetyl)-(1H-imidazol-4-ylmethyl)amino]carbamoyl]-3-methyl-butyl]carbamate;
tert-Butyl N-[(1R)-1-[[(3-amino-3-oxo-propyl)-(2-chloroacetyl)amino]carbamoyl]-3-methyl-butyl]carbamate;
4-Methoxy-N-[(1R)-1-[[(3-amino-3-oxo-propyl)-(2-chloroacetyl)amino]carbamoyl]-3-methyl-butyl]-1H-indole-2-carboxamide;
N-[(1R)-1-[[(3-amino-3-oxo-propyl)-(2-chloroacetyl)amino]carbamoyl]-3-methyl-butyl]-1H-indole-2-carboxamide;
N-[(1R)-1-[[(3-amino-3-oxo-propyl)-(2-chloroacetyl)amino]carbamoyl]-3-methyl-butyl]-2-methyl-oxazole-4-carboxamide;
N-[(1R)-1-[[(3-Amino-3-oxo-propyl)-(2-fluoroacetyl)amino]carbamoyl]-3-methyl-butyl]-4-methoxy-1H-indole-2-carboxamide;
N-[(1R)-1-[[(3-Amino-3-oxo-propyl)-(2-fluoroacetyl)amino]carbamoyl]-3-methyl-butyl]-1H-indole-2-carboxamide;
N-[(1R)-2-[2-(3-Amino-3-oxo-propyl)-2-(2-chloroacetyl)hydrazino]-1-(cyclohexylmethyl)-2-axo-ethyl]-4-methoxy-1H-indole-2-carboxamide;
3-[(2-Chloroacetyl)-[[(2R)-2-[[(E)-3-(4-chloro-2-fluorophenyl)prop-2-enoyl]amino]-3-cyclohexyl-propanoyl]amino]propanamide;
3-[(2-Chloroacetyl)-[[(2R)-2-[[(E)-3-(4-chloro-2-fluorophenyl)prop-2-enoyl]amino]-4-methyl-pentanoyl]amino]propanamide;
N-[(1R)-2-[2-(3-Amino-3-oxo-propyl)-2-(2-chloroacetyl)hydrazino]-1-(cyclohexylmethyl)-2-axo-ethyl]-1H-indole-2-carboxamide;
N-[(1R)-2-[2-(3-Amino-3-oxo-propyl)-2-(2-fluoroacetyl)hydrazino]-1-(cyclohexylmethyl)-2-axo-ethyl]-1H-indole-2-carboxamide;
N-[(1R)-2-[2-(3-Amino-3-oxo-propyl)-2-(2-fluoroacetyl)hydrazino]-1-(cyclohexylmethyl)-2-axo-ethyl]-4-methoxy-1H-indole-2-carboxamide;
N-[(1R)-1-[[(2-fluoroacetyl)-[(2-oxo-pyrrolidin-3-yl)methyl]amino]carbamoyl]-3-methyl-butyl]-1H-indole-2-carboxamide;
N-[(1R)-1-[[(2-Fluoroacetyl)-[[(3S)-2-oxo-pyrrolidin-3-yl]methyl]amino]carbamoyl]-3-methyl-butyl]-1H-indole-2-carboxamide;
N-[(1R)-1-[[(2-fluoroacetyl)-[[(3R)-2-oxo-pyrrolidin-3-yl]methyl]amino]carbamoyl]-3-methyl-butyl]-1H-indole-2-carboxamide;
N-[(1R)-2-[2-(3-Amino-3-oxo-propyl)-2-(2-chloroacetyl)hydrazino]-1-(cyclohexylmethyl)-2-axo-ethyl]-N-methyl-1H-indole-2-carboxamide;
N-[(1R)-1-[[(3-Amino-3-oxo-propyl)-(2-chloroacetyl)amino]carbamoyl]-3-methyl-butyl]-N-methyl-1H-indole-2-carboxamide;
N-[(1R)-1-[[(3-Amino-3-oxo-propyl)-(2-chloro-2-fluoroacetyl)amino]carbamoyl]-3-methyl-butyl]-1H-indole-2-carboxamide;
N-[(1R)-1-[[(3-amino-3-oxo-propyl)-[(2S)-2-chloro-2-fluoro-acetyl]amino]carbamoyl]-3-methyl-butyl]-1H-indole-2-carboxamide;
N-[(1R)-1-[[(3-amino-3-oxo-propyl)-[(2R)-2-chloro-2-fluoro-acetyl]amino]carbamoyl]-3-methyl-butyl]-1H-indole-2-carboxamide;
N-[(1R)-1-[[(3-Amino-3-oxo-propyl)-(2-chloroacetyl)amino]carbamoyl]-3-methyl-butyl]-1H-benzimidazole-2-carboxamide;
N-[(1R)-1-[[(3-Amino-3-oxo-propyl)-(2-chloroacetyl)amino]carbamoyl]-3-methyl-butyl]isoxazole-3-carboxamide;
N-[(1R)-1-[[(3-Amino-3-oxo-propyl)-(2-chloroacetyl)amino]carbamoyl]-3-methyl-butyl]-1H-pyrrolo[2,3-b]pyridine-2-carboxamide;
N-[(1R)-1-[[(3-Amino-3-oxo-propyl)-(2-chloroacetyl)amino]carbamoyl]-3-methyl-butyl]-2-methyl-oxazole-4-carboxamide;
N-[(1R)-1-[[(3-Amino-3-oxo-propyl)-(2-chloroacetyl)amino]carbamoyl]-3-methyl-butyl]-5-methyl-isoxazole-4-carboxamide;
N-[(1R)-1-[[(3-Amino-3-oxo-propyl)-(2-chloroacetyl)amino]carbamoyl]-3-methyl-butyl]-5-methoxy-6H-pyrrolo[2,3-c]pyridine-2-carboxamide;
N-[(1R)-2-[2-(3-amino-3-oxo-propyl)-2-(2-chloroacetyl)hydrazino]-1-(cyclohexylmethyl)-2-axo-ethyl]-5-methyl-isoxazole-3-carboxamide;
4-Methoxy-N-[(1R)-1-[[(3-amino-3-oxo-propyl)-(2-chloro-2-fluoro-acetyl)amino]carbamoyl]-3-methyl-butyl]-1H-indole-2-carboxamide;
N-[(1R)-1-[[(2-Chloroacetyl)-[3-(methylamino)-3-oxo-propyl]amino]carbamoyl]-3-methyl-butyl]-N-methyl-1H-indole-2-carboxamide;
N-[(1R)-1-[[(2-Chloroacetyl)-[(2-oxo-pyrrolidin-3-yl)methyl]amino]carbamoyl]-3-methyl-butyl]-1H-indole-2-carboxamide;
N-[(1R)-1-[[(2-chloroacetyl)-[[(3S)-2-oxo-pyrrolidin-3-yl]methyl]amino]carbamoyl]-3-methyl-butyl]-1H-indole-2-carboxamide;
N-[(1R)-1-[[(2-chloroacetyl)-[[(3R)-2-oxo-pyrrolidin-3-yl]methyl]amino]carbamoyl]-3-methyl-butyl]-1H-indole-2-carboxamide;
N-[(1R)-1-[[(3-amino-3-oxo-propyl)-(2-chloroacetyl)amino]carbamoyl]-3-methyl-butyl]-1H-pyrrolo[3,2-c]pyridine-2-carboxamide;

or a pharmaceutically acceptable salt thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^5$ and L are as defined above unless otherwise indicated. Furthermore, and unless explicitly otherwise stated, all reactions, reaction conditions, abbreviations and symbols have the meanings well known to a person of ordinary skill in organic chemistry.

General synthetic routes for preparing the compound of formula (I) or (Ia) are shown below.

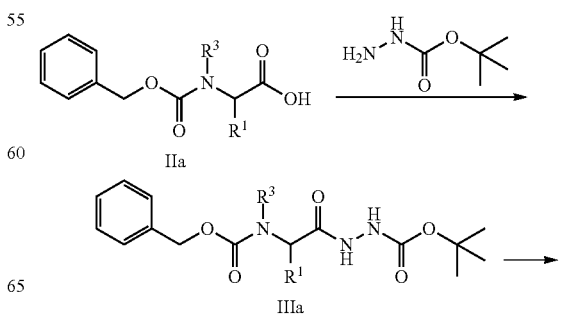

Scheme 1

-continued

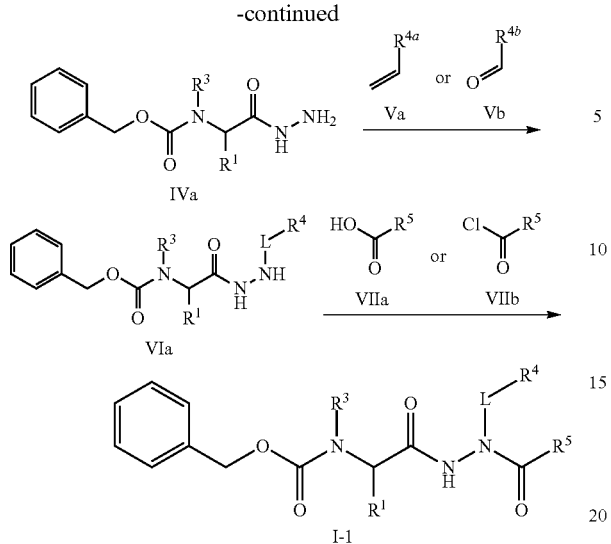

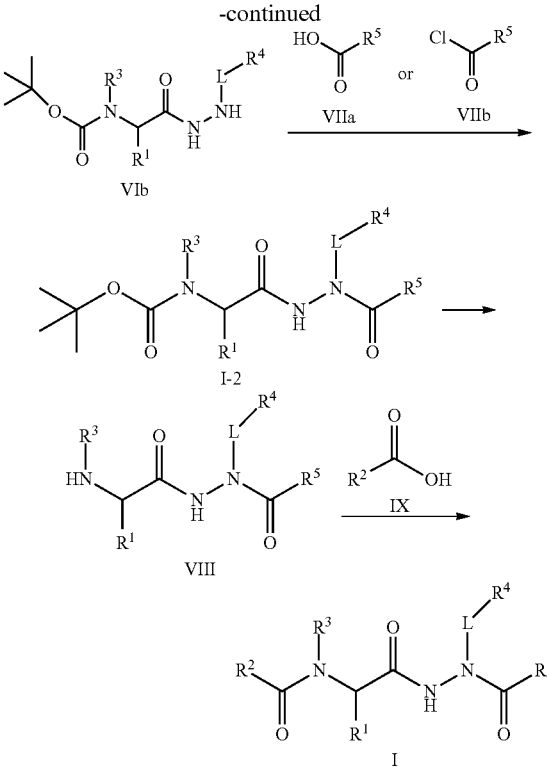

Wherein R$^{4a}$ is R$^4$—C$_y$H$_{2y}$—, y is 0, 1, 2, 3, or 4, and wherein R$^{4b}$ is R$^4$—C$_z$H$_{2z}$—, z is 0, 1, 2, 3, 4, or 5.

Compound of formula (IIIa) can be prepared by a coupling reaction of (IIa), tert-butyl N-aminocarbamate and coupling reagent(s) in the presence of an organic base. Deprotection of compound of formula (IIIa) in the presence of a strong acid can afford compound of formula (IVa). Compound of formula (VIa) can be prepared by Michael addition of compound of formula (IVa) with compound for formula (Va) in the presence of an organic base in alcoholic solvent. Alternatively a reduction amination of compound of formula (IVa) with compound of formula (Vb) using NaBH$_4$, NaBH$_3$CN in the presence of TsOH affords compound of formula (VIa). Compound of formula (I-1) can be obtained by a coupling reaction using acid (VIIa), compound of formula (VIa), and coupling reagent(s), such as T$_3$P, HATU, PyBOP or EDCI/HOBt, in the presence of an organic base, such TEA, DIEPA or DMAP. Alternatively, compound of formula (I-1) can be obtained by a reaction of compound of formula (VIa) and acylchloride (VIIb) in the presence of an organic base, such as TEA, DIEPA or DMAP.

Scheme 2

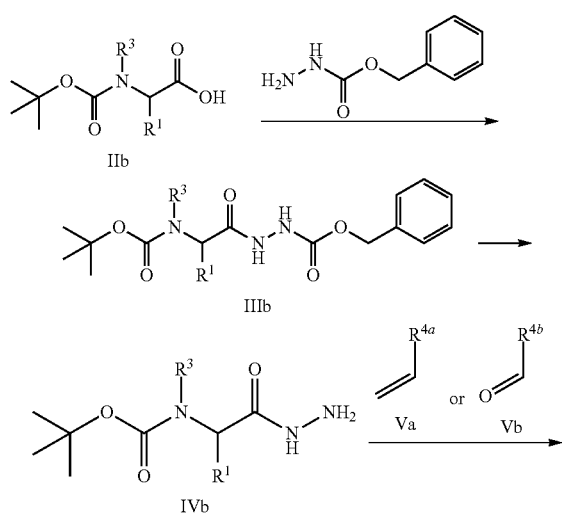

Wherein R$^{4a}$ and R$^{4b}$ are as defined in Scheme 1.

Compound of formula (IIIb) can be prepared by a coupling reaction of compound of formula (IIb) with benzyl N-aminocarbamate and coupling reagent(s) in the presence of an organic base. Hydrogenolysis of compound of formula (IIIb) can afford compound of formula (IVb). Compound of formula (VIb) can be prepared by Michael addition of compound of formula (IVb) with compound of formula (Va) in the presence of an organic base in alcoholic solvent. Alternatively a reduction amination of compound of formula (IVb) with compound of formula (Vb) using NaBH$_4$, NaBH$_3$CN in the presence of TsOH affords compound of formula (VIb). Compound of formula (I-2) can be obtained by a coupling reaction using acid (VIIa), compound of formula (VIb), and coupling reagent(s), such as T$_3$P, HATU, PyBOP or EDCI/HOBt, in the presence of an organic base, such TEA, DIEPA or DMAP. Alternatively, compound of formula (I-2) can be obtained by a reaction of compound of formula (VIb) and acylchloride (VIIb) in the presence of an organic base, such as TEA, DIEPA or DMAP. Deprotection of compound of formula (I-2) can afford compound of formula (VIII) in the presence of a strong acid, such as TFA. Compound of formula (I) can be prepared by a coupling reaction of compound of formula (IX) with compound of formula (VIII) and coupling reagent(s), such as T$_3$P, HATU, PyBOP or EDCI/HOBt in the presence of an organic base, such as TEA, DIEPA or DMAP.

Scheme 3

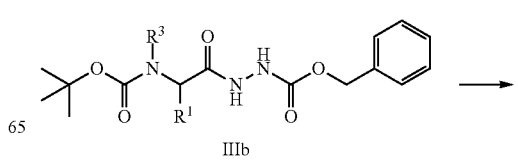

-continued

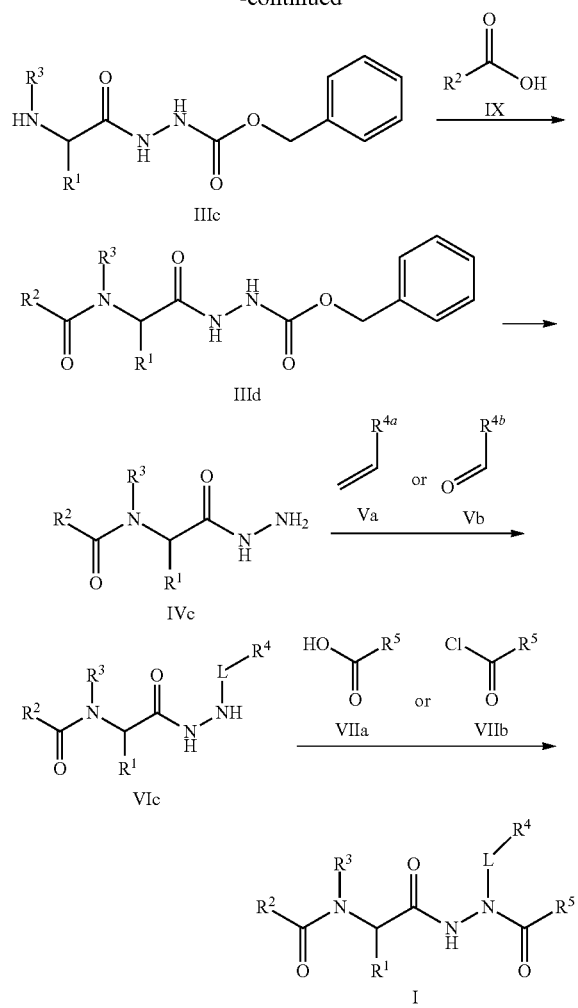

Scheme 4

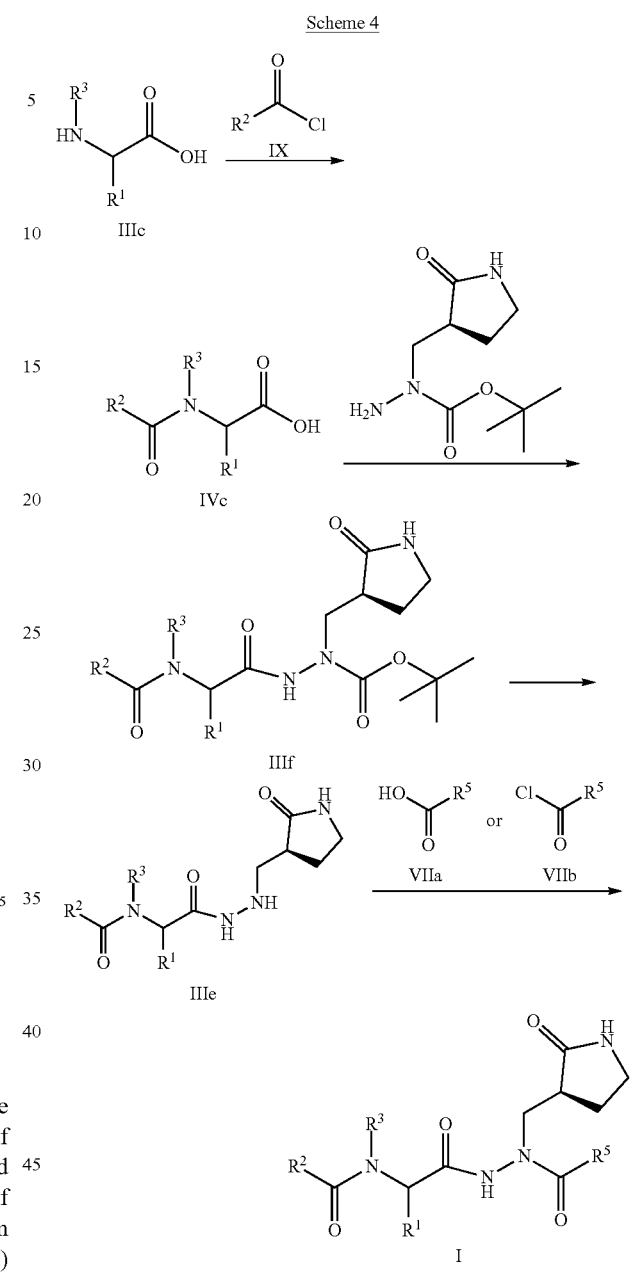

Wherein $R^{4a}$ and $R^{4b}$ are as defined in Scheme 1.

Deprotection of compound of formula (IIIb) from Scheme 2 can afford compound of formula (IIIc) in the presence of a strong acid. Compound of formula (IIId) can be prepared by a coupling reaction of compound (IIIc) with compound of formula (IX) and coupling reagent(s) in the presence of an organic base. Hydrogenolysis of compound of formula (IIId) in the presence of Pd/C in organic solvent can afford compound of formula (IVc). Compound of formula (VIc) can be prepared by Michael addition of compound of formula (IVc) and compound of formula (Va) in the presence of an organic base in alcoholic solvent. Alternatively a reduction amination of compound of formula (IVc) with aldehyde (Vb) using $NaBH_4$, $NaBH_3CN$ in the presence of TsOH affords compound of formula (VIc). Compound of formula (I) can be obtained by a coupling reaction using acid (VIIa), compound of formula (VIc), and coupling reagent(s), such as $T_3P$, HATU, PyBOP or EDCI/HOBt, in the presence of an organic base, such TEA, DIEPA or DMAP. Alternatively, compound of formula (I) can be obtained by a reaction of compound of formula (VIc) and acylchloride (VIIb) in the presence of an organic base, such as TEA, DIEPA or DMAP.

Compound of formula (IVc) can be prepared by a coupling reaction of compound (IIIc) with carbonyl chloride compound of formula (IX) in the presence of base, such as DIEPA. Compound of formula (IIIf) can be prepared by a coupling reaction of compound (IVc) with (S)-tert-butyl 1-((2-axopyrrolidin-3-yl)methyl)hydrazinecarboxylate in the prensence of coupling reagent(s) such as $T_3P$, HATU, PyBOP or EDCI/HOBt, in the presence of an organic base, such TEA, DIEPA or DMAP. Deprotection of compound of formula (IIIf) can afford compound of formula (IIIe) in the presence of a strong acid, such as HCl, TFA. Compound of formula (I) can be obtained by a coupling reaction using acid (VIIa), and coupling reagent(s), such as $T_3P$, HATU, PyBOP or EDCI/HOBt, in the presence of an organic base, such TEA, DIEPA or DMAP, or using carbonyl chloride (VIIb) in the prensence of organic base, such as DIEPA.

This invention also relates to a process for the preparation of a compound of formula (I) or (Ia) comprising one of the following steps:

a) coupling reaction using compound of formula (VIII), compound of formula (IX),

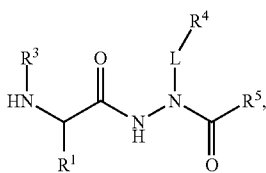

VIII

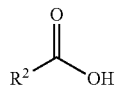

IX and a coupling reagent in the presence of an organic base;

b) a reaction of compound of formula (VIc), and

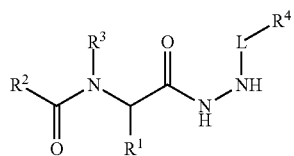

VIc acid (VIIa)

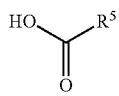

VIIa and a coupling reagent in the presence of an organic base; or c) a reaction of compound of formula (VIc), with acylchloride (VIIb), and

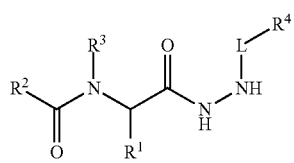

VIc in the presence of an organic base;

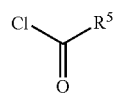

VIIb wherein the coupling agent is selected from $T_3P$, HATU, PyBOP or EDCI/HOBt, the organic base is selected from TEA, DIEPA, and DMAP.

Compounds of this invention can be obtained as mixtures of diastereomers or enantiomers, which can be separated by methods well known in the art, e.g. (chiral) HPLC or SFC.

Chiral compounds, such as compound of formula (Ia), can be obtained according to the schemes above with chiral starting materials.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (II) or (IIa) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (II) or (IIa) is formulated in an acetate buffer, at pH 5. In another embodiment, the compounds of formula (II) or (IIa) are sterile. The compound may be stored, for example, as a solid or amorphous composition, as a lyophilized formulation or as an aqueous or nonaqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit 3CL protease. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.1 to 100 mg/kg of patient body weight per day, with the typical initial range of compound used being 0.3 to 15 mg/kg/day. In another embodiment, oral unit dosage forms, such as tablets and capsules, preferably contain from about 1 to about 500 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.01 to 500 mg of the compound of the invention compounded with about 50 to 400 mg anhydrous lactose, about 5 to 40 mg sodium croscarmellose, about 5 to 30 mg polyvinylpyrrolidone (PVP) K30, and about 0.1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.01 to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (II) or (IIa), or a stereoisomer or pharmaceutically acceptable salt thereof. In a further embodiment includes a pharmaceutical composition comprising a compound of Formula (II) or (IIa), or a stereoisomer or pharmaceutically acceptable salt thereof, together with a pharmaceutically acceptable carrier or excipient.

Another embodiment includes a pharmaceutical composition comprising a compound of Formula (II) or (IIa) for use in the treatment of coronavirus infections.

The following embodiments illustrate typical compositions of the present invention, but serve merely as representative thereof.

Composition A

A compound of the present invention can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Composition B

A compound of the present invention can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The present invention provides peptidomimetic (or peptide-like) compounds that inhibit the enzymatic activity of 3C-like proteases from coronaviruses including, but not limited to, severe acute respiratory syndrome coronavirus (SARS-CoV), severe acute respiratory syndrome coronavirus 2 (SARS-CoV-2) and Middle East Respiratory Syndrome Coronavirus (MERS-CoV). Accordingly, the compounds of the invention are useful for blocking coronavirus replication in infected cells. As such, the compounds can be used as a therapeutic or prophylactic agent for treatments of coronavirus infections.

In one aspect, the present invention provides a compound of formula (II) as described herein, or a pharmaceutically acceptable salt thereof, for use as therapeutically active substance.

The present invention also provides methods for treatment or prophylaxis of viral infections caused by coronaviruses including, but not limited to, SARS-CoV, SARS-CoV-2 and MERS-CoV in a patient in need thereof.

Another embodiment includes a method of treating or preventing viral infections caused by coronaviruses including, but not limited to, SARS-CoV, SARS-CoV-2 and MERS-CoV in a mammal in need of such treatment, wherein the method comprises administering to said mammal a therapeutically effective amount of a compound of formula (II), a stereoisomer, tautomer, prodrug or pharmaceutically acceptable salt thereof.

In one aspect, the present invention provides the use of a compound of formula (II) as described herein, or a pharmaceutically acceptable salt thereof, for the treatment or prophylaxis of coronavirus infections, e.g. for the treatment or prophylaxis of severe acute respiratory syndrome coronavirus (SARS-CoV), severe acute respiratory syndrome coronavirus 2 (SARS-CoV-2) or Middle East Respiratory Syndrome Coronavirus (MERS-CoV).

In one aspect, the present invention provides the use of a compound of formula (II) as described herein, or a pharmaceutically acceptable salt thereof, for the preparation of a medicament for the treatment or prophylaxis of coronavirus infections, e.g. for the preparation of a medicament for the treatment or prophylaxis of SARS-CoV, SARS-CoV-2 or MERS-CoV infections.

In one aspect, the present invention provides the use of a compound of formula (II) as described herein, or a pharmaceutically acceptable salt thereof, for the preparation of a medicament for inhibiting enzymatic activity of 3C-like proteases.

In one aspect, the present invention provides a compound of formula (II) as described herein, or a pharmaceutically acceptable salt thereof, for use in the treatment or prophylaxis of coronavirus infections, e.g. for use in the treatment or prophylaxis of SARS-CoV, SARS-CoV-2 or MERS-CoV infections.

EXAMPLES

The invention will be more fully understood by reference to the following examples. They should not, however, be construed as limiting the scope of the invention.

ABBREVIATIONS

Abbreviations Used Herein are as Follows:
aq. aqueous
ACN acetonitrile
CbzCl benzyl chloroformate
$CDCl_3$: deuterated chloroform
$CD_3OD$: deuterated methanol
CHAPS 3-[(3-cholamidopropyl)dimethylammonio]-1-propanesulfonate
DEA: diethyl amine
DIEA: N,N-Diisopropylethylamine
DIEPA: N,N-diethylpropylamine
DMF: dimethyl formamide
DMSO: dimethyl sulfoxide
DBU: 1,8-diazabicycloundec-7-ene
EDCI: N-ethyl-N'-(3-dimethylaminopropyl)carbodiimide hydrochloride
EDTA ethylenediaminetetraacetic acid
EtOAc or EA: ethyl acetate
FAM carboxyfluorescein
FRET fluorescence resonance energy transfer
HATU: (1-[bis(dimethylamino)methylene]-1H-1,2,3-triazolo[4,5-b]pyridinium 3-oxid hexafluorophosphate)
HEPES 4-(2-hydroxyethyl)-1-piperazineethanesulfonic acid
hr(s): hour(s)
HPLC: high performance liquid chromatography
HOBt: N-hydroxybenzotriazole
LiHMDS lithium bis(trimethylsilyl)amide
MS (ESI): mass spectroscopy (electron spray ionization)
MTBE methyl tert-butyl ether
min(s) minute(s)
NMR: nuclear magnetic resonance
obsd. observed
prep-HPLC preparative high performance liquid chromatography
PyBOP benzotriazol-1-yl-oxytripyrrolidinophosphonium hexafluorophosphate
RT or rt: room temperature
sat. saturated
SFC supercritical fluid chromatography
TAMRA carboxytetramethylrhodamine
TCEP tris(2-carboxyethyl)phosphine
TEA: triethylamine
TFA: trifluoroacetic acid
THF: tetrahydrofuran
TEA: triethylamine
$T_3P$: propylphosphonic anhydride General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Alternatively, intermediates and final compounds were purified by preparative HPLC on reversed phase column using X Bridge™ Perp $C_{18}$ (5 μm, OBD™ 30×100 mm) column, SunFire™ Perp $C_{18}$ (5 μm, OBD™ 30×100 mm) column, Phenomenex Luna C18 75*30 mm*3 μm column or Phenomenex Synergi C18 150*25 mm*10 μm column.

For SFC chiral separation, intermediates were separated by chiral column (Daicel chiralpak IC, 5 μm, 30×250 mm), AS (10 μm, 30×250 mm) or AD (10 μm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3·H_2O$ in MeOH), back pressure 100 bar, detection UV@ 254 or 220 nm.

LC/MS spectra were obtained using a Waters UPLC-SQD Mass. Standard LC/MS conditions were as follows (running time 3 mins):
Acidic condition: A: 0.1% formic acid and 1% acetonitrile in $H_2O$; B: 0.1% formic acid in acetonitrile;
Basic condition: A: 0.05% $NH_3·H_2O$ in $H_2O$; B: acetonitrile.
Mass spectra (MS): generally only ions which indicate the parent mass are reported, and unless otherwise stated the mass ion quoted is the positive mass ion $(M+H)^+$.
NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Preparation of Intermediate

Intermediate AA (2S)-2-(Benzyloxycarbonylamino)-3-cyclopropyl-propanoic acid (Intermediate AA)

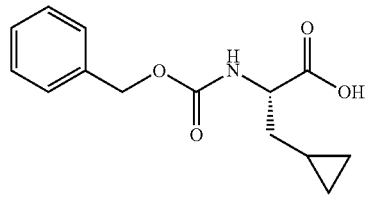 [SMILES: O=C(N[C@@H](CC1CC1)C(=O)O)OCc1ccccc1]

Intermediate AA

To a solution of (2S)-2-amino-3-cyclopropyl-propanoic acid (1.0 g, 7.74 mmol, Shanghai Titan Scientific Co., Ltd, CAS number: 102735-53-5), $Na_2CO_3$ (1.6 g, 15.48 mmol) and $NaHCO_3$ (0.65 g, 7.74 mmol) in water (30 mL) and acetone (4 mL) was added CbzCl (1.65 g, 9.68 mmol) at 0° C. After being stirred at 20° C. for 3 hrs, the reaction mixture was extracted with EtOAc (20 mL) twice. The aqueous layer was acidized by HCl (1M) until pH=2 and then extracted with EtOAc (20 mL) three times. The combined organic layers were washed with brine (10 mL), dried over Na$_2$SO$_4$ and concentrated in vacuo. (2S)-2-(Benzyloxycarbonylamino)-3-cyclopropyl-propanoic acid (1.3 g, Intermediate AA) was obtained as a yellow oil, which was used in next step without further purification. MS obsd. (ESI$^+$) [(M+Na)$^+$]: 286.1.

Intermediate AB (S)-2-(((Benzyloxy)carbonyl)amino)-3-cyclopentyl-propanoic acid (Intermediate AB)

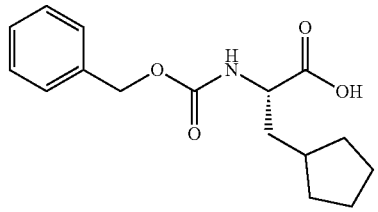 [SMILES: O=C(N[C@@H](CC1CCCC1)C(=O)O)OCc1ccccc1]

Intermediate AB

Intermediate AB was prepared in analogy to Intermediate AA by using (2S)-2-amino-3-cyclopentyl-propanoic acid (1.0 g, 6.36 mmol, Bidepharm, CAS number: 99295-82-6) instead of (2S)-2-amino-3-cyclopropyl-propanoic acid. (S)-2-(((Benzyloxy)carbonyl)amino)-3-cyclopentylpropanoic acid (1.3 g, Intermediate AB) was obtained as a light yellow oil. $^1$H NMR (400 MHz, CDCl$_3$) δ ppm: 7.33-7.36 (m, 5H), 5.22 (d, J=8.8 Hz, 1H), 5.16 (s, 2H), 4.37-4.40 (m, 1H), 1.80-1.89 (m, 5H), 1.61-1.63 (m, 2H), 1.52-1.56 (m, 2H), 1.11-1.15 (m, 2H).

Intermediate AC tert-Butyl N-[[(2S)-2-amino-4-methyl-pentanoyl]amino]carbamate

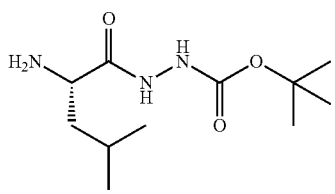 [SMILES: CC(C)C[C@H](N)C(=O)NNC(=O)OC(C)(C)C]

Intermediate AC

Step 1: Preparation of tert-butyl N-[[(2S)-2-(benzyloxycarbonylamino)-4-methyl-pentanoyl]amino]carbamate

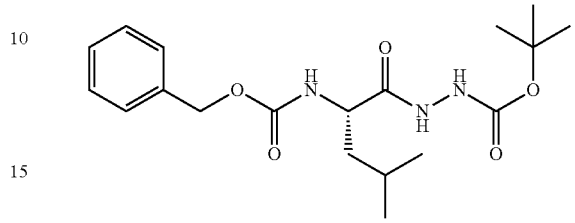

Intermediate AC-1

To a solution of (S)-2-(((benzyloxy) carbonyl)amino)-4-methylpentanoic acid (10.0 g, 37.69 mmol, Wuxi Apptec (Wuhan) Co., Ltd.) and tert-butyl hydrazinecarboxylate (5.48 g, 41.46 mmol) in EtOAc (150 mL) was added T$_3$P (33.6 mL, 56.54 mmol, 50% in EtOAc) and DIEPA (18.7 mL, 113.1 mmol) at 0° C. After being stirred at 25° C. for 3 hrs, the reaction mixture was poured into water (200 mL) and extracted with EtOAc (200 mL) three times. The combined organic phases were washed with HCl (1M, 200 mL) twice, saturated aqueous NaHCO$_3$ (200 mL) twice, brine (200 mL) twice, dried over anhydrous Na$_2$SO$_4$ and concentrated in vacuo. (S)-tert-Butyl 2-(2-(((benzyloxy)carbonyl)amino)-4-methyl pentanoyl) hydrazinecarboxylate (14.0 g, Intermediate AC-1) was obtained as a light yellow oil and used in next step without further purification. MS obsd. (ESI$^+$) [(M-tBu+H)$^+$]: 323.9.

Step 2: Preparation of tert-butyl N-[[(2S)-2-amino-4-methyl-pentanoyl]amino]carbamate

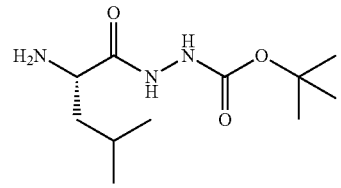 [SMILES: CC(C)C[C@H](N)C(=O)NNC(=O)OC(C)(C)C]

Intermediate AC

To a solution of (S)-tert-butyl 2-(2-(((benzyloxy)carbonyl)amino)-4-methyl pentanoyl) hydrazinecarboxylate (5.0 g, Intermediate AC-1) in methanol (50 mL) was added Pd/C (500.0 mg, 10% purity). The mixture was degassed in vacuo and purged with H$_2$ three times. After being stirred under H$_2$ balloon at 25° C. for 12 hrs, the resulting mixture was filtered through a pad of celite. The filtrate was concentrated in vacuo to give (S)-tert-butyl 2-(2-amino-4-methylpentanoyl) hydrazinecarboxylate (3.0 g, Intermediate AC) as a light yellow oil and used in next step without further purification. $^1$H NMR (400 MHz, CDCl$_3$) δ ppm: 3.48-3.51 (m, 1H), 1.67-1.76 (m, 2H), 1.46 (s, 9H), 1.38-1.44 (m, 1H), 0.94 (dd, J=6.4 Hz, J=15.6 Hz, 6H).

Intermediate AD (2S)-2-(benzyloxycarbonylamino)-3-(1-methylcyclopropyl)propanoic acid

Intermediate AD

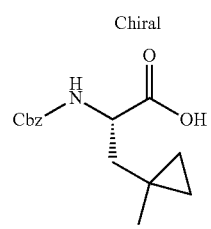

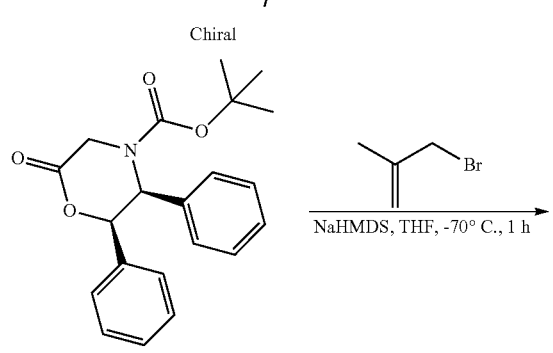

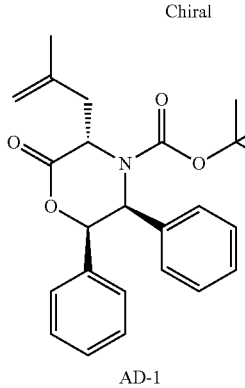

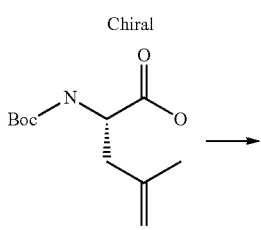

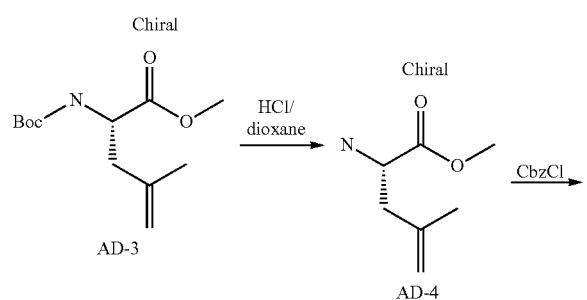

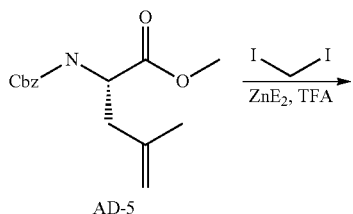

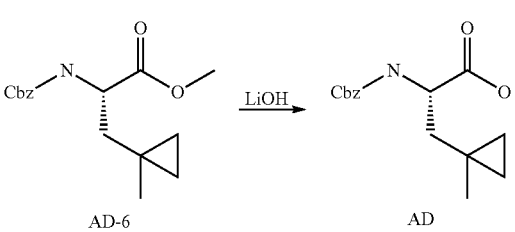

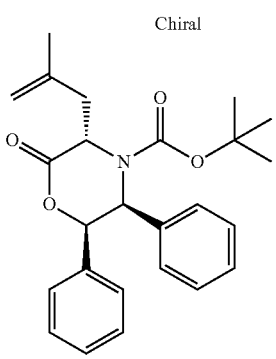 [SMILES: C=C(C)C[C@H]1C(=O)O[C@H](c2ccccc2)[C@H](c2ccccc2)N1C(=O)OC(C)(C)C]

Step 1: Preparation of tert-butyl(3S,5S,6R)-3-(2-methylallyl)-2-oxo-5,6-diphenyl-morpholine-4-carboxylate Intermediate AD-1

To a solution of tert-butyl(2R,3S)-6-oxo-2,3-diphenylmorpholine-4-carboxylate (1.0 g, 2.83 mmol, GL Biochem, CAS 112741-49-8), 3-bromo-2-methylprop-1-ene (413 mg, 3.06 mmol, Shanghai Titan, CAS: 1458-98-6) and HMPA (1.0 mL) in THF (10 mL) was added NaHMDS (3.08 mL, 3.08 mmol, 1M) at −70° C. under $N_2$. The reaction mixture was stirred at −70° C. for 1 hr, then quenched with sat. aq. solution of $NH_4Cl$ (30 mL), extracted with EtOAc (50 mL) 3 times. The combined organic layers were washed with brine (20 mL) and concentrated in vacuo. The residue was purified by column, eluted with EtOAc (0~2%) in petroleum ether to afford tert-butyl(3S,5S,6R)-3-(2-methylallyl)-2-oxo-5,6-diphenylmorpholine-4-carboxylate (600 mg, Intermediate AD-1) as a yellow oil. MS obsd. (ESI⁺) [M-$C_4H_8$+H]⁺: 352.2.

Step 2: Preparation of (S)-2-((tert-butoxycarbonyl)amino)-4-methylpent-4-enoic acid

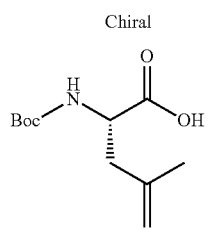

Intermediate AD-2

To a solution of liquid NH₃ (500.0 mL) in ethanol (40 mL) and THF (400 mL) was added tert-butyl(3S,5S,6R)-3-(2-methylallyl)-2-oxo-5,6-diphenylmorpholine-4-carboxylate (47.0 g, AD-1) at −70° C. Then Li (7.2 g) was added. After stirred at −70° C. for 1 hr, the reaction mixture was quenched with NH₄Cl solution (41 mL, 20%) at 0° C. After addition, the mixture was warmed to 25° C. and diluted with water (300 mL). The aqueous phase was washed with MTBE (300 mL) 2 times. Then the aqueous layers was adjusted by HCl (1M) until pH=1 at 0° C. and extracted with EtOAc (500 mL) 3 times. The combined organic layers were concentrated in vacuo to afford (S)-2-((tert-butoxycarbonyl)amino)-4-methylpent-4-enoic acid (18.93 g, Intermediate AD-2) as a light yellow oil. ¹H NMR (400 MHz, CDCl₃) δ ppm: 5.00-4.76 (m, 3H), 4.41 (d, J=4.4 Hz, 1H), 2.67-2.50 (m, 1H), 2.43-2.38 (m, 1H), 1.77 (s, 3H), 1.45 (s, 9H) Step 3: Preparation of methyl(S)-2-((tert-butoxycarbonyl)amino)-4-methylpent-4-enoate

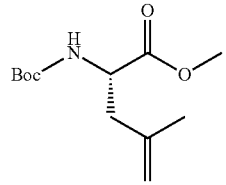 [SMILES: C=C(C)C[C@H](NC(=O)OC(C)(C)C)C(=O)OC]

Intermediate AD-3

To a mixture of (S)-2-((tert-butoxycarbonyl)amino)-4-methylpent-4-enoic acid (18.9 g, Intermediate AD-2) and K₂CO₃ (34.19 g) in DMF (300 mL) was added MeI (23.4 g) at 20° C. After stirred at 20° C. for 1 hr, the reaction mixture was filtered and the mother liquor was diluted with brine (400 mL) and extracted with EtOAc (300 mL) three times. The combined organic layers were washed with brine (300 mL) two times, dried over anhydrous Na₂SO₄, and concentrated in vacuo. The residue was purified by column, eluted with EtOAc (0~6%) in petroleum ether to afford methyl(S)-2-((tert-butoxycarbonyl)amino)-4-methylpent-4-enoate (17.2 g, Intermediate AD-3) as a colorless oil.

¹H NMR (400 MHz, CDCl₃) δ ppm: 4.94 (d, J=6.8 Hz, 1H), 4.86 (s, 1H), 4.76 (s, 1H), 4.48-4.34 (m, 1H), 3.74 (s, 3H), 2.59-2.45 (m, 1H), 2.39-2.34 (m, 1H), 1.75 (s, 3H), 1.44 (s, 9H)

Step 4: Preparation of methyl(S)-2-amino-4-methylpent-4-enoate

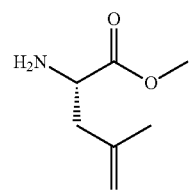

Intermediate AD-4

A mixture of methyl(S)-2-((tert-butoxycarbonyl)amino)-4-methylpent-4-enoate (17.2 g, Intermediate AD-3) in HCl/dioxane (200.0 mL, 4M) was stirred at 20° C. for 2 hrs. Then the reaction mixture was concentrated in vacuo to afford methyl(S)-2-amino-4-methylpent-4-enoate hydrochloride (12.7 g, Intermediate AD-4) and used directly without purification.

Step 5: Preparation of methyl(S)-2-(((benzyloxy)carbonyl)amino)-4-methylpent-4-enoate

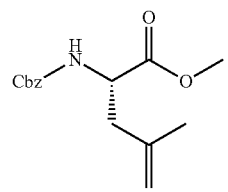 [SMILES: C=C(C)C[C@H](NC(=O)OCc1ccccc1)C(=O)OC]

Intermediate AD-5

To a solution of methyl(S)-2-amino-4-methylpent-4-enoate hydrochloride (12.7 g, Intermediate AD-4) in THF (100 mL) was added a solution of Na₂CO₃ (29.97 g) in water (100 mL) at 0° C. CbzCl (18.09 g) was added to the mixture at 0° C. After stirred at 20° C. for 1 hr, the reaction mixture was diluted with water (200 mL) and extracted with EtOAc (200 mL) three times. The combined organic layers were dried over anhydrous Na₂SO₄ and concentrated in vacuo. The residue was purified by column, eluted with EtOAc (0%~7%) in petroleum ether to afford methyl(S)-2-(((benzyloxy)carbonyl)amino)-4-methylpent-4-enoate (14.03 g, Intermediate AD-5) as a colorless oil. ¹H NMR (400 MHz, CDCl₃) δ ppm: 7.43-7.29 (m, 5H), 5.20 (d, J=7.2 Hz, 1H), 5.12 (s, 2H), 4.89-4.83 (m, 1H), 4.76 (s, 1H), 4.55-4.45 (m, 1H), 3.75 (s, 3H), 2.60-2.50 (m, 1H), 2.43-2.38 (m, 1H), 1.75 (s, 3H). MS obsd. (ESI⁺) [(M+H)⁺]: 278.2.

Step 6: Preparation of methyl(S)-2-(((benzyloxy)carbonyl)amino)-3-(1-methylcyclopropyl)propanoate

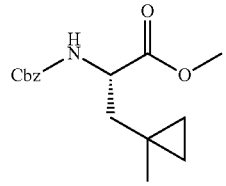 [SMILES: COC(=O)[C@H](CC1(C)CC1)NC(=O)OCc1ccccc1]

Intermediate AD-6

ZnEt$_2$ (196.2 mL, 1 M in hexane) was added to DCM (200 mL) at 0° C. Then TFA (15.0 mL) in DCM (75 mL) was added at 0° C. under N$_2$ protection. After stirred at 0° C. for 20 mins, Diiodomethane (16.0 mL, Energy Chemical, CAS: 75-11-6) in DCM (35 mL) was added into above solution at 0° C. under N$_2$ protection. The mixture was stirred at 0° C. for another 20 min. Then to the mixture, methyl(S)-2-(((benzyloxy)carbonyl)amino)-4-methylpent-4-enoate (5.0 g AD-5) in DCM (35 mL) was added at 0° C. The resulting mixture was stirred at 20° C. for 2 hrs. After reaction, the reaction mixture was quenched with 1 M aq. solution of HCl (80 mL) at 0° C. The aqueous layer was separated. The organic layer was washed with sat.aq. NaHCO$_3$ (30 mL) and concentrated in vacuo. The residue was purified by column, eluted with EtOAc (0~7.5%) in petroleum ether to afford methyl(S)-2-(((benzyloxy)carbonyl)amino)-3-(1-methylcyclopropyl)propanoate (4.16 g, Intermediate AD-6) as a yellow oil. $^1$H NMR (400 MHz, CDCl$_3$) δ ppm: 7.40-7.32 (m, 5H), 5.21 (d, J=7.6 Hz, 1H), 5.17-5.03 (m, 2H), 4.51 (q, J=8.0 Hz, 1H), 3.75 (s, 3H), 1.76-1.68 (m, 1H), 1.67-1.58 (m, 1H), 1.10 (s, 3H), 0.36-0.17 (m, 4H). MS obsd. (ESI$^+$) [(M+H)$^+$]: 292.1.

Step 7: Preparation of (S)-2-(((benzyloxy)carbonyl)amino)-3-(1-methylcyclopropyl) propanoic acid

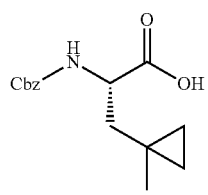 [SMILES: CC1(C[C@H](NC(=O)OCc2ccccc2)C(=O)O)CC1]

Intermediate AD

To a mixture of methyl(S)-2-(((benzyloxy)carbonyl)amino)-3-(1-methylcyclopropyl)propanoate (4.16 g, Intermediate AD-6) in THF (20 mL) was added a solution of LiOH H$_2$O (1.2 g) in water (20 mL) at 0° C. After stirred at 0° C. for 2 hrs, the reaction mixture was extracted with EtOAc (100 mL) two times. The combined organic layers were dried over anhydrous Na$_2$SO$_4$ and concentrated in vacuo to afford (S)-2-(((benzyloxy)carbonyl)amino)-3-(1-methylcyclopropyl)propanoic acid (3.58 g, Intermediate AD) as a light yellow oil. $^1$H NMR (400 MHz, CDCl$_3$) δ ppm: 8.18 (br. s, 1H), 7.40-7.29 (m, 5H), 5.27 (d, J=8.0 Hz, 1H), 5.20-5.10 (m, 2H), 4.60-4.48 (m, 1H), 1.87 (dd, J$_1$=5.6 Hz, J$_2$=14.0 Hz, 1H), 1.60 (dd, J$_1$=8.4 Hz, J$_2$=14.0 Hz, 1H), 1.11 (s, 3H), 0.38-0.21 (m, 4H). MS obsd. (ESI$^+$) [(M+H)$^+$]: 278.2.

Intermediate AE

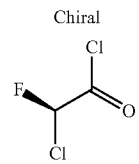

Step 1: Preparation of 2-chloro-2-fluoroacetic acid

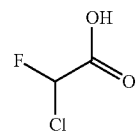

AE-1

To a solution of ethyl chlorofluoroacetate (1000 g) in ethanol (9 L) was added water (1 L) and NaOH (313 g). After stirred at 25° C. for 12 hrs, the reaction mixture was concentrated under reduced pressure to remove most of EtOH. Then the residue was diluted with water (1500 mL) and acidified with HCl (2M) until pH=4~5. The mixture was extracted with MTBE (1 L) 4 times. The combined organic layers were dried over Na$_2$SO$_4$, filtered and concentrated in vacuo to give crude compound without further purification. The compound 2-chloro-2-fluoro-acetic acid (718 g, AE-1) was obtained as a colorless oil which was used directly. $^1$H NMR (400 MHz, CDCl$_3$) δ 6.16 (d, J=50.4 Hz, 1H)

Step 2: Preparation of (R)-2-chloro-2-fluoroacetic acid

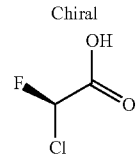

AE-2

To a solution of 2-chloro-2-fluoro-acetic acid (718.0 g, AE-1) in EtOAc (3000 mL) was added 0° C. solution of (S)-1-phenylethanamine (386.73 g) in EtOAc (3000 mL). The mixture was stirred at 0° C. for 2 hrs and then stood over night. The reaction mixture was filtered and the solid was dissolved with acetone (760 g, 7600 mL) under 80° C. The resulting solution was slowly cooled to 20° C. and stood overnight. The precipitate was filtrated, collected and dissolved with acetone (100 g/1 L) at 80°. The recrystallization operation was repeated for 2 times. The collected solid was triturated with acetone for 3 times (acetone, 100 g/0.5 L). The solid was collected and dissolved with water (1000 mL) and acidified with HCl (1M, 750 mL). The mixture was extracted with MTBE (1 L) three times. The combined organic layers were dried over $Na_2SO_4$, filtered and concentrated under reduced pressure to afford (R)-2-chloro-2-fluoroacetic acid (121.15 g, 1080 mmol, 61% purity, containing MTBE, Intermediate AE-2) as a yellow oil.

$^1$H NMR (400 MHz, CDCl$_3$) δ 6.29 (d, J=50.8 Hz, 1H)

Step 3: Preparation of (R)-2-chloro-2-fluoroacetyl chloride

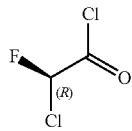

To (R)-2-chloro-2-fluoroacetic acid (12.0 g) was added PCl$_5$ (24.46 g). The reaction mixture was stirred at 20° C. for 1 hr. Then the reaction mixture was stirred at 70° C. for 1 hr. $^1$H NMR showed the reaction was finished. (R)-2-chloro-2-fluoroacetyl chloride (22.84 g, 40% purity with POCl$_3$ and MTBE) was collected by distillation (70° C., 20 mmHg) as a colorless liquid. $^1$H NMR (400 MHz, CDCl$_3$) δ 6.40 (d, J=50.8 Hz, 1H).

Intermediate AF tert-Butyl N-amino-N-[[(3S)-2-axopyrrolidin-3-yl]methyl]carbamate

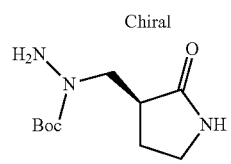 [SMILES: CC(C)(C)OC(=O)N(N)C[C@@H]1CCNC1=O]

Intermediate AF

Step 1: Preparation of tert-butyl 3-methylene-2-axopyrrolidine-1-carboxylate

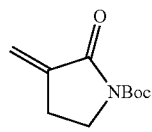

AF-1

To a solution of tert-butyl 2-axopyrrolidine-1-carboxylate (100.0 g, Wuxi catalog: CAS number: 85909-08-6) in THF (1000 mL) was added to a stirring solution of LiHMDS (1133.79 mL) at 0° C. The reaction mixture was allowed to warm up to 20° C. over 30 min before 2,2,2-trifluoroethyl trifluoroacetate (211.69 g, 1080 mmol) was added. After stirred for additional 20 min at 20° C., the reaction mixture was extracted with EtOAc (600 mL) two times. The combined organic phases were dried over $Na_2SO_4$, filtered and concentrated in vacuo. The oil was dissolved in toluene (1000 mL) then formaldehyde (48.64 g) and $K_2CO_3$ (164.16 g) were added into the solution. The reaction mixture was heated at 110° C. for 2 hours. The mixture was diluted with ethyl acetate (800 mL), washed with brine (200 mL) three times, dried over anhydrous $Na_2SO_4$, filtered and concentrated in vacuo to afford the desired product (tert-butyl 3-methylene-2-oxo-pyrrolidine-1-carboxylate (80 g, AF-1) as a light yellow oil which was used directly. MS obsd. (ESI$^+$) [M−Bu+H]$^+$: 142.1.

Step 2: Preparation of tert-butyl 3-((2-((benzyloxy)carbonyl)hydrazinyl)methyl)-2-axopyrrolidine-1-carboxylate

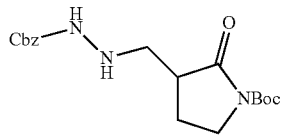 [SMILES: CC(C)(C)OC(=O)N1CCC(CNNC(=O)OCc2ccccc2)C1=O]

AF-2

To a solution of tert-butyl 3-methylene-2-oxo-pyrrolidine-1-carboxylate (80.0 g) in IPA (800 mL) was added benzyl carbazate (67.41 g). After stirred at 85° C. for 12 hrs under N$_2$ protection, the reaction mixture was concentrated in vacuo to afford crude tert-butyl 3-[(2-benzyloxycarbonylhydrazino)methyl]-2-oxo-pyrrolidine-1-carboxylate (147 g, AF-2) as a yellow oil which was used directly. MS obsd. (ESI+) [2M+H]$^+$: 727.2

Step 3: Preparation of benzyl 2-((2-axopyrrolidin-3-yl)methyl)hydrazinecarboxylate

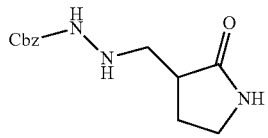 [SMILES: O=C(NNCC1CCNC1=O)OCc1ccccc1]

Intermediate AF-3

To a solution of tert-butyl 3-[(2-benzyloxycarbonylhydrazino)methyl]-2-oxo-pyrrolidine-1-carboxylate (147.0 g, Intermediate AF-2) in DCM (700 mL) was added TFA (500.0 mL). After stirred at 20° C. for 2 hrs, the reaction mixture was concentrated in vacuo to afford benzyl 2-((2-axopyrrolidin-3-yl)methyl)hydrazinecarboxylate (147.0 g, Intermediate AF-3) as a yellow oil which was used directly. MS obsd. (ESI$^+$) [M+H]$^+$: 264.0.

Step 4: Preparation of 2-benzyl 1-tert-butyl 1-((2-axopyrrolidin-3-yl)methyl)hydrazine-1,2-dicarboxylate

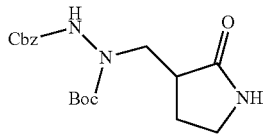 [SMILES: CC(C)(C)OC(=O)N(CC1CCNC1=O)NC(=O)OCc1ccccc1]

Intermediate AF-4

To a solution of benzyl N-[(2-axopyrrolidin-3-yl)methylamino]carbamate (150.0 g, Intermediate AF-3) in ethanol (800 mL) was added DIEA (220.89 g) and Boc₂O (149.21 g). After stirred at 50° C. for 12 hrs, the reaction mixture was concentrated in vacuo. The residue was diluted with ethyl acetate (1000 mL), washed with brine (200 mL), dried over anhydrous Na₂SO₄, filtered and concentrated in vacuo. The residue was purified by silica gel column, eluted with petroleum ether/ethyl acetate from 1:1 to 0:1 to afford an impure product which was conducted a further purification by reverse flash (0.1% TFA) to afford 2-benzyl 1-tert-butyl 1-((2-axopyrrolidin-3-yl)methyl)hydrazine-1,2-dicarboxylate (50 g, Intermediate AF-4) as a light yellow oil. MS obsd. (ESI+) [M−Boc+H]⁺: 264.2

Step 5: Preparation of (S)-tert-butyl 1-((2-axopyrrolidin-3-yl)methyl)hydrazinecarboxylate

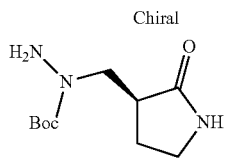 [SMILES: CC(C)(C)OC(=O)N(N)C[C@@H]1CCNC1=O]

Intermediate AF

To a solution of tert-butyl N-(benzyloxycarbonylamino)-N-[(2-axopyrrolidin-3-yl)methyl]carbamate (160.0 g, Intermediate AF-4) in methanol (1500 mL) was added Pd/C (15.0 g, 10% purity) and Pd(OH)₂/C (15.0 g) under N₂. The reaction mixture was degassed under vacuum and purged H₂ for 3 times. After stirred at 25° C. for 12 hrs under H₂ balloon, the resulting mixture was filtered through a pad of celite and the filtrate was concentrated in vacuo to afford tert-butyl 1-((2-axopyrrolidin-3-yl)methyl)hydrazinecarboxylate (100 g) as a colorless oil.

The racemate was purified with SFC preparation: (Column: Phenomenex-Cellulose-2 (250 mm*50 mm, 10 um); Condition: Neu-MeOH; B %: 45-45%; FlowRate (ml/min): 220) to afford (S)-tert-butyl 1-((2-axopyrrolidin-3-yl)methyl)hydrazinecarboxylate (faster eluting, 41.4 g, Intermediate AF) as a light yellow solid. ¹H NMR (400 MHz, CDCl₃) δ 5.77 (s, 1H), 3.55-3.75 (m, 2H), 3.30-3.45 (m, 2H), 2.75-2.85 (m, 1H), 2.20-2.30 (m, 1H), 1.89-1.99 (m, 1H), 1.42-1.51 (m, 9H). MS obsd. (ESI⁺) [M+H]⁺: 230.1. SFC: RT=1.615 min, ee %=98.05%.

The absolute configuration was determined by X-Ray.

Intermediate AG

Methyl(2S)-2-amino-3-(1-bicyclo[1.1.1]pentanyl)propanoate

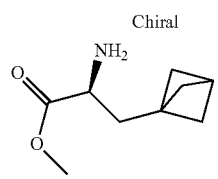

Step 1: Preparation of tricyclo[1.1.1.01,3]pentane

Intermediate AG-1

To a suspension of 1,1-dibromo-2,2-bis(chloromethyl)cyclopropane (10 g, WuXi catalog, CAS number: 98577-44-7) in diethyl ether (11.49 mL) was added methyllithium (3.1 M, 20.56 g) dropwise at −50 to −60° C. under N₂ atmosphere. Then the reaction mixture was allowed to warm to 0° C. and stirred for 2 hrs. After reaction, a distillation apparatus is connected and the receiving flask is cooled to −78° C. Tricyclo[1.1.1.01,3]pentane (Intermediate AG-1) is obtained as a solution in Et₂O (0.3 to 0.6 M) in 70-95% yield.

Step 2: Preparation of methyl(2S)-2-(tert-butoxycarbonylamino)-3-(3-iodo-1-bicyclo[1.1.1]pentanyl)propanoate

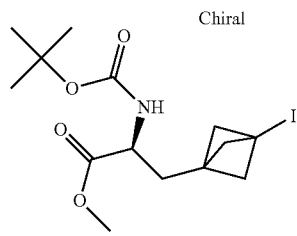 [SMILES: COC(=O)[C@H](CC12CC(I)(C1)C2)NC(=O)OC(C)(C)C]

Intermediate AG-2

A solution of (2R)-2-(tert-butoxycarbonylamino)-3-iodopropionic acid methyl ester (658 mg) in diethyl ether (5 mL) was added 0.300 M tricyclo[1.1.1.01,3]pentane (6.66 mL, Intermediate AG-1) at room temperature. After stirred at this temperature for 15 min, triethylborane (199.92 uL, 1M) was added and stirred for another 2 hrs. The reaction mixture was concentrated and purified by silica gel chromatography (EtOAc/PE form 0% to 12%) to afford (2S)-2-(tert-butoxycarbonylamino)-3-(3-iodo-1-bicyclo[1.1.1]pentanyl)propionic acid methyl ester (788 mg, Intermediate AG-2) as a white solid. MS obsd. (ESI$^+$) [M+H]$^+$: 396.

Step 3: Preparation of methyl(2S)-3-(1-bicyclo[1.1.1]pentanyl)-2-(tert-butoxycarbonylamino)propanoate

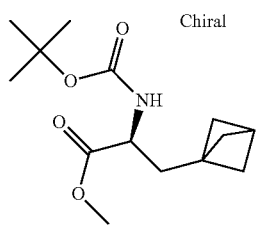 [SMILES: COC(=O)[C@H](CC12CC(C1)C2)NC(=O)OC(C)(C)C]

Intermediate AG-3

To a solution of (2S)-2-(tert-butoxycarbonylamino)-3-(3-iodo-1-bicyclo[1.1.1]pentanyl)propionic acid methyl ester (287 mg, Intermediate AG-2) and 2,6-lutidine (233.42 mg) in tetrahydrofuran (2 mL) was added bis(trimethylsilyl)silyl-trimethyl-silane (180.57 mg) and stirred at rt for 30 min. Then triethylborane (142.31 mg) was added and stirred for another 1 hr. The resulting mixture was stirred for 15 min at rt and concentrated in vacuo. The residue was purified by column chromatography (EtOAc/PE from 10% to 30%) to afford (2S)-3-(1-bicyclo[1.1.1]pentanyl)-2-(tert-butoxycarbonylamino)propionic acid methyl ester (85 mg intermediate AG-3) as a colorless oil.

Step 4: Preparation of (2S)-2-amino-3-(1-bicyclo[1.1.1]pentanyl)propionic acid methyl ester

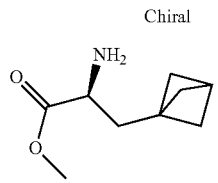

Intermediate AG

A solution of (2S)-3-(1-bicyclo[1.1.1]pentanyl)-2-(tert-butoxycarbonylamino)propionic acid methyl ester (85 mg, Intermediate AG-3) in dichloromethane (1 mL) was added TFA (1.48 g, 1 mL) at 0° C. After stirred at rt for 1 hour, the resulting mixture was concentrated in vacuo to afford crude (2S)-2-amino-3-(1-bicyclo[1.1.1]pentanyl)propionic acid methyl ester TFA salt (80 mg, Intermediate AG) as a light yellow oil which can be used for next step without purification.

Example 1

Benzyl N-[2-[2-(3-amino-3-oxo-propyl)-2-(2-chloroacetyl)hydrazino]-2-axo-ethyl]carbamate

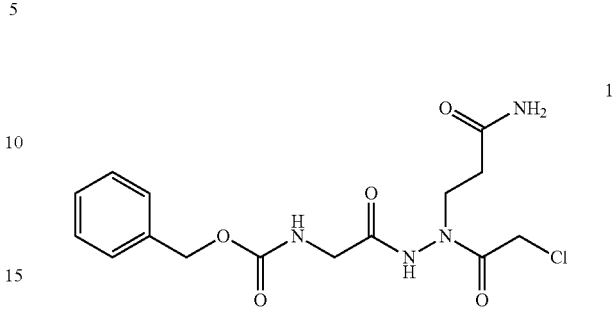

Step 1: Preparation of tert-butyl N-[[2-(benzyloxycarbonylamino)acetyl]amino]carbamate

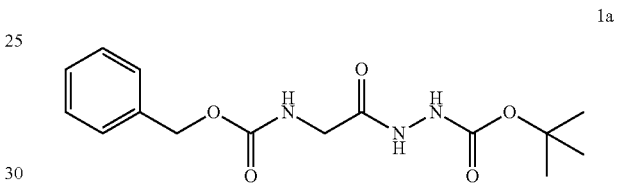

To a solution of 2-(benzyloxycarbonylamino)acetic acid (5.0 g, 23.9 mmol) and tert-butyl carbazate (3.16 g, 23.9 mmol, Wuxi Apptec (Wuhan) Co., Ltd.) in EtOAc (80 mL) was added T$_3$P (21.3 mL, 35.9 mmol) and DIEPA (11.9 mL, 71.7 mmol) at 0° C. The mixture was stirred at 25° C. for 3 hrs, and then diluted with water (100 mL), extracted with EtOAc (100 mL) three times. The combined organic layer was washed with HCl (1M, 100 mL) twice, saturated aqueous NaHCO$_3$ (100 mL) twice, and brine (100 mL) twice, dried over anhydrous Na$_2$SO$_4$ and concentrated in vacuo. tert-Butyl N-[[2-(benzyloxycarbonylamino)acetyl]amino]carbamate (8.0 g, compound 1a) was obtained as a light yellow oil and used in next step without further purification. MS obsd. (ESI$^+$) [(M-Boc+H)$^+$]: 223.9.

Step 2: Preparation of benzyl(2-hydrazinyl-2-axo-ethyl)carbamate

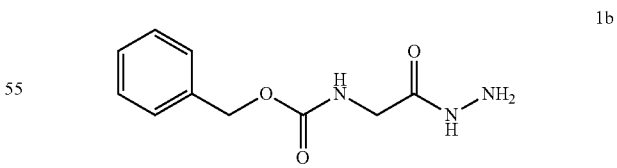

A solution of tert-butyl N-[[2-(benzyloxycarbonylamino)acetyl]amino]carbamate (2.0 g, compound 1a) in HCl/dioxane (4 M, 20.0 mL) was stirred at 25° C. for 2 hrs. After reaction, the resulting reaction mixture was concentrated in vacuo to afford benzyl(2-hydrazinyl-2-axo-ethyl)carbamate (1.7 g, compound 1b) as a yellow solid and used in next step without further purification. MS obsd. (ESI$^+$) [(M+H)$^+$]: 223.9.

Step 3: Preparation of benzyl N-[2-[2-(3-amino-3-oxo-propyl)hydrazino]-2-axo-ethyl]carbamate

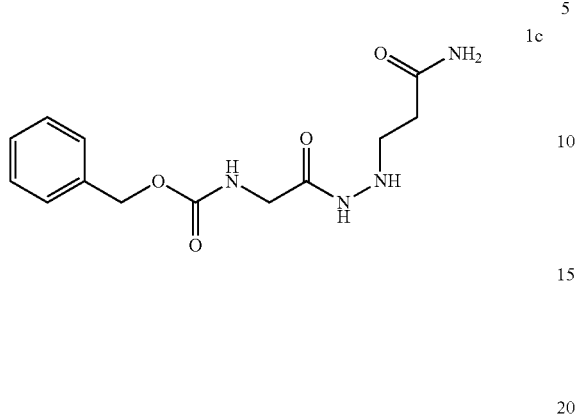

1c

To a solution of benzyl(2-hydrazinyl-2-axo-ethyl)carbamate (300.0 mg, compound 1b) in 2-propanol (3 mL) was added acrylamide (49.3 mg). After stirred at 60° C. for 1.5 hrs and at 85° C. for another 2 hrs, the reaction mixture was concentrated in vacuo. The residue was purified by prep-HPLC to afford benzyl N-[2-[2-(3-amino-3-oxo-propyl)hydrazino]-2-axo-ethyl]carbamate (80 mg, compound 1c) as a light yellow oil. MS obsd. (ESI$^+$) [(M+H)$^+$]: 295.0.

Step 4: Preparation of benzyl N-[2-[2-(3-amino-3-oxo-propyl)-2-(2-chloroacetyl)hydrazino]-2-axo-ethyl]carbamate

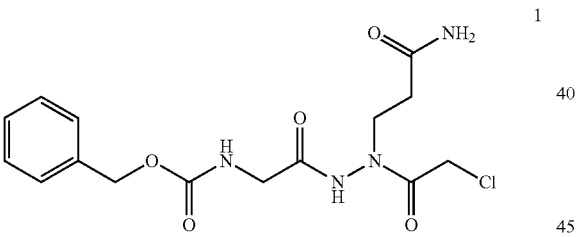

1

To a solution of benzyl N-[2-[2-(3-amino-3-oxo-propyl)hydrazino]-2-axo-ethyl]carbamate (80.0 mg, 0.270 mmol, compound 1c) and TEA (55.0 mg, 0.540 mmol) in THF (2 mL) was added chloroacetyl chloride (30.7 mg, 0.270 mmol) at 0° C. The mixture was warmed to 25° C. and stirred for 2 hrs. After reaction, the resulting mixture was diluted with H$_2$O (10 mL) and extracted with EtOAc (10 mL) three times. The combined organic phases were dried over anhydrous Na$_2$SO$_4$ and concentrated in vacuo. The residue was purified by prep-HPLC to afford benzyl N-[2-[2-(3-amino-3-oxo-propyl)-2-(2-chloroacetyl)hydrazino]-2-axo-ethyl]carbamate (23.0 mg, Example 1)) as a white solid. $^1$H NMR (400 MHz, DMSO-d$_6$) δ ppm: 10.47 (s, 1H), 7.65 (t, J=5.6 Hz, 1H), 7.33-7.39 (m, 5H), 7.29-7.32 (m, 1H), 6.85 (s, 1H), 5.04 (s, 2H), 4.10-4.31 (m, 2H), 3.70 (s, 2H), 3.60-3.62 (m, 2H), 2.29-2.32 (m, 2H). MS obsd. (ESI$^+$) [(M+H)$^+$]: 371.3.

Example 2

Benzyl N-[(1S)-1-[[(3-amino-3-oxo-propyl)-(2-chloroacetyl)amino]carbamoyl]-3-methyl-butyl]carbamate

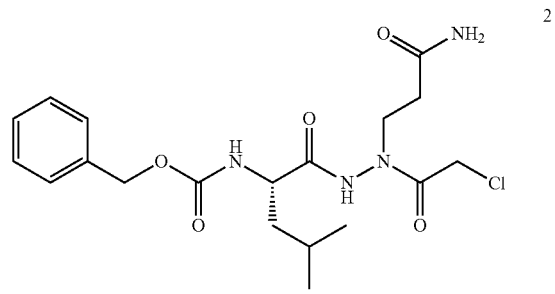 [SMILES: CC(C)C[C@H](NC(=O)OCc1ccccc1)C(=O)NN(CCC(N)=O)C(=O)CCl]

2

Step 1: Preparation of tert-butyl N-[[(2S)-2-(benzyloxycarbonylamino)-4-methyl-pentanoyl]amino]carbamate

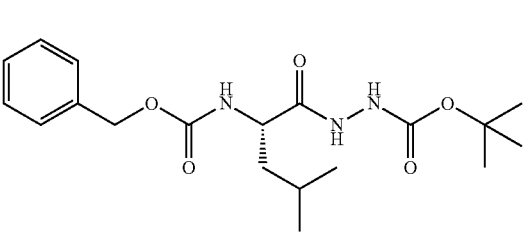

2a

Compound 2a was prepared in analogy to Example 1, Step 1 by using (2S)-2-(benzyloxycarbonylamino)-4-methyl-pentanoic acid (Shanghai Titan Scientific Co., Ltd. CAS number: 2018-66-8) instead of (2-(benzyloxycarbonylamino) acetic acid. tert-Butyl N-[[(2S)-2-(benzyloxycarbonylamino)-4-methyl-pentanoyl]amino]carbamate (3.8 g, compound 2a) was obtained as a white solid.

Step 2: Preparation of benzyl N-[(1S)-1-(hydrazinecarbonyl)-3-methyl-butyl]carbamate

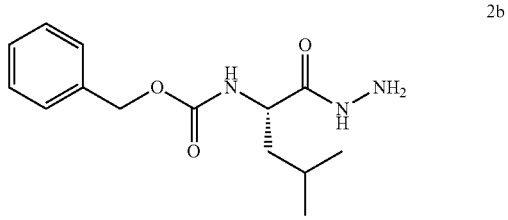 [SMILES: CC(C)C[C@H](NC(=O)OCc1ccccc1)C(=O)NN]

2b

Compound 2b was prepared in analogy to Example 1, Step 2 by using tert-butyl N-[[(2S)-2-(benzyloxycarbonylamino)-4-methyl-pentanoyl]amino]carbamate (compound 2a) instead of tert-butyl N-[[2-(benzyloxycarbonylamino)acetyl]amino]carbamate (compound 1a). Benzyl N-[(1S)-1-(hydrazinecarbonyl)-3-methyl-butyl]carbamate (730 mg, compound 2b) was obtained as a yellow oil. MS obsd. (ESI+) [(M+H)+]: 280.

Step 3: Preparation of benzyl N-[(1S)-1-[[(3-amino-3-oxo-propyl)amino]carbamoyl]-3-methyl-butyl]carbamate

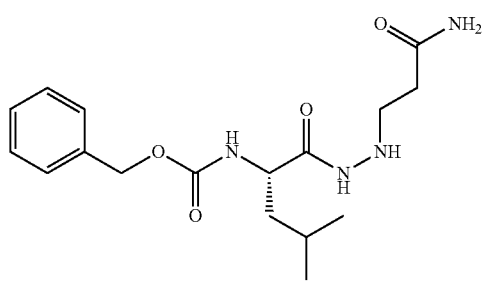

2c

Compound 2c was prepared in analogy to Example 1, Step 3 by using benzyl N-[(1S)-1-(hydrazinecarbonyl)-3-methyl-butyl]carbamate (compound 2b) instead of benzyl (2-hydrazinyl-2-axo-ethyl)carbamate (compound 1b). Benzyl N-[(1S)-1-[[(3-amino-3-oxo-propyl)amino]carbamoyl]-3-methyl-butyl]carbamate (500 mg, compound 2c) was obtained as a viscous oil. MS obsd. (ESI+) [(M+H)+]: 351.

Step 4: Preparation of benzyl N-[(1S)-1-[[(3-amino-3-oxo-propyl)-(2-chloroacetyl)amino]carbamoyl]-3-methyl-butyl]carbamate

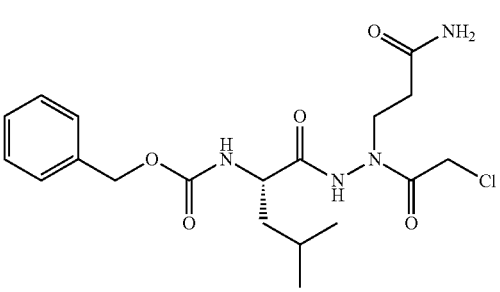

2

The title compound was prepared in analogy to Example 1, Step 4 by using benzyl N-[(1S)-1-[[(3-amino-3-oxo-propyl)amino]carbamoyl]-3-methyl-butyl]carbamate (compound 2c) instead of benzyl N-[2-[2-(3-amino-3-oxo-propyl)hydrazino]-2-axo-ethyl]carbamate (80 mg, compound 1c). Benzyl N-[(1S)-1-[[(3-amino-3-oxo-propyl)-(2-chloroacetyl)amino]carbamoyl]-3-methyl-butyl]carbamate (7.3 mg, Example 2) was obtained as a white solid. $^1$H NMR (400 MHz, CD$_3$OD, 25° C.) δ ppm: 7.14-7.34 (m, 5H), 5.01 (br d, J=5.14 Hz, 2H), 3.40-4.32 (m, 5H), 2.15-2.53 (m, 2H), 1.38-1.77 (m, 3H), 0.87 (dd, J=12.72, 6.48 Hz, 6H). MS obsd. (ESI+) [(M+H)+]: 427.

Example 3

Benzyl N-[(1S)-1-[[(3-amino-3-oxo-propyl)-(2-chloro-2-phenyl-acetyl)amino]carbamoyl]-3-methyl-butyl]carbamat

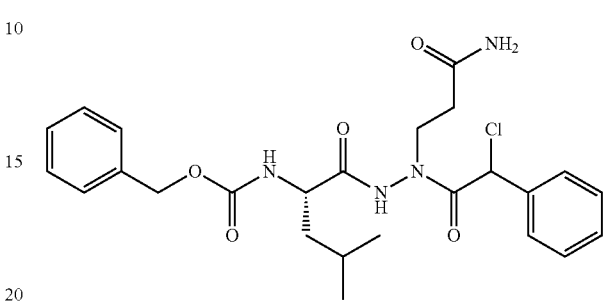

3

The title compound was prepared in analogy to Example 1, Step 4 by using benzyl N-[(1S)-1-[[(3-amino-3-oxo-propyl)amino]carbamoyl]-3-methyl-butyl]carbamate (50.0 mg, compound 2c) and 2-chloro-2-phenylacetyl chloride (Sigma-Aldrich, CAS number: 2018-66-8) instead of benzyl N-[2-[2-(3-amino-3-oxo-propyl)hydrazino]-2-axo-ethyl]carbamate (compound 1c) and chloroacetyl chloride. Benzyl N-[(1S)-1-[[(3-amino-3-oxo-propyl)-(2-chloro-2-phenyl-acetyl)amino]carbamoyl]-3-methyl-butyl]carbamate (20.4 mg, Example 3) was obtained as a white solid. $^1$H NMR (400 MHz, DMSO-d$_6$) δ ppm: 10.59-11.06 (m 1H), 7.52-7.81 (m, 1H), 7.47-7.59 (m, 1H), 7.23-7.46 (m, 10H), 6.84 (br. s, 1H), 5.85-5.88 (m, 1H), 4.99-5.19 (m, 2H), 3.95-4.03 (m, 1H), 3.59-3.86 (m, 1H), 3.29 (s, 1H), 2.24-2.37 (m, 2H), 1.62-1.75 (m, 1H), 1.49-1.60 (m, 1H), 1.32-1.47 (m, 1H), 0.84-0.95 (m, 6H). MS obsd. (ESI+) [(M+H)+]: 503.2.

Example 4

Benzyl N-[(1S)-1-[[(3-amino-3-oxo-propyl)-(2-chloropropanoyl)amino]carbamoyl]-3-methyl-butyl]carbamate

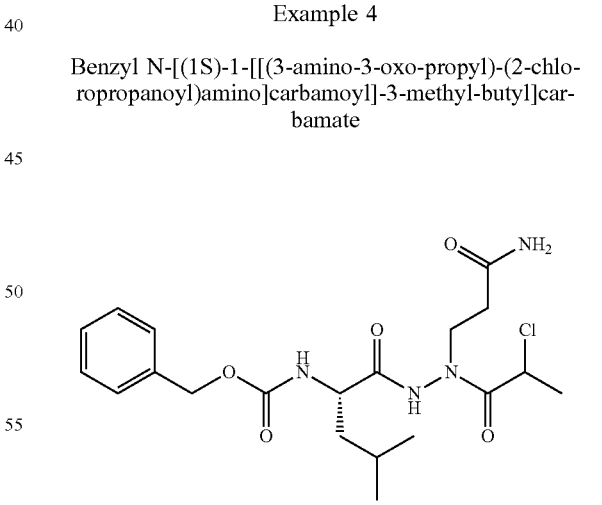

4

To a solution of benzyl N-[(1S)-1-[[(3-amino-3-oxo-propyl)amino]carbamoyl]-3-methyl-butyl]carbamate (50.0 mg, compound 2c) and 2-chloropropanoic acid (18.6 mg) in DMF (0.500 mL) was added DIEPA (0.1 mL, 0.570 mmol) and T$_3$P (0.13 mL, 50% in EtOAc) at 0° C. for 1 hr. The resulting mixture was diluted with water (15 mL) and extracted with EtOAc (10 mL) three times. The combined organic layers were washed with brine (15 mL), dried over anhydrous Na$_2$SO$_4$ and concentrated in vacuo. The residue was purified by prep-HPLC to afford benzyl N-[(1S)-1-[[(3-amino-3-oxo-propyl)-(2-chloropropanoyl)amino]carbamoyl]-3-methyl-butyl]carbamate (22.3 mg, Example 4) as a light yellow solid. $^1$H NMR (400 MHz, CDCl$_3$) δ ppm: 9.37-9.71 (m, 1H), 7.29-7.40 (m, 5H), 6.10-6.31 (m, 1H), 5.75 (br. s, 1H), 5.36-5.57 (m, 1H), 5.13 (s, 2H), 4.50-4.55 (m, 1H), 4.20-4.27 (m, 1H), 3.83-4.16 (m, 1H), 3.52-3.63 (m, 1H), 2.40-2.60 (m, 2H), 1.67-1.89 (m, 3H), 1.51-1.61 (m, 3H), 0.95-1.00 (m, 6H). MS obsd. (ESI$^+$) [(M+H)$^+$]: 441.1.

Example 5

Benzyl N-[(1S)-1-[[(3-amino-3-oxo-propyl)-(2-chlorobutanoyl)amino]carbamoyl]-3-methyl-butyl]carbamate

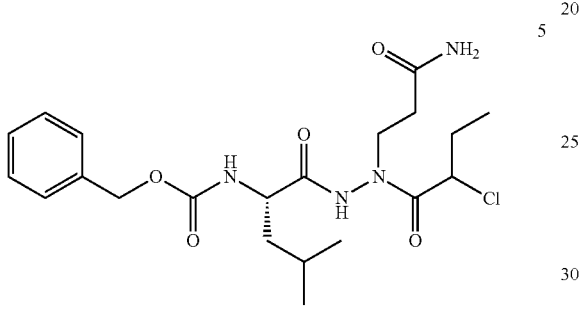

The title compound was prepared in analogy to Example 4 by using 2-chlorobutanoic acid instead of 2-chloropropanoic acid (Shanghai Aladdin Bio-Chem Technology Co., Ltd, CAS number: 7623-11-2). Benzyl N-[(1S)-1-[[(3-amino-3-oxo-propyl)-(2-chlorobutanoyl)amino]carbamoyl]-3-methyl-butyl]carbamate (33.9 mg, Example 5) was obtained as a white yellow solid. $^1$H NMR (400 MHz, CDCl$_3$) δ ppm: 9.28-9.65 (m, 1H), 7.29-7.43 (m, 5H), 6.03-6.19 (m, 1H), 5.67 (br. s, 1H), 5.45-5.29 (m, 1H), 5.12-5.14 (m, 2H), 4.18-4.42 (m, 2H), 4.00-4.16 (m, 1H), 3.43-3.66 (m, 1H), 2.38-2.76 (m, 2H), 1.95-2.04 (m, 1H), 1.80-1.87 (m, 1H), 1.51-1.71 (m, 3H), 0.90-1.05 (m, 9H). MS obsd. (ESI$^+$) (M+H)$^+$: 455.1.

Example 7

Benzyl N-[(1S)-1-[[(3-amino-3-oxo-propyl)-(2-bromoacetyl)amino]carbamoyl]-3-methyl-butyl]carbamate

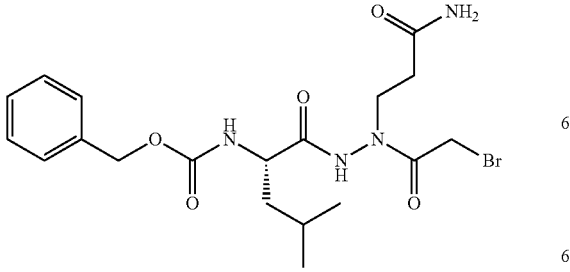

The title compound was prepared in analogy to Example 1, Step 4 by using benzyl N-[(1S)-1-[[(3-amino-3-oxo-propyl)amino]carbamoyl]-3-methyl-butyl]carbamate (50.0 mg, compound 2c) and bromoacetyl bromide instead of benzyl(2-(2-(3-amino-3-oxo-propyl)hydrazinyl)-2-axo-ethyl)carbamate (compound 1c) and chloroacetyl chloride. (S)-Benzyl(1-(2-(3-amino-3-oxo-propyl)-2-(2-bromoacetyl)hydrazinyl)-4-methyl-1-oxo-pentan-2-yl)carbamate (4 mg, Example 7) was obtained as a white solid. $^1$H NMR (400 MHz, DMSO-d$_6$) δ ppm: 10.52-10.65 (m, 1H), 7.66-7.71 (m, 1H), 7.33-7.48 (m, 5H), 7.29-7.32 (m, 1H), 6.86 (s, 1H), 5.04 (s, 2H), 3.97-4.10 (m, 1H), 3.64-3.95 (m, 2H), 3.43-3.50 (m, 2H), 2.20-2.33 (m, 2H), 1.60-1.74 (m, 1H), 1.35-1.58 (m, 2H), 0.77-0.91 (m, 6H). MS obsd. (ESI$^+$) [M+H]$^+$: 471.1.

Example 8

Benzyl N-[(1S)-2-[2-(3-amino-3-oxo-propyl)-2-(2-chloroacetyl)hydrazino]-1-(cyclohexylmethyl)-2-axo-ethyl]carbamate

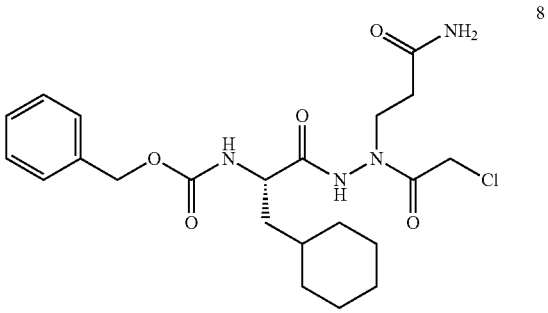 [SMILES: NC(=O)CCN(NC(=O)[C@H](CC1CCCCC1)NC(=O)OCc1ccccc1)C(=O)CCl]

Step 1: Preparation of tert-butyl N-[[(2S)-2-(benzyloxycarbonylamino)-3-cyclohexyl-propanoyl]amino]carbamate

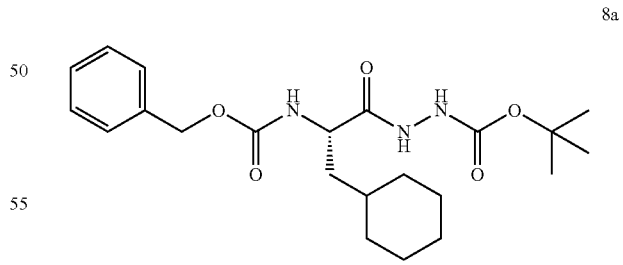

Compound 8a was prepared in analogy to Example 1, Step 1 by using (2S)-2-(benzyloxycarbonylamino)-3-cyclohexyl-propanoic acid (10 g, Bidepharm, CAS number: 25341-42-8) instead of (2-(benzyloxycarbonylamino)acetic acid. tert-Butyl N-[[(2S)-2-(benzyloxycarbonylamino)-3-cyclohexyl-propanoyl]amino]carbamate (13.0 g, compound 8a) was obtained as a white solid. MS obsd. (ESI$^+$) [(M-Boc+H)$^+$]: 319.9.

Step 2: Preparation of benzyl N-[(1S)-1-(cyclohexylmethyl)-2-hydrazino-2-axo-ethyl]carbamate

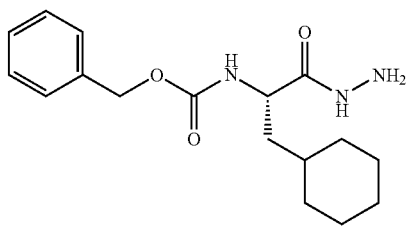

8b

Compound 8b was prepared in analogy to Example 1, Step 2 by using tert-butyl N-[[(2S)-2-(benzyloxycarbonylamino)-3-cyclohexyl-propanoyl]amino]carbamate (3.0 g, compound 8a) instead of tert-butyl N-[[2-(benzyloxycarbonylamino)acetyl]amino]carbamate (compound 1a). Benzyl N-[(1S)-1-(cyclohexylmethyl)-2-hydrazino-2-axo-ethyl]carbamate (2.2 g, compound 8b) was obtained as a white solid. MS obsd. (ESI$^+$) [(M+H)$^+$]: 320.

Step 3: Preparation of benzyl N-[(1S)-2-[2-(3-amino-3-axo-propyl)hydrazino]-1-(cyclohexylmethyl)-2-axo-ethyl]carbamate

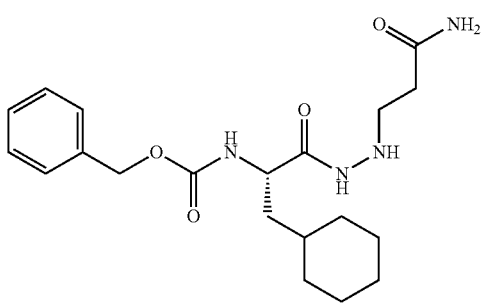 [SMILES: NC(=O)CCNNC(=O)[C@H](CC1CCCCC1)NC(=O)OCc1ccccc1]

8c

Compound 8c was prepared in analogy to Example 1, Step 3 by using benzyl N-[(1S)-1-(cyclohexylmethyl)-2-hydrazino-2-axo-ethyl]carbamate (2.2 g, compound 8b) instead of benzyl(2-hydrazinyl-2-axo-ethyl)carbamate (compound 1b). Benzyl N-[(1S)-2-[2-(3-amino-3-oxo-propyl)hydrazino]-1-(cyclohexylmethyl)-2-axo-ethyl]carbamate (650 mg, compound 8c) was obtained as a white solid. MS obsd. (ESI$^+$) [(M+H)$^+$]: 391.0.

Step 4: Preparation of benzyl N-[(1S)-2-[2-(3-amino-3-axo-propyl)-2-(2-chloroacetyl)hydrazino]-1-(cyclohexylmethyl)-2-axo-ethyl]carbamate

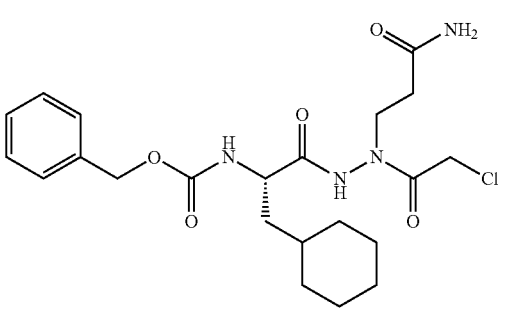

8

The title compound was prepared in analogy to Example 1, Step 4 by using benzyl N-[(1S)-2-[2-(3-amino-3-oxo-propyl)hydrazino]-1-(cyclohexylmethyl)-2-axo-ethyl]carbamate (50.0 mg, compound 8c) instead of benzyl N-[2-[2-(3-amino-3-oxo-propyl)hydrazino]-2-axo-ethyl]carbamate (compound 1c). Benzyl N-[(1S)-2-[2-(3-amino-3-oxo-propyl)-2-(2-chloroacetyl)hydrazino]-1-(cyclohexylmethyl)-2-axo-ethyl]carbamate (12.2 mg, Example 8) was obtained as a white solid. $^1$H NMR (400 MHz, DMSO-d$_6$) δ ppm: 10.51-10.70 (m, 1H), 7.72 (br. s, 1H), 7.32-7.38 (m, 6H), 6.87 (s, 1H), 5.01 (s, 2H), 4.21-4.39 (m, 1H), 3.95-4.03 (m, 2H), 3.75-3.81 (m, 1H), 2.22-2.33 (m, 2H), 1.48-1.67 (m, 8H), 1.24-1.33 (m, 1H), 1.09-1.16 (m, 3H), 0.84-0.95 (m, 2H). MS obsd. (ESI$^+$) [(M+H)$^+$]: 467.2.

Example 10

Benzyl N-[(1S)-2-[2-(3-amino-3-oxo-propyl)-2-(2-chloroacetyl)hydrazino]-1-(cyclopentylmethyl)-2-axo-ethyl]carbamate

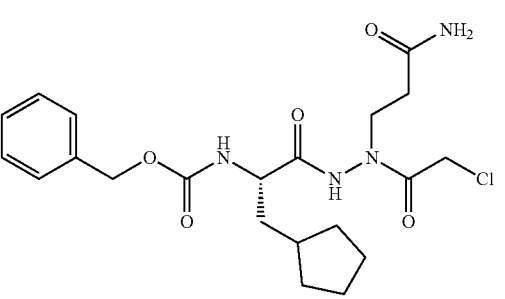

10

Step 1: Preparation of tert-butyl N-[[(2S)-2-(benzyloxycarbonylamino)-3-cyclopentyl-propanoyl]amino]carbamate

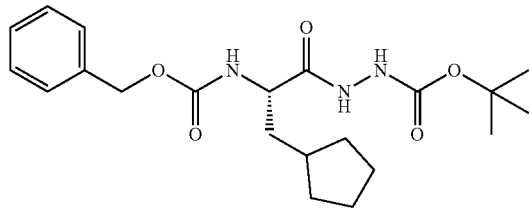

10a

Compound 10a was prepared in analogy to Example 1, Step 1 by using (2S)-2-(benzyloxycarbonylamino)-3-cyclopentyl-propanoic acid (0.9 g, Intermediate AB) instead of (2-(benzyloxycarbonylamino)acetic acid. tert-Butyl N-[[(2S)-2-(benzyloxycarbonylamino)-3-cyclopentyl-propanoyl]amino]carbamate (1.0 g, compound 10a) was obtained as a white solid. MS obsd. (ESI⁺) [(M+H)⁺]: 406.2.

Step 2: Preparation of benzyl N-[(1S)-1-(cyclopentylmethyl)-2-hydrazino-2-axo-ethyl]carbamate

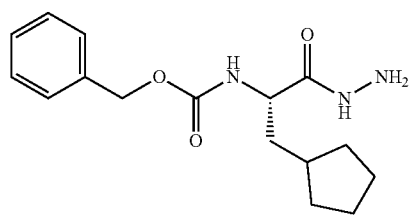

10b

Compound 10b was prepared in analogy to Example 1, Step 2 by using tert-butyl N-[[(2S)-2-(benzyloxycarbonylamino)-3-cyclopentyl-propanoyl]amino]carbamate (700 mg, compound 10a) instead of tert-butyl N-[[2-(benzyloxycarbonylamino)acetyl]amino]carbamate (compound 1a). Benzyl N-[(1S)-1-(cyclopentylmethyl)-2-hydrazino-2-axo-ethyl]carbamate (300 mg, compound 10b) was obtained as a light yellow solid. (ESI⁺) [(M+H)⁺]: 306.

Step 3: Preparation of benzyl N-[(1S)-2-[2-(3-amino-3-axo-propyl)hydrazino]-1-(cyclopentylmethyl)-2-axo-ethyl]carbamate

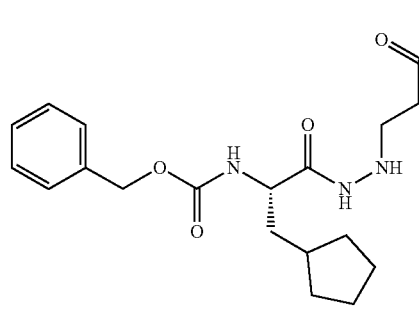

10c

Compound 10c was prepared in analogy to Example 1, Step 3 by using benzyl N-[(1S)-1-(cyclopentylmethyl)-2-hydrazino-2-axo-ethyl]carbamate (500 mg, compound 10b) instead of benzyl(2-hydrazinyl-2-axo-ethyl)carbamate (compound 1b). Benzyl N-[(1S)-2-[2-(3-amino-3-oxo-propyl)hydrazino]-1-(cyclopentylmethyl)-2-axo-ethyl]carbamate (300 mg, compound 10c) was obtained as a light yellow solid. (ESI⁺) [(M+H)⁺]: 377.

Step 4: Preparation of benzyl N-[(1S)-2-[2-(3-amino-3-axo-propyl)-2-(2-chloroacetyl)hydrazino]-1-(cyclopentylmethyl)-2-axo-ethyl]carbamate

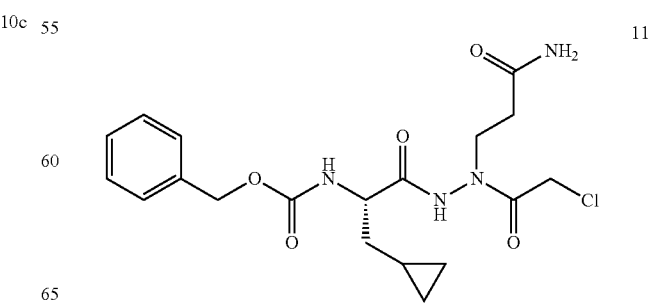

10

The title compound was prepared in analogy to Example 1, Step 4 by using benzyl N-[(1S)-2-[2-(3-amino-3-oxo-propyl)hydrazino]-1-(cyclopentylmethyl)-2-axo-ethyl]carbamate (80 mg, compound 10c) instead of benzyl N-[2-[2-(3-amino-3-oxo-propyl)hydrazino]-2-axo-ethyl]carbamate (compound 1c). Benzyl N-[(1S)-2-[2-(3-amino-3-oxo-propyl)-2-(2-chloroacetyl)hydrazino]-1-(cyclopentylmethyl)-2-axo-ethyl]carbamate (48 mg, Example 10) was obtained as a light yellow solid. ¹H NMR (400 MHz, DMSO-d₆) δ ppm: 10.49-10.89 (m, 1H), 7.71 (br. s, 1H), 7.33-7.39 (m, 6H), 6.85 (s, 1H), 5.04 (s, 2H), 4.19-4.35 (m, 1H), 3.96-4.12 (m, 2H), 3.77-3.84 (m, 1H), 3.36-3.45 (m, 1H), 2.29-2.33 (m, 2H), 1.58-1.85 (m, 7H), 1.45-1.51 (m, 2H), 1.11-1.18 (m, 2H), MS obsd. (ESI⁺) [(M+H)⁺]: 453.1.

Example 11

Benzyl N-[(1S)-2-[2-(3-amino-3-oxo-propyl)-2-(2-chloroacetyl)hydrazino]-1-(cyclopropylmethyl)-2-axo-ethyl]carbamate Step 1: Preparation of tert-butyl N-[[(2S)-2-(benzyloxycarbonylamino)-3-cyclopropyl-propanoyl]amino]carbamate

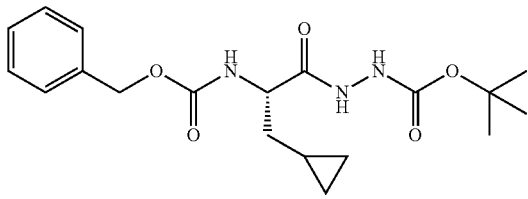

11a

Compound 11a was prepared in analogy to Example 1, Step 1 by using (2S)-2-(benzyloxycarbonylamino)-3-cyclopropyl-propanoic acid (1.6 g, Intermediate AA) instead of (2-(benzyloxycarbonylamino)acetic acid. tert-Butyl N-[[(2S)-2-(benzyloxycarbonylamino)-3-cyclopropyl-propanoyl]amino]carbamate (2 g, compound 11a) was obtained as a yellow oil.

Step 2: Preparation of benzyl N-[(1S)-1-(cyclopropylmethyl)-2-hydrazino-2-axo-ethyl]carbamate hydrochloride

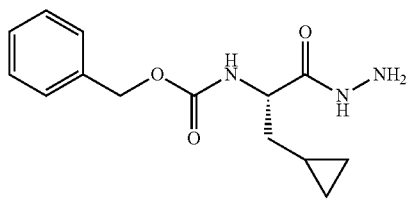

11b

Compound 11b was prepared in analogy to Example 1, Step 2 by using tert-butyl N-[[(2S)-2-(benzyloxycarbonylamino)-3-cyclopropyl-propanoyl]amino]carbamate (2 g, compound 11a) instead of tert-butyl N-[[2-(benzyloxycarbonylamino)acetyl]amino]carbamate (compound 1a). Benzyl N-[(1S)-1-(cyclopropylmethyl)-2-hydrazino-2-axo-ethyl]carbamate hydrochloride (1.6 g, compound 11b) was obtained as a yellow solid. MS obsd. (ESI$^+$) [(M+H)$^+$]: 278.

Step 3: Preparation of benzyl N-[(1S)-2-[2-(3-amino-3-axo-propyl)hydrazino]-1-(cyclopropylmethyl)-2-axo-ethyl]carbamate

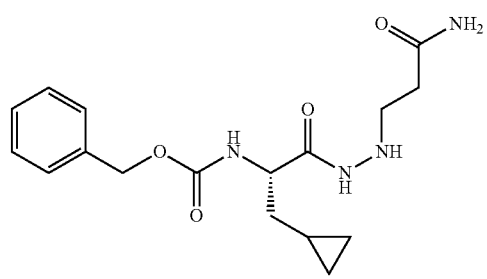

11c

Compound 11c was prepared in analogy to Example 1, Step 3 by using benzyl N-[(1S)-1-(cyclopropylmethyl)-2-hydrazino-2-axo-ethyl]carbamate hydrochloride (1.6 g, compound 11b) instead of benzyl(2-hydrazinyl-2-axo-ethyl)carbamate (compound 1b). Benzyl N-[(1S)-2-[2-(3-amino-3-oxo-propyl)hydrazino]-1-(cyclopropylmethyl)-2-axo-ethyl]carbamate (400 mg, compound 11c) was obtained as a yellow oil. MS obsd. (ESI$^+$) [(M+H)$^+$]: 349.0.

Step 4: Preparation of benzyl N-[(1S)-2-[2-(3-amino-3-axo-propyl)-2-(2-chloroacetyl)hydrazino]-1-(cyclopropylmethyl)-2-axo-ethyl]carbamate

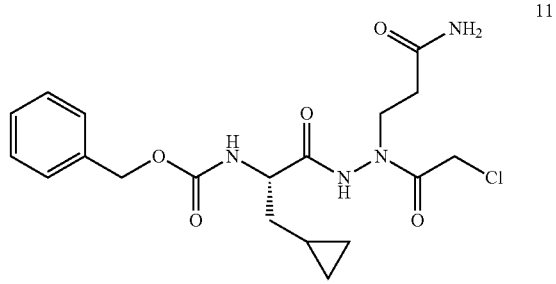 [SMILES: NC(=O)CCN(NC(=O)[C@H](CC1CC1)NC(=O)OCc1ccccc1)C(=O)CCl]

11

The title compound was prepared in analogy to Example 1, Step 4 by using benzyl N-[(1S)-2-[2-(3-amino-3-oxo-propyl)hydrazino]-1-(cyclopropylmethyl)-2-axo-ethyl]carbamate (50.0 mg, compound 11c) instead of benzyl(2-(2-(3-amino-3-oxo-propyl)hydrazinyl)-2-axo-ethyl)carbamate (compound 1c). Benzyl N-[(1S)-2-[2-(3-amino-3-oxo-propyl)-2-(2-chloroacetyl)hydrazino]-1-(cyclopropylmethyl)-2-axo-ethyl]carbamate (19.4 mg, Example 11) was obtained as a white solid. $^1$H NMR (400 MHz, DMSO-$d_6$) δ ppm: 10.45-10.73 (m, 1H), 7.74-7.76 (m, 1H), 7.29-7.37 (m, 6H), 6.85 (s, 1H), 5.02 (s, 2H), 4.21-4.41 (m, 1H), 4.06-4.21 (m, 2H), 3.70-3.92 (m, 1H), 2.52-2.58 (m, 1H), 2.22-2.34 (m, 2H), 1.60-1.72 (m, 1H), 1.33-1.45 (m, 1H), 0.72-0.83 (m 1H), 0.37-0.47 (m, 2H), 0.14-0.20 (m, 1H), 0.04-0.11 (m, 1H). MS obsd. (ESI$^+$) [(M+H)$^+$]: 425.1.

Example 15

Benzyl N-[(1S)-2-[2-(3-amino-3-oxo-propyl)-2-(2-fluoroacetyl)hydrazino]-1-(cyclohexylmethyl)-2-axo-ethyl]carbamate

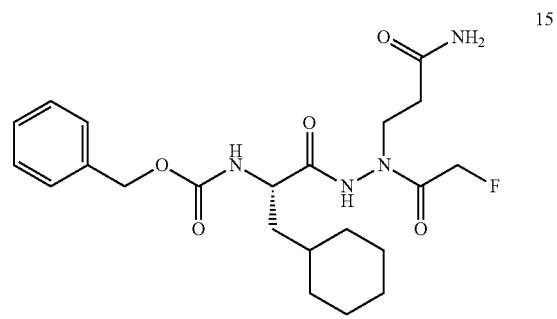 [SMILES: NC(=O)CCN(NC(=O)[C@H](CC1CCCCC1)NC(=O)OCc1ccccc1)C(=O)CF]

15

The title compound was prepared in analogy to Example 1, Step 4 by using benzyl N-[(1S)-2-[2-(3-amino-3-oxopropyl)hydrazino]-1-(cyclohexylmethyl)-2-axo-ethyl]carbamate (compound 8c) and 2-fluoroacetyl chloride instead of benzyl N-[2-[2-(3-amino-3-oxo-propyl)hydrazino]-2-axo-ethyl]carbamate (compound 1c) and chloroacetyl chloride. Benzyl N-[(1S)-2-[2-(3-amino-3-oxo-propyl)-2-(2-fluoroacetyl)hydrazino]-1-(cyclohexylmethyl)-2-axo-ethyl]carbamate (32.5 mg, compound 15) was obtained as a white solid. ¹H NMR (400 MHz, DMSO-d$_6$) δ ppm: 10.19-10.52 (m, 1H), 7.70 (br.s, 1H), 7.28-7.35 (m, 7H), 6.86 (br.s, 1H), 5.03 (br.s, 2H), 4.59-4.75 (m, 1H), 3.95-4.08 (m, 1H), 3.74-3.86 (m, 1H), 2.20-2.27 (m, 2H), 1.54-1.82 (m, 6H), 1.31-1.48 (m, 3H), 1.10-1.18 (m, 3H), 0.86-0.90 (m, 2H). MS obsd. (ESI⁺)[(M+H)⁺]: 451.

Example 16

Benzyl N-[(1S)-2-[2-(3-amino-3-oxo-propyl)-2-(2-chloro-2-fluoro-acetyl)hydrazino]-1-(cyclohexylmethyl)-2-axo-ethyl]carbamate

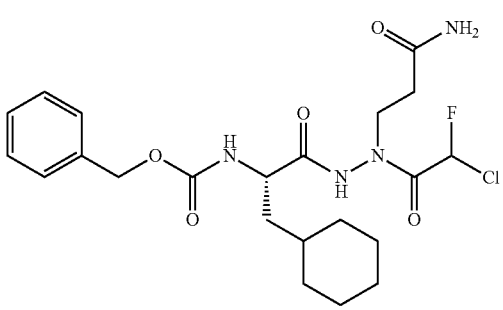

Step 1: Preparation of 2-chloro-2-fluoroacetic acid

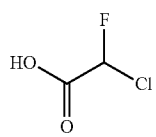

16a

To a solution of ethyl chlorofluoroacetate (8.0 g) in ethanol (114 mL) and water (7 mL) was added NaOH (2.73 g). After stirred at 20° C. for 12 hr, the solvent was removed in vacuo. The residue was dissolved in HCl (3 M, 80 mL). The aqueous solution was extracted with MTBE (100 mL) four times. The combined organic phase was dried over anhydrous Na$_2$SO$_4$ and concentrated to afford 2-chloro-2-fluoro-acetic acid (4.2 g, compound 16a) as a yellow liquid. ¹H NMR (400 MHz, DMSO-d$_6$) δ ppm: 6.88 (s, 0.5H), 6.76 (s, 0.5H).

Step 2: Preparation of benzyl N-[(1S)-2-[2-(3-amino-3-axo-propyl)-2-(2-chloro-2-fluoro-acetyl)hydrazino]-1-(cyclohexylmethyl)-2-axo-ethyl]carbamate

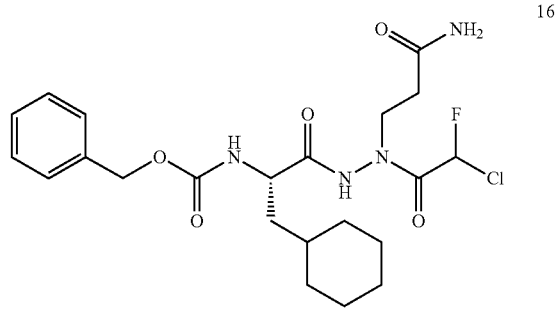 [SMILES: NC(=O)CCN(NC(=O)[C@H](CC1CCCCC1)NC(=O)OCc1ccccc1)C(=O)C(F)Cl]

16

Example 16 was prepared in analogy to Example 4 by using benzyl N-[(1S)-2-[2-(3-amino-3-oxo-propyl)hydrazino]-1-(cyclohexylmethyl)-2-axo-ethyl]carbamate (50.0 mg, compound 8c) and 2-chloro-2-fluoro-acetyl chloride instead of benzyl N-[(1S)-1-[[(3-amino-3-oxo-propyl)amino]carbamoyl]-3-methyl-butyl]carbamate (compound 2c) and 2-chloropropanoic acid. Benzyl N-[(1S)-2-[2-(3-amino-3-oxo-propyl)-2-(2-chloro-2-fluoro-acetyl)hydrazino]-1-(cyclohexylmethyl)-2-axo-ethyl]carbamate (Example 16) obtained as a white solid. MS obsd. (ESI⁺) [(M+H)⁺]: 485.4.

Separation of Example 16 by chiral HPLC afforded Example 16-A (faster eluting, 6.3 mg) and Example 16-B (slower eluting, 6.2 mg) as a white solid with 5%-40% MeOH (0.05% DEA)/CO$_2$ on CHIRALCEL OJ-3 column.

Benzyl((S)-1-(2-(3-amino-3-oxo-propyl)-2-((S)-2-chloro-2-fluoroacetyl)hydrazinyl)-3-cyclohexyl-1-oxo-propan-2-yl)carbamate and Benzyl((S)-1-(2-(3-amino-3-oxo-propyl)-2-((R)-2-chloro-2-fluoroacetyl)hydrazinyl)-3-cyclohexyl-1-oxo-propan-2-yl)carbamate (16-A and 16-B)

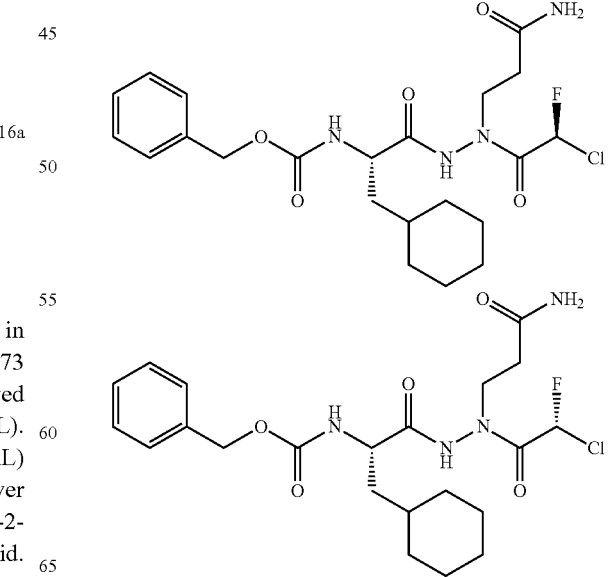

Example 16-A: $^1$H NMR (400 MHz, CDCl$_3$) δ ppm: 9.54 (br. s, 1H), 7.23-7.33 (m, 5H), 6.07-6.58 (m, 2H), 5.63 (br. s, 1H), 5.44 (br. s, 1H), 5.02-5.10 (m, 2H), 4.15-4.21 (m, 1H), 3.83-4.02 (m, 1H), 3.25-3.60 (m, 1H), 2.31-2.63 (m, 2H), 1.44-1.70 (m, 4H), 0.99-1.37 (m, 6H), 0.89-0.99 (m, 3H). MS obsd. (ESI$^+$) [(M+H)$^+$]: 485.4.

Example 16-B: $^1$H NMR (400 MHz, CDCl$_3$) δ ppm: 9.48 (br. s, 1H), 7.28-7.39 (m, 5H), 6.28-6.47 (m, 1H), 5.94-6.13 (m, 1H), 5.63 (br. s, 1H), 5.27 (br. s, 1H), 5.05 (s, 2H), 4.13-4.19 (m, 1H), 3.70-4.00 (m, 1H), 3.20-3.60 (m, 1H), 2.35-2.68 (m, 2H), 1.49-1.60 (m, 4H), 1.08-1.41 (m, 6H), 0.85-0.92 (m, 3H). 485.4.

Example 17

Benzyl N-[(1S)-1-[[(3-amino-3-oxo-propyl)-(2-chloro-2-fluoro-acetyl)amino]carbamoyl]-3-methyl-butyl]carbamate

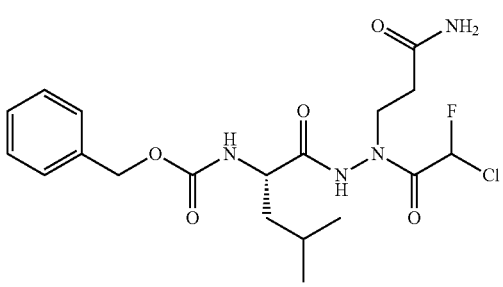

17

Example 17 was prepared in analogy to Example 4 by using 2-chloro-2-fluoro-acetic acid instead of 2-chloropropanoic acid. Benzyl N-[(1S)-1-[[(3-amino-3-oxo-propyl)-(2-chloro-2-fluoro-acetyl)amino]carbamoyl]-3-methyl-butyl]carbamate (60 mg, Example 17) was obtained as a white solid. MS obsd. (ESI$^+$) [(M+H)$^+$]: 445.4.

Separation of example of 17 by chiral SFC afford Example 17-A (faster eluting, 28 mg) and Example 17-B (Slower eluting, 40 mg) with isopropanol 5%-40% (0.05% DEA)/CO$_2$ on Chiralcel OD-3 column.

benzyl N-[(1S)-1-[[(3-amino-3-oxo-propyl)-[(2S)-2-chloro-2-fluoro-acetyl]amino]carbamoyl]-3-methyl-butyl]carbamate and benzyl N-[(1S)-1-[[(3-amino-3-oxo-propyl)-[(2R)-2-chloro-2-fluoro-acetyl]amino]carbamoyl]-3-methyl-butyl]carbamate (17-A and 17-B)

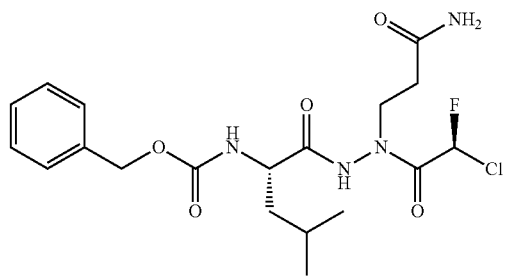

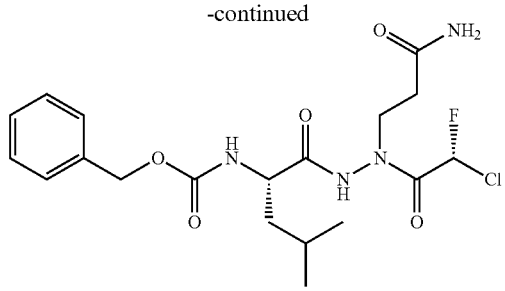

Example 17-A: $^1$H NMR (400 MHz, DMSO-d$_6$) δ ppm: 10.64-10.70 (m, 1H), 7.72-7.76 (m, 1H), 7.29-7.41 (m, 6H), 6.50-7.02 (m, 2H), 5.02-5.06 (m, 2H), 3.98-4.02 (m, 1H), 3.66-3.92 (m, 1H), 3.37-3.43 (m, 1H), 2.32-2.36 (m, 2H), 1.46-1.66 (m, 3H), 0.88 (dd, J=6.4 Hz, 12.8 Hz, 6H). MS obsd. (ESI$^+$) [(M+H)$^+$]: 445.4.

Example 17-B: $^1$H NMR (400 MHz, DMSO-d$_6$) δ ppm: 10.44-10.97 (m, 1H), 7.65-7.82 (m, 1H), 7.34-7.43 (m, 5H), 7.29-7.33 (m, 1H), 6.60-7.20 (m, 2H), 5.03-5.06 (m, 2H), 3.92-4.10 (m, 1H), 3.66-3.90 (m, 1H), 3.42-3.57 (m, 1H), 2.28-2.36 (m, 2H), 1.66-1.69 (m, 1H), 1.52-1.56 (m, 1H), 1.32-1.49 (m, 1H), 0.88 (dd, J=6.4, 10.4 Hz, 6H). MS obsd. (ESI$^+$) [(M+H)$^+$]: 445.3.

Example 18

Benzyl N-[(1S)-1-[[(2-chloroacetyl)-[(2-oxo-pyrrolidin-3-yl)methyl]amino]carbamoyl]-3-methyl-butyl]carbamate

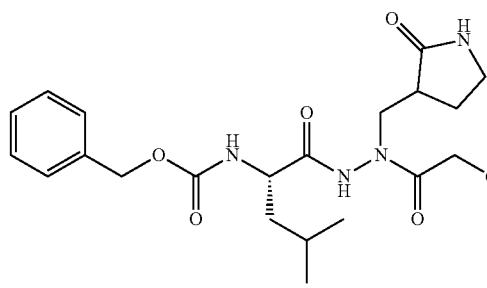

18

Step 1: Preparation of tert-butyl 3-methylene-2-oxo-pyrrolidine-1-carboxylate

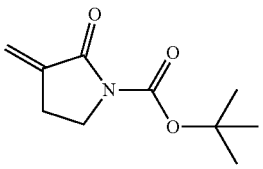

18a

To a solution of tert-butyl 2-oxo-pyrrolidine-1-carboxylate (10.0 g, 53.99 mmol, Wuxi Apptec (Wuhan) Co., Ltd) in THF (100 mL) was added a solution of LiHMDS (113.4 mL) at 0° C. The reaction mixture was allowed to warm up to rt over 30 mins before 2,2,2-trifluoroethyl trifluoroacetate (21.2 g) was added. After additional 20 mins at rt, the reaction mixture was quenched with saturated NH₄Cl (500 mL) and extracted with EtOAc (500 mL) twice. The combined organic phases were dried over anhydrous Na₂SO₄ and concentrated in vacuo. The residue was dissolved in toluene (100 mL), then formaldehyde (40.53 g) and K₂CO₃ (16.42 g) were added to the solution. After stirred at 108° C. for 2 hrs, the reaction mixture was diluted with EtOAc (500 mL). The organic layer was washed with brine (500 mL) twice, dried over anhydrous Na₂SO₄ and concentrated in vacuo. The residue was purified by flash chromatography on silica gel to afford tert-butyl 3-methylene-2-oxo-pyrrolidine-1-carboxylate (3.5 g, compound 18a) as a yellow oil. MS obsd. (ESI⁺) [(M−C4H8+H)⁺]: 142.1.

Step 2: Preparation of tert-butyl 3-[[2-[(2S)-2-(benzyloxycarbonylamino)-4-methyl-pentanoyl]hydrazino]methyl]-2-oxo-pyrrolidine-1-carboxylate

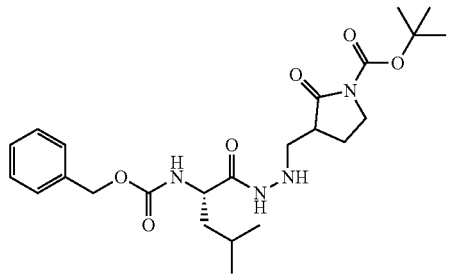

18b

To a solution of benzyl N-[(1S)-1-(hydrazinecarbonyl)-3-methyl-butyl]carbamate (700.0 mg, compound 2a) in 2-propanol (10 mL) was added tert-butyl 3-methylene-2-oxo-pyrrolidine-1-carboxylate (494.3 mg, compound 18a). After stirred at 90° C. for 48 hrs, the reaction mixture was purified by reversed flash chromatography to afford tert-butyl 3-[[2-[(2S)-2-(benzyloxycarbonylamino)-4-methyl-pentanoyl]hydrazino]methyl]-2-oxo-pyrrolidine-1-carboxylate (450 mg, compound 18b) as a yellow oil. MS obsd. (ESI⁺) [(M−Boc+Na)⁺]: 399.4.

Step 3: Preparation of benzyl N-[(1S)-3-methyl-1-[[(2-oxo-pyrrolidin-3-yl)methylamino]carbamoyl]butyl]carbamate

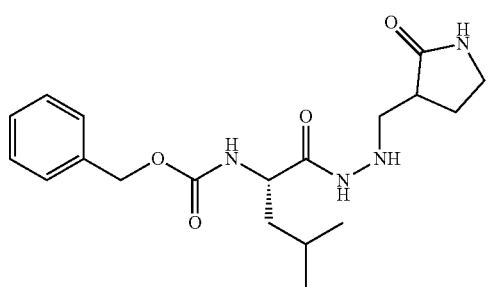

18c

To a solution of tert-butyl 3-[[2-[(2S)-2-(benzyloxycarbonylamino)-4-methyl-pentanoyl]hydrazino]methyl]-2-oxo-pyrrolidine-1-carboxylate (450.0 mg, compound 18b) in 1,4-dioxane (5 mL) was added HCl/dioxane (2.0 mL). After stirred at 20° C. for 2 hrs, the reaction mixture was concentrated in vacuo. The residue was purified by reversed flash chromatography to afford benzyl N-[(1S)-3-methyl-1-[[(2-oxo-pyrrolidin-3-yl)methylamino]carbamoyl]butyl] carbamate (150 mg, compound 18c) as a yellow oil. MS obsd. (ESI⁺) [(M+H)⁺]: 377.2.

Step 4: Preparation of benzyl N-[(1S)-1-[[(2-chloroacetyl)-[(2-oxo-pyrrolidin-3-yl)methyl]amino]carbamoyl]-3-methyl-butyl]carbamate

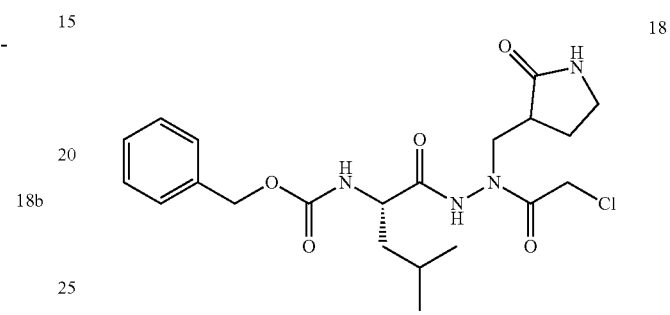

18

The title compound was prepared in analogy to Example 1, Step 4 by using benzyl N-[(1S)-3-methyl-1-[[(2-oxo-pyrrolidin-3-yl)methylamino]carbamoyl]butyl]carbamate (150 mg, compound 18c) instead of benzyl N-[2-[2-(3-amino-3-oxo-propyl)hydrazino]-2-axo-ethyl]carbamate (compound 1c). Benzyl N-[(1S)-1-[[(2-chloroacetyl)-[(2-oxo-pyrrolidin-3-yl)methyl]amino]carbamoyl]-3-methyl-butyl]carbamate (15.1 mg, Example 18) was obtained as a white solid. ¹H NMR (400 MHz, CDCl₃) δ ppm: 9.68-10.23 (m, 1H), 7.34-7.38 (m, 5H), 5.60-5.78 (m, 1H), 5.16-5.42 (m, 1H), 5.10 (s, 2H), 4.24-4.56 (m, 3H), 3.74-4.24 (m, 1H), 3.24-3.38 (m, 2H), 2.67-2.87 (m, 1H), 2.17-2.44 (m, 1H), 1.64-1.78 (m, 2H), 1.47-1.51 (m, 3H), 0.89-1.04 (m, 6H). MS obsd. (ESI⁺) (M+H)⁺: 453.2.

Example 20

Benzyl N-[(1S)-1-[[(2-chloroacetyl)-[(2-oxo-3-piperidyl)methyl]amino]carbamoyl]-3-methyl-butyl]carbamate

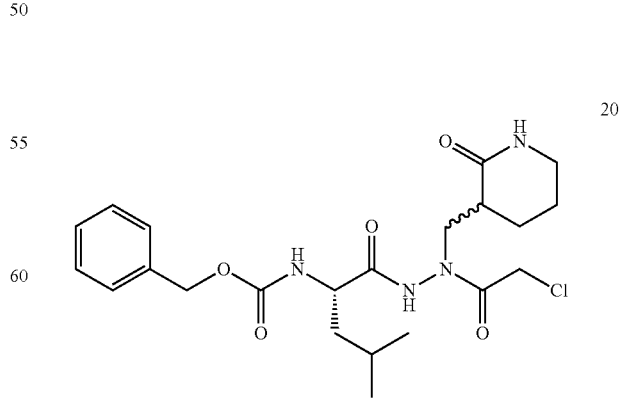

20

Step 1: Preparation of tert-butyl 3-methylene-2-oxo-piperidine-1-carboxylate

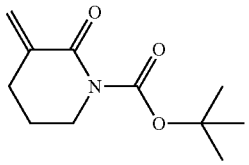

20a

Compound 20a was prepared in analogy to Example 18, Step 1 by using tert-butyl 2-oxo-piperidine-1-carboxylate instead of tert-butyl 2-oxo-pyrrolidine-1-carboxylate (Wuxi Apptec (Wuhan) Co., Ltd). tert-Butyl 3-methylene-2-oxo-piperidine-1-carboxylate (1.0 g, compound 20a) was obtained as a yellow oil. MS obsd. (ESI$^+$) [2M+Na]$^+$: 445.1

Step 2: Preparation of tert-butyl 3-((2-((S)-2-(((benzyloxy)carbonyl)amino)-4-methylpentanoyl)hydrazinyl)methyl)-2-oxo-piperidine-1-carboxylate

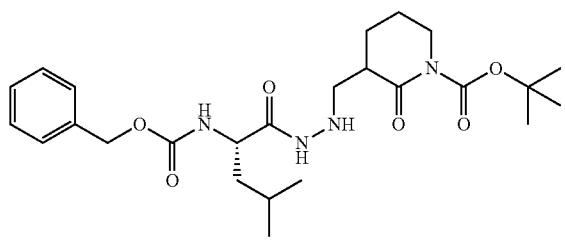

20b

Compound 20b was prepared in analogy to Example 18, Step 2 by using tert-butyl 3-methylene 2-oxo-piperidine-1-carboxylate (1.0 g, compound 20a) instead of tert-butyl 3-methylene-2-oxo-pyrrolidine-1-carboxylate (compound 18a). tert-Butyl 3-((2-((S)-2-(((benzyloxy)carbonyl)amino)-4-methylpentanoyl)hydrazinyl)methyl)-2-oxo-piperidine-1-carboxylate (170 mg, compound 20b) was obtained as a colorless oil. MS obsd. (ESI$^+$) [2M+H]$^+$: 981.7.

Step 3: Preparation of benzyl N-[(1S)-3-methyl-1-[[(2-oxo-3-piperidyl)methylamino]carbamoyl]butyl]carbamate

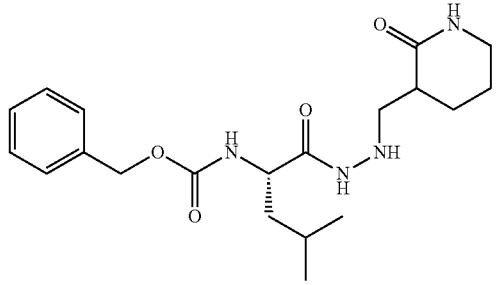

20c

Compound 20c was prepared in analogy to Example 18, Step 3 by using tert-butyl 3-((2-((S)-2-(((benzyloxy)carbonyl)amino)-4-methylpentanoyl)hydrazinyl)methyl)-2-oxo-piperidine-1-carboxylate (190 mg, compound 20b) instead of tert-butyl 3-[[2-[(2S)-2-(benzyloxycarbonylamino)-4-methyl-pentanoyl]hydrazino]methyl]-2-oxo-pyrrolidine-1-carboxylate (compound 18b). Benzyl N-[(1S)-3-methyl-1-[[(2-oxo-3-piperidyl)methylamino]carbamoyl]butyl]carbamate (100 mg, compound 20c) was obtained as a yellow oil. MS obsd. (ESI$^+$) [(M+H)$^+$]: 391.4.

Step 4: Preparation of benzyl N-[(1S)-1-[[(2-chloroacetyl)-[(2-oxo-3-piperidyl)methyl]amino]carbamoyl]-3-methyl-butyl]carbamate

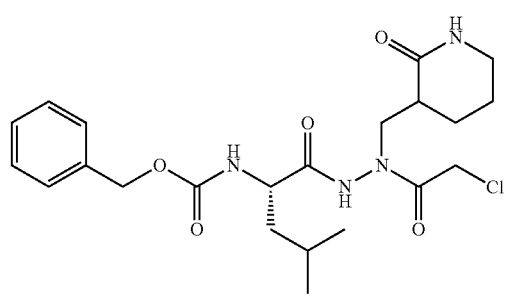

20

The title compound was prepared in analogy to Example 1, Step 4 by using benzyl((2S)-4-methyl-1-oxo-1-(2-((2-oxo-piperidin-3-yl)methyl)hydrazinyl)pentan-2-yl)carbamate (50 mg, compound 20c) instead of benzyl N-[2-[2-(3-amino-3-oxo-propyl)hydrazino]-2-axo-ethyl]carbamate (compound 1c). Benzyl N-[(1S)-1-[[(2-chloroacetyl)-[(2-oxo-3-piperidyl)methyl]amino]carbamoyl]-3-methyl-butyl]carbamate (7.2 mg, Example 20) was obtained as a white solid. $^1$H NMR (400 MHz, DMSO-d$_6$) δ ppm: 10.44-10.79 (m, 1H), 7.62-7.77 (m, 1H), 7.43-7.57 (m, 1H), 7.24-7.42 (m, 5H), 4.97-5.11 (m, 2H), 4.20-4.40 (m, 1H), 3.92-4.10 (m, 2H), 3.46-3.57 (m, 3H), 3.10 (s, 2H), 1.62-1.93 (m, 3H), 1.30-1.58 (m, 4H), 0.86-0.91 (m, 6H). MS obsd. (ESI$^+$) [(M+H)$^+$]: 467.2.

Example 21

Benzyl N-[(1S)-1-[[(2-chloroacetyl)-propyl-amino]carbamoyl]-3-methyl-butyl]carbamate

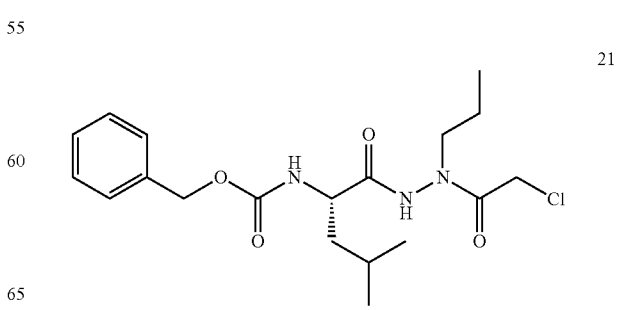

21

Step 1: Preparation of benzyl N-[(1S)-3-methyl-1-(propylaminocarbamoyl)butyl]carbamate

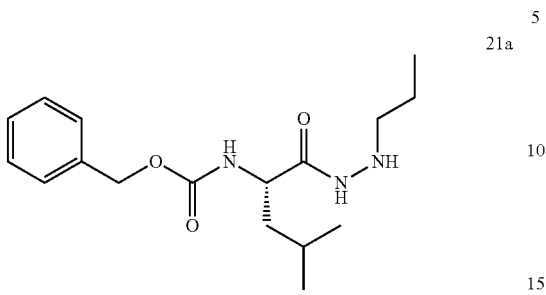

21a

To a solution of benzyl N-[(1S)-1-(hydrazinecarbonyl)-3-methyl-butyl]carbamate (450.0 mg, compound 2b) in toluene (2 mL) was added propionaldehyde (102.92 mg). After being stirred at 60° C. for 2 hrs and at 20° C. for another 12 hrs, the reaction mixture was concentrated in vacuo. The residue was dissolve in THF (2 mL), then TsOH (831.27 mg, 4.83 mmol) and NaBH$_3$CN (10.12 mg, 0.160 mmol) were added. After being stirred at 40° C. for 2 hrs, the reaction mixture was concentrated in vacuo. The residue was purified by prep-HPLC to afford benzyl N-[(1S)-3-methyl-1-(propylaminocarbamoyl)butyl]carbamate (160 mg, compound 21a) as a colorless oil. MS obsd. (ESI$^+$) [(M+H)$^+$]: 322.0.

Step 2: Preparation of benzyl N-[(1S)-1-[[(2-chloroacetyl)-propyl-amino]carbamoyl]-3-methyl-butyl]carbamate

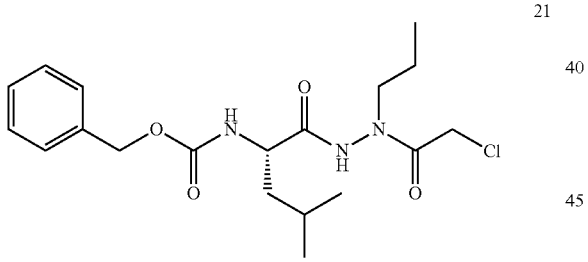

21

The title compound was prepared in analogy to Example 1, Step 4 by using benzyl N-[(1S)-3-methyl-1-(propylaminocarbamoyl)butyl]carbamate (160 mg, compound 21a) instead of benzyl N-[2-[2-(3-amino-3-oxo-propyl)hydrazino]-2-axo-ethyl]carbamate (compound 1c). Benzyl N-[(1S)-1-[[(2-chloroacetyl)-propyl-amino]carbamoyl]-3-methyl-butyl]carbamate (8.5 mg, Example 21) was obtained as a light yellow solid. $^1$H NMR (400 MHz, DMSO-d$_6$) δ ppm: 10.49-10.74 (m, 1H), 7.70-7.71 (br. s, 1H), 7.31-7.36 (m, 5H), 4.99-5.08 (m, 2H), 4.21-4.37 (m, 1H), 3.96-4.10 (m, 2H), 3.41-3.43 (m, 1H), 3.01-3.17 (m, 1H), 1.61-1.68 (m, 1H), 1.50-1.57 (m, 1H), 1.41-1.46 (m, 2H), 1.23 (s, 1H), 0.80-0.91 (m, 9H). MS obsd. (ESI$^+$) [(M+H)$^+$]: 398.

Example 23

Benzyl N-[(1S)-1-[[(2-chloroacetyl)-(1H-pyrazol-3-ylmethyl)amino]carbamoyl]-3-methyl-butyl]carbamate

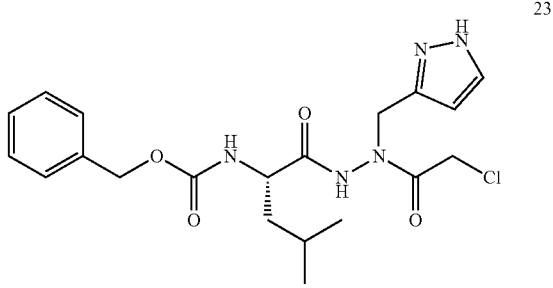 [SMILES: CC(C)C[C@H](NC(=O)OCc1ccccc1)C(=O)NN(Cc1cc[nH]n1)C(=O)CCl]

23

Step 1: Preparation of benzyl N-[(1S)-3-methyl-1-[(1H-pyrazol-3-ylmethylamino)carbamoyl]butyl]carbamate

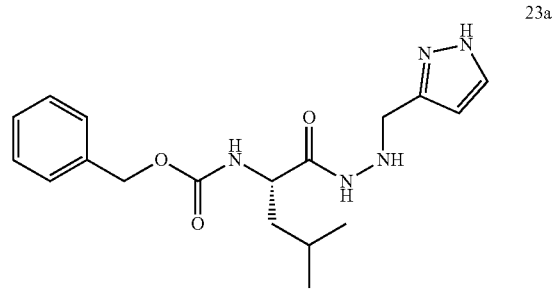 [SMILES: CC(C)C[C@H](NC(=O)OCc1ccccc1)C(=O)NNCc1cc[nH]n1]

23a

Compound 23a was prepared in analogy to Example 21, Step 1 by using 1H-pyrazole-3-carbaldehyde (276.0 mg, Wuxi Apptec (Wuhan) Co., Ltd) instead of propionaldehyde. Benzyl N-[(1S)-3-methyl-1-[(1H-pyrazol-3-ylmethylamino) carbamoyl]butyl]carbamate (500 mg, compound 23a) was obtained as a yellow oil. MS obsd. (ESI$^+$) [(M+H)$^+$]: 360.4.

Step 2: Preparation of benzyl N-[(1S)-1-[[(2-chloroacetyl)-(1H-pyrazol-3-ylmethyl)amino]carbamoyl]-3-methyl-butyl]carbamate

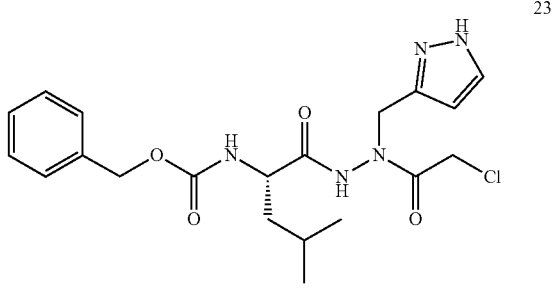

23

The title compound was prepared in analogy to Example 1, Step 4 by using benzyl N-[(1S)-3-methyl-1-[(1H-pyrazol-3-ylmethylamino) carbamoyl]butyl]carbamate (500 mg, compound 23a) instead of benzyl(2-(2-(3-amino-3-oxo-propyl)hydrazinyl)-2-axo-ethyl)carbamate (compound 1c). Benzyl N-[(1S)-1-[[(2-chloroacetyl)-(1H-pyrazol-3-ylmethyl)amino]carbamoyl]-3-methyl-butyl]carbamate (20 mg, Example 23) was obtained as a white solid. $^1$H NMR (400 MHz, DMSO-$d_6$) δ ppm: 12.70 (br. s, 1H), 10.51-10.58 (m, 1H), 7.62-7.63 (m, 2H), 7.30-7.34 (m, 5H), 6.14-6.15 (m, 1H), 5.01-5.03 (m, 3H), 4.25-4.40 (m, 1H), 3.91-4.16 (m, 3H), 1.23-1.55 (m, 3H), 0.82 (s, 6H). MS obsd. (ESI$^+$) [(M+H)$^+$]: 436.1.

Example 24

Benzyl N-[(1S)-1-[[(2-chloroacetyl)-(1H-imidazol-4-ylmethyl)amino]carbamoyl]-3-methyl-butyl]carbamate

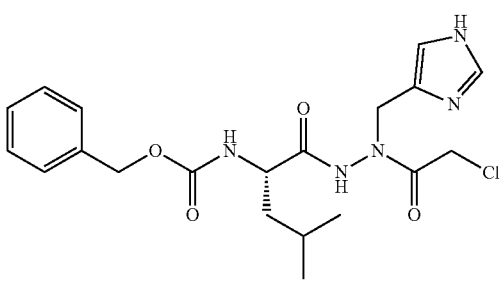

24

Step 1: Preparation of benzyl N-[(1S)-1-[(1H-imidazol-4-ylmethylamino)carbamoyl]-3-methyl-butyl]carbamate

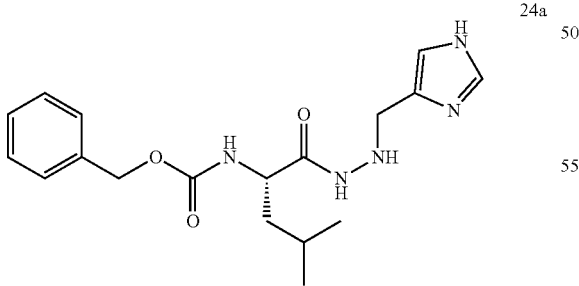

24a

Compound 24a was prepared in analogy to Example 21, Step 1 by using 1H-imidazole-4-carbaldehyde (34.4 mg, Wuxi Apptec (Wuhan) Co., Ltd) instead of propionaldehyde. Benzyl N-[(1S)-1-[(1H-imidazol-4-ylmethylamino)carbamoyl]-3-methyl-butyl]carbamate (40 mg, compound 24a) was obtained as a yellow oil. MS obsd. (ESI$^+$) [(M+H)$^+$]: 360.0.

Step 2: Preparation of benzyl N-[(1S)-1-[[(2-chloroacetyl)-(1H-imidazol-4-ylmethyl)amino]carbamoyl]-3-methyl-butyl]carbamate

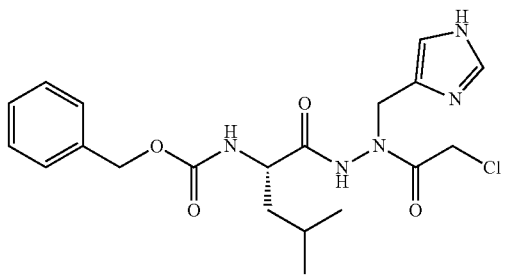

24

The title compound was prepared in analogy to Example 1, Step 4 by using (S)-benzyl(1-(2-((1H-imidazol-4-yl) methyl) hydrazinyl)-4-methyl-1-oxo-pentan-2-yl)carbamate (40 mg, compound 24a) instead of benzyl N-[2-[2-(3-amino-3-oxo-propyl)hydrazino]-2-axo-ethyl]carbamate (compound 1c). Benzyl N-[(1S)-1-[[(2-chloroacetyl)-(1H-imidazol-4-ylmethyl)amino]carbamoyl]-3-methyl-butyl] carbamate (20.2 mg, Example 24) was obtained as a yellow solid. $^1$H NMR (400 MHz, DMSO-$d_6$) δ ppm: 14.24 (br. S, 1H), 10.55-10.73 (m, 1H), 8.98 (s, 1H), 7.71 (s, 1H), 7.53 (s, 1H), 7.30-7.36 (m, 5H), 5.03 (s, 2H), 4.88 (d, J=14.4 Hz, 1H), 4.30-4.50 (m, 2H), 4.13 (d, J=15.6 Hz, 1H), 3.92 (m, 1H), 1.30-1.53 (m, 3H), 0.83 (d, J=6.0 Hz, 6H). MS obsd. (ESI$^+$) [(M+H)$^+$]: 436.1.

Example 26 tert-Butyl N-[(1S)-1-[[(3-amino-3-oxo-propyl)-(2-chloroacetyl)amino]carbamoyl]-3-methyl-butyl]carbamate

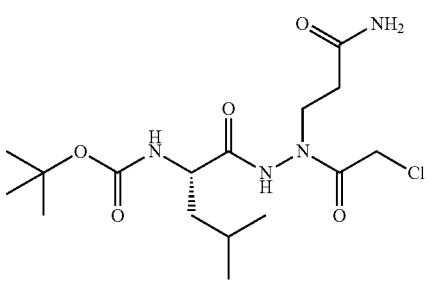

26

Step 1: Preparation of tert-butyl N-[(1S)-1-(benzyloxycarbonylaminocarbamoyl)-3-methyl-butyl]carbamate

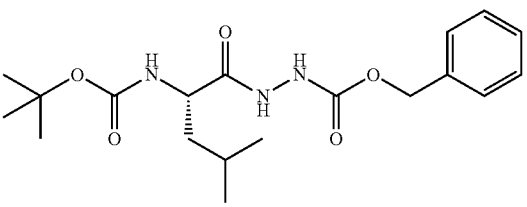

26a

To a solution of benzyl hydrazinecarboxylate (8 g, 48.14 mmol), (S)-2-((tert-butoxycarbonyl)amino)-4-methylpentanoic acid (10 g, 43.24 mmol, Wuxi Apptec (Wuhan) Co., Ltd) and DIEPA (22.6 mL, 129.71 mmol) in EtOAc (100 mL) was added T$_3$P (38.57 mL, 64.85 mmol, 50% solution in EtOAc) at 0° C. The reaction mixture was stirred for 1 hr at 0° C., then diluted with EtOAc (300 mL), washed with HCl (1N, 100 mL), saturated aqueous NaHCO$_3$ (200 mL) and brine (300 mL). The organic layer was dried over anhydrous Na$_2$SO$_4$, and concentrated in vacuo to afford (S)-benzyl 2-(2-((tert-butoxycarbonyl)amino)-4-methylpentanoyl)hydrazinecarboxylate (16 g, compound 26a) as a yellow oil and used in next step without further purification. MS obsd. (ESI$^+$) [(M+H)$^+$]: 380.0.

Step 2: Preparation of tert-butyl N-[(1S)-1-(hydrazinecarbonyl)-3-methyl-butyl]carbamate

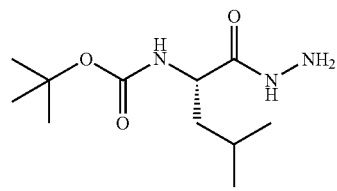

26b

To a solution of tert-butyl N-[(1S)-1-(benzyloxycarbonylaminocarbamoyl)-3-methyl-butyl]carbamate (16.0 g, compound 26a) in methanol (150 mL) was added Pd/C (1.0 g, 10% purity) under N$_2$. The mixture was degassed in vacuo and purged with H$_2$ three times. The resulting mixture was stirred at 25° C. for 4 hrs under H$_2$ balloon. The reaction mixture was filtered and concentrated in vacuo to afford tert-butyl N-[(1S)-1-(hydrazinecarbonyl)-3-methyl-butyl]carbamate (10 g, compound 26b) as a yellow gum and used in next step without further purification. MS obsd. (ESI$^+$) [M−C4H8+H]$^+$]: 189.9.

Step 3: Preparation of tert-butyl N-[(1S)-1-[[(3-amino-3-oxo-propyl)amino]carbamoyl]-3-methyl-butyl]carbamate

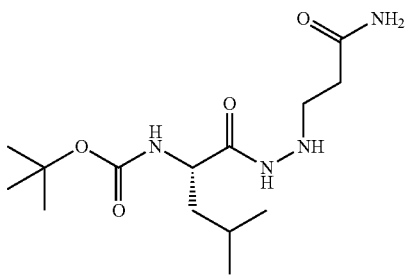

26c

Compound 26c was prepared in analogy to Example 1, Step 3 by using tert-butyl N-[(1S)-1-(hydrazinecarbonyl)-3-methyl-butyl]carbamate (10 g, compound 26b) instead of benzyl(2-hydrazinyl-2-axo-ethyl)carbamate (compound 1b). tert-Butyl N-[(1S)-1-[[(3-amino-3-oxo-propyl)amino]carbamoyl]-3-methyl-butyl]carbamate (350 mg, compound 26c) was obtained as a yellow oil and used in next step without further purification. MS obsd. (ESI$^+$) [(M+H)$^+$]: 317.1

Step 4: Preparation of tert-butyl N-[(1S)-1-[[(3-amino-3-axo-propyl)-(2-chloroacetyl)amino]carbamoyl]-3-methyl-butyl]carbamate

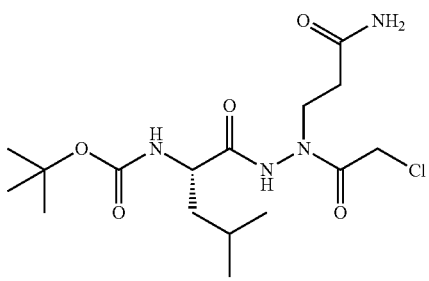

26

The title compound was prepared in analogy to Example 1, Step 4 by using tert-butyl N-[(1S)-1-[[(3-amino-3-oxo-propyl)amino]carbamoyl]-3-methyl-butyl]carbamate (50.0 mg, compound 26c) instead of benzyl N-[2-[2-(3-amino-3-oxo-propyl)hydrazino]-2-axo-ethyl]carbamate (compound 1c). tert-Butyl N-[(1S)-1-[[(3-amino-3-oxo-propyl)-(2-chloroacetyl)amino]carbamoyl]-3-methyl-butyl]carbamate (18.4 mg, Example 26) was obtained as a white solid. $^1$H NMR (400 MHz, DMSO-d$_6$) δ ppm: 10.35-10.63 (m, 1H), 7.29-7.38 (m, 2H), 6.83 (s, 1H), 4.15-4.34 (m, 1H), 3.97-4.14 (m, 1H), 3.82-3.89 (m, 1H), 3.67-3.80 (m, 1H), 3.33-3.41 (m, 1H), 2.28-2.33 (m, 2H), 1.58-1.69 (m, 1H), 1.49-1.53 (m, 1H), 1.40-1.44 (m, 1H), 1.38 (s, 9H), 0.88 (dd, J=6.4, 13.2 Hz, 6H). MS obsd. (ESI$^+$) [(M+H)$^+$]: 393.2.

Example 27

4-Methoxy-N-[(1S)-1-[[(3-amino-3-oxo-propyl)-(2-chloroacetyl)amino]carbamoyl]-3-methyl-butyl]-1H-indole-2-carboxamide

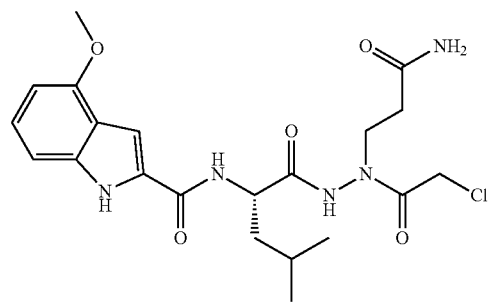

27

Step 1: Preparation of 3-[[[(2S)-2-amino-4-methyl-pentanoyl]amino]-(2-chloroacetyl)amino]propana-mide

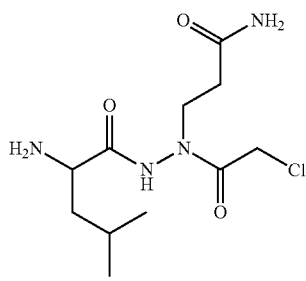

27a

To a solution of tert-butyl N-[(1S)-1-[[(3-amino-3-oxo-propyl)-(2-chloroacetyl)amino]carbamoyl]-3-methyl-butyl] carbamate (350.0 mg, Example 26) in 1,4-dioxane (5 mL) was added HCl/dioxane (4 M, 5.0 mL). After being stirred at 25° C. for 3 hrs, the reaction mixture was concentrated in vacuo to afford 3-[[[(2S)-2-amino-4-methyl-pentanoyl]amino]-(2-chloroacetyl)amino]propanamide (290 mg, compound 27a) as a yellow solid and used in next step without further purification.

Step 2: Preparation of N-[(1S)-1-[[(3-amino-3-oxo-propyl)-(2-chloroacetyl)amino]carbamoyl]-3-methyl-butyl]-4-methoxy-1H-indole-2-carboxamide

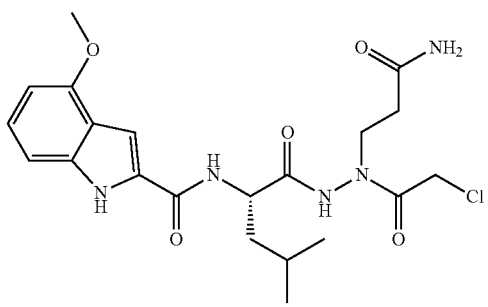

27

To a solution of 3-[[[(2S)-2-amino-4-methyl-pentanoyl]amino]-(2-chloroacetyl)amino]propanamide (80.0 mg, compound 27a) and 4-methoxy-1H-indole-2-carboxylic acid (69.7 mg, Shanghai Haohong Pharmaceutical Co., Ltd, CAS number: 103260-65-7) in DMF (1.5 mL) at 0° C. was added DIEPA (0.17 mL) and T$_3$P (0.29 mL, 50% in EtOAc). After stirred at 0° C. for 1 hr, the reaction mixture was diluted with H$_2$O (50 mL) and extracted with EtOAc (20 mL) twice. The combined organic layers were washed with brine (50 mL), dried over anhydrous Na$_2$SO$_4$ and concentrated in vacuo. The residue was purified by prep-HPLC to afford N-[(1S)-1-[[(3-amino-3-oxo-propyl)-(2-chloroacetyl)amino]carbamoyl]-3-methyl-butyl]-4-methoxy-1H-indole-2-carboxamide (16 mg, Example 27) as a yellow solid. $^1$H NMR (400 MHz, DMSO-d$_6$) δ ppm: 11.61 (s, 1H), 10.43-10.95 (br. s, 1H), 8.59 (d, J=6.8 Hz, 1H), 7.39 (d, J=2.0 Hz, 1H), 7.38 (br. s, 1H), 7.08-7.14 (m, 1H), 6.98-7.05 (m, 1H), 6.86 (s, 1H), 6.51 (d, J=7.6 Hz, 1H), 4.13-4.41 (m, 2H), 3.98-4.17 (m, 1H), 3.89 (s, 3H), 3.72-3.84 (m, 1H), 3.40-3.53 (m, 1H), 2.32-2.33 (m, 2H), 1.69-1.87 (m, 2H), 1.45-1.63 (m, 1H), 0.86-0.98 (m, 6H). MS obsd. (ESI$^+$) [(M+H)$^+$]: 466.4.

Example 28

N-[(1S)-1-[[(3-amino-3-oxo-propyl)-(2-chloroacetyl)amino]carbamoyl]-3-methyl-butyl]-1H-indole-2-carboxamide

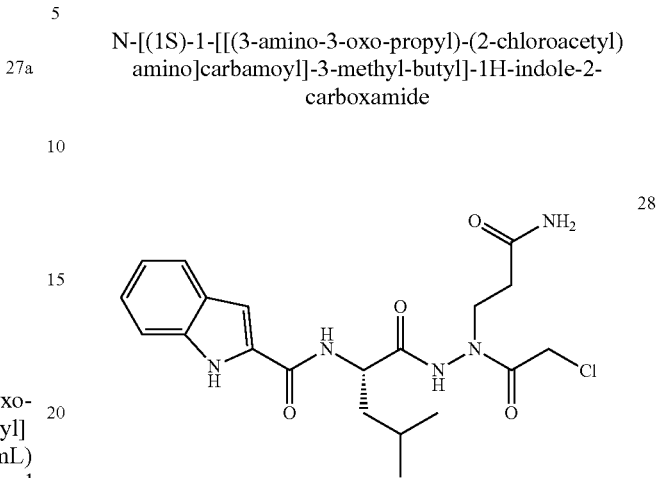

28

The title compound was prepared in analogy to Example 27, Step 2 by using 1H-indole-2-carboxylic acid instead of 4-methoxy-1H-indole-2-carboxylic acid. N-[(1S)-1-[[(3-Amino-3-oxo-propyl)-(2-chloroacetyl)amino]carbamoyl]-3-methyl-butyl]-1H-indole-2-carboxamide (36.2 mg, Example 28) was obtained as a white solid. $^1$H NMR (400 MHz, DMSO-d$_6$) δ ppm: 11.61 (s, 1H), 10.51-10.85 (m, 1H), 8.66 (d, J=7.2 Hz, 1H), 7.63 (d, J=8.0 Hz, 1H), 7.42-7.44 (m, 1H), 7.37 (br. s, 1H), 7.29 (d, J=1.6 Hz, 1H), 7.17-7.21 (m, 1H), 7.00-7.07 (m, 1H), 6.86 (br. s, 1H), 4.12-4.43 (m, 2H), 3.95-4.19 (m, 1H), 3.69-3.94 (m, 1H), 3.39-3.54 (m, 1H), 2.26-2.37 (m, 2H), 1.71-1.89 (m, 2H), 1.48-1.65 (m, 1H), 0.89-0.99 (m, 6H). (ESI$^+$) [(M+Na)$^+$]: 458.4.

Example 29

N-[(1S)-1-[[(3-amino-3-oxo-propyl)-(2-chloroacetyl)amino]carbamoyl]-3-methyl-butyl]-2-methyl-oxazole-4-carboxamide

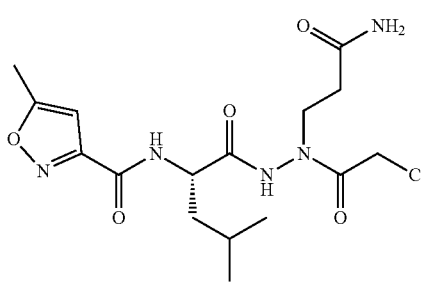

29

The title compound was prepared in analogy to Example 27, Step 2 by using 5-methylisoxazole-3-carboxylic acid instead of 4-methoxy-1H-indole-2-carboxylic acid (Bidepharm, CAS number: 3405-77-4). N-[(1S)-1-[[(3-Amino-3-oxo-propyl)-(2-chloroacetyl)amino]carbamoyl]-3-methyl-butyl]-2-methyl-oxazole-4-carboxamide (31.9 mg, Example 29) was obtained as a white solid. $^1$H NMR (400 MHz, DMSO-d$_6$) δ ppm: 10.50-10.69 (br. s, 1H), 8.85-9.04 (m, 1H), 7.36 (br. s, 1H), 6.85 (br. s, 1H), 6.58 (s, 1H), 4.36-4.50 (m, 1H), 4.18-4.30 (m, 1H), 3.95-4.17 (m, 1H), 3.72-3.86 (m, 1H), 3.37-3.46 (m, 1H), 2.47 (d, J=0.4 Hz, 3H), 2.24-2.34 (m, 2H), 1.74-1.85 (m, 1H), 1.61-1.71 (m, 1H), 1.51-1.60 (m, 1H), 0.91 (dd, J=6.4, 14.8 Hz, 6H). MS obsd. (ESI$^+$) [(M+Na)$^+$]: 424.4.

Example 30

N-[(1S)-1-[[(3-Amino-3-axo-propyl)-(2-fluoroacetyl)amino]carbamoyl]-3-methyl-butyl]-4-methoxy-1H-indole-2-carboxamide

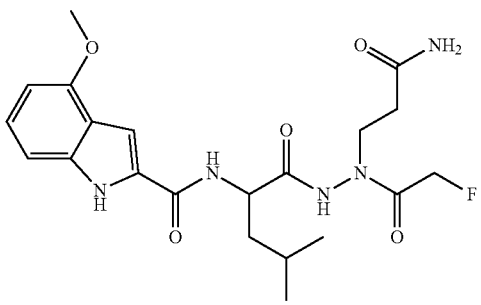

Step 1: Preparation of tert-butyl N-[(1S)-1-[[(3-amino-3-oxo-propyl)-(2-fluoroacetyl)amino]carbamoyl]-3-methyl-butyl]carbamate

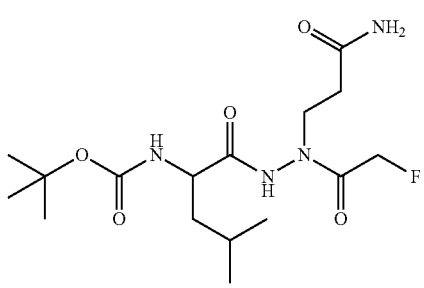

30a

Compound 30a was prepared in analogy to Example 4 by using (S)-tert-butyl(1-(2-(3-amino-3-oxo-propyl)hydrazinyl)-3-cyclohexyl-1-oxo-propan-2-yl)carbamate (compound 26c) and fluoroacetic acid instead of benzyl N-[(1S)-1-[[(3-amino-3-oxo-propyl)amino]carbamoyl]-3-methyl-butyl]carbamate (compound 2c) and 2-chloropropanoic acid. tert-Butyl N-[(1S)-1-[[(3-amino-3-oxo-propyl)-(2-fluoroacetyl)amino]carbamoyl]-3-methyl-butyl]carbamate (400 mg, compound 30a) was obtained as a white solid. MS obsd. (ESI$^+$) [M+H]$^+$: 377.2.

Step 2: Preparation of 3-[[[(2S)-2-amino-4-methyl-pentanoyl]amino]-(2-fluoroacetyl)amino]propanamide

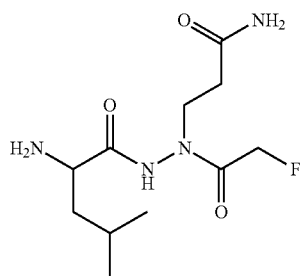

30b

Compound 30b was prepared in analogy to Example 27, step 1 by using (S)-tert-butyl(1-(2-(3-amino-3-oxo-propyl)-2-(2-fluoroacetyl)hydrazinyl)-4-methyl-1-oxo-pentan-2-yl)carbamate (400 mg, compound 30a) instead of N-[(1S)-1-[[(3-amino-3-oxo-propyl)-(2-chloroacetyl)amino]carbamoyl]-3-methyl-butyl]carbamate (Example 26). 3-[[[(2S)-2-Amino-4-methyl-pentanoyl]amino]-(2-fluoroacetyl)amino]propanamide (400 mg, compound 30b) was obtained as a yellow oil.

Step 3: Preparation of N-[(1S)-1-[[(3-amino-3-oxo-propyl)-(2-fluoroacetyl)amino]carbamoyl]-3-methyl-butyl]-4-methoxy-1H-indole-2-carboxamide

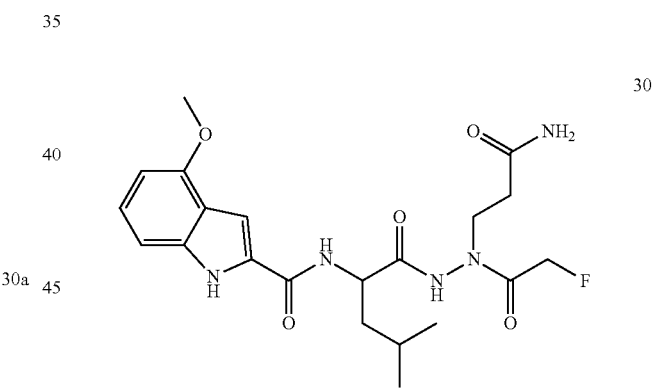

30

The title compound was prepared in analogy to Example 27, Step 2 by using (S)-3-(2-(2-amino-4-methylpentanoyl)-1-(2-fluoroacetyl)hydrazinyl)propanamide (100 mg, compound 30b) instead of (S)-3-(2-(2-amino-4-methylpentanoyl)-1-(2-chloroacetyl)hydrazinyl)propanamide (compound 27a). N-[(1S)-1-[[(3-Amino-3-oxo-propyl)-(2-fluoroacetyl)amino]carbamoyl]-3-methyl-butyl]-4-methoxy-1H-indole-2-carboxamide (32.1 mg, Example 30) was obtained as a white solid. $^1$H NMR (400 MHz, DMSO-d$_6$) δ ppm: 11.60 (s, 1H), 10.46-10.62 (m, 1H), 8.61 (d, J=6.8 Hz, 1H), 7.39 (s, 2H), 7.05-7.16 (m, 1H), 7.01 (d, J=8.0 Hz, 1H), 6.86 (s, 1H), 6.51 (d, J=7.6 Hz, 1H), 4.91-5.24 (m, 1H), 4.51-4.87 (m, 1H), 4.29-4.49 (m, 1H), 3.88 (s, 3H), 3.72-3.84 (m, 1H), 3.41-3.46 (m, 1H), 2.20-2.39 (m, 2H), 1.73-1.81 (m, 2H), 1.52-1.60 (m, 1H), 0.88-0.98 (m, 6H). MS obsd. (ESI$^+$) [M+H]$^+$: 450.1.

Example 31

N-[(1S)-1-[[(3-Amino-3-axo-propyl)-(2-fluoro-acetyl)amino]carbamoyl]-3-methyl-butyl]-1H-indole-2-carboxamide

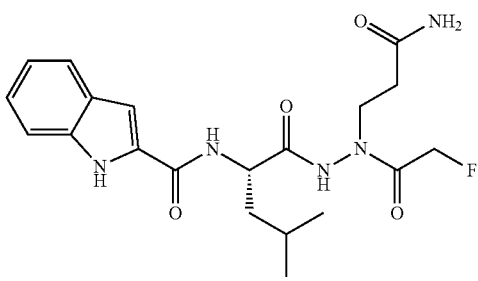

The title compound was prepared in analogy to Example 27, Step 2 by using (S)-3-(2-(2-amino-4-methylpentanoyl)-1-(2-fluoroacetyl)hydrazinyl)propanamide (100 mg, compound 30b) and 1H-indole-2-carboxylic acid instead of (S)-3-(2-(2-amino-4-methylpentanoyl)-1-(2-chloroacetyl) hydrazinyl)propanamide (compound 27a) and 4-methoxy-1H-indole-2-carboxylic acid. N-[(1S)-1-[[(3-Amino-3-oxo-propyl)-(2-fluoroacetyl)amino]carbamoyl]-3-methyl-butyl]-1H-indole-2-carboxamide (30.8 mg, Example 31) was obtained as a white solid. $^1$H NMR (400 MHz, DMSO-$d_6$) δ ppm: 11.60 (s, 1H), 10.47-10.63 (m, 1H), 8.67 (d, J=7.2 Hz, 1H), 7.63 (d, J=8.0 Hz, 1H), 7.43 (d, J=8.8 Hz, 1H), 7.38 (s, 1H), 7.29 (s, 1H), 7.17-7.21 (m, 1H), 7.01-7.07 (m, 1H), 6.86 (s, 1H), 4.72-5.13 (m, 2H), 4.33-4.39 (m, 1H), 3.69-3.91 (m, 1H), 3.37-3.45 (m, 1H), 2.31-2.33 (m, 2H), 1.72-1.85 (m, 2H), 1.51-1.62 (m, 1H), 1.02-0.87 (m, 6H). MS obsd. (ESI$^+$) [M+H]$^+$: 420.1.

Example 32

N-[(1S)-2-[2-(3-Amino-3-axo-propyl)-2-(2-chloroacetyl)hydrazino]-1-(cyclohexylmethyl)-2-axo-ethyl]-4-methoxy-1H-indole-2-carboxamide

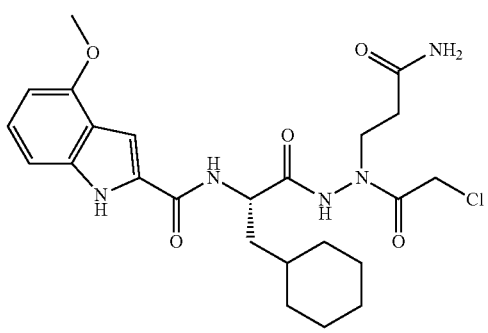

Step 1: Preparation of tert-butyl N-[(1S)-2-(2-benzyloxycarbonylhydrazino)-1-(cyclohexylmethyl)-2-axo-ethyl]carbamate

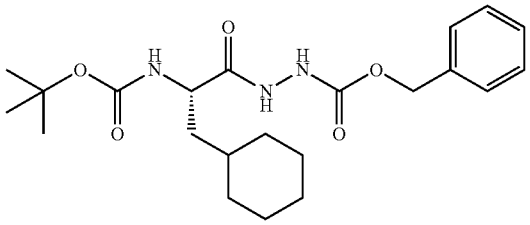

Compound 32a was prepared in analogy to Example 26, Step 1 by using (S)-2-((tert-butoxycarbonyl)amino)-3-cyclohexylpropanoic acid (8.6 g, 31.69 mmol, Thbiochem, CAS number: 37736-82-6) instead of (S)-2-((tert-butoxycarbonyl)amino)-4-methylpentanoic acid. tert-Butyl N-[(1S)-2-(2-benzyloxycarbonylhydrazino)-1-(cyclohexylmethyl)-2-axo-ethyl]carbamate (12 g, compound 32a) was obtained as a white solid. MS obsd. (ESI$^+$) [(M+H)$^+$]: 420.5.

Step 2: Preparation of tert-butyl N-[(1S)-1-(cyclohexylmethyl)-2-hydrazino-2-axo-ethyl]carbamate

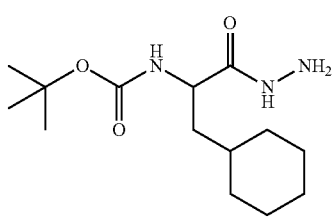

Compound 32b was prepared in analogy to Example 26, Step 2 by using (S)-benzyl 2-(2-((tert-butoxycarbonyl)amino)-3-cyclohexylpropanoyl)hydrazinecarboxylate (compound 32a) instead of (S)-benzyl 2-(2-((tert-butoxycarbonyl)amino)-4-methylpentanoyl)hydrazinecarboxylate (compound 26a). tert-Butyl N-[(1S)-1-(cyclohexylmethyl)-2-hydrazino-2-axo-ethyl]carbamate (6.5 g, compound 32b) was obtained as a white solid. MS obsd. (ESI$^+$) [(M−Bu+H)$^+$]: 230.4.

Step 3: Preparation of tert-butyl N-[(1S)-2-[2-(3-amino-3-oxo-propyl)hydrazino]-1-(cyclohexylmethyl)-2-axo-ethyl]carbamate

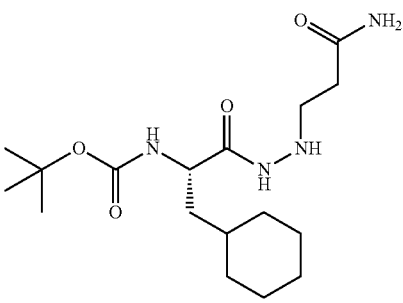

Compound 32c was prepared in analogy to Example 26, Step 3 by using (S)-tert-butyl(3-cyclohexyl-1-hydrazinyl-1-oxo-propan-2-yl)carbamate (compound 32b) instead of tert-butyl N-[(1S)-1-(hydrazinecarbonyl)-3-methyl-butyl]carbamate (compound 26b). tert-Butyl N-[(1S)-2-[2-(3-amino-3-oxo-propyl)hydrazino]-1-(cyclohexylmethyl)-2-axo-ethyl]carbamate (2.2 g, compound 32c) was obtained as a white solid. MS obsd. (ESI⁺) [(M+H)⁺]: 357.0.

Step 4: Preparation of tert-butyl N-[(1S)-2-[2-(3-amino-3-oxo-propyl)-2-(2-chloroacetyl)hydrazino]-1-(cyclohexylmethyl)-2-axo-ethyl]carbamate

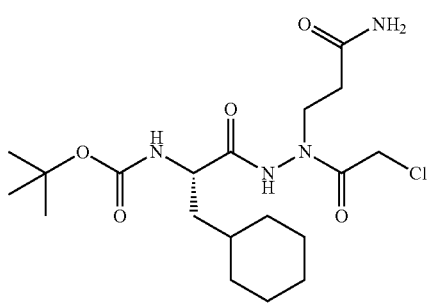

32d

Compound 32d was prepared in analogy to Example 1, Step 4 by using tert-butyl N-[(1S)-2-[2-(3-amino-3-oxo-propyl)hydrazino]-1-(cyclohexylmethyl)-2-axo-ethyl]carbamate (2.2 g, compound 32c) instead of benzyl N-[2-[2-(3-amino-3-oxo-propyl)hydrazino]-2-axo-ethyl]carbamate (compound 1c). tert-Butyl N-[(1S)-2-[2-(3-amino-3-oxo-propyl)-2-(2-chloroacetyl)hydrazino]-1-(cyclohexylmethyl)-2-axo-ethyl]carbamate (140 mg, compound 32d) was obtained as a light yellow oil.

Step 5: Preparation of 3-[[[(2S)-2-amino-3-cyclohexyl-propanoyl]amino]-(2-chloroacetyl)amino]propanamide

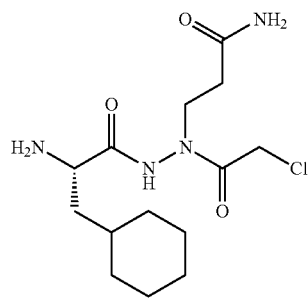

32e

Compound 32e was prepared in analogy to Example 27, Step 1 by using tert-butyl N-[(1S)-2-[2-(3-amino-3-oxo-propyl)-2-(2-chloroacetyl)hydrazino]-1-(cyclohexylmethyl)-2-axo-ethyl]carbamate (140 mg, compound 32d) instead of tert-butyl N-[(1S)-1-[[(3-amino-3-oxo-propyl)-(2-chloroacetyl)amino]carbamoyl]-3-methyl-butyl]carbamate (350.0 mg, Example 26). 3-[[[(2S)-2-Amino-3-cyclohexyl-propanoyl]amino]-(2-chloroacetyl)amino]propanamide (100 mg, compound 32e) was obtained as a colorless oil. MS obsd. (ESI⁺) [(M+H)⁺]: 333.4.

Step 6: Preparation of N-[(1S)-2-[2-(3-amino-3-oxo-propyl)-2-(2-chloroacetyl)hydrazino]-1-(cyclohexylmethyl)-2-axo-ethyl]-4-methoxy-1H-indole-2-carboxamide

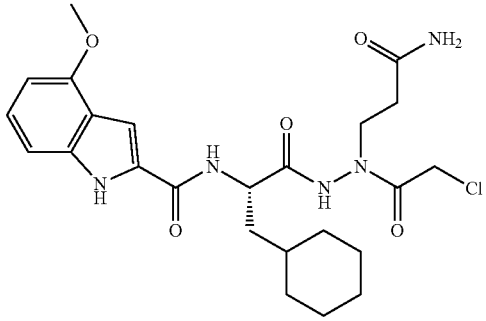

32

The title compound was prepared in analogy to Example 27, Step 2 by using 3-[[[(2S)-2-amino-3-cyclohexyl-propanoyl]amino]-(2-chloroacetyl)amino]propanamide (50.0 mg, compound 32e) instead of 3-[[[(2S)-2-amino-4-methyl-pentanoyl]amino]-(2-chloroacetyl)amino]propanamide (compound 27a). N-[(1S)-2-[2-(3-Amino-3-oxo-propyl)-2-(2-chloroacetyl)hydrazino]-1-(cyclohexylmethyl)-2-axo-ethyl]-4-methoxy-1H-indole-2-carboxamide (14.1 mg, Example 32) was obtained as a light yellow solid. ¹H NMR (400 MHz, DMSO-d₆) δ 11.60 (s, 1H), 10.60-10.75 (m, 1H), 8.57 (d, J=6.8 Hz, 1H), 7.39 (d, J=2.0 Hz, 1H), 7.37 (br. s, 1H), 7.10 (t, J=8.0 Hz, 1H), 7.01 (d, J=8.0 Hz, 1H), 6.86 (br. s, 1H), 6.51 (d, J=8.0 Hz, 1H), 4.39-4.42 (m, 3H), 4.08-4.14 (m, 1H), 3.89 (s, 3H), 2.27-2.32 (m, 2H), 1.72-1.79 (m, 3H), 1.60-1.70 (m, 4H), 1.39-1.41 (m, 1H), 1.21-1.25 (m, 1H), 1.11-1.19 (m, 3H), 0.89-0.99 (m, 2H). MS obsd. (ESI⁺) [(M+H)⁺]: 506.3.

Example 33

3-[(2-Chloroacetyl)-[[(2S)-2-[[(E)-3-(4-chloro-2-fluoro-phenyl)prop-2-enoyl]amino]-3-cyclohexyl-propanoyl]amino]amino]propanamide

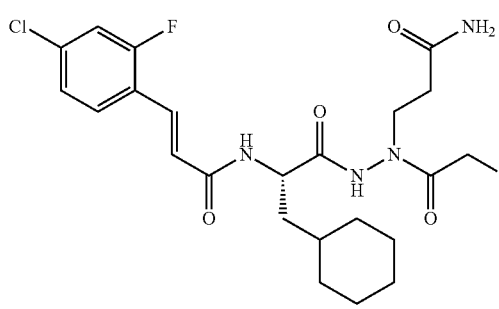

33

The title compound was prepared in analogy to Example 27, Step 2 by using 3-[[[(2S)-2-amino-3-cyclohexyl-propanoyl]amino]-(2-chloroacetyl)amino]propanamide (compound 32e) and (E)-3-(4-chloro-2-fluoro-phenyl)prop-2-enoic acid instead of 3-[[[(2S)-2-amino-4-methyl-pentanoyl]amino]-(2-chloroacetyl)amino]propanamide (compound 27a) and 4-methoxy-1H-indole-2-carboxylic acid. 3-[(2-Chloroacetyl)-[[(2S)-2-[[(E)-3-(4-chloro-2-fluoro-phenyl)prop-2-enoyl]amino]-3-cyclohexyl-propanoyl]amino]amino]propanamide (33 mg, Example 33) was obtained as a white solid. ¹H NMR (400 MHz, CDCl₃) δ ppm: 9.74 (s, 1H), 7.66 (d, J=7.6 Hz, 1H), 7.42 (t, J=8.4 Hz, 1H), 7.14 (t, J=8.4 Hz, 2H), 6.59-6.63 (m, 2H), 6.27 (s, 1H), 5.81 (s, 1H), 4.65 (q, J=7.4 Hz, 1H), 4.11-3.70 (m, 4H), 2.57 (s, 2H), 1.75-1.81 (m, 5H), 1.35-1.48 (m, 2H), 0.93-1.26 (m, 6H). MS obsd. (ESI⁺) [M+H]⁺: 515.2.

Example 34

3-[(2-Chloroacetyl)-[[(2S)-2-[[(E)-3-(4-chloro-2-fluoro-phenyl)prop-2-enoyl]amino]-4-methyl-pentanoyl]amino]amino]propanamide

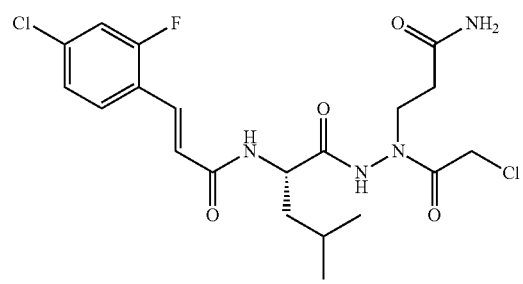

Step 1: Preparation of tert-butyl N-[[(2S)-2-[[(E)-3-(4-chloro-2-fluoro-phenyl)prop-2-enoyl]amino]-4-methyl-pentanoyl]amino]carbamate

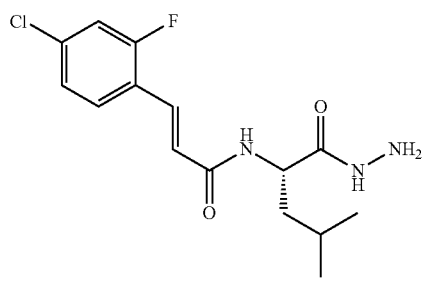

Compound 34a was prepared in analogy to Example 27, Step 2 by using (E)-3-(4-chloro-2-fluorophenyl)acrylic acid (Yantai ChengKaiLun Chemical technology Co., Ltd, CAS number: 312693-55-3) and tert-butyl N-[[(2S)-2-amino-4-methyl-pentanoyl]amino]carbamate (Intermediate AC) instead of 4-methoxy-1H-indole-2-carboxylic acid and 3-[[[(2S)-2-amino-4-methyl-pentanoyl]amino]-(2-chloroacetyl)amino]propanamide (compound 27a). tert-Butyl N-[[(2S)-2-[[(E)-3-(4-chloro-2-fluoro-phenyl)prop-2-enoyl]amino]-4-methyl-pentanoyl]amino]carbamate (1.29 g, compound 34a) was obtained as a yellow solid.

Step 2: Preparation of (E)-3-(4-chloro-2-fluoro-phenyl)-N-[(1S)-1-(hydrazinecarbonyl)-3-methyl-butyl]prop-2-enamide

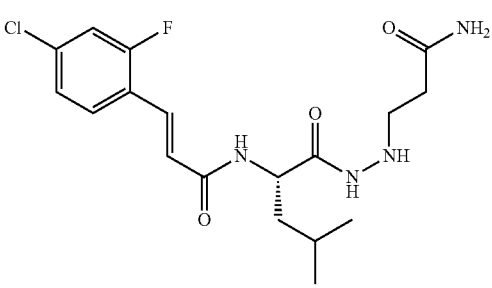

Compound 34b was prepared in analogy to Example 1, Step 2 by using tert-butyl N-[[(2S)-2-[[(E)-3-(4-chloro-2-fluoro-phenyl)prop-2-enoyl]amino]-4-methyl-pentanoyl]amino]carbamate (1.29 g, compound 34a) instead of tert-butyl N-[[2-(benzyloxycarbonylamino)acetyl]amino] carbamate (compound 1a). (E)-3-(4-chloro-2-fluoro-phenyl)-N-[(1S)-1-(hydrazinecarbonyl)-3-methyl-butyl] prop-2-enamide (420 mg, compound 34b) was obtained as a yellow solid. MS obsd. (ESI⁺) [(M+H)⁺]: 328.1.

Step 3: Preparation of 3-[2-[(2S)-2-[[(E)-3-(4-chloro-2-fluoro-phenyl)prop-2-enoyl]amino]-4-methyl-pentanoyl]hydrazino]propanamide Compound 34c was prepared in analogy to Example 1, Step 3 by using (E)-3-(4-chloro-2-fluoro-phenyl)-N-[(1S)-1-(hydrazinecarbonyl)-3-methyl-butyl]prop-2-enamide (compound 34b) instead of benzyl(2-hydrazinyl-2-axo-ethyl)carbamate (compound 1b). 3-[2-[(2S)-2-[[(E)-3-(4-Chloro-2-fluoro-phenyl)prop-2-enoyl]amino]-4-methyl-pentanoyl]hydrazino]propanamide (110 mg, compound 34c) was obtained as a yellow solid. MS obsd. (ESI⁺) [(M+H)⁺]: 399.3

Step 4: Preparation of 3-[(2-chloroacetyl)-[[(2S)-2-[[(E)-3-(4-chloro-2-fluoro-phenyl)prop-2-enoyl]amino]-4-methyl-pentanoyl]amino]amino]propanamide

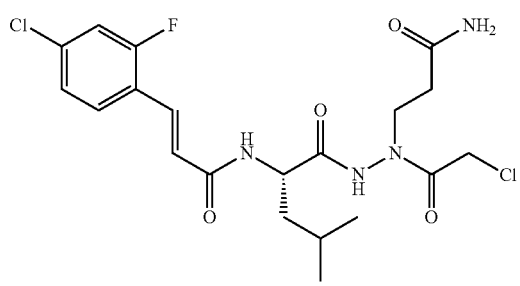

The title compound was prepared in analogy to Example 1, Step 4 by using 3-[2-[(2S)-2-[[(E)-3-(4-chloro-2-fluoro-phenyl)prop-2-enoyl]amino]-4-methyl-pentanoyl]hydrazino]propanamide (110 mg, compound 34c) instead of benzyl N-[2-[2-(3-amino-3-oxo-propyl)hydrazino]-2-axo-ethyl]carbamate (compound 1c). 3-[(2-Chloroacetyl)-[[(2S)-2-[[(E)-3-(4-chloro-2-fluoro-phenyl)prop-2-enoyl]amino]-4-methyl-pentanoyl]amino]amino]propanamide (9 mg, Example 34) was obtained as a white solid. $^1$H NMR (400 MHz, CDCl$_3$) δ ppm: 9.72 (br. s, 1H), 7.65 (d, J=16.0 Hz, 1H), 7.42 (t, J=8.4 Hz, 1H), 7.14 (t, J=8.0 Hz, 2H), 6.59 (d, J=16.0 Hz, 1H), 6.53 (br. s 1H), 6.21 (br. s, 1H), 5.82 (br. s, 1H), 4.62-4.65 (m, 1H), 3.40-4.12 (m, 4H), 2.52-2.60 (m, 2H), 1.71-1.78 (m, 3H), 1.00 (dd, J=5.6, 10.4 Hz, 6H). MS obsd. (ESI$^+$) [(M+H)$^+$]: 475.1.

Example 35

N-[(1S)-2-[2-(3-Amino-3-axo-propyl)-2-(2-chloroacetyl)hydrazino]-1-(cyclohexylmethyl)-2-axo-ethyl]-1H-indole-2-carboxamide

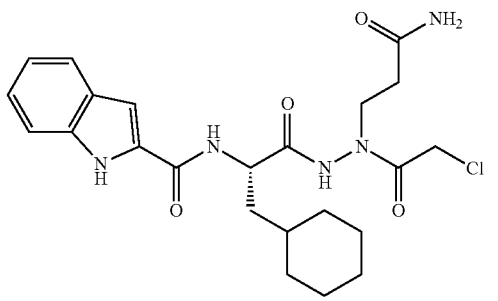

The title compound was prepared in analogy to Example 27, Step 2 by using 3-[[[(2S)-2-amino-3-cyclohexyl-propanoyl]amino]-(2-chloroacetyl)amino]propanamide (compound 32e) and indole-2-carboxylic acid instead of 3-[[[(2S)-2-amino-4-methyl-pentanoyl]amino]-(2-chloroacetyl)amino]propanamide (compound 27a) and 4-methoxy-1H-indole-2-carboxylic acid. N-[(1S)-2-[2-(3-Amino-3-oxo-propyl)-2-(2-chloroacetyl)hydrazino]-1-(cyclohexylmethyl)-2-axo-ethyl]-1H-indole-2-carboxamide (31.6 mg, Example 35) was obtained as a white solid. $^1$H NMR (400 MHz, DMSO-d$_6$) δ ppm: 11.60 (s, 1H), 10.59-10.78 (m, 1H), 8.65 (d, J=6.4 Hz, 1H), 7.63 (d, J=8.4 Hz, 1H), 7.43 (d, J=8.4 Hz, 1H), 7.37 (s, 1H), 7.29 (d, J=2.0 Hz, 1H), 7.19 (t, J=8.0 Hz, 1H), 7.04 (d, J=8.0 Hz, 1H), 6.86 (s, 1H), 4.01-4.49 (m, 3H), 3.71-3.85 (m, 1H), 2.27-2.32 (m, 2H), 1.72-1.79 (m, 3H), 1.60-1.70 (m, 4H), 1.39-1.49 (m, 1H), 1.21-1.24 (m, 1H), 1.03-1.17 (m, 3H), 0.89-0.99 (m, 2H). MS obsd. (ESI$^+$) [(M+H)$^+$]: 476.2.

Example 36

N-[(1S)-2-[2-(3-Amino-3-axo-propyl)-2-(2-fluoroacetyl)hydrazino]-1-(cyclohexylmethyl)-2-axo-ethyl]-1H-indole-2-carboxamide

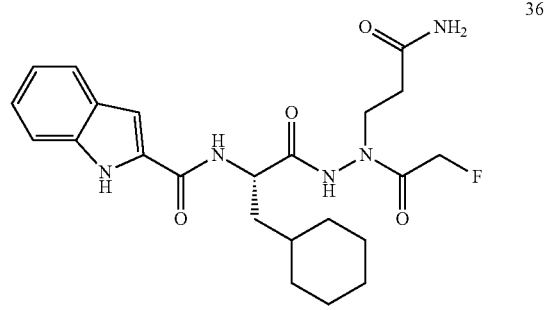 [SMILES: NC(=O)CCN(NC(=O)[C@H](CC1CCCCC1)NC(=O)c1cc2ccccc2[nH]1)C(=O)CF]

Step 1: Preparation of (S)-tert-butyl(1-(2-(3-amino-3-oxo-propyl)-2-(2-fluoroacetyl)hydrazinyl)-3-cyclohexyl-1-oxo-propan-2-yl)carbamate

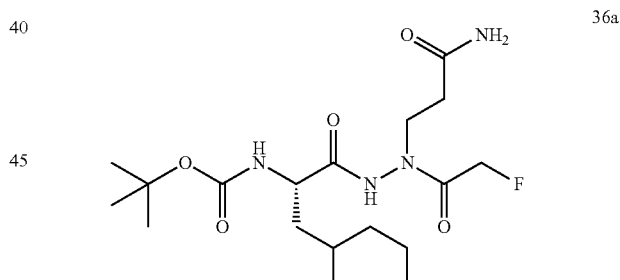

Compound 36a was prepared in analogy to Example 4 by using (S)-tert-butyl(1-(2-(3-amino-3-oxo-propyl)hydrazinyl)-3-cyclohexyl-1-oxo-propan-2-yl)carbamate (compound 32c) and fluoroacetic acid instead of benzyl N-[(1S)-1-[[(3-amino-3-oxo-propyl)amino]carbamoyl]-3-methyl-butyl]carbamate (compound 2c) and 2-chloropropanoic acid. (S)-tert-Butyl(1-(2-(3-amino-3-oxo-propyl)-2-(2-fluoroacetyl)hydrazinyl)-3-cyclohexyl-1-oxo-propan-2-yl)carbamate (320 mg, compound 36a) was obtained as a light yellow solid. MS obsd. (ESI$^+$) [(M+H)$^+$]: 417.1.

Step 2: Preparation of (S)-3-(2-(2-amino-3-cyclohexylpropanoyl)-1-(2-fluoroacetyl)hydrazinyl)propanamide

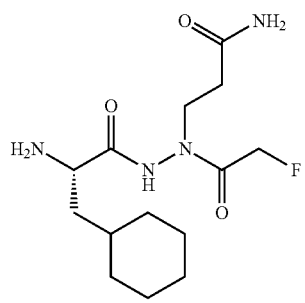
36b

Compound 36b was prepared in analogy to Example 27, Step 1 by using (S)-tert-butyl(1-(2-(3-amino-3-oxo-propyl)-2-(2-fluoroacetyl)hydrazinyl)-3-cyclohexyl-1-oxo-propan-2-yl)carbamate (200.0 mg, compound 36a) instead of tert-butyl N-[(1S)-1-[[(3-amino-3-oxo-propyl)-(2-chloroacetyl)amino]carbamoyl]-3-methyl-butyl]carbamate (Example 26).

(S)-3-(2-(2-Amino-3-cyclohexylpropanoyl)-1-(2-fluoroacetyl)hydrazinyl)propanamide (150 mg, compound 36b) was obtained as a light yellow oil.

Step 3: Preparation of N-[(1S)-2-[2-(3-amino-3-oxo-propyl)-2-(2-fluoroacetyl)hydrazino]-1-(cyclohexylmethyl)-2-axo-ethyl]-1H-indole-2-carboxamide

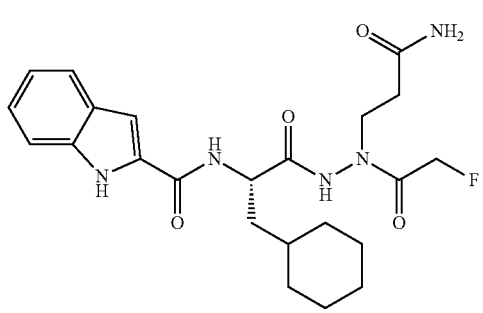
36

The title compound was prepared in analogy to Example 27, Step 2 by using (S)-3-(2-(2-amino-3-cyclohexylpropanoyl)-1-(2-fluoroacetyl)hydrazinyl)propanamide (150 mg, compound 36b) and 1H-indole-2-carboxylic acid instead of 3-[[[(2S)-2-amino-4-methyl-pentanoyl]amino]-(2-chloroacetyl)amino]propanamide (compound 27a) and 4-methoxy-1H-indole-2-carboxylic acid. N-[(1S)-2-[2-(3-Amino-3-oxo-propyl)-2-(2-fluoroacetyl)hydrazino]-1-(cyclohexylmethyl)-2-axo-ethyl]-1H-indole-2-carboxamide (12.8 mg, Example 36) was obtained as a white solid. ¹H NMR (400 MHz, DMSO-d₆) δ ppm: 11.60 (s, 1H), 10.40-10.62 (m, 1H), 8.65 (d, J=6.0 Hz, 1H), 7.63 (d, J=8.0 Hz, 1H), 8.65 (dd, J=0.8, 8.4 Hz, 1H), 7.37 (s, 1H), 7.29 (d, J=1.2 Hz, 1H), 7.17-7.21 (m, 1H), 7.02-7.07 (m, 1H), 6.87 (s, 1H), 4.46-5.26 (m, 2H), 4.38-4.49 (m, 1H), 3.79-3.88 (m, 1H), 3.32-3.34 (m, 1H), 2.27-2.34 (m, 2H), 1.71-1.82 (m, 3H), 1.68-1.78 (m, 3H), 1.40-1.47 (m, 1H), 1.23-1.29 (m, 2H), 1.06-1.19 (m, 2H), 0.89-1.03 (m, 2H). MS obsd. (ESI⁺) [(M+H)⁺]: 460.3.

Example 37

N-[(1S)-2-[2-(3-Amino-3-axo-propyl)-2-(2-fluoroacetyl)hydrazino]-1-(cyclohexylmethyl)-2-axo-ethyl]-4-methoxy-1H-indole-2-carboxamide

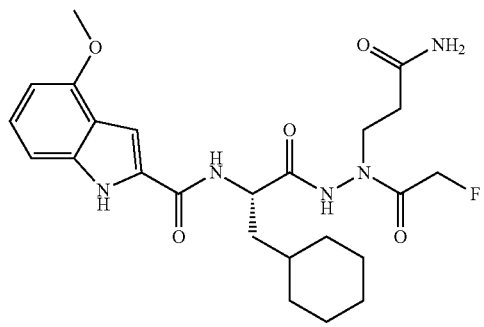
37

The title compound was prepared in analogy to Example 27, Step 2 by using (S)-3-(2-(2-amino-3-cyclohexylpropanoyl)-1-(2-fluoroacetyl)hydrazinyl)propanamide (150 mg, compound 36b) instead of 3-[[[(2S)-2-amino-4-methyl-pentanoyl]amino]-(2-chloroacetyl)amino]propanamide (compound 27a). (S)—N-(1-(2-(3-Amino-3-oxo-propyl)-2-(2-fluoroacetyl)hydrazinyl)-3-cyclohexyl-1-oxo-propan-2-yl)-4-methoxy-1H-indole-2-carboxamide (35.2 mg, Example 37) was obtained as a white solid. ¹H NMR (400 MHz, DMSO-d₆) δ ppm: 11.60 (s, 1H), 10.40-10.60 (m, 1H), 8.57 (d, J=6.4 Hz, 1H), 7.34-7.43 (m, 2H), 7.06-7.15 (m, 1H), 7.00-7.02 (m, 1H), 6.86 (s, 1H), 6.51 (d, J=8.0 Hz, 1H), 4.55-5.33 (m, 2H), 4.30-4.50 (m, 1H), 3.89 (s, 3H), 3.49-3.80 (m, 2H), 2.31-2.32 (m, 2H), 1.63-1.81 (m, 5H), 1.55-1.62 (m, 2H), 1.42-1.44 (m, 1H), 1.14-1.26 (m, 3H), 0.87-1.05 (m, 2H). MS obsd. (ESI⁺) [(M+H)⁺]: 490.2.

Example 38

N-[(1S)-1-[[(2-fluoroacetyl)-[(2-oxo-pyrrolidin-3-yl)methyl]amino]carbamoyl]-3-methyl-butyl]-1H-indole-2-carboxamide

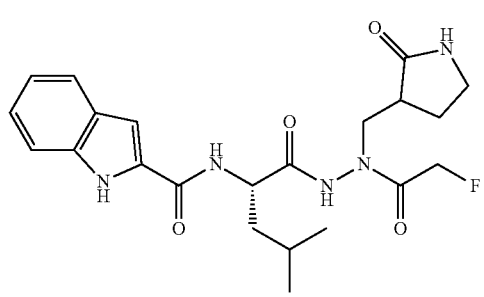
38

Step 1: Preparation of tert-butyl N-[[(2S)-2-(1H-indole-2-carbonylamino)-4-methyl-pentanoyl]amino]carbamate

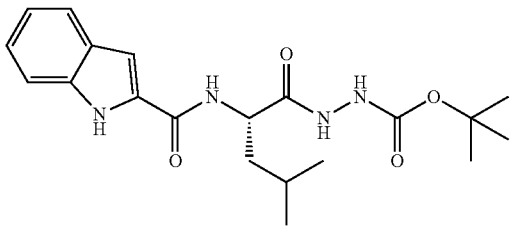

38a

Compound 38a was prepared in analogy to Example 27, Step 2 by using 1H-indole-2-carboxylic acid and tert-butyl N-[[(2S)-2-amino-4-methyl-pentanoyl]amino]carbamate (Intermediate AC) instead of 4-methoxy-1H-indole-2-carboxylic acid and 3-[[[(2S)-2-amino-4-methyl-pentanoyl]amino]-(2-chloroacetyl)amino]propanamide (compound 27a). tert-Butyl N-[[(2S)-2-(1H-indole-2-carbonylamino)-4-methyl-pentanoyl]amino]carbamate (3.0 g, compound 38a) was obtained as a yellow solid. MS obsd. (ESI⁺) [(M−tBu+H)⁺]: 333.0.

Step 2: Preparation of N-[(1S)-1-(hydrazinecarbonyl)-3-methyl-butyl]-1H-indole-2-carboxamide

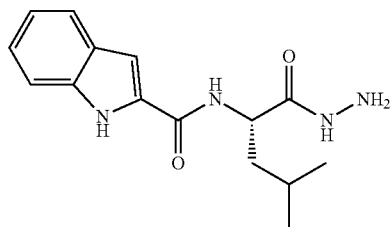

38b

Compound 38b was prepared in analogy to Example 1, Step 2 by using tert-butyl N-[[(2S)-2-(1H-indole-2-carbonylamino)-4-methyl-pentanoyl]amino]carbamate (2.5 g, compound 38a) instead of tert-butyl N-[[2-(benzyloxycarbonylamino)acetyl]amino]carbamate (compound 1a). N-[(1S)-1-(Hydrazinecarbonyl)-3-methyl-butyl]-1H-indole-2-carboxamide (1.4 g, compound 38b) was obtained as a yellow solid. MS obsd. (ESI⁺) [(M+H)⁺]: 289.0.

Step 3: Preparation of tert-butyl 3-[[2-[(2S)-2-(1H-indole-2-carbonylamino)-4-methyl-pentanoyl]hydrazino]methyl]-2-oxo-pyrrolidine-1-carboxylate

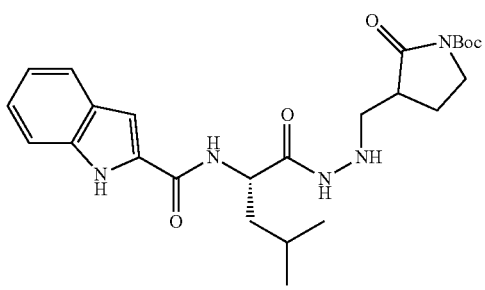

38c

Compound 38c was prepared in analogy to Example 18, Step 2 by using N-[(1S)-1-(hydrazinecarbonyl)-3-methyl-butyl]-1H-indole-2-carboxamide (1.4 g, compound 38b) instead of benzyl N-[(1S)-1-(hydrazinecarbonyl)-3-methyl-butyl]carbamate (compound 2a). tert-Butyl 3-[[2-[(2S)-2-(1H-indole-2-carbonylamino)-4-methyl-pentanoyl]hydrazino]methyl]-2-oxo-pyrrolidine-1-carboxylate (350 mg, compound 38c) was obtained as a yellow solid. MS obsd. (ESI⁺) [(M-Boc+H)⁺]: 386.2.

Step 4: Preparation of N-[(1S)-3-methyl-1-[[(2-oxo-pyrrolidin-3-yl)methylamino]carbamoyl]butyl]-1H-indole-2-carboxamide

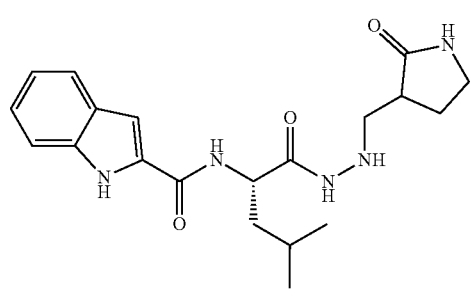

38d

Compound 38d was prepared in analogy to Example 18, Step 3 by using tert-Butyl 3-[[2-[(2S)-2-(1H-indole-2-carbonylamino)-4-methyl-pentanoyl]hydrazino]methyl]-2-oxo-pyrrolidine-1-carboxylate (320 mg, compound 38c) instead of (compound 18c). N-((2S)-4-Methyl-1-oxo-1-(2-((2-oxo-pyrrolidin-3-yl)methyl)hydrazinyl) pentan-2-yl)-1H-indole-2-carboxamide (228.0 mg, compound 38d) was obtained as a yellow solid.

Step 5: preparation of N-[(1S)-1-[[(2-fluoroacetyl)-[(2-oxo-pyrrolidin-3-yl)methyl]amino]carbamoyl]-3-methyl-butyl]-1H-indole-2-carboxamide

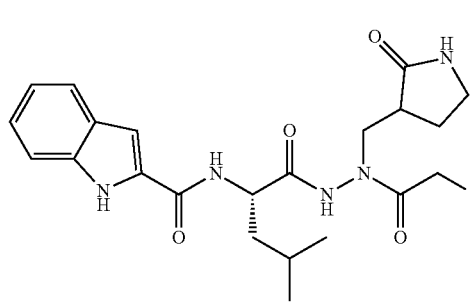

38

The title compound was prepared in analogy to Example 4 by using N-((2S)-4-methyl-1-oxo-1-(2-((2-oxo-pyrrolidin-3-yl)methyl)hydrazinyl) pentan-2-yl)-1H-indole-2-carboxamide (80 mg, compound 38d) and fluoroacetic acid instead of benzyl N-[(1S)-1-[[(3-amino-3-oxo-propyl)amino]carbamoyl]-3-methyl-butyl]carbamate (compound 2c) and 2-chloropropanoic acid. N—((S)-1-(2-(2-Fluoroacetyl)-2-((2-oxo-pyrrolidin-3-yl)methyl) hydrazinyl)-4-methyl-1-oxo-pentan-2-yl)-1H-indole-2-carboxamide (65.6 mg, Example 38) was obtained as a white solid. MS obsd. (ESI⁺) [(M+H)⁺]: 446.4.

Step 6: Preparation of N-[(1S)-1-[[(2-Fluoroacetyl)-[[(3S)-2-oxo-pyrrolidin-3-yl]methyl]amino]carbamoyl]-3-methyl-butyl]-1H-indole-2-carboxamide and N-[(1S)-1-[[(2-fluoroacetyl)-[[(3R)-2-oxo-pyrrolidin-3-yl]methyl]amino]carbamoyl]-3-methyl-butyl]-1H-indole-2-carboxamide (38-A and 38-B)

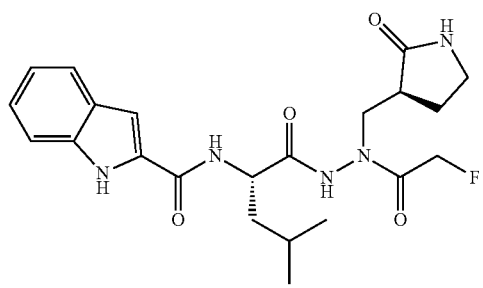

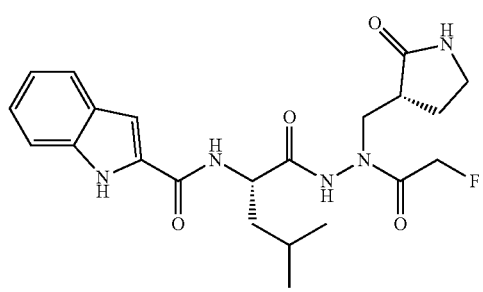

Separation of compound 38 by chiral SFC separation afforded Example 38-A (faster eluting, 18.3 mg) and Example 38-B (slower eluting, 15.9 mg) as a white solid with 40% MeOH+ACN(0.05% DEA) (0.05% DEA)/CO₂ on Chiralpak IC-3 column.

Example 38-A: ¹H NMR (400 MHz, DMSO-d₆) δ ppm: 11.60 (s, 1H), 10.38-10.69 (m, 1H), 8.63-8.69 (m, 1H), 7.69-7.74 (m, 1H), 7.63 (d, J=8.0 Hz, 1H), 7.43 (d, J=8.0 Hz, 1H), 7.29 (d, J=1.2 Hz, 1H), 7.16-7.20 (m, 1H), 7.02-7.06 (m, 1H), 4.62-5.22 (m, 2H), 4.37-4.44 (m, 1H), 3.77-3.88 (m, 1H), 3.11-3.26 (m, 3H), 2.45 (br s, 1H), 2.06-2.17 (m, 1H), 1.73-1.78 (m, 3H), 1.54-1.58 (m, 1H), 0.94 (dd, J=5.6 Hz, 21.2 Hz, 6H). MS obsd. (ESI⁺) [(M+H)⁺]: 446.4.

Example 38-A: ¹H NMR (400 MHz, DMSO-d₆) δ ppm: 11.61 (s, 1H), 10.44-10.58 (m, 1H), 8.66 (d, J=6.8 Hz, 1H), 7.70-7.73 (m, 1H), 7.62 (d, J=8.0 Hz, 1H), 7.42 (d, J=8.0 Hz, 1H), 7.29 (d, J=1.6 Hz, 1H), 7.16-7.20 (m, 1H), 7.02-7.06 (m, 1H), 4.68-5.20 (m, 2H), 4.37-4.46 (m, 1H), 3.76-3.89 (m, 1H), 3.26-3.30 (m, 1H), 3.08-3.19 (m, 2H), 2.40 (br.s, 1H), 2.06-2.20 (br. s, 1H), 1.76-1.78 (m, 3H), 1.54-1.58 (m, 1H), 0.94 (dd, J=6.4, 20.8 Hz, 6H). MS obsd. (ESI⁺) [(M+H)⁺]: 446.4.

Example 39

N-[(1S)-2-[2-(3-Amino-3-axo-propyl)-2-(2-chloroacetyl)hydrazino]-1-(cyclohexylmethyl)-2-axoethyl]-N-methyl-1H-indole-2-carboxamide

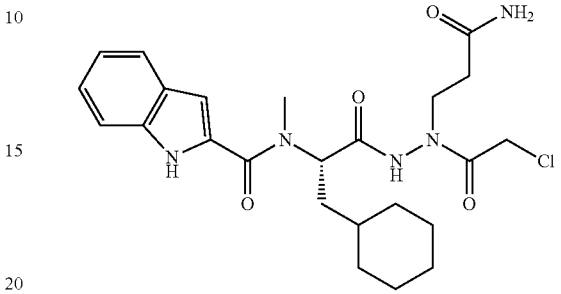

Step 1: Preparation of tert-butyl N-[(1S)-2-(2-benzyloxycarbonylhydrazino)-1-(cyclohexylmethyl)-2-axo-ethyl]-N-methyl-carbamate

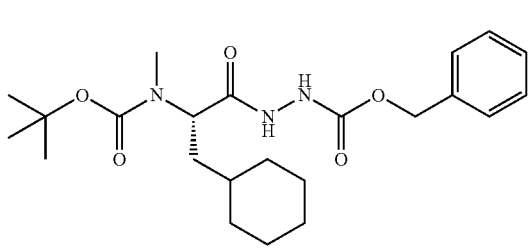

Compound 39a was prepared in analogy to Example 26, Step 1 by using (2S)-2-[tert-butoxycarbonyl(methyl)amino]-3-cyclohexyl-propanoic acid (270 mg, GL Biochem, CAS number: 97269-22-2) instead of (S)-2-((tert-butoxycarbonyl)amino)-4-methylpentanoic acid. (S)-Benzyl 2-(2-((tert-butoxycarbonyl)(methyl)amino)-3-cyclohexylpropanoyl)hydrazinecarboxylate (360 mg, compound 39a) was obtained as a colorless oil. MS obsd. (ESI⁺) [M−Boc+H]⁺: 334.1.

Step 2: Preparation of (S)-tert-butyl(3-cyclohexyl-1-hydrazinyl-1-oxo-propan-2-yl)carbamate

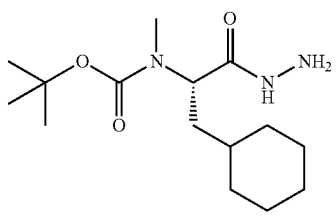

Compound 39b was prepared in analogy to Example 26, Step 2 by using (S)-benzyl 2-(2-((tert-butoxycarbonyl)

(methyl)amino)-3-cyclohexylpropanoyl)hydrazinecarboxylate (360 mg, compound 39a) instead of (S)-benzyl 2-(2-((tert-butoxycarbonyl)amino)-4-methylpentanoyl)hydrazinecarboxylate (compound 26a). (S)-tert-Butyl(3-cyclohexyl-1-hydrazinyl-1-oxo-propan-2-yl)(methyl)carbamate (240 mg, compound 38b) was obtained as a light yellow oil. MS obsd. (ESI$^+$) [(M−Boc)$^+$]: 200.1.

Step 3: Preparation of tert-butyl N-[(1S)-2-[2-(3-amino-3-oxo-propyl)hydrazino]-1-(cyclohexylmethyl)-2-axo-ethyl]-N-methyl-carbamate

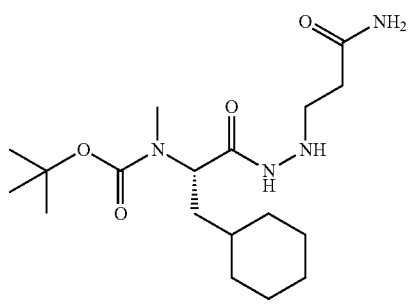

39c

Compound 39c was prepared in analogy to Example 26, Step 3 by using tert-butyl N-[(1S)-2-[2-(3-amino-3-oxo-propyl)hydrazino]-1-(cyclohexylmethyl)-2-axo-ethyl]-N-methyl-carbamate (compound 39b) instead of tert-butyl N-[(1S)-1-(hydrazinecarbonyl)-3-methyl-butyl]carbamate (compound 26b). tert-Butyl N-[(1S)-2-[2-(3-amino-3-oxo-propyl)hydrazino]-1-(cyclohexylmethyl)-2-axo-ethyl]-N-methyl-carbamate (300 mg, compound 39c) was obtained as a colorless oil. MS obsd. (ESI$^+$) [(M+H)$^+$]: 371.1.

Step 4: Preparation of tert-butyl N-[(1S)-2-[2-(3-amino-3-oxo-propyl)-2-(2-chloroacetyl)hydrazino]-1-(cyclohexylmethyl)-2-axo-ethyl]-N-methyl-carbamate

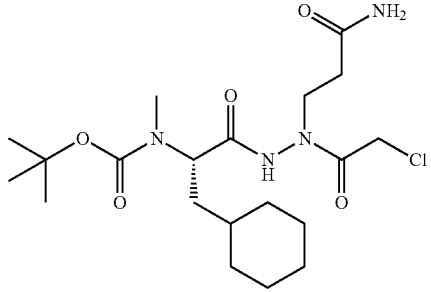

39d

Compound 39d was prepared in analogy to Example 1, Step 4 by using tert-butyl N-[(1S)-2-[2-(3-amino-3-oxo-propyl)hydrazino]-1-(cyclohexylmethyl)-2-axo-ethyl]-N-methyl-carbamate (300 mg, compound 39c) instead of benzyl N-[2-[2-(3-amino-3-oxo-propyl)hydrazino]-2-axo-ethyl]carbamate (compound 1c). tert-Butyl N-[(1S)-2-[2-(3-amino-3-oxo-propyl)-2-(2-chloroacetyl)hydrazino]-1-(cyclohexylmethyl)-2-axo-ethyl]-N-methyl-carbamate (100 mg, compound 39d) was obtained as a colorless oil. MS obsd. (ESI$^+$) [(M+H)$^+$]: 447.1

Step 5: Preparation of 3-[(2-chloroacetyl)-[[(2S)-3-cyclohexyl-2-(methylamino)propanoyl]amino]amino]propanamide 39e Compound 39e was prepared in analogy to Example 27, Step 1 by using tert-butyl N-[(1S)-2-[2-(3-amino-3-oxo-propyl)-2-(2-chloroacetyl)hydrazino]-1-(cyclohexylmethyl)-2-axo-ethyl]-N-methyl-carbamate (100 mg, compound 39d) instead of tert-butyl N-[(1S)-1-[[(3-amino-3-oxo-propyl)-(2-chloroacetyl)amino]carbamoyl]-3-methyl-butyl]carbamate (350.0 mg, Example 26). (S)-3-(1-(2-Chloroacetyl)-2-(3-cyclohexyl-2-(methylamino)propanoyl)hydrazinyl)propanamide (70 mg, compound 39e) was obtained as a light yellow oil. MS obsd. (ESI$^+$) [(M+H)$^+$]: 347.0.

Step 6: Preparation of N-[(1S)-2-[2-(3-amino-3-oxo-propyl)-2-(2-chloroacetyl)hydrazino]-1-(cyclohexylmethyl)-2-axo-ethyl]-N-methyl-1H-indole-2-carboxamide

39

The title compound was prepared in analogy to Example 27, Step 2 by using 3 (S)-3-(1-(2-chloroacetyl)-2-(3-cyclohexyl-2-(methylamino)propanoyl)hydrazinyl)propanamide (70 mg, compound 39e) instead of 3-[[[(2S)-2-amino-4-methyl-pentanoyl]amino]-(2-chloroacetyl)amino]propanamide (compound 27a). N-[(1S)-2-[2-(3-Amino-3-oxo-propyl)-2-(2-chloroacetyl)hydrazino]-1-(cyclohexylmethyl)-2-axo-ethyl]-N-methyl-1H-indole-2-carboxamide (13.2 mg, Example 39) was obtained as a white solid. $^1$H NMR (400 MHz, DMSO-d$_6$) δ ppm: 11.61 (s, 1H), 10.54 (br. s, 1H), 7.64 (d, J=8.0 Hz, 1H), 7.45 (d, J=8.0 Hz, 1H), 7.38 (s, 1H), 7.18-7.22 (m, 1H), 6.92-7.08 (m, 2H), 6.88 (s, 1H), 5.13 (br.

s, 1H), 4.16-4.30 (m, 2H), 3.80 (br. s, 1H), 3.38 (m, 1H), 3.32 (s, 3H), 2.32-2.33 (m, 2H), 1.59-1.86 (m, 7H), 0.98-1.23 (m, 6H). MS obsd. (ESI$^+$) [(M+H)$^+$]: 490.4.

Example 40

N-[(1S)-1-[[(3-Amino-3-axo-propyl)-(2-chloro-acetyl)amino]carbamoyl]-3-methyl-butyl]-N-methyl-1H-indole-2-carboxamide

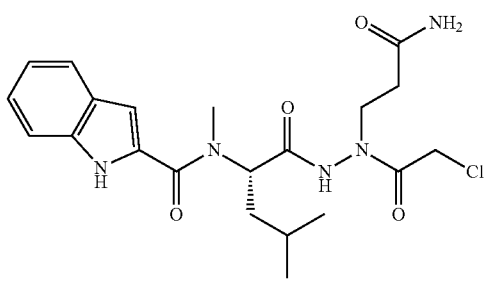

40

Step 1: Preparation of tert-butyl N-[(1S)-1-(benzy-loxycarbonylaminocarbamoyl)-3-methyl-butyl]-N-methyl-carbamat

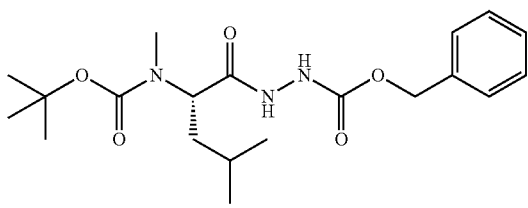

40a

Compound 40a was prepared in analogy to Example 26, Step 1 by using (S)-2-((tert-butoxycarbonyl)(methyl)amino)-4-methylpentanoic acid (2.0 g, Shanghai Haohong Pharmaceutical Co., Ltd, CAS number: 53363-89-6) instead of (S)-2-((tert-butoxycarbonyl)amino)-4-methylpentanoic acid. tert-Butyl N-[(1S)-1-(benzyloxycarbonylaminocarbamoyl)-3-methyl-butyl]-N-methyl-carbamate (2.9 g, compound 40a) was obtained as a light yellow oil. MS obsd. (ESI$^+$) [M−Boc+H]$^+$: 294.2.

Step 2: Preparation of tert-butyl N-[(1S)-1-(hydrazinecarbonyl)-3-methyl-butyl]-N-methyl-carbamate

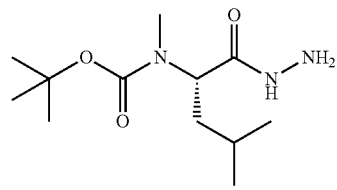

40b

Compound 40b was prepared in analogy to Example 26, Step 2 by using tert-butyl N-[(1S)-1-(benzyloxycarbonylaminocarbamoyl)-3-methyl-butyl]-N-methyl-carbamate (2.9 g, compound 40a) instead of (S)-benzyl 2-(2-((tert-butoxycarbonyl)amino)-4-methylpentanoyl)hydrazinecarboxylate (compound 26a). tert-Butyl N-[(1S)-1-(hydrazinecarbonyl)-3-methyl-butyl]-N-methyl-carbamate (900 mg, compound 40b) was obtained as a colorless oil. MS obsd. (ESI$^+$) [M−Boc+H]$^+$: 160.4.

Step 3: Preparation of tert-butyl N-[(1S)-1-[[(3-amino-3-oxo-propyl)amino]carbamoyl]-3-methyl-butyl]-N-methyl-carbamate

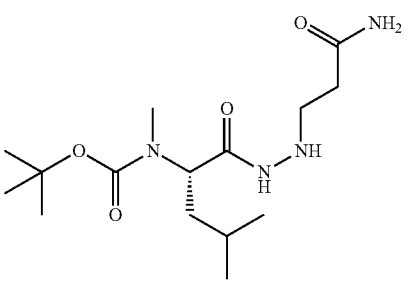

40c

Compound 40c was prepared in analogy to Example 26, Step 3 by using tert-butyl N-[(1S)-1-(hydrazinecarbonyl)-3-methyl-butyl]-N-methyl-carbamate (compound 40b) instead of tert-butyl N-[(1S)-1-(hydrazinecarbonyl)-3-methyl-butyl]carbamate (compound 26b). tert-Butyl N-[(1S)-1-[[(3-amino-3-oxo-propyl)amino]carbamoyl]-3-methyl-butyl]-N-methyl-carbamate (480 mg, compound 40c) was obtained as a colorless oil. MS obsd. (ESI$^+$) [(M−Boc+H)]: 230.9.

Step 4: Preparation of tert-butyl N-[(1S)-1-[[(3-amino-3-oxo-propyl)-(2-chloroacetyl)amino]carbamoyl]-3-methyl-butyl]-N-methyl-carbamate

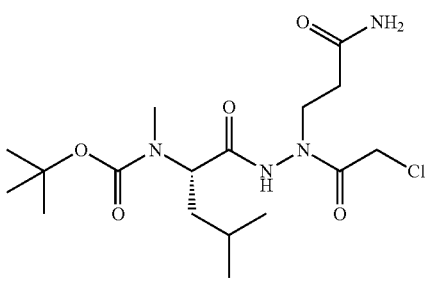

40d

Compound 40d was prepared in analogy to Example 1, Step 4 by using tert-butyl N-[(1S)-1-[[(3-amino-3-oxo-propyl)amino]carbamoyl]-3-methyl-butyl]-N-methyl-carbamate (240 mg, compound 40c) instead of benzyl N-[2-[2-(3-amino-3-oxo-propyl)hydrazino]-2-axo-ethyl]carbamate (compound 1c). tert-Butyl N-[(1S)-1-[[(3-amino-3-oxo-propyl)-(2-chloroacetyl)amino]carbamoyl]-3-methyl-butyl]-N-methyl-carbamate (270 mg, compound 40d) was obtained as a colorless oil. MS obsd. (ESI$^+$) [M−Boc+H]$^+$: 307.2.

Step 5: Preparation of 3-[(2-chloroacetyl)-[[(2S)-4-methyl-2-(methylamino)pentanoyl]amino]amino]propanamide

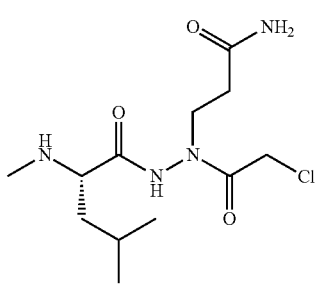
40e

Compound 40e was prepared in analogy to Example 27, Step 1 by using 3-[(2-chloroacetyl)-[[(2S)-4-methyl-2-(methylamino)pentanoyl]amino]amino]propanamide (compound 40d) instead of tert-butyl N-[(1S)-1-[[(3-amino-3-oxo-propyl)-(2-chloroacetyl)amino]carbamoyl]-3-methyl-butyl]carbamate (350.0 mg, Example 26). 3-[(2-Chloroacetyl)-[[(2S)-4-methyl-2-(methylamino)pentanoyl]amino]amino]propanamide (60 mg, compound 40e) was obtained as a light yellow oil.

Step 6: Preparation of N-[(1S)-1-[[(3-amino-3-oxo-propyl)-(2-chloroacetyl)amino]carbamoyl]-3-methyl-butyl]-N-methyl-1H-indole-2-carboxamide

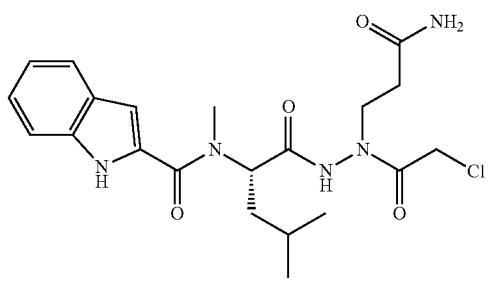
40

The title compound was prepared in analogy to Example 27, Step 2 by using 3-[(2-chloroacetyl)-[[(2S)-4-methyl-2-(methylamino)pentanoyl]amino]amino]propanamide (60 mg, compound 40e) (70 mg, compound 39e) instead of 3-[[[(2S)-2-amino-4-methyl-pentanoyl]amino]-(2-chloroacetyl)amino]propanamide (compound 27a). N-[(1S)-1-[[(3-Amino-3-oxo-propyl)-(2-chloroacetyl)amino]carbamoyl]-3-methyl-butyl]-N-methyl-1H-indole-2-carboxamide (29.2 Example 40) was obtained as a white solid. $^1$H NMR (400 MHz, CDCl$_3$) δ ppm: 9.83 (br. s, 1H), 9.51 (br. s, 1H), 7.67 (d, J=7.6 Hz, 1H), 7.44 (d, J=8.4 Hz, 1H), 7.32 (t, J=8.0 Hz, 1H), 7.16 (t, J=7.2 Hz, 1H), 6.93 (s, 1H), 5.80-6.05 (m, 2H), 5.15-5.25 (m, 1H), 3.95-4.15 (m, 2H), 3.39 (s, 3H), 2.45-2.65 (m, 2H), 1.84-1.91 (m, 2H), 1.60-1.65 (m, 1H), 1.21-1.29 (m, 2H), 1.02 (d, J=6.8 Hz, 3H), 0.96 (d, J=6.0 Hz, 3H). MS obsd. (ESI$^+$) [(M+H)$^+$]: 450.4.

Example 41

N-[(1S)-1-[[(3-Amino-3-axo-propyl)-(2-chloro-2-fluoro-acetyl)amino]carbamoyl]-3-methyl-butyl]-1H-indole-2-carboxamide

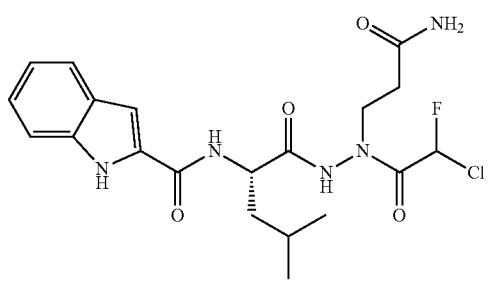
41

Step 1: Preparation of N-[(1S)-1-[[(3-amino-3-oxo-propyl)amino]carbamoyl]-3-methyl-butyl]-1H-indole-2-carboxamide

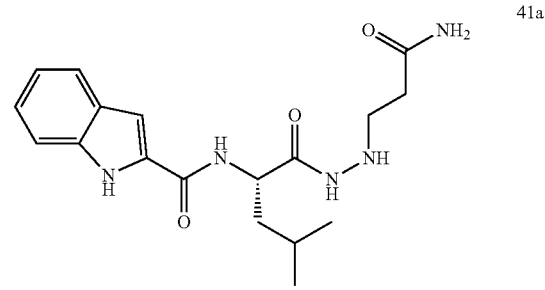 [SMILES: CC(C)C[C@H](NC(=O)c1cc2ccccc2[nH]1)C(=O)NNCCC(N)=O]
41a

Compound 41a was prepared in analogy to Example 1, Step 3 by using N-[(1S)-1-(hydrazinecarbonyl)-3-methyl-butyl]-1H-indole-2-carboxamide (200 mg, compound 38b) instead of benzyl(2-hydrazinyl-2-axo-ethyl)carbamate (compound 1b). N-[(1S)-1-[[(3-Amino-3-oxo-propyl)amino]carbamoyl]-3-methyl-butyl]-1H-indole-2-carboxamide (100 mg, compound 41a) was obtained as a light yellow solid. MS obsd. (ESI$^+$) [(M+H)$^+$]: 360.4.

Step 2: Preparation of N-[(1S)-1-[[(3-Amino-3-oxo-propyl)-(2-chloro-2-fluoro-acetyl)amino]carbamoyl]-3-methyl-butyl]-1H-indole-2-carboxamide

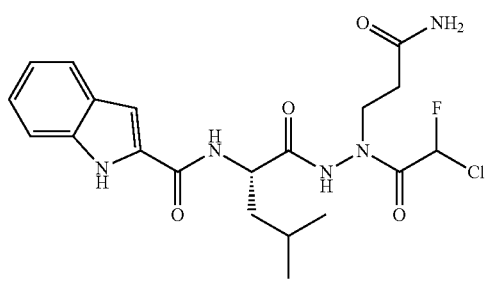
41

The title compound was prepared in analogy to Example 4 by using N-[(1S)-1-[[(3-amino-3-oxo-propyl)amino]carbamoyl]-3-methyl-butyl]-1H-indole-2-carboxamide (50.0 mg, compound 41a) and 2-chloro-2-fluoro-acetic acid instead of benzyl N-[(1S)-1-[[(3-amino-3-oxo-propyl)amino]carbamoyl]-3-methyl-butyl]carbamate (compound 2c) and 2-chloropropanoic acid. N-[(1S)-1-[[(3-Amino-3-oxo-propyl)-(2-chloro-2-fluoro-acetyl)amino]carbamoyl]-3-methyl-butyl]-1H-indole-2-carboxamide was obtained as a white solid (11.0 mg, Example 41, MS obsd. (ESI+) [(M+H)+]: 454.1).

Step 3: Preparation of N-[(1S)-1-[[(3-amino-3-oxo-propyl)-[(2S)-2-chloro-2-fluoro-acetyl]amino]carbamoyl]-3-methyl-butyl]-1H-indole-2-carboxamide and N-[(1S)-1-[[(3-amino-3-oxo-propyl)-[(2R)-2-chloro-2-fluoro-acetyl]amino]carbamoyl]-3-methyl-butyl]-1H-indole-2-carboxamide (41-A and 41-B)

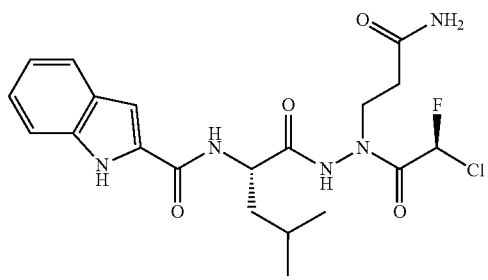

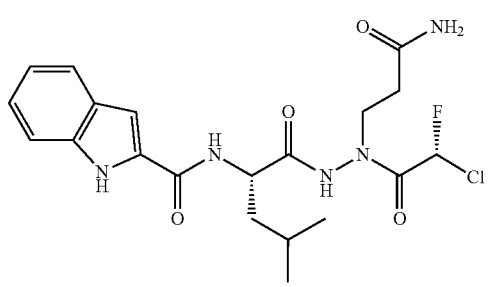

Separation of Example 41 by chiral SFC separation afforded Example 41-A (faster eluting, 2.1 mg) and Example 41-B (slower eluting, 1.9 mg) as a white solid with 5%-40% MeOH(0.05% DEA)/CO₂ on DAICEL CHIRALCEL OJ column.

Example 41-A: ¹H NMR (400 MHz, CD₃OD) δ ppm: 7.61 (d, J=8.0 Hz, 1H), 7.43 (d, J=8.0 Hz, 1H), 7.21-7.24 (m, 2H), 7.06 (t, J=8.0 Hz, 1H), 6.81 (d, J=50.4 Hz, 1H), 4.45-4.51 (m, 1H), 3.68-3.94 (m, 2H), 2.46-2.55 (m, 2H), 1.84-1.89 (m, 2H), 1.68-1.72 (m, 1H), 1.04 (dd, J=6.4, 16.8 Hz, 6H). MS obsd. (ESI+) [(M+H)+]: 454.1.

Example 41-B: ¹H NMR (400 MHz, CD₃OD) δ ppm: 7.62 (d, J=8.0 Hz, 1H), 7.44 (d, J=8.0 Hz, 1H), 7.21-7.24 (m, 2H), 7.06 (t, J=7.2 Hz, 1H), 6.54 (d, J=50.4 Hz, 1H), 4.54-4.56 (m, 1H), 3.72-3.92 (m, 2H), 2.48-2.53 (m, 2H), 1.82-1.88 (m, 2H), 1.72-1.77 (m, 1H), 1.04 (dd, J=6.0, 18.0 Hz, 6H). MS obsd. (ESI+) [(M+H)+]: 454.1.

Example 42

N-[(1S)-1-[[(3-Amino-3-axo-propyl)-(2-chloro-acetyl)amino]carbamoyl]-3-methyl-butyl]-1H-benzimidazole-2-carboxamide

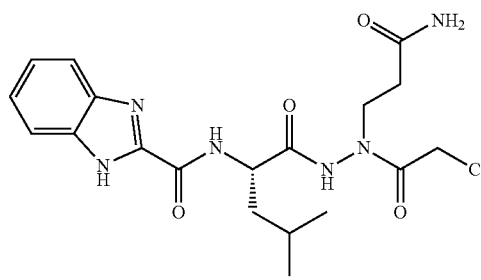

The title compound was prepared in analogy to Example 27, Step 2 by using 1H-benzimidazole-2-carboxylic acid instead of 4-methoxy-1H-indole-2-carboxylic acid. (S)—N-(1-(2-(3-Amino-3-oxo-propyl)-2-(2-chloroacetyl)hydrazinyl)-4-methyl-1-oxo-pentan-2-yl)-1H-benzo[d]imidazole-2-carboxamide (10.1 mg, Example 42) was obtained as a white solid.

¹H NMR (400 MHz, CD₃OD) δ ppm: 7.52-7.79 (m, 2H), 7.35 (dd, J=2.4, 5.6 Hz, 2H), 3.59 (s, 1H), 4.01-4.49 (m, 2H), 3.52-3.99 (m, 2H), 2.52 (s, 2H), 1.86-1.93 (m, 2H), 1.75-1.80 (m, 1H), 1.04 (dd, J=6.4, 14.0 Hz, 6H). MS obsd. (ESI+) [(M+H)+]: 437.1.

Example 43

N-[(1S)-1-[[(3-Amino-3-oxo-propyl)-(2-chloroacetyl)amino]carbamoyl]-3-methyl-butyl]isoxazole-3-carboxamide

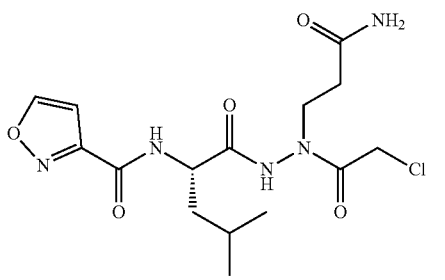

The title compound was prepared in analogy to Example 27, Step 2 by using 3-isoxazolecarboxylic acid (Wuxi Apptec (Wuhan) Co., Ltd) instead of 4-methoxy-1H-indole-2-carboxylic acid. N-[(1S)-1-[[(3-Amino-3-oxo-propyl)-(2-chloroacetyl)amino]carbamoyl]-3-methyl-butyl]isoxazole-3-carboxamide (6.7 mg, Example 43) was obtained as a colorless gum. ¹H NMR (400 MHz, CD₃OD) δ ppm: 8.96 (d, J=6.0 Hz, 1H), 8.81 (d, J=1.6 Hz, 1H), 6.85 (d, J=1.6 Hz, 1H), 4.59-4.52 (m, 1H), 4.09-4.45 (m, 1H), 3.55-4.05 (m, 3H), 2.46-2.55 (m, 2H), 1.68-1.91 (m, 3H), 1.02 (dd, J=6.4, 14.4 Hz, 6H). MS obsd. (ESI+) [(M+H)+]: 388.0.

Example 44

N-[(1S)-1-[[(3-Amino-3-oxo-propyl)-(2-chloroacetyl)amino]carbamoyl]-3-methyl-butyl]-1H-pyrrolo[2,3-b]pyridine-2-carboxamide

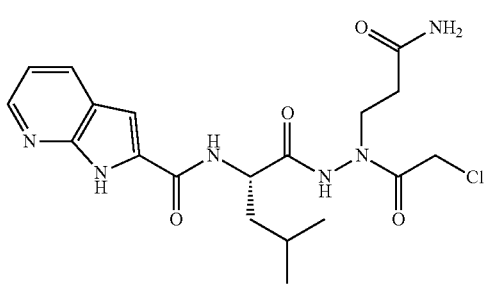

44

The title compound was prepared in analogy to Example 27, Step 2 by using 1H-pyrrolo[2,3-b]pyridine-2-carboxylic acid (Wuxi Apptec (Wuhan) Co., Ltd) instead of 4-methoxy-1H-indole-2-carboxylic acid. N-[(1S)-1-[[(3-Amino-3-oxo-propyl)-(2-chloroacetyl)amino]carbamoyl]-3-methyl-butyl]-1H-pyrrolo[2,3-b]pyridine-2-carboxamide (7.9 mg, Example 44) was obtained as a white solid. $^1$H NMR (400 MHz, DMSO-$d_6$) δ ppm: 12.16 (s, 1H), 10.65-10.68 (m, 1H), 8.69 (d, J=6.8 Hz, 1H), 8.34 (dd, J=1.2, 4.4 Hz, 1H), 8.07-8.12 (m, 1H), 7.36 (s, 1H), 7.26 (d, J=2.0 Hz, 1H), 7.13 (dd, J=4.4, 8.0 Hz, 1H), 6.86 (s, 1H), 4.42-4.53 (m, 1H), 3.99-4.32 (m, 2H), 3.73-3.93 (m, 2H), 2.23-2.33 (m, 2H), 1.73-1.79 (m, 2H), 1.58-1.64 (m, 1H), 0.95 (dd, J=6.4, 20.0 Hz, 6H). MS obsd. (ESI$^+$) [(M+H)$^+$]: 436.9.

Example 45

N-[(1S)-1-[[(3-Amino-3-oxo-propyl)-(2-chloroacetyl)amino]carbamoyl]-3-methyl-butyl]-2-methyl-oxazole-4-carboxamide

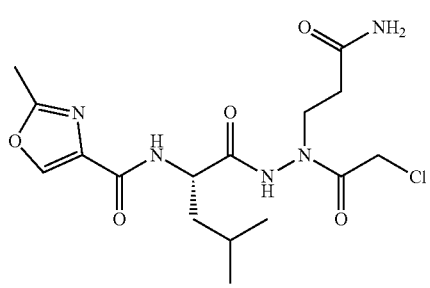

45

The title compound was prepared in analogy to Example 27, Step 2 by using 2-methyloxazole-4-carboxylic acid (Bidepharm, CAS number 23012-17-1) instead of 4-methoxy-1H-indole-2-carboxylic acid. N-[(1S)-1-[[(3-Amino-3-oxo-propyl)-(2-chloroacetyl)amino]carbamoyl]-3-methyl-butyl]-2-methyl-oxazole-4-carboxamide (4.9 mg, Example 45) was obtained as a white solid. $^1$H NMR (400 MHz, CDCl$_3$) δ ppm: 9.86 (s, 1H), 8.13 (s, 1H), 7.35 (d, J=6.0 Hz, 1H), 6.44 (s, 1H), 6.09 (br. s, 1H), 4.58-4.63 (m, 1H), 3.88-4.29 (m, 4H), 2.56 (br. s, 2H), 2.48 (s, 3H), 1.75-1.77 (m, 3H), 0.98 (dd, J=6.0, 17.6 Hz, 6H). MS obsd. (ESI$^+$) [(M+H)$^+$]: 402.3.

Example 46

N-[(1S)-1-[[(3-Amino-3-oxo-propyl)-(2-chloroacetyl)amino]carbamoyl]-3-methyl-butyl]-5-methyl-isoxazole-4-carboxamide

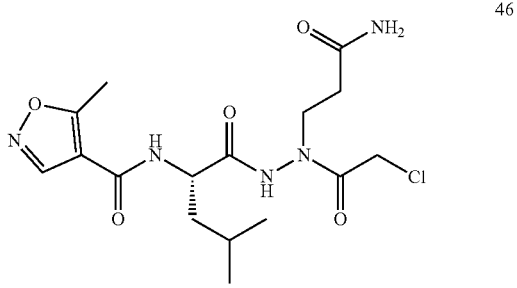 [SMILES: Cc1oncc1C(=O)N[C@@H](CC(C)C)C(=O)NN(CCC(N)=O)C(=O)CCl]

46

The title compound was prepared in analogy to Example 27, Step 2 by using 5-methylisoxazole-4-carboxylic acid (Bidepharm, CAS number: 42831-50-5) instead of 4-methoxy-1H-indole-2-carboxylic acid. (S)—N-(1-(2-(3-Amino-3-oxo-propyl)-2-(2-chloroacetyl)hydrazinyl)-4-methyl-1-oxo-pentan-2-yl)-5-methylisoxazole-4-carboxamide (6.7 mg, Example 46) was obtained as a colorless gum. $^1$H NMR (400 MHz, CD$_3$OD) δ ppm: 8.74 (s, 1H), 4.34-4.51 (m, 2H), 3.94-4.20 (m, 2H), 3.55-3.80 (m, 1H), 2.66 (s, 3H), 2.45-2.60 (m, 2H), 1.75-1.85 (m, 2H), 1.64-1.71 (m, 1H), 1.02 (dd, J=6.4, 16.8 Hz, 6H). MS obsd. (ESI$^+$) [(M+H)$^+$]: 402.1.

Example 47

N-[(1S)-1-[[(3-Amino-3-axo-propyl)-(2-chloroacetyl)amino]carbamoyl]-3-methyl-butyl]-5-methoxy-6H-pyrrolo[2,3-c]pyridine-2-carboxamide

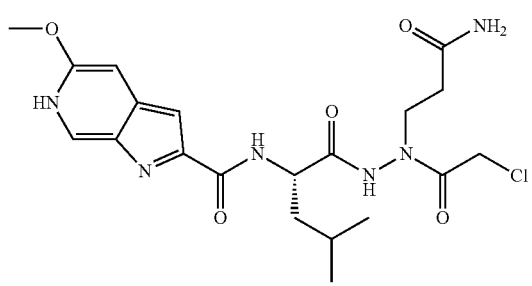

47

The title compound was prepared in analogy to Example 27, Step 2 by using 5-methoxy-1H-pyrrolo[2,3-c]pyridine-2-carboxylic acid (Bidepharm, CAS number: 17288-36-7) instead of 4-methoxy-1H-indole-2-carboxylic acid. N-[(1S)-1-[[(3-Amino-3-oxo-propyl)-(2-chloroacetyl)amino]carbamoyl]-3-methyl-butyl]-5-methoxy-6H-pyrrolo[2,3-c]pyridine-2-carboxamide (5.5 mg, Example 47) was obtained as a white solid. $^1$H NMR (400 MHz, CD$_3$OD) δ ppm: 8.42

(s, 1H), 7.13 (s, 1H), 7.00 (s, 1H), 4.61-4.64 (m, 2H), 4.56-4.58 (m, 1H), 4.07-4.25 (m, 1H), 3.91 (s, 3H), 3.60-3.90 (m, 1H), 2.49-2.57 (m, 2H), 1.79-1.92 (m, 2H), 1.71-1.76 (m, 1H), 1.03 (dd, J=6.4, 17.2 Hz, 6H). MS obsd. (ESI$^+$) [(M+H)$^+$]: 467.1.

Example 48

N-[(1S)-2-[2-(3-amino-3-oxo-propyl)-2-(2-chloro-acetyl)hydrazino]-1-(cyclohexylmethyl)-2-axo-ethyl]-5-methyl-isoxazole-3-carboxamide

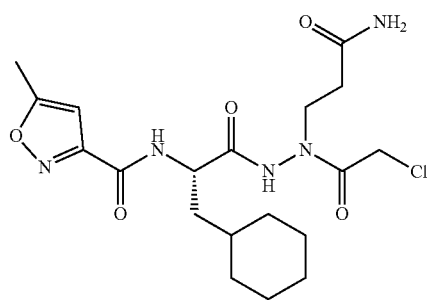

48

The title compound was prepared in analogy to Example 27, Step 2 by using 3-[[[(2S)-2-amino-3-cyclohexyl-propanoyl]amino]-(2-chloroacetyl)amino]propanamide (70.0 mg, compound 32e) and 5-methylisoxazole-3-carboxylic acid instead of 3-[[[(2S)-2-amino-4-methyl-pentanoyl]amino]-(2-chloroacetyl)amino]propanamide (compound 27a) and 4-methoxy-1H-indole-2-carboxylic acid. (S)—N-(1-(2-(3-Amino-3-oxo-propyl)-2-(2-chloroacetyl)hydrazinyl)-3-cyclohexyl-1-oxo-propan-2-yl)-5-methylisoxazole-3-carboxamide (48.9 mg, Example 36) was obtained as a white solid. $^1$H NMR (400 MHz, DMSO-d$_6$) δ ppm: 10.30-10.73 (m, 1H), 8.87-8.94 (m, 1H), 7.36 (s, 1H), 6.85 (s, 1H), 6.58 (s, 1H), 4.20-4.50 (m, 2H), 3.98-4.12 (m, 1H), 3.72-3.82 (m, 1H), 2.46 (s, 3H), 2.25-2.35 (m, 2H), 1.71-1.79 (m, 2H), 1.57-1.70 (m, 5H), 1.27-1.37 (m, 1H), 1.05-1.45 (m, 4H), 0.87-0.99 (m, 2H). MS obsd. (ESI$^+$) [(M+H)$^+$]: 442.4.

Example 49

4-Methoxy-N-[(1S)-1-[[(3-amino-3-oxo-propyl)-(2-chloro-2-fluoro-acetyl)amino]carbamoyl]-3-methyl-butyl]-1H-indole-2-carboxamide

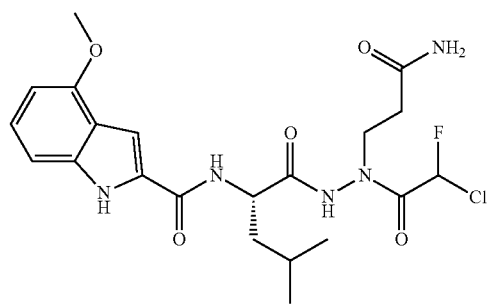

49

Step 1: Preparation of tert-butyl N-[[(2S)-2-[(4-methoxy-1H-indole-2-carbonyl)amino]-4-methyl-pentanoyl]amino]carbamate

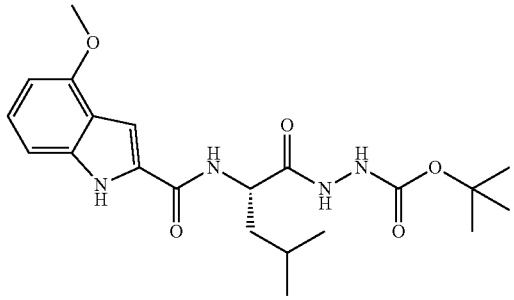

49a

Compound 49a was prepared in analogy to Example 27, Step 2 by using tert-butyl N-[[(2S)-2-amino-4-methyl-pentanoyl]amino]carbamate (Intermediate AC) instead of 3-[[[(2S)-2-amino-4-methyl-pentanoyl]amino]-(2-chloroacetyl)amino]propanamide (compound 27a). tert-Butyl N-[[(2S)-2-[(4-methoxy-1H-indole-2-carbonyl)amino]-4-methyl-pentanoyl]amino]carbamate (1.3 g, compound 49a) was obtained as a yellow solid. MS obsd. (ESI$^+$) [(M–C$_4$H$_8$+H)$^+$]: 363.2.

Step 2: Preparation of 4-methoxy-N-[(1S)-1-(hydrazinecarbonyl)-3-methyl-butyl]-1H-indole-2-carboxamide

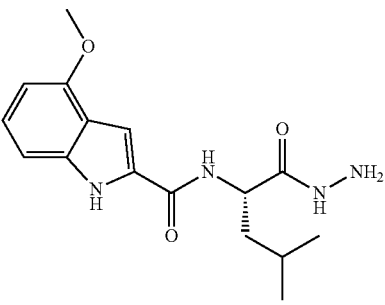

49b

Compound 49b was prepared in analogy to Example 1, Step 2 by using tert-Butyl N-[[(2S)-2-[(4-methoxy-1H-indole-2-carbonyl)amino]-4-methyl-pentanoyl]amino]carbamate (1.3 g, compound 49a) instead of tert-butyl N-[[2-(benzyloxycarbonylamino)acetyl]amino]carbamate (compound 1a). 4-Methoxy-N-[(1S)-1-(hydrazinecarbonyl)-3-methyl-butyl]-1H-indole-2-carboxamide (428 mg, Compound 49b) was obtained as a yellow solid. MS obsd. (ESI$^+$) [(M+H)$^+$]: 319.1.

Step 3: Preparation of N-[(1S)-1-[[(3-amino-3-oxo-propyl)amino]carbamoyl]-3-methyl-butyl]-4-methoxy-1H-indole-2-carboxamide

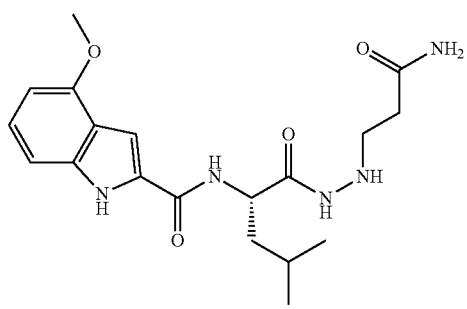

49c

Compound 49c was prepared in analogy to Example 1, Step 3 by using 4-methoxy-N-[(1S)-1-(hydrazinecarbonyl)-3-methyl-butyl]-1H-indole-2-carboxamide (100 mg, Compound 49b) instead of benzyl(2-hydrazinyl-2-axo-ethyl)carbamate (compound 1b). N-[(1S)-1-[[(3-Amino-3-oxo-propyl)amino]carbamoyl]-3-methyl-butyl]-4-methoxy-1H-indole-2-carboxamide (100 mg, compound 49c) was obtained as a yellow oil. MS obsd. (ESI$^+$) [(M+H)$^+$]: 390.4

Step 4: Preparation of 4-methoxy-N-[(1S)-1-[[(3-amino-3-oxo-propyl)-(2-chloro-2-fluoro-acetyl)amino]carbamoyl]-3-methyl-butyl]-1H-indole-2-carboxamide

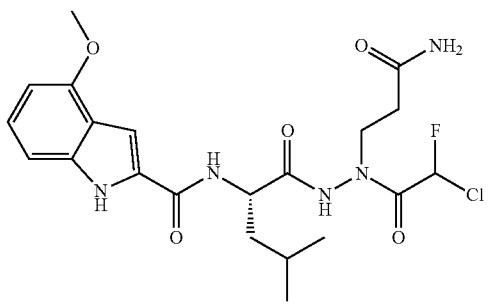

49

The title compound was prepared in analogy to Example 4 by using (S)—N-(1-(2-(3-amino-3-oxo-propyl)hydrazinyl)-4-methyl-1-oxo-pentan-2-yl)-4-methoxy-1H-indole-2-carboxamide (50.0 mg, compound 49c) and 2-chloro-2-fluoro-acetic acid instead of benzyl N-[(1S)-1-[[(3-amino-3-oxo-propyl)amino]carbamoyl]-3-methyl-butyl]carbamate (compound 2c) and 2-chloropropanoic acid. N-((2S)-1-(2-(3-Amino-3-oxo-propyl)-2-(2-chloro-2-fluoroacetyl)hydrazinyl)-4-methyl-1-oxo-pentan-2-yl)-4-methoxy-1H-indole-2-carboxamide (6.1 mg, Example 49) was obtained as a white solid. $^1$H NMR (400 MHz, CDCl$_3$) δ ppm: 10.09 (br. s, 1H), 7.16-7.20 (m, J=7.6 Hz, 2H), 7.05-6.94 (m, 1H), 6.64, (br. s, 1H), 6.46 (d, J=7.6 Hz, 1H), 6.35-6.15 (m, 1H), 4.63-4.68 (m, 1H), 3.29-4.25 (m, 5H), 2.12-2.66 (m, 2H), 1.62-1.87 (m, 3H), 0.64-1.11 (m, 6H). MS obsd. (ESI$^+$) [(M+H)$^+$]: 484.0.

Example 50

N-[(1S)-1-[[(2-Chloroacetyl)-[3-(methylamino)-3-oxo-propyl]amino]carbamoyl]-3-methyl-butyl]-N-methyl-1H-indole-2-carboxamide

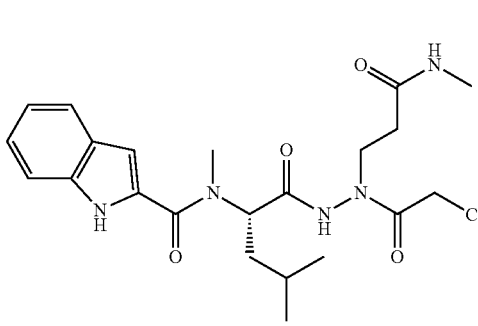

50

Step 1: Preparation of (S)-tert-butyl methyl(4-methyl-1-(2-(3-(methylamino)-3-oxo-propyl)hydrazinyl)-1-oxo-pentan-2-yl)carbamate

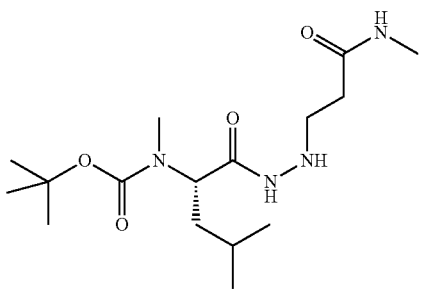

50a

Compound 50a was prepared in analogy to Example 1, Step 3 by using of (S)-tert-butyl(1-hydrazinyl-4-methyl-1-oxo-pentan-2-yl)(methyl)carbamate (900.0 mg, compound 40b) and N-methylprop-2-enamide (Bidepharm) instead of benzyl(2-hydrazinyl-2-axo-ethyl)carbamate (compound 1b) and acrylamide. (S)-tert-Butyl methyl(4-methyl-1-(2-(3-(methylamino)-3-oxo-propyl)hydrazinyl)-1-oxo-pentan-2-yl)carbamate (160 mg, compound 50a) was obtained as a colorless oil. MS obsd. (ESI$^+$) [(M+H)$^+$]: 345.1.

Step 2: Preparation of (S)-tert-butyl(1-(2-(2-chloro-acetyl)-2-(3-(methylamino)-3-oxo-propyl)hydrazinyl)-4-methyl-1-oxo-pentan-2-yl)(methyl)carbamate

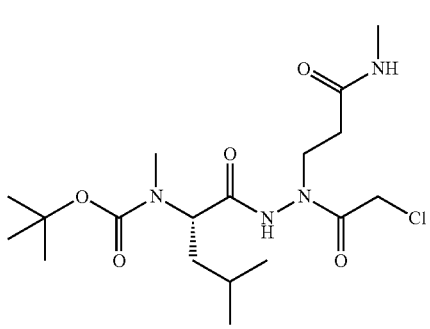

50b

Compound 50d was prepared in analogy to Example 1, Step 4 by using (S)-tert-butyl methyl(4-methyl-1-(2-(3-(methylamino)-3-oxo-propyl)hydrazinyl)-1-oxo-pentan-2-yl)carbamate (160 mg, compound 50a) instead of benzyl N-[2-[2-(3-amino-3-oxo-propyl)hydrazino]-2-axo-ethyl] carbamate (compound 1c). (S)-tert-Butyl(1-(2-(2-chloroacetyl)-2-(3-(methylamino)-3-oxo-propyl)hydrazinyl)-4-methyl-1-oxo-pentan-2-yl)(methyl)carbamate (180 mg, compound 50b) was obtained as a colorless oil. MS obsd. (ESI⁺) [(M+H)⁺]: 421.4.

Step 3: Preparation of (S)-3-(1-(2-chloroacetyl)-2-(4-methyl-2-(methylamino)pentanoyl)hydrazinyl)-N-methylpropanamide

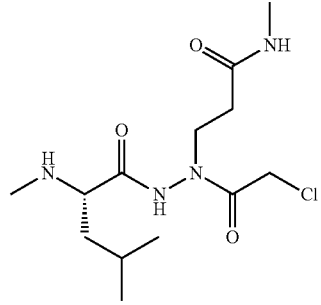

50c

Compound 50c was prepared in analogy to Example 27, step 1 by using ((S)-tert-butyl(1-(2-(2-chloroacetyl)-2-(3-(methylamino)-3-oxo-propyl)hydrazinyl)-4-methyl-1-oxo-pentan-2-yl)(methyl)carbamate (90 mg, compound 50b) instead of N-[(1S)-1-[[(3-amino-3-oxo-propyl)-(2-chloroacetyl)amino]carbamoyl]-3-methyl-butyl]carbamate (Example 26). (S)-3-(1-(2-Chloroacetyl)-2-(4-methyl-2-(methylamino)pentanoyl)hydrazinyl)-N-methylpropanamide (60 mg, compound 50c) was obtained as a colorless oil.

Step 4: Preparation of (S)—N-(1-(2-(2-chloroacetyl)-2-(3-(methylamino)-3-oxo-propyl)hydrazinyl)-4-methyl-1-oxo-pentan-2-yl)-N-methyl-1H-indole-2-carboxamide

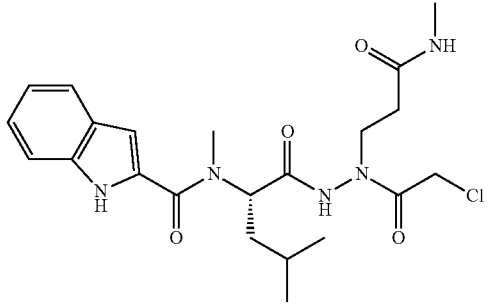

50

The title compound was prepared in analogy to Example 27, Step 2 by using (S)-3-(1-(2-chloroacetyl)-2-(4-methyl-2-(methylamino)pentanoyl)hydrazinyl)-N-methylpropanamide (60 mg, compound 50c)) and 1H-indole-2-carboxylic acid instead of (S)-3-(2-(2-amino-4-methylpentanoyl)-1-(2-chloroacetyl)hydrazinyl)propanamide; hydrochloride (compound 27a) and 4-methoxy-1H-indole-2-carboxylic acid. (S)—N-(1-(2-(2-Chloroacetyl)-2-(3-(methylamino)-3-oxo-propyl)hydrazinyl)-4-methyl-1-oxo-pentan-2-yl)-N-methyl-1H-indole-2-carboxamide (9.7 mg, Example 50) was obtained as a white solid. ¹H NMR (400 MHz, CDCl₃) δ ppm: 9.83 (br. s, 1H), 9.49 (br. s, 1H), 7.68 (d, J=8.4 Hz, 1H), 7.44 (d, J=8.8 Hz, 1H), 7.32 (t, J=7.2 Hz, 1H), 7.16 (t, J=7.6 Hz, 1H), 6.93 (s, 1H), 5.77 (br. s, 1H), 5.21 (t, J=7.6 Hz, 1H), 3.95-4.15 (m, 2H), 3.36 (s, 3H), 2.77 (d, J=4.8 Hz, 3H), 2.35-2.65 (m, 2H), 1.89 (t, J=7.6 Hz, 2H), 1.69-1.66 (m, 1H), 1.35-1.21 (m, 2H), 1.03 (d, J=6.4 Hz, 3H), 0.98 (d, J=6.4 Hz, 3H). MS obsd. (ESI⁺) [(M+H)⁺]: 464.1.

Example 51

N-[(1S)-1-[[(2-Chloroacetyl)-[(2-oxo-pyrrolidin-3-yl)methyl]amino]carbamoyl]-3-methyl-butyl]-1H-indole-2-carboxamide

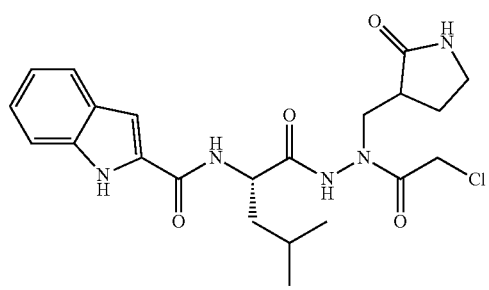

51

The title compound was prepared in analogy to Example 1, step 4 by using N-((2S)-4-methyl-1-oxo-1-(2-((2-oxo-pyrrolidin-3-yl)methyl)hydrazinyl) pentan-2-yl)-1H-indole-2-carboxamide (80 mg, compound 38d) instead of benzyl N-[2-[2-(3-amino-3-oxo-propyl)hydrazino]-2-axo-ethyl] carbamate (compound 1c). N-[(1S)-1-[[(2-chloroacetyl)-[(2-oxo-pyrrolidin-3-yl)methyl]amino]carbamoyl]-3-methyl-butyl]-1H-indole-2-carboxamide (70.8 mg, Example 51) was obtained as a white solid.

Separation of compound of Example 51 by chiral SFC separation afford Example 51-A (faster eluting, 20.1 mg) and Example 51-B (slower eluting, 23.8 mg) as a white solid with 40% MeOH+ACN(0.05% DEA) (0.05% DEA)/CO₂ on Chiralpak IC-3 column.

N-[(1S)-1-[[(2-chloroacetyl)-[[(3S)-2-oxo-pyrrolidin-3-yl]methyl]amino]carbamoyl]-3-methyl-butyl]-1H-indole-2-carboxamide and N-[(1S)-1-[[(2-chloroacetyl)-[[(3R)-2-oxo-pyrrolidin-3-yl]methyl]amino]carbamoyl]-3-methyl-butyl]-1H-indole-2-carboxamide (51-A and 51-B)

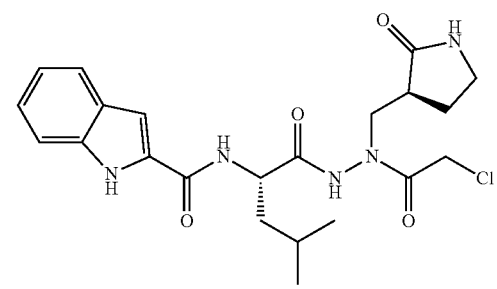

107

-continued

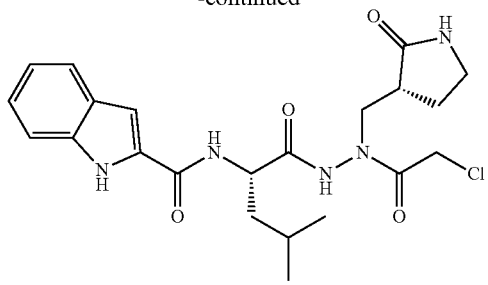

Example 51-A: $^1$H NMR (400 MHz, DMSO-$d_6$) δ ppm: 11.60 (m, 1H), 10.52-10.84 (m, 1H), 8.67 (br. s, 1H), 7.70-7.74 (m, 1H), 7.62 (d, J=7.6 Hz, 1H), 7.43 (d, J=8.4 Hz, 1H), 7.29 (d, J=1.6 Hz, 1H), 7.16-7.20 (m, 1H), 7.02-7.05 (m, 1H), 4.30-4.57 (m, 2H), 4.06-4.16 (m, 1H), 3.77-3.90 (m, 1H), 3.23-3.27 (m, 1H), 3.14 (br. s, 2H), 2.44-2.50 (m, 1H), 2.05-2.11 (m, 1H), 1.72-1.79 (m, 3H), 1.57-1.59 (m, 1H), 0.94 (dd, J=10.0, 20.0 Hz, 6H). MS obsd. (ESI$^+$) [(M+H)$^+$]: 462.3.

Example 51-B: $^1$H NMR (400 MHz, DMSO-$d_6$) δ ppm: 11.60 (m, 1H), 10.58-10.73 (m, 1H), 8.65 (d, J=6.8 Hz, 1H), 7.71 (br s, 1H), 7.62 (d, J=8.0 Hz, 1H), 7.43 (d, J=8.4 Hz, 1H), 7.29 (d, J=1.2 Hz, 1H), 7.16-7.20 (m, 1H), 7.02-7.06 (m, 1H), 4.31-4.46 (m, 2H), 4.08-4.15 (m, 1H), 3.78-3.90 (m, 1H), 3.28-3.30 (m, 1H), 3.08-3.19 (m, 2H), 2.38-2.43 (m, 1H), 2.16-2.23 (m, 1H), 1.73-1.82 (m, 3H), 1.51-1.59 (m, 1H), 0.94 (dd, J=6.4, 19.6 Hz, 6H). MS obsd. (ESI$^+$) [(M+H)$^+$]: 462.3.

Example 52

N-[(1S)-1-[[(3-amino-3-oxo-propyl)-(2-chloroacetyl)amino]carbamoyl]-3-methyl-butyl]-1H-pyrrolo[3,2-c]pyridine-2-carboxamide

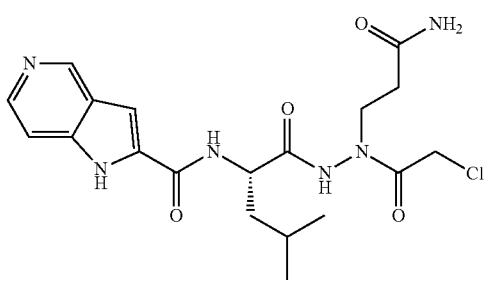

52

The title compound was prepared in analogy to Example 27, Step 2 by using 1H-pyrrolo[3,2-c]pyridine-2-carboxylic acid (38.4 mg) instead of 4-methoxy-1H-indole-2-carboxylic acid. N-[(1S)-1-[[(3-Amino-3-oxo-propyl)-(2-chloroacetyl)amino]carbamoyl]-3-methyl-butyl]-1H-pyrrolo[3,2-c]pyridine-2-carboxamide (23.2 mg, Example 52) was obtained as a yellow solid. $^1$H NMR (400 MHz, DMSO-$d_6$) δ ppm: 13.33 (s, 1H), 10.90-10.92 (m, 1H), 9.50 (s, 1H), 9.30 (d, J=6.8 Hz, 1H), 8.48 (s, 1H), 7.72-8.02 (m, 2H), 7.40 (s, 1H), 6.89 (s, 1H), 4.26-4.67 (m, 2H), 4.01-4.16 (m, 1H), 3.63-3.93 (m, 2H), 2.30-2.33 (m, 2H), 1.72-1.95 (m, 2H), 1.56-1.63 (m, 1H), 0.90-0.99 (m, 6H). MS obsd. (ESI$^+$) [(M+H)$^+$]: 436.9.

108

Example 53

N-[(1S)-1-[[(3-amino-3-oxo-propyl)-[(2S)-2-chloro-2-fluoro-acetyl]amino]carbamoyl]-3-methyl-butyl]-4-chloro-1H-indole-2-carboxamide and N-[(1S)-1-[[(3-amino-3-oxo-propyl)-[(2R)-2-chloro-2-fluoro-acetyl]amino]carbamoyl]-3-methyl-butyl]-4-chloro-1H-indole-2-carboxamide (Example 53-A and Example 53-B)

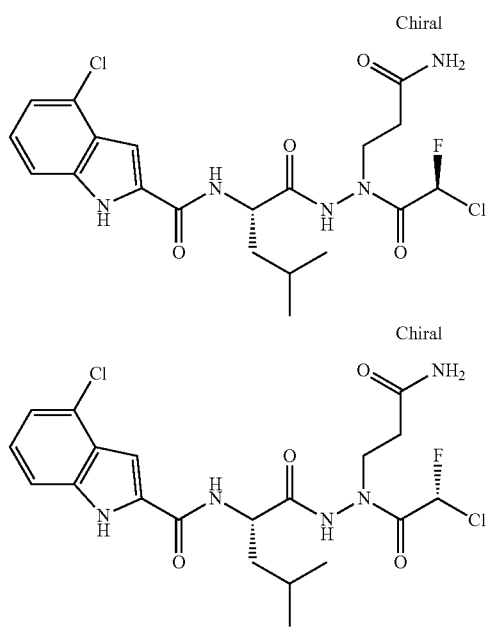

Example 53-A and Example 53-B

Step 1: Preparation of tert-butyl N-[(1S)-1-[[(3-amino-3-oxo-propyl)-(2-chloro-2-fluoro-acetyl)amino]carbamoyl]-3-methyl-butyl]carbamate

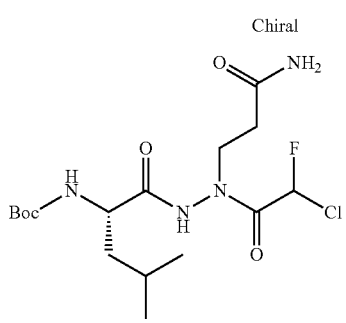

53a

To a solution of (S)-tert-butyl(1-(2-(3-amino-3-oxopropyl)hydrazinyl)-4-methyl-1-oxopentan-2-yl)carbamate (3.0 g, 26c), (2-chloro-2-fluoro-acetyl)oxysodium (6.38 g, 47.41 mmol) and DIEA (3.68 g, 28.45 mmol) in DMF (60 mL) was added T$_3$P (9.05 g, 14.22 mmol, 50% in EtOAc) at 0° C. After stirred at 20° C. for 12 hrs, the reaction mixture was poured into ice-water (50 mL) and extracted with EtOAc (100 mL) three times. The combined organic phase was washed with brine (60 mL) and over anhydrous Na₂SO₄ and concentrated in vacuo. The residue was purified by silica gel column (eluted with EtOAc:MeOH=1:0~100:1) to afford tert-butyl N-[(1S)-1-[[(3-amino-3-oxo-propyl)-(2-chloro-2-fluoro-acetyl)amino]carbamoyl]-3-methyl-butyl]carbamate (1.3 g, compound 53a) as a white solid. MS obsd. (ESI⁺) [(M+H)⁺]: 411.1.

Step 2: Preparation of 3-[[[(2S)-2-amino-4-methyl-pentanoyl]amino]-(2-chloro-2-fluoro-acetyl)amino]propanamide

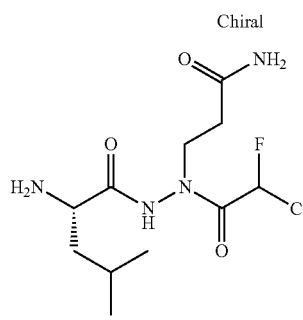

53b

To a solution of tert-butyl N-[(1S)-1-[[(3-amino-3-oxo-propyl)-(2-chloro-2-fluoro-acetyl)amino]carbamoyl]-3-methyl-butyl]carbamate (200.0 mg, compound 53a) in DCM (2 mL) was added TFA (0.5 mL). After stirred at 20° C. for 1 hr, the reaction mixture was concentrated in vacuo to afford 3-[[[(2S)-2-amino-4-methyl-pentanoyl]amino]-(2-chloro-2-fluoro-acetyl)amino]propanamide (151 mg, compound 53b) as a yellow oil.

Step 3: Preparation of N-((2S)-1-(2-(3-amino-3-oxopropyl)-2-(2-chloro-2-fluoroacetyl)hydrazinyl)-4-methyl-1-oxopentan-2-yl)-4-chloro-1H-indole-2-carboxamide

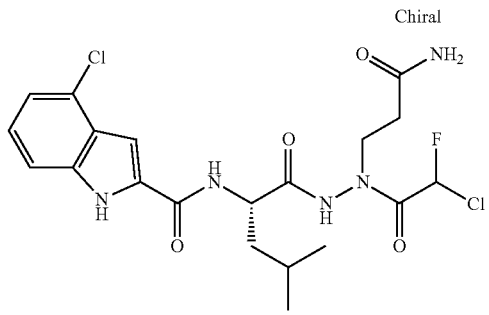

53

To a solution of 3-[[[(2S)-2-amino-4-methyl-pentanoyl]amino]-(2-chloro-2-fluoro-acetyl)amino]propanamide (74.61 mg, 53b), 4-chloro-1H-indole-2-carboxylic acid (46.97 mg, Bidepharm, CAS number: 24621-73-6) and DIEA (92.92 mg) in DMF (1 mL) was added T₃P (198.6 mg) at 0° C. After stirred at 25° C. for 2 hrs, the reaction mixture was purified by prep-HPLC) to afford N-((2S)-1-(2-(3-amino-3-oxopropyl)-2-(2-chloro-2-fluoroacetyl)hydrazinyl)-4-methyl-1-oxopentan-2-yl)-4-chloro-1H-indole-2-carboxamide (30 mg, Example 53) as a white solid.

Separation of compound of compound 53 by chiral SFC separation afford Example 53-A (faster eluting, 6.3 mg) and Example 53-B (slower eluting, 4.5 mg) as a white solid with 40% MeOH+ACN(0.05% DEA) (0.05% DEA)/CO₂ on Chiralpak IC-3 column.

Example 53-A: ¹H NMR (400 MHz, CD₃OD) δ ppm: 7.39 (d, J=8.4 Hz, 1H). 7.34 (s, 1H), 7.18 (t, J=8.0 Hz, 1H), 7.09 (d, J=7.6 Hz, 1H), 6.88 (d, J=50.0 Hz, 1H), 4.43-4.46 (m, 1H), 3.93-3.97 (m, 1H), 3.66-3.71 (m, 1H), 2.48-2.56 (m, 2H), 1.84-1.96 (m, 2H), 1.65-1.72 (m, 1H), 1.07 (d, J=6.4 Hz, 3H), 1.03 (d, J=6.4 Hz, 3H). MS obsd. (ESI⁺) [(M+H)⁺]: 488.1. SFC: RT=1.664 min, ee %=100%.

Example 53-B: ¹H NMR (400 MHz, CD₃OD) δ ppm: 7.40 (d, J=8.0 Hz, 1H). 7.36 (s, 1H), 7.19 (t, J=8.0 Hz, 1H), 7.09 (d, J=7.6 Hz, 1H), 6.48-6.98 (m, 1H), 4.54-5.58 (m, 1H), 3.92-3.96 (m, 1H), 3.70-3.76 (m, 1H), 2.47-2.63 (m, 2H), 1.73-1.93 (m, 3H), 1.06 (d, J=6.0 Hz, 3H), 1.00 (d, J=6.0 Hz, 3H). MS obsd. (ESI⁺) [(M+H)⁺]: 488.3 SFC: RT=1.862 min, ee %=97.7%.

Example 54-A and Example 54-B

4-Methoxy-N-[rac-(1S)-1-[[(3-amino-3-oxo-propyl)-[(2S)-2-chloro-2-fluoro-acetyl]amino]carbamoyl]-3-methyl-butyl]-1H-indole-2-carboxamide and 4-methoxy-N-[rac-(1S)-1-[[(3-amino-3-oxo-propyl)-[(2R)-2-chloro-2-fluoro-acetyl]amino]carbamoyl]-3-methyl-butyl]-1H-indole-2-carboxamide

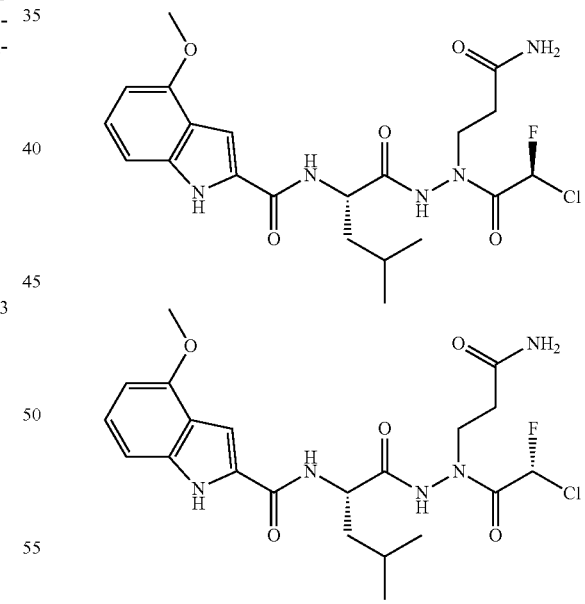

Example 54-A and Example 54-B

The title compound was prepared in analogy to Example 53, Step 3 by using 4-methoxy-1H-indole-2-carboxylic acid instead of 4-chloro-1H-indole-2-carboxylic acid. N-[(1S)-1-[[(3-amino-3-oxo-propyl)-(2-chloro-2-fluoro-acetyl)amino]carbamoyl]-3-methyl-butyl]-4-methoxy-1H-indole-2-carboxamide (compound 54) was obtained as a yellow solid.

Separation of compound of compound 54 by chiral SFC separation afford Example 54-A (faster eluting, 14 mg) and Example 54-B (slower eluting, 10.7 mg) as a white solid with mobile phase: [0.1% NH₃H₂O MEOH]; 40%-40%, 70 min on DAICEL CHIRALCEL OJ column.

Example 54-A: ¹H NMR (400 MHz, CDCl₃) δ ppm: 10.30-10.11 (m, 2H), 7.37-7.27 (m, 1H), 7.16 (s, 2H), 7.05-6.97 (m, 1H), 6.70-6.52 (m, 1H), 6.51-6.12 (m, 2H), 4.73-4.67 (m, 1H), 4.05-3.96 (m, 1H), 3.95 (s, 3H), 3.68-3.49 (m, 1H), 2.53-2.31 (m, 2H), 1.79-1.72 (m, 2H), 1.27-1.23 (m, 1H), 0.99-0.90 (m, 6H). MS obsd. (ESI⁺) [(M+H)⁺]: 484.2 SFC: RT=0.972 min, ee %=100%

Example 54-B: ¹H NMR (400 MHz, CD₃Cl₃) δ ppm: 10.50-9.86 (m, 1H), 7.27-7.20 (m, 2H), 7.03 (br. s, 1H), 6.88-5.87 (m, 3H), 4.69-4.67 (m, 1H), 4.32-3.03 (m, 5H), 2.58-2.22 (m, 2H), 1.83-1.69 (m, 3H), 1.00-0.87 (m, 6H). MS obsd. (ESI⁺) [(M+H)⁺]: 441.3. SFC: RT=2.503 min, ee %=97.734%

Example 56-A and Example 56-B

N-[(1S)-2-[2-(3-amino-3-oxo-propyl)-2-[(2R)-2-chloro-2-fluoro-acetyl]hydrazino]-1-(cyclohexylmethyl)-2-axo-ethyl]-4-methoxy-1H-indole-2-carboxamide and N-[(1S)-2-[2-(3-amino-3-oxo-propyl)-2-[(2S)-2-chloro-2-fluoro-acetyl]hydrazino]-1-(cyclohexylmethyl)-2-axo-ethyl]-4-methoxy-1H-indole-2-carboxamide

56-A

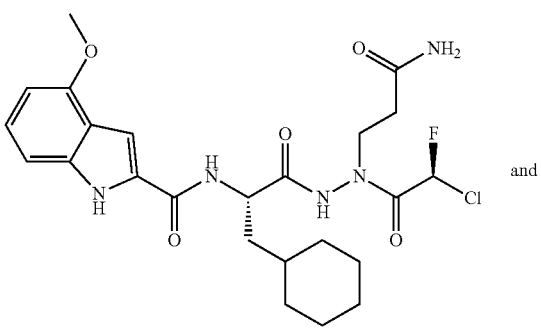

and

56-B

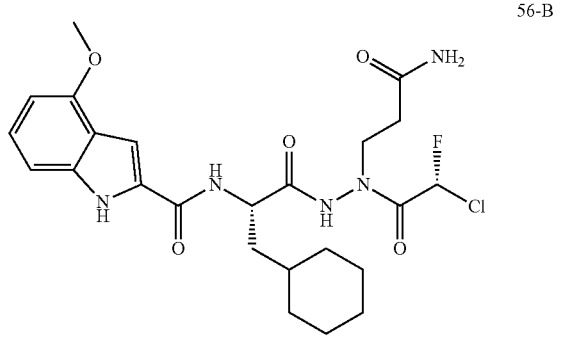

Step 1: Preparation of tert-butyl N-[(1S)-2-[2-(3-amino-3-oxo-propyl)-2-(2-chloro-2-fluoro-acetyl)hydrazino]-1-(cyclohexylmethyl)-2-axo-ethyl]carbamate

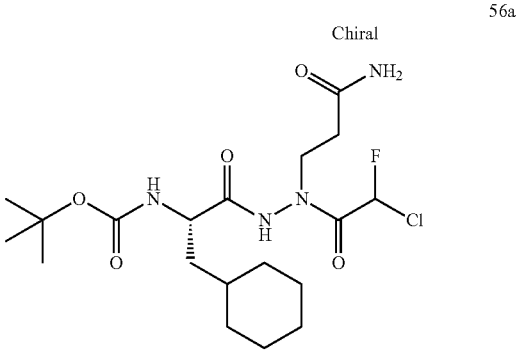 [SMILES: CC(C)(C)OC(=O)N[C@@H](CC1CCCCC1)C(=O)NN(CCC(N)=O)C(=O)C(F)Cl]

Compound 56a was prepared in analogy to Example 53, step 1 by using tert-butyl N-[(1S)-2-[2-(3-amino-3-oxo-propyl)hydrazino]-1-(cyclohexylmethyl)-2-axo-ethyl]carbamate (2.0 g, compound 32c) instead of (S)-tert-butyl(1-(2-(3-amino-3-oxopropyl)hydrazinyl)-4-methyl-1-oxopentan-2-yl)carbamate (26c). tert-Butyl N-[(1S)-2-[2-(3-amino-3-oxo-propyl)-2-(2-chloro-2-fluoro-acetyl)hydrazino]-1-(cyclohexylmethyl)-2-axo-ethyl]carbamate (470 mg, 56a) was obtained as a white solid MS obsd. (ESI⁺) [(M+H)⁺]: 451.42.

Step 2: Preparation of 3-(2-((S)-2-amino-3-cyclohexylpropanoyl)-1-(2-chloro-2-fluoroacetyl)hydrazinyl)propanamide

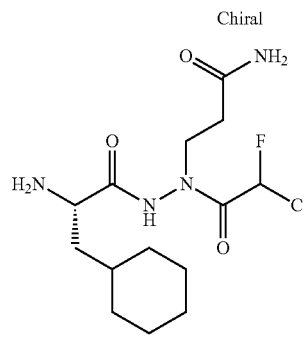

Compound 56b was prepared in analogy to Example 53, step 2 by using tert-butyl N-[(1S)-2-[2-(3-amino-3-oxo-propyl)-2-(2-chloro-2-fluoro-acetyl)hydrazino]-1-(cyclohexylmethyl)-2-axo-ethyl]carbamate (470 mg, 56a) instead of tert-butyl N-[(1S)-1-[[(3-amino-3-oxo-propyl)-(2-chloro-2-fluoro-acetyl)amino]carbamoyl]-3-methyl-butyl]carbamate (53a). 3-(2-((S)-2-amino-3-cyclohexylpropanoyl)-1-(2-chloro-2-fluoroacetyl)hydrazinyl)propanamide (compound 56b, 370 mg) was obtained as as a yellow oil. MS obsd. (ESI⁺) [(M+H)⁺]: 351.2.

Step 3: Preparation of N-[(1S)-2-[2-(3-amino-3-oxo-propyl)-2-[(2R)-2-chloro-2-fluoro-acetyl]hydrazino]-1-(cyclohexylmethyl)-2-axo-ethyl]-4-methoxy-1H-indole-2-carboxamide and N-[(1S)-2-[2-(3-amino-3-oxo-propyl)-2-[(2S)-2-chloro-2-fluoro-acetyl]hydrazino]-1-(cyclohexylmethyl)-2-axo-ethyl]-4-methoxy-1H-indole-2-carboxamide

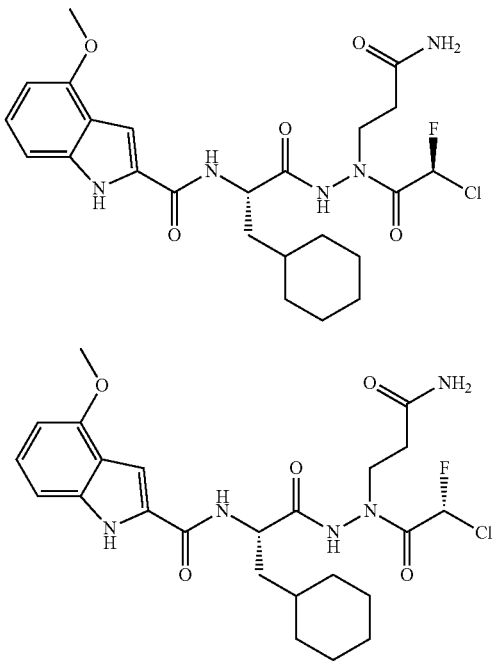

56-A

56-B

The title compounds were prepared in analogy to Example 53, Step 3 by using 4-methoxy-1H-indole-2-carboxylic acid and 3-(2-((S)-2-amino-3-cyclohexylpropanoyl)-1-(2-chloro-2-fluoroacetyl)hydrazinyl)propanamide (compound 56b) instead of 4-chloro-1H-indole-2-carboxylic acid and 3-[[[(2S)-2-amino-4-methyl-pentanoyl]amino]-(2-chloro-2-fluoro-acetyl)amino]propanamide (53b). N-[(1S)-2-[2-(3-Amino-3-oxo-propyl)-2-(2-chloro-2-fluoro-acetyl)hydrazino]-1-(cyclohexylmethyl)-2-axo-ethyl]-4-methoxy-1H-indole-2-carboxamide (mg, compound 56) was obtained as a yellow solid.

Separation of compound 56 by chiral prep-SFC afforded Example 56-A (faster eluting, 20.3 mg) and Example 56-B (slower eluting, 8.4 mg) as a white solid with on column as a white solid with mobile phase: [0.1% NH₃H₂O MEOH]; 40%-40%, 70 min on DAICEL CHIRALCEL OJ column.

Example 56-A: ¹H NMR (400 MHz, DMSO-d₆) δ ppm 11.62-11.64 (m, 1H), 10.76 (d, J=27.2 Hz, 1H), 8.59-8.65 (m, 1H), 7.40-7.48 (m, 2H), 7.11 (t, J=8.0 Hz, 1H), 6.91-7.03 (m, 1.7H), 6.66 (s, 0.3H), 6.50-6.55 (m, 1H), 4.39-4.50 (m, 1H), 3.70-3.88 (m, 4H), 3.45-3.51 (m, 1H), 2.50-2.57 (m, 2H), 1.52-1.84 (m, 6H), 1.06-1.50 (m, 5H), 0.79-1.01 (m, 2H). MS obsd. (ESI⁺) [(M+H)⁺]: 524.4. SFC: RT=1.661 min, ee %=100%.

Example 56-B

¹H NMR (400 MHz, CD₃OD) δ ppm: 7.31 (s, 1H), 7.15 (t, J=8.0 Hz, 1H), 7.04 (d, J=8.0 Hz, 1H), 6.87 (d, J=50.0 Hz, 1H), 6.52 (d, J=8.0 Hz, 1H), 4.44-4.52 (m, 1H), 3.80-4.20 (m, 4H), 3.63-3.76 (m, 1H), 2.48-2.59 (m, 2H), 1.67-1.90 (m, 6H), 1.18-1.58 (m, 5H), 0.97-1.12 (m, 2H) MS obsd. (ESI⁺) [(M+H)⁺]: 524.4. SFC: RT=1.922 min, ee %=100%.

Example 57-A and Example 57-B 5-fluoro-N-[rac-(1S)-1-[[(3-amino-3-oxo-propyl)-[rac-(2S)-2-chloro-2-fluoro-acetyl]amino]carbamoyl]-3-methyl-butyl]-1H-indole-2-carboxamide and 5-fluoro-N-[rac-(1S)-1-[[(3-amino-3-oxo-propyl)-[rac-(2R)-2-chloro-2-fluoro-acetyl]amino]carbamoyl]-3-methyl-butyl]-1H-indole-2-carboxamide

57-A

57-B

The title compound was prepared in analog to Example 53, step 3 by using 5-fluoro-1H-indole-2-carboxylic acid (Wuxi catalog, CAS Number: 399-76-8) instead of 4-chloro-1H-indole-2-carboxylic acid. 5-Fluoro-N-[rac-(1S)-1-[[(3-amino-3-oxo-propyl)-(2-chloro-2-fluoro-acetyl)amino]carbamoyl]-3-methyl-butyl]-1H-indole-2-carboxamide was obtained (50 mg, compound 57) was obtained as a white solid.

Separation of compound 57 by chiral prep-SFC afforded Example 57-A (faster eluting, 19.1 mg) and Example 56-B (slower eluting, 20.7 mg) as a white solid with Neu-MeOH B:30 Gradient Time (min): 4.2; 25 FlowRate (ml/min): 60 on DAICEL CHIRALCEL OJ-H column.

Example 57-A: ¹H NMR (400 MHz, CD₃OD) δ ppm: 7.42 (q, J=4.4 Hz, 1H), 7.29 (dd, J=3.2 Hz, 9.6 Hz, 1H), 7.18 (s, 1H), 7.01 (td, J=2.4 Hz, 9.2 Hz, 1H), 6.76-6.89 (d, J=50.4 Hz, 1H), 4.43-4.45 (m, 1H), 3.94-4.10 (m, 1H), 3.61-3.69 (m, 1H), 2.44-2.55 (m, 2H), 1.81-1.92 (m, 2H), 1.69-1.72 (m, 1H), 1.06 (d, J=6.4 Hz, 3H), 1.02 (d, J=6.4 Hz, 3H). MS obsd. (ESI⁺) [(M+H)⁺]: 472.3.

Example 57-B: ¹H NMR (400 MHz, CD₃OD) δ ppm. 7.43 (q, J=4.4 Hz, 1H), 77.29 (dd, J=2.4 Hz, 9.2 Hz, 1H), 7.19 (s, 1H), 7.02 (td, J=2.4 Hz, 9.2 Hz, 1H), 6.48-6.90 (m, 1H), 4.54-4.57 (m, 1H), 3.91-3.96 (m, 1H), 3.65-3.72 (m, 1H), 2.46-2.66 (m, 2H), 1.69-1.91 (m, 3H), 1.06 (d, J=6.4 Hz, 3H), 1.02 (d, J=6.4 Hz, 3H). MS obsd. (ESI⁺) [(M+H)⁺]: 472.4.

Example 58-A and Example 58-B

5-Chloro-N-[rac-(1S)-1-[[(3-amino-3-oxo-propyl)-[rac-(2S)-2-chloro-2-fluoro-acetyl]amino]carbamoyl]-3-methyl-butyl]-1H-indole-2-carboxamide and 5-chloro-N-[rac-(1S)-1-[[(3-amino-3-oxo-propyl)-[rac-(2R)-2-chloro-2-fluoro-acetyl]amino]carbamoyl]-3-methyl-butyl]-1H-indole-2-carboxamide

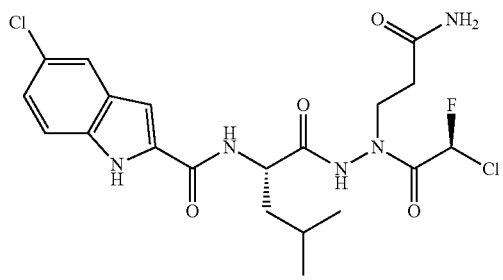

58-A and

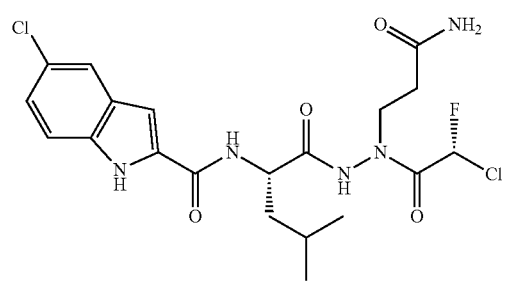

58-B

The title compound was prepared in analogy to Example 53, Step 3 by using 5-chloro-1H-indole-2-carboxylic acid instead of 4-chloro-1H-indole-2-arboxylic acid. 5-Chloro-N-[rac-(1S)-1-[[(3-amino-3-oxo-propyl)-(2-chloro-2-fluoro-acetyl)amino]carbamoyl]-3-methyl-butyl]-1H-indole-2-carboxamide (10 mg) was obtained as a white solid.

Separation of compound 58 by chiral prep-SFC afforded Example 58-A (faster eluting, 17.8 mg) and Example 58-B (slower eluting, 10 mg) as a white solid with Neu-MeOH; MeOH %: 30%~30%; Flow Rate (mL/min): 60 on DAICEL CHIRALCEL OJ-H column.

Example 58-A: $^1$H NMR (400 MHz, CD$_3$OD) δ ppm: 7.62 (d, J=1.6 Hz, 1H), 7.41 (d, J=8.8 Hz, 1H), 7.17-7.22 (m, 2H), 6.80 (d, J=50.0 Hz, 1H), 4.44-4.52 (m, 1H), 3.79-4.04 (m, 1H), 3.60-3.73 (m, 1H), 2.49-2.59 (m, 2H), 1.65-1.90 (m, 3H), 1.05 (d, J=6.4 Hz, 3H), 1.02 (d, J=6.4 Hz, 3H). MS obsd. (ESI$^+$) [(M+H)$^+$]: 488.4.

Example 58-B: $^1$H NMR (400 MHz, CD$_3$OD) δ ppm: 7.62 (d, J=2.8 Hz, 1H), 7.42 (d, J=8.8 Hz, 1H), 7.17-7.21 (m, 2H), 6.47-6.95 (m, 1H), 4.54-4.57 (m, 1H), 3.77-4.05 (m, 1H), 3.62-3.76 (m, 1H), 2.47-2.63 (m, 2H), 1.71-1.89 (m, 3H), 1.05 (d, J=6.4 Hz, 3H), 1.02 (d, J=6.0 Hz, 3H). MS obsd. (ESI$^+$) [(M+H)$^+$]: 488.3.

Example 59-A and Example 59-B

N-[(1S)-2-[2-(3-amino-3-oxo-propyl)-2-[(2S)-2-chloro-2-fluoro-acetyl]hydrazino]-1-(cyclohexylmethyl)-2-axo-ethyl]-1H-indole-2-carboxamide and N-[(1S)-2-[2-(3-amino-3-oxo-propyl)-2-[(2R)-2-chloro-2-fluoro-acetyl]hydrazino]-1-(cyclohexylmethyl)-2-axo-ethyl]-1H-indole-2-carboxamide

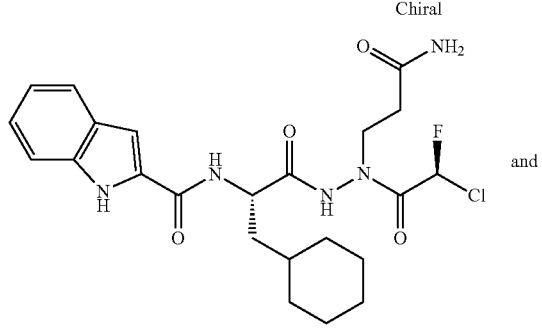

59-A
Chiral and

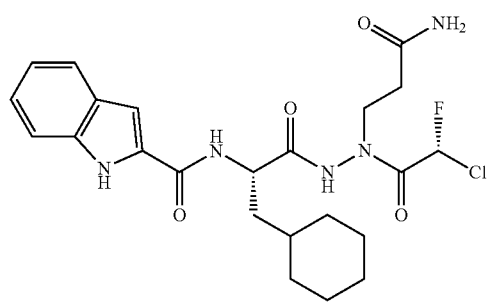

59-B
Chiral

The title compound was prepared in analogy to Example 53, Step 3 by using 1H-indole-2-carboxylic acid and 3-(2-((S)-2-amino-3-cyclohexylpropanoyl)-1-(2-chloro-2-fluoro-acetyl)hydrazinyl)propanamide (compound 56b) instead of 4-chloro-1H-indole-2-carboxylic acid and 3-[[[(2S)-2-amino-4-methyl-pentanoyl]amino]-(2-chloro-2-fluoro-acetyl)amino]propanamide (53b). N-[(1S)-2-[2-(3-Amino-3-oxo-propyl)-2-(2-chloro-2-fluoro-acetyl)hydrazino]-1-(cyclohexylmethyl)-2-axo-ethyl]-1H-indole-2-carboxamide (20 mg, compound 59) was obtained as a yellow solid.

Separation of compound 59 by chiral SFC separation afforded Example 59-A (faster eluting, 20.3 mg) and Example 59-B (slower eluting, 8.4 mg) by prep-SFC with Neu-MeOH; MeOH %: 50%-50%; FlowRate (mL/min): 70 on DAICEL CHIRALCEL OJ column.

Example 59-A: $^1$H NMR (400 MHz, DMSO-d6) δ ppm: 11.60-11.62 (m, 1H), 10.71-10.79 (m, 1H), 8.68-8.71 (m, 1H), 7.63 (d, J=8.0 Hz, 1H), 7.45 (d, J=8.0 Hz, 1H), 7.45 (s, 1H), 7.30 (s, 1H), 7.19 (t, J=8.0 Hz, 1H), 7.04 (t, J=8.0 Hz, 1H), 6.51-6.98 (m, 2H), 4.47-4.48 (m, 1H), 3.72-3.89 (m, 1H), 3.45-3.52 (m, 1H), 2.32-2.41 (m, 2H), 1.55-1.85 (m, 7H), 1.35-1.48 (m, 1H), 1.11-1.25 (m, 3H), 0.79-1.02 (m, 2H). MS obsd. (ESI$^+$) [(M+H)$^+$]: 494.1. ee %=100%.

Example 59-B: $^1$H NMR (400 MHz, DMSO-d6) δ ppm: 11.59-11.62 (m, 1H), 11.05 (s, 1H), 8.69 (d, J=4.8 Hz, 1H), 7.63 (d, J=8.0 Hz, 1H), 7.43 (t, J=7.6 Hz, 2H), 7.31 (s, 1H), 7.19 (t, J=6.8 Hz, 1H), 7.04 (t, J=7.6 Hz, 1H), 6.79-6.98 (m, 2H), 4.31-4.52 (m, 1H), 3.75-3.89 (m, 1H), 3.39-3.49 (m, 1H), 2.27-2.41 (m, 2H), 1.55-1.92 (m, 7H), 1.42-1.54 (m, 1H), 1.11-1.28 (m, 3H), 0.88-1.02 (m, 2H). MS obsd. (ESI$^+$) [(M+H)$^+$]: 494.1. SFC: RT=2.002 min, ee %=100%

Example 60-A and Example 60-B 5-chloro-N-[rac-(1S)-1-[[(3-amino-3-axo-propyl)-[rac-(2S)-2-chloro-2-fluoro-acetyl]amino]carbamoyl]-3-methyl-butyl]-1H-benzimidazole-2-carboxamide and 5-chloro-N-[rac-(1S)-1-[[(3-amino-3-oxo-propyl)-[rac-(2R)-2-chloro-2-fluoro-acetyl]amino]carbamoyl]-3-methyl-butyl]-1H-benzimidazole-2-carboxamide

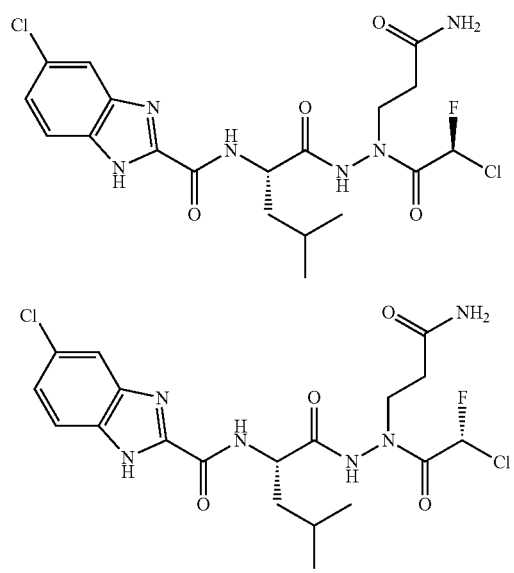

60-A and

60-B

The title compound was prepared in analogy to Example 53, Step 3 by using 5-chloro-1H-benzimidazole-2-carboxylic acid instead of 4-chloro-1H-indole-2-carboxylic acid. 5-Chloro-N-[rac-(1S)-1-[[(3-amino-3-oxo-propyl)-(2-chloro-2-fluoro-acetyl)amino]carbamoyl]-3-methyl-butyl]-1H-benzimidazole-2-carboxamide (20 mg, compound 60) was obtained as a yellow solid.

Separation of compound 60 by chiral SFC separation afforded Example 60-A (faster eluting, 3.1 mg) and Example 60-B (slower eluting, 5 mg) with Neu-ETOH; B %: 30-30%; FlowRate (ml/min): 60) on DAICEL CHIRALPAK AD-H column.

Example 60-A: $^1$H NMR (400 MHz, CD$_3$OD) δ ppm: 7.83-7.71 (m, 1H), 7.68-7.53 (m, 1H), 7.39-7.30 (m, 1H), 7.05-6.48 (m, 1H), 4.59-4.54 (m, 1H), 4.05-3.85 (m, 1H), 3.73-3.62 (m, 1H), 2.58-2.45 (m, 2H), 1.89-1.75 (m, 3H), 1.06 (d, J=6.0 Hz, 3H), 1.02 (d, J=6.0 Hz, 3H). MS obsd. (ESI$^+$) [(M+H)$^+$]: 489.0. SFC: RT=6.523 min, ee %=100%

Example 60-B: $^1$H NMR (400 MHz, CD$_3$OD) δ ppm: 7.75-7.52 (m, 2H), 7.34-7.31 (m, 1H), 6.92-6.75 (m, 1H), 4.55-4.45 (m, 1H), 4.02-3.82 (m, 1H), 3.71-3.60 (m, 1H), 2.57-2.47 (m, 2H), 1.92-1.73 (m, 3H), 1.06 (d, J=6.0 Hz, 3H), 1.02 (d, J=6.0 Hz, 3H). MS obsd. (ESI$^+$) [(M+H)$^+$]: 489.0. SFC: RT=6.199 min, ee %=100%

Example 62

N-[rac-(1S)-2-[2-(3-amino-3-oxo-propyl)-2-(2-chloro-2-fluoro-acetyl)hydrazino]-1-(cyclopropylmethyl)-2-axo-ethyl]-1H-indole-2-carboxamide

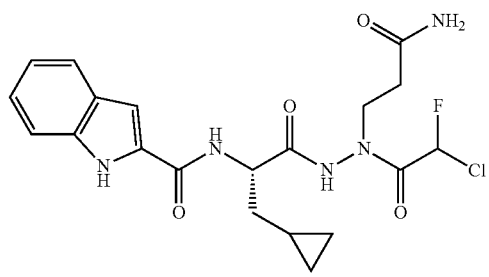 [SMILES: NC(=O)CCN(NC(=O)[C@H](CC1CC1)NC(=O)c1cc2ccccc2[nH]1)C(=O)C(F)Cl]

Step 1: Preparation of tert-butyl N-[rac-(1S)-1-(cyclopropylmethyl)-2-oxo-2-[2-(2-phenoxyacetyl)hydrazino]ethyl]carbamate

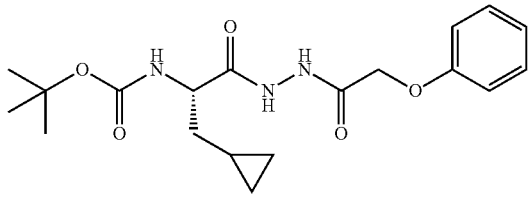

62a

To a solution of (S)-2-((tert-butoxycarbonyl)amino)-3-cyclopropylpropanoic acid (10.0 g) and benzyl hydrazinecarboxylate (7.97 g, 48.0 mmol) in DMF (150 mL) was added DIEA (31.14 mL). The reaction mixture was cooled down to 0° C. and T$_3$P (38.91 mL, 65.43 mmol, 50% purity in EtOAc) was added. After stirred at 0° C. for 2 hrs, the reaction mixture was added into water (500 mL) and extracted with EtOAc (200 mL) for three times. The combined organic layers were washed with sat. aq. solution of sodium bicarbonate (200 mL), sat. aq. solution of citric acid (200 mL) and brine (200 mL), dried over anhydrous Na$_2$SO$_4$, concentrated in vacuo to afford tert-butyl N-[rac-(1S)-1-(cyclopropylmethyl)-2-oxo-2-[2-(2-phenoxyacetyl)hydrazino]ethyl]carbamate (16 g, compound 62a) as a yellow oil. MS obsd. (ESI$^+$) [M+Na]$^+$: 400.2.

Step 2: Preparation of tert-butyl N-[rac-(1S)-1-(cyclopropylmethyl)-2-hydrazino-2-axo-ethyl]carbamate

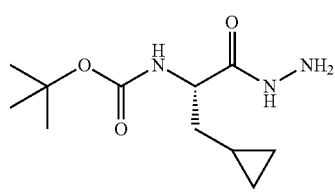

62b

A solution of tert-butyl N-[rac-(1S)-1-(cyclopropylmethyl)-2-oxo-2-[2-(2-phenoxyacetyl)hydrazino]ethyl]carbamate (16.0 g, compound 62a) in methanol (30 mL) was purged with nitrogen three times. Then Pd/C (1.5 g, 10% purity) was added to the solution under nitrogen. The mixture was degassed under vacuum and purged H$_2$ for hydrogen three times. After stirred at 20° C. for 16 hrs under H$_2$ balloon, the reaction mixture was filtered, concentrated in vacuo to afford tert-butyl (S)-(3-cyclopropyl-1-hydrazineyl-1-oxopropan-2-yl)carbamate (11 g, compound 62b) as a yellow oil. MS obsd. (ESI$^+$) [M-C$_4$H$_8$+H]$^+$: 187.8.

Step 3: Preparation of tert-butyl (S)-(1-(2-(3-amino-3-oxopropyl)hydrazineyl)-3-cyclopropyl-1-oxopropan-2-yl)carbamate

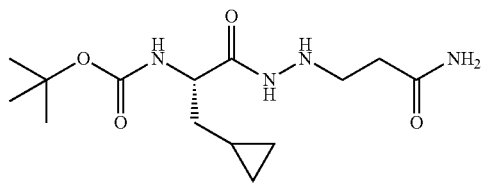

62c

To a solution of acrylamide (876.45 mg) in 2-propanol (10 mL) was added tert-butyl (S)-(3-cyclopropyl-1-hydrazineyl-1-oxopropan-2-yl)carbamate (11 g, compound 62b) (HCl salt). The mixture was purged and degassed with nitrogen for three times. After stirred at 50° C. for 2 hrs, the reaction mixture was added water (200 mL) and basified with sodium bicarbonate until pH=7, extracted with EtOAc (50 mL) three times. The combined organic layers were washed with brine (200 mL), dried over anhydrous Na$_2$SO$_4$ and concentrated in vacuo. The residue was purified by silica gel column (eluted with ethyl acetate in petroleum ether: EtOAc=30~100% to methanol in ethyl acetate=0~10%) to afford tert-butyl (S)-(1-(2-(3-amino-3-oxopropyl)hydrazineyl)-3-cyclopropyl-1-oxopropan-2-yl)carbamate (4.5 g, compound 62c) as a white solid. MS obsd. (ESI$^+$) [M-C$_4$H$_8$+H]$^+$: 258.8.

Step 4: Preparation of tert-butyl((2S)-1-(2-(3-amino-3-oxopropyl)-2-(2-chloro-2-fluoroacetyl)hydrazineyl)-3-cyclopropyl-1-oxopropan-2-yl)carbamate

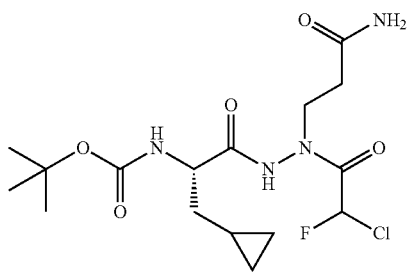

62d

Compound 62d was prepared in analogy to Example 53, step 1 by using tert-butyl (S)-(1-(2-(3-amino-3-oxopropyl)hydrazineyl)-3-cyclopropyl-1-oxopropan-2-yl)carbamate (4.5 g, compound 62c) instead of (S)-tert-butyl(1-(2-(3-amino-3-oxopropyl)hydrazinyl)-4-methyl-1-oxopentan-2-yl)carbamate (26c). tert-Butyl((2S)-1-(2-(3-amino-3-oxopropyl)-2-(2-chloro-2-fluoroacetyl) hydrazineyl)-3-cyclopropyl-1-oxopropan-2-yl)carbamate (200 mg, compound 62d) was obtained as a white solid. MS obsd. (ESI$^+$) [M-C$_4$H$_8$+H]$^+$: 352.8.

Step 5: Preparation of 3-(2-((S)-2-amino-3-cyclopropylpropanoyl)-1-(2-chloro-2-fluoroacetyl)hydrazineyl)propanamide

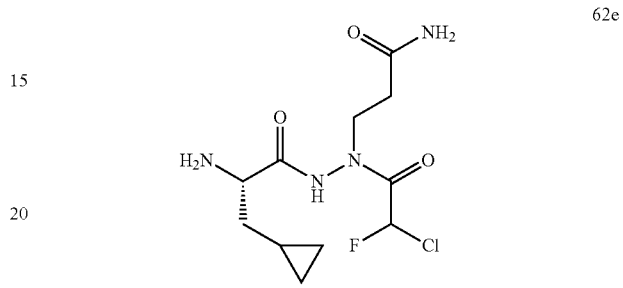

62e

Compound 62e was prepared in analogy to Example 53, step 2 by using tert-butyl((2S)-1-(2-(3-amino-3-oxopropyl)-2-(2-chloro-2-fluoroacetyl) hydrazineyl)-3-cyclopropyl-1-oxopropan-2-yl)carbamate (200 mg, compound 62d) instead of tert-butyl N-[(1S)-1-[[(3-amino-3-oxo-propyl)-(2-chloro-2-fluoro-acetyl)amino]carbamoyl]-3-methyl-butyl]carbamate (200.0 mg, compound 53a). 3-(2-((S)-2-Amino-3-cyclopropylpropanoyl)-1-(2-chloro-2-fluoroacetyl)hydrazineyl) propanamide (120 mg, compound 62e) was obtained as a yellow oil.

Step 6: Preparation of N-((2S)-1-(2-(3-amino-3-oxopropyl)-2-(2-chloro-2-fluoroacetyl) hydrazineyl)-3-cyclopropyl-1-oxopropan-2-yl)-1H-indole-2-carboxamide

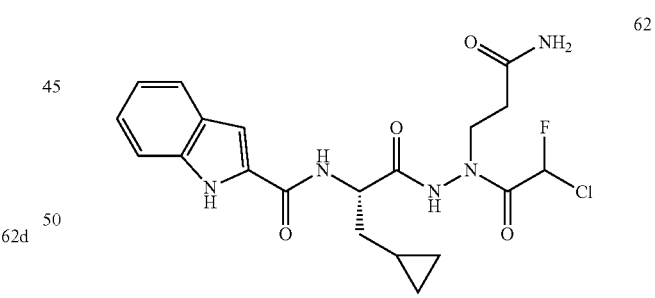

62

The title compound was prepared in analogy to Example 53, Step 3 by using 1H-indole-2-carboxylic acid (22.87 mg) and 3-(2-((S)-2-amino-3-cyclopropylpropanoyl)-1-(2-chloro-2-fluoroacetyl)hydrazineyl)propanamide (TFA salt) (40.0 mg, compound 62e) instead of 4-chloro-1H-indole-2-carboxylic acid and 3-[[[(2S)-2-amino-4-methyl-pentanoyl]amino]-(2-chloro-2-fluoro-acetyl)amino]propanamide (74.61 mg, compound 53b). N-((2S)-1-(2-(3-Amino-3-oxopropyl)-2-(2-chloro-2-fluoroacetyl)hydrazineyl)-3-cyclopropyl-1-oxopropan-2-yl)-1H-indole-2-carboxamide (4.89 mg, Example 62) was obtained as a white solid.

$^1$H NMR (400 MHz, CD$_3$OD) δ ppm: 7.63 (d, J=8.4 Hz, 1H), 7.50-7.43 (m, 1H), 7.27-7.17 (m, 2H), 7.13-6.90 (m, 1H), 7.02-6.81 (m, 1H), 4.02-3.50 (m, 1H), 3.26-3.17 (m, 2H), 2.77-2.37 (m, 2H), 2.10-1.54 (m, 2H), 1.05-0.76 (m, 1H), 0.66-0.45 (m, 2H), 0.32-0.11 (m, 2H) MS obsd. (ESI+) [(M+H)+]: 452.3.

Example 63

N-[(1S)-1-[[(3-amino-3-oxo-propyl)-[(2S)-2-chloro-2-fluoro-acetyl]amino]carbamoyl]-3-methyl-butyl]-1H-benzimidazole-2-carboxamide and N-[(1S)-1-[[(3-amino-3-oxo-propyl)-[(2R)-2-chloro-2-fluoro-acetyl]amino]carbamoyl]-3-methyl-butyl]-1H-benzimidazole-2-carboxamide

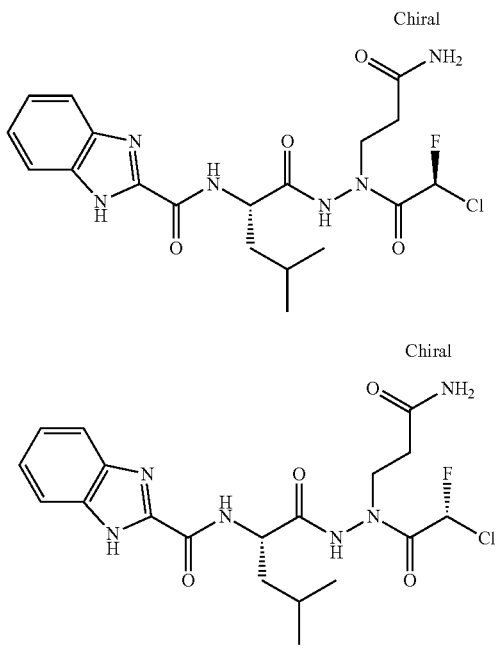

The title compound was prepared in analogy to Example 53, Step 3 by using 1H-benzimidazole-2-carboxylic acid instead of 4-chloro-1H-indole-2-carboxylic acid. N-[(1S)-1-[[(3-Amino-3-oxo-propyl)-(2-chloro-2-fluoro-acetyl)amino]carbamoyl]-3-methyl-butyl]-1H-benzimidazole-2-carboxamide (40 mg, compound 63) was obtained as a yellow solid.

Separation of compound 63 by chiral SFC afforded Example 63-A (faster eluting, 11.8 mg) and Example 63-B (slower eluting, 12.9 mg) with Neu-ETOH; B %: 30-30%; FlowRate (ml/min): 60) on DAICEL CHIRALCEL OJ-H column.

Example 63-A: 1H NMR (400 MHz, CD3OD) δ ppm: 7.68-7.72 (m, 2H), 7.33-7.42 (m, 2H), 6.67-6.95 (m, 1H), 4.42-4.53 (m, 1H), 3.94-4.02 (m, 1H), 3.67-3.72 (m, 1H), 2.49-2.59 (m, 2H), 1.82-1.99 (m, 2H), 1.66-1.80 (m, 1H), 1.05 (dd, J=6.0 Hz, 15.2 Hz, 6H). MS obsd. (ESI+) [(M+H)+]: 455.1.SFC: RT=1.030 min, ee %=100%

Example 63-B: 1H NMR (400 MHz, CD3OD) δ ppm: 7.59-7.76 (m, 2H), 7.29-7.42 (m, 2H), 6.38-6.85 (m, 1H), 4.42-4.53 (m, 1H), 3.84-4.02 (m, 1H), 3.57-3.83 (m, 1H), 2.49-2.59 (m, 2H), 1.78-1.95 (m, 3H), 1.05 (dd, J=6.4 Hz, 17.2 Hz, 6H). MS obsd. (ESI+) [(M+H)+]: 455.2. SFC: RT=1.177 min, ee %=96.564%

Example 64

N-[(1S)-1-[[(3-amino-3-oxo-propyl)-(2-chloro-2-fluoro-acetyl)amino]carbamoyl]-3-methyl-butyl] pyrazolo[1,5-a]pyridine-2-carboxamide

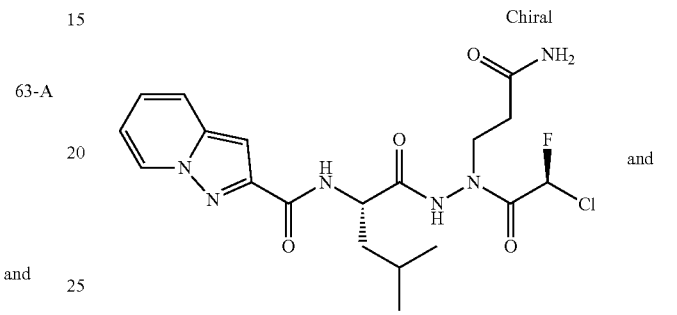

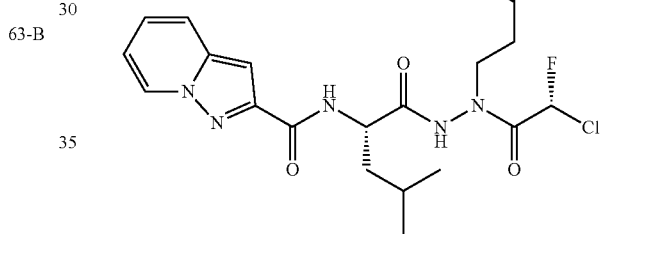

The title compound was prepared in analogy to Example 53, Step 3 by using pyrazolo[1,5-a]pyridine-2-carboxylic acid (Bidepharm, CAS Number: 63237-88-7) instead of 4-chloro-1H-indole-2-carboxylic acid. N-[(1S)-2-[2-(3-Amino-3-oxo-propyl)-2-(2-chloro-2-fluoro-acetyl)hydrazino]-1-(cyclohexylmethyl)-2-axo-ethyl]-1H-indole-2-carboxamide (compound 64) was obtained as a yellow solid.

Separation of compound 64 by chiral SFC afforded Example 64-A (faster eluting, 4.0 mg) and Example 64-B (slower eluting, 6.5 mg) with Neu-ETOH; B %: 30-30%; FlowRate (ml/min): 60) on DAICEL CHIRALPAK AD-H column Example 64-A: 1H NMR (400 MHz, CD3OD) δ ppm: 8.61 (d, J=6.4 Hz, 1H), 7.72 (d, J=9.2 Hz, 1H), 7.25-7.29 (m, 1H), 7.08 (s, 1H), 6.99-7.03 (m, 1H), 6.46-6.60 (m, 1H), 4.63-4.70 (m, 1H), 3.92-4.01 (m, 1H), 3.65-3.75 (m, 1H), 2.45-2.59 (m, 2H), 1.74-1.90 (m, 3H), 1.05 (d, J=6.4 Hz, 3H), 1.02 (d, J=6.4 Hz, 3H). MS obsd. (ESI+) [(M+H)+]: 455.3. SFC: RT=1.909 min, ee %=96.9%

Example 64-B: 1H NMR (400 MHz, CD3OD) δ ppm: 8.61 (d, J=6.4 Hz, 1H), 7.72 (d, J=8.8 Hz, 1H), 7.25-7.29 (m, 1H), 7.08 (s, 1H), 7.01-7.07 (m, 1H), 6.82 (d, J=50.0 Hz, 1H), 4.54-4.58 (m, 1H), 3.93-3.97 (m, 1H), 3.66-3.70 (m, 1H), 2.46-2.61 (m, 2H), 1.70-1.90 (m, 3H), 1.06 (d, J=6.0 Hz, 3H), 1.03 (d, J=6.4 Hz, 3H). MS obsd. (ESI+) [(M+H)+]: 455.3. SFC: RT=2.104 min, ee %=96.5% Example 65

123

N-[(1S)-1-[[(3-amino-3-oxo-propyl)-(2-chloro-2-fluoro-acetyl)amino]carbamoyl]-3,3-dimethyl-butyl]-1H-benzimidazole-2-carboxamide

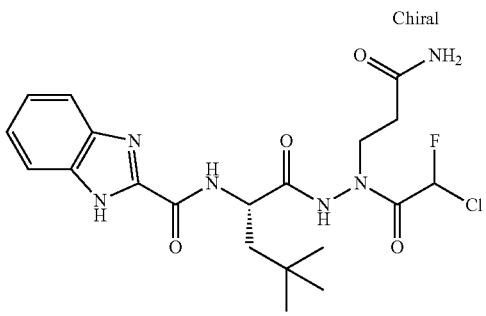 [SMILES: CC(C)(C)C[C@H](NC(=O)c1nc2ccccc2[nH]1)C(=O)NN(CCC(N)=O)C(=O)C(F)Cl]

Step 1: Preparation of (2S)-2-(1H-benzimidazole-2-carbonylamino)-4,4-dimethyl-pentanoic acid

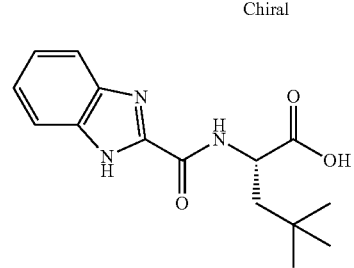

To a solution of (S)-2-amino-4,4-dimethylpentanoic acid (TFA salt) (230.0 mg, compound 65a, GL Biochem, CAS number: 57224-50-7) in DCM (10 mL) was added DIEA (1023.6 mg) and 1H-benzimidazole-2-carbonyl chloride (310.0 mg). After stirred at 25° C. for 2 hrs, the reaction mixture was concentrated in vacuo. The residue was dissolved with EtOAc (60 mL), washed with HCl (1 M, 30 mL), brine (20 mL), dried over anhydrous Na$_2$SO$_4$ and concentrated in vacuo. The residue was purified by silica gel column, eluted with MeOH in DCM: MeOH=0~10% to afford (S)-2-(1H-benzo[d]imidazole-2-carboxamido)-4,4-dimethylpentanoic acid (120 mg, compound 65b) as a yellow solid. MS obsd. (ESI$^+$) [(M+H)$^+$]: 290.1

Step 2: Preparation of tert-butyl(S)-2-(2-(1H-benzo[d]imidazole-2-carboxamido)-4,4-dimethylpentanoyl)-1-(3-amino-3-oxopropyl)hydrazine-1-carboxylate

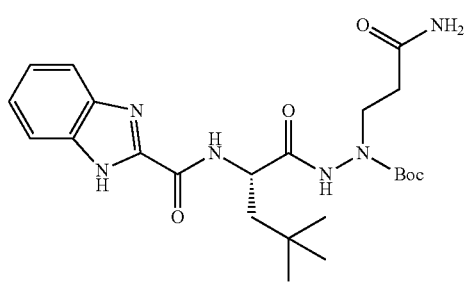

124

To a solution of (S)-2-(1H-benzo[d]imidazole-2-carboxamido)-4,4-dimethylpentanoic acid (120.0 mg, compound 65b), tert-butyl 1-(3-Amino-3-oxopropyl)hydrazine-1-carboxylate (84.29 mg) and DIEA (160.81 mg) in DCM (3 mL) was added T$_3$P (395.67 mg, 0.620 mmol, 50% purity in EtOAc). After stirred at 25° C. for 12 hrs, the reaction mixture was concentrated in vacuo. The residue was purified by silica gel column, eluted with MeOH in DCM: =0~10% to afford tert-butyl(S)-2-(2-(1H-benzo[d]imidazole-2-carboxamido)-4,4-dimethylpentanoyl)-1-(3-amino-3-oxopropyl)hydrazine-1-carboxylate (100 mg, compound 65c) as a yellow solid. MS obsd. (ESI$^+$) [(M+H)$^+$]: 475.2.

Step 3: Preparation of (S)—N-(1-(2-(3-amino-3-oxopropyl)hydrazineyl)-4,4-dimethyl-1-oxopentan-2-yl)-1H-benzo[d]imidazole-2-carboxamide

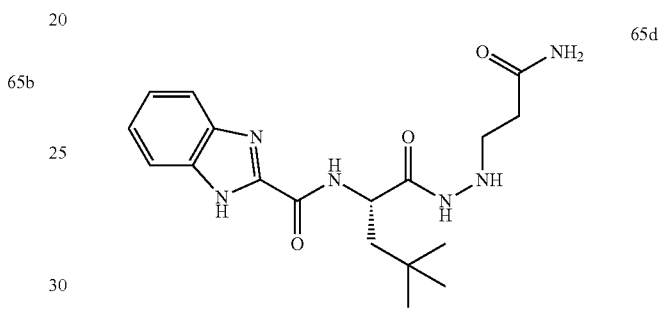

To a solution of tert-butyl(S)-2-(2-(1H-benzo[d]imidazole-2-carboxamido)-4,4-dimethylpentanoyl)-1-(3-amino-3-oxopropyl)hydrazine-1-carboxylate (100.0 mg, compound 65c) in DCM (2 mL) was added TFA (2.0 mL). After stirred at 25° C. for 1 hr, the reaction mixture was concentrated in vacuo to afford (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75 mg, compound 65d) as a light yellow oil.

Step 4: Preparation of N-((2S)-1-(2-(3-amino-3-oxopropyl)-2-(2-chloro-2-fluoroacetyl) hydrazineyl)-4,4-dimethyl-1-oxopentan-2-yl)-1H-benzo[d]imidazole-2-carboxamide

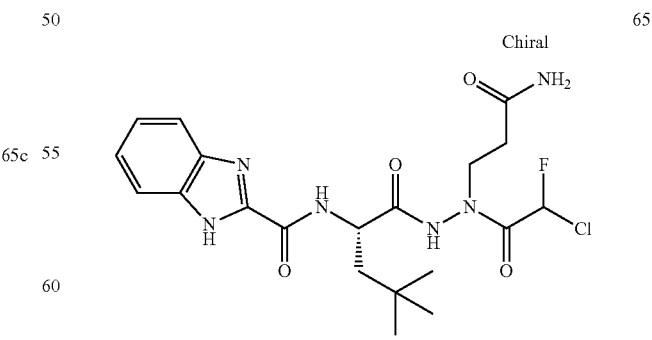

To a solution of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d), 2-chloro-2-fluoroacetic acid (66.5 mg) and DIEA (129.43 mg) in DMF (2 mL) was added T₃P (191.09 mg, 0.300 mmol, 50% purity in EtOAc) at 0° C. After stirred at 25° C. for 12 hrs, the reaction mixture was purified by prep-HPLC (Phenomenex Synergi C$_{18}$ 150*25 mm*10 um; ACN in water (0.1% TFA): 30%-60%) to afford N-((2S)-1-(2-(3-amino-3-oxopropyl)-2-(2-chloro-2-fluoroacetyl)hydrazineyl)-4,4-dimethyl-1-oxopentan-2-yl)-1H-benzo[d]imidazole-2-carboxamide (1.82 mg, Example 65) as a yellow solid. ¹H NMR (400 MHz, CD₃OD) δ ppm: 7.69 (dd, J$_1$=3.2 Hz, J$_2$=6.0 Hz, 2H), 7.38 (dd, J$_1$=3.2 Hz, J$_2$=6.0 Hz, 2H), 6.82-6.50 (m, 1H), 4.71-4.48 (m, 1H), 4.13-3.80 (m, 1H), 3.76-3.61 (m, 1H), 2.61-2.46 (m, 2H), 2.02-1.82 (m, 2H), 1.07-1.00 (m, 9H). MS obsd. (ESI⁺) [(M+H)⁺]: 469.4.

Example 66

N-[rac-(1S)-2-[2-(3-amino-3-oxo-propyl)-2-(2-chloro-2-fluoro-acetyl)hydrazino]-1-(cyclobutylmethyl)-2-axo-ethyl]-1H-benzimidazole-2-carboxamide

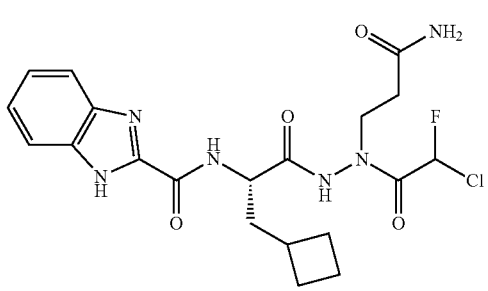

Step 1: Preparation of (S)-2-(1H-benzo[d]imidazole-2-carboxamido)-3-cyclobutylpropanoic acid

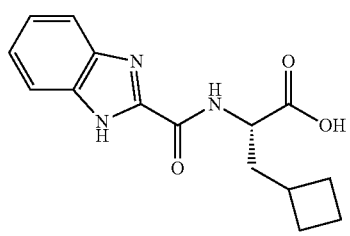

Compound 66a was prepared in analogy to Example 65, step 1 by using (S)-2-amino-3-cyclobutylpropanoic acid (150.56 mg, GL Biochem) instead of (S)-2-amino-4,4-dimethylpentanoic acid. (S)-2-(1H-benzo[d]imidazole-2-carboxamido)-3-cyclobutylpropanoic acid (140 mg, compound 66a) was obtained as a yellow oil. MS obsd. (ESI⁺) [(M+Na)⁺]: 309.8.

Step 2: Preparation of tert-butyl(S)-2-(2-(1H-benzo[d]imidazole-2-carboxamido)-3-cyclobutylpropanoyl)-1-(3-amino-3-oxopropyl)hydrazine-1-carboxylate

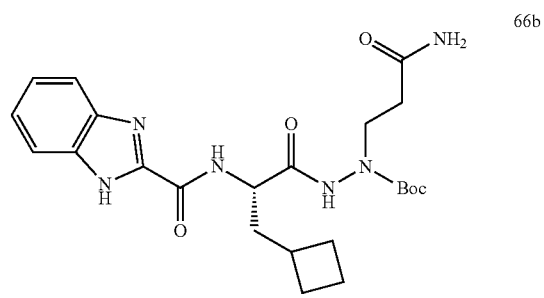 [SMILES: CC(C)(C)OC(=O)N(CCC(N)=O)NC(=O)[C@H](CC1CCC1)NC(=O)c1nc2ccccc2[nH]1]

Compound 66b was prepared in analogy to Example 65, step 2 by using (S)-2-(1H-benzo[d]imidazole-2-carboxamido)-3-cyclobutylpropanoic acid (140 mg, compound 66a) instead of (2S)-2-(1H-benzimidazole-2-carbonylamino)-4,4-dimethyl-pentanoic acid (compound 65b). tert-Butyl(S)-2-(2-(1H-benzo[d]imidazole-2-carboxamido)-3-cyclobutylpropanoyl)-1-(3-amino-3-oxopropyl)hydrazine-1-carboxylate (100 mg, compound 66b) was obtained as a light yellow solid. MS obsd. (ESI⁺) [(M+H)⁺]:473.2.

Step 3: Preparation of (S)—N-(1-(2-(3-amino-3-oxopropyl)hydrazineyl)-3-cyclobutyl-1-oxopropan-2-yl)-1H-benzo[d]imidazole-2-carboxamide

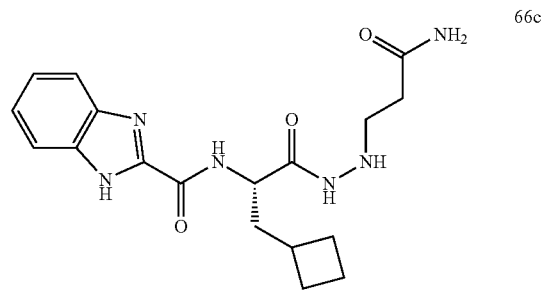 [SMILES: NC(=O)CCNNC(=O)[C@H](CC1CCC1)NC(=O)c1nc2ccccc2[nH]1]

Compound 66c was prepared in analogy to Example 65, step 3 by using tert-butyl(S)-2-(2-(1H-benzo[d]imidazole-2-carboxamido)-3-cyclobutylpropanoyl)-1-(3-amino-3-oxopropyl)hydrazine-1-carboxylate (100 mg, compound 66b) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (100.0 mg, compound 65c). (S)—N-(1-(2-(3-Amino-3-oxopropyl)hydrazineyl)-3-cyclobutyl-1-oxopropan-2-yl)-1H-benzo[d]imidazole-2-carboxamide (75 mg, compound 66c) was obtained as a light yellow oil.

Step 4: Preparation of N-((2S)-1-(2-(3-amino-3-oxopropyl)-2-(2-chloro-2-fluoroacetyl) hydrazineyl)-3-cyclobutyl-1-oxopropan-2-yl)-1H-benzo[d]imidazole-2-carboxamide

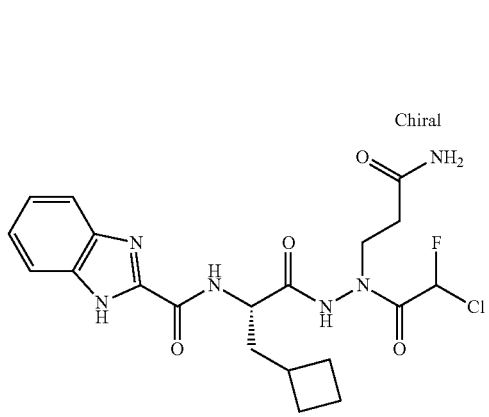

66

Chiral

The title compound was prepared in analogy to Example 65, step 4 by using (S)—N-(1-(2-(3-amino-3-oxopropyl)hydrazineyl)-3-cyclobutyl-1-oxopropan-2-yl)-1H-benzo[d]imidazole-2-carboxamide (75 mg, compound 66c) instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d). N-((2S)-1-(2-(3-Amino-3-oxopropyl)-2-(2-chloro-2-fluoroacetyl)hydrazineyl)-3-cyclobutyl-1-oxopropan-2-yl)-1H-benzo[d]imidazole-2-carboxamide (1.77 mg, Example 66) was obtained as a white solid. $^1$H NMR (400 MHz, CD$_3$OD) δ ppm: 7.68-7.66 (m, 2H), 7.37-7.35 (m, 2H), 6.92-6.50 (m, 1H), 4.51-4.46 (m, 1H), 4.15-3.88 (m, 1H), 3.76-3.61 (m, 1H), 2.64-2.46 (m, 2H), 2.21-2.13 (m, 2H), 2.12-1.99 (m, 2H), 1.99-1.76 (m, 4H), 1.28-1.25 (m, 1H). MS obsd. (ESI$^+$) [(M+H)$^+$]: 467.4.

Example 67

N-[rac-(1S)-2-[2-(3-amino-3-oxo-propyl)-2-(2-chloro-2-fluoro-acetyl)hydrazino]-1-(1-bicyclo[1.1.1]pentanylmethyl)-2-axo-ethyl]-1H-benzimidazole-2-carboxamide

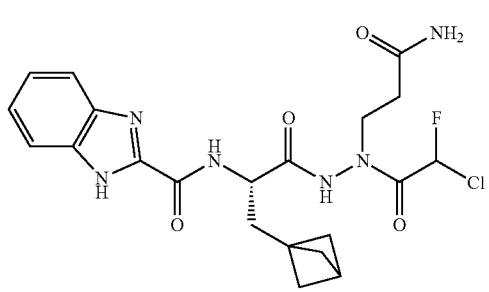

67

Step 1: Preparation of tert-butyl 2-(3-amino-3-oxopropyl)hydrazine-1-carboxylate

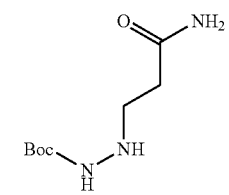

67a

To a solution of tert-butyl hydrazinecarboxylate (10.0 g) in IPA (100 mL) was added acrylamide (5.38 g). After stirred at 70° C. for 3 hrs, the reaction mixture was concentrated in vacuo. The residue was dissolved with ethyl acetate (60 mL), washed with HCl (1 M, 30 mL), brine (20 mL) and dried over anhydrous Na$_2$SO$_4$ and concentrated in vacuo. tert-Butyl 2-(3-amino-3-oxopropyl)hydrazine-1-carboxylate (8 g, compound 67a) was obtained as a colorless oil.

Step 2: Preparation of 1-benzyl 2-(tert-butyl) 1-(3-amino-3-oxopropyl)hydrazine-1,2-dicarboxylate

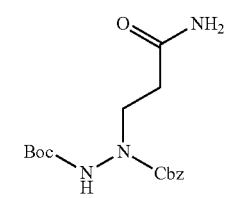

67b

To a solution of tert-butyl 2-(3-amino-3-oxopropyl)hydrazine-1-carboxylate (1.2 g) was added benzyl(2,5-dioxopyrrolidin-1-yl) carbonate (1.47 g) in DMF (30 mL) at 25° C. After stirred at 25° C. for 12 hrs, the reaction mixture was diluted with H$_2$O (100 mL) and extracted with EtOAc (100 mL) three times. The combined organic phase was washed with brine (80 mL) three times, dried over anhydrous Na$_2$SO$_4$ and filtrated. The filtrate was concentrated in vacuo. The residue was purified by silica gel column, eluted with MeOH in DCM=0~10% to afford 1-benzyl 2-(tert-butyl) 1-(3-amino-3-oxopropyl)hydrazine-1,2-dicarboxylate (580 mg, compound 67b) as a white solid. MS obsd. (ESI$^+$) [(M+Na)$^+$]: 360.1

Step 3: Preparation of benzyl 1-(3-amino-3-oxopropyl)hydrazine-1-carboxylate

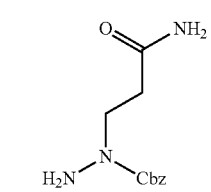

67c

To a solution of 1-benzyl 2-(tert-butyl) 1-(3-amino-3-oxopropyl)hydrazine-1,2-dicarboxylate (1.0 g) in DCM (10 mL) was added TFA (10 mL). After stirred at 25° C. for 2 hrs, the reaction mixture was concentrated in vacuo to afford benzyl 1-(3-amino-3-oxopropyl)hydrazine-1-carboxylate (TFA salt) (145 mg, 67c) as a colorless oil.

Step 4: Preparation of benzyl(S)-1-(3-amino-3-oxopropyl)-2-(3-(bicyclo[1.1.1]pentan-1-yl)-2-((tert-butoxycarbonyl)amino)propanoyl)hydrazine-1-carboxylate

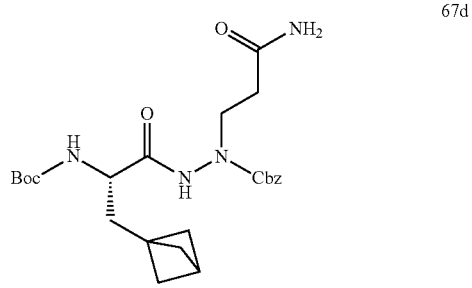 [SMILES: CC(C)(C)OC(=O)N[C@@H](CC12CC(C1)C2)C(=O)NN(CCC(N)=O)C(=O)OCc1ccccc1]

To a solution of (S)-3-(bicyclo[1.1.1]pentan-1-yl)-2-((tert-butoxycarbonyl)amino)propanoic acid (550.0 mg, compound 67c) and benzyl 1-(3-amino-3-oxopropyl)hydrazine-1-carboxylate (511.12 mg) in DCM (10 mL) was added DIEA (1.11 g) and T$_3$P (1.37 g, 50% purity in EtOAc) at 0° C. After stirred at 20° C. for 12 hrs, the reaction mixture was concentrated in vacuo. The residue was purified by silica gel column, eluted with MeOH in DCM=0~1% to afford benzyl (S)-1-(3-amino-3-oxopropyl)-2-(3-(bicyclo[1.1.1]pentan-1-yl)-2-((tert-butoxycarbonyl)amino)propanoyl)hydrazine-1-carboxylate (500 mg, compound 67d) as a yellow oil.

MS obsd. (ESI$^+$) [M+H]$^+$: 475.3.

Step 5: Preparation of tert-butyl (S)-(1-(2-(3-amino-3-oxopropyl)hydrazineyl)-3-(bicyclo[1.1.1]pentan-1-yl)-1-oxopropan-2-yl)carbamate

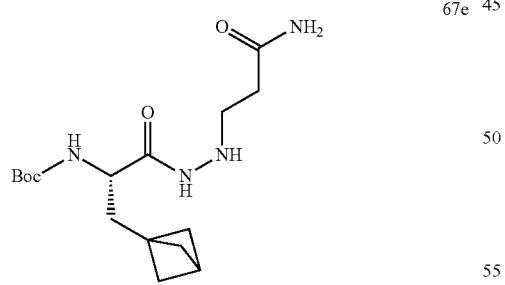

To a solution of benzyl(S)-1-(3-amino-3-oxopropyl)-2-(3-(bicyclo[1.1.1]pentan-1-yl)-2-((tert-butoxycarbonyl)amino) propanoyl)hydrazine-1-carboxylate (500.0 mg) in methanol (10 mL) was added Pd/C (50.0 mg, 10% purity). The mixture was degassed under vacuum and purged H$_2$ three times. The mixture was stirred at 20° C. for 2 hrs uner H$_2$ balloon. LCMS showed the reaction was completed. The reaction mixture was filtered. The filtrate was concentrated in vacuo to afford tert-butyl (S)-(1-(2-(3-amino-3-oxopropyl)hydrazineyl)-3-(bicyclo[1.1.1]pentan-1-yl)-1-oxopropan-2-yl)carbamate (300 mg, compound 67e) as a yellow solid. MS obsd. (ESI$^+$) [M+H]$^+$: 341.2.

Step 6: Preparation of tert-butyl((2S)-1-(2-(3-amino-3-oxopropyl)-2-(2-chloro-2-fluoroacetyl)hydrazineyl)-3-(bicyclo[1.1.1]pentan-1-yl)-1-oxopropan-2-yl)carbamate

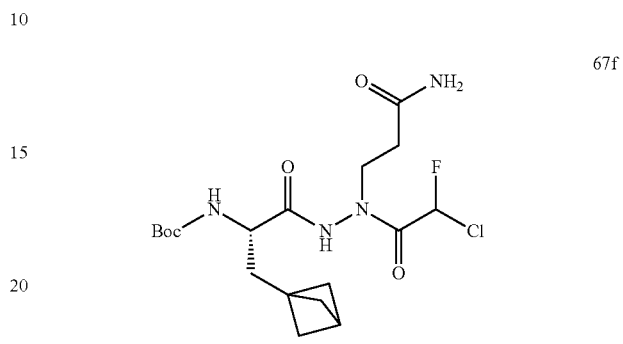

To a solution of tert-butyl (S)-(1-(2-(3-amino-3-oxopropyl)hydrazineyl)-3-(bicyclo[1.1.1]pentan-1-yl)-1-oxopropan-2-yl)carbamate (300.0 mg, compound 67e) in DCM (6 mL) was added DIEA (569.47 mg) and 2-chloro-2-fluoroacetyl chloride (346.15 mg) at 0° C. The mixture was stirred at 0° C. for 1 hr. LCMS showed the reaction was completed. It was concentrated in vacuo. The residue was purified by silica gel column, eluted with MeOH in DCM=0~2% to afford tert-butyl((2S)-1-(2-(3-amino-3-oxopropyl)-2-(2-chloro-2-fluoroacetyl)hydrazineyl)-3-(bicyclo[1.1.1]pentan-1-yl)-1-oxopropan-2-yl)carbamate (260 mg, compound 67f) as a yellow oil. MS obsd. (ESI$^+$) [M+H]$^+$: 435.2.

Step 7: Preparation of 3-(2-((S)-2-amino-3-(bicyclo[1.1.1]pentan-1-yl)propanoyl)-1-(2-chloro-2-fluoroacetyl)hydrazineyl)propanamide

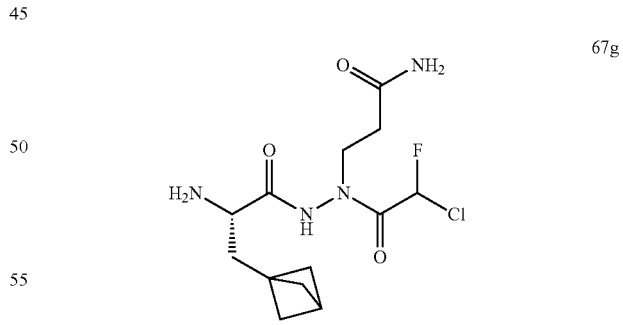

To a solution of tert-butyl((2S)-1-(2-(3-amino-3-oxopropyl)-2-(2-chloro-2-fluoroacetyl) hydrazineyl)-3-(bicyclo[1.1.1]pentan-1-yl)-1-oxopropan-2-yl)carbamate (260.0 mg, compound 67f) in DCM (3 mL) was added TFA (3.0 mL). After stirred at 20° C. for 1 hr, the reaction mixture was concentrated in vacuo to afford 3-(2-((S)-2-amino-3-(bicyclo[1.1.1]pentan-1-yl) propanoyl)-1-(2-chloro-2-fluoroacetyl)hydrazineyl)propanamide (200 mg, compound 67g) as a yellow oil.

Step 8: Preparation of N-((2S)-1-(2-(3-amino-3-oxopropyl)-2-(2-chloro-2-fluoroacetyl) hydrazineyl)-3-(bicyclo[1.1.1]pentan-1-yl)-1-oxopropan-2-yl)-1H-benzo[d]imidazole-2-carboxamide

67

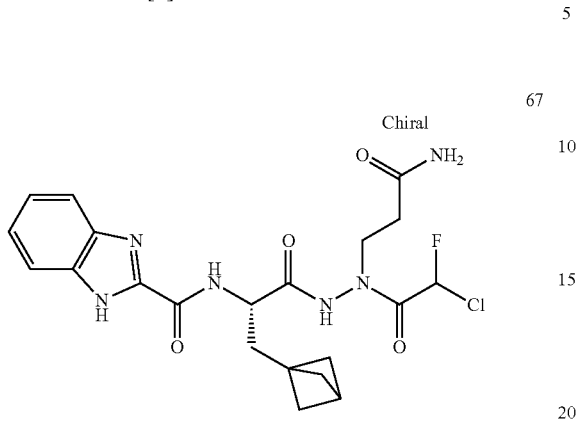

The title compound was prepared in analogy to Example 53, Step 3 by using 1H-benzimidazole-2-carboxylic acid and 3-(2-((S)-2-amino-3-(bicyclo[1.1.1]pentan-1-yl) propanoyl)-1-(2-chloro-2-fluoroacetyl)hydrazineyl)propanamide (compound 67g) instead of 4-chloro-1H-indole-2-carboxylic acid and 3-[[[(2S)-2-amino-4-methyl-pentanoyl]amino]-(2-chloro-2-fluoro-acetyl)amino]propanamide (74.61 mg, 53b). N-((2S)-1-(2-(3-Amino-3-oxopropyl)-2-(2-chloro-2-fluoroacetyl) hydrazineyl)-3-(bicyclo[1.1.1]pentan-1-yl)-1-oxopropan-2-yl)-1H-benzo[d]imidazole-2-carboxamide (145 mg, Example 67) was obtained as a white solid. $^1$H NMR (400 MHz, CDCl$_3$) δ ppm: 9.97 (br. s, 1H), 7.72 (m, 2H), 7.53 (m, 2H), 6.68-6.42 (m, 2H), 4.66 (m, 1H), 4.15-3.73 (m, 4H), 2.52 (m, 1H), 2.44-2.42 (m, 1H), 2.11 (m, 2H), 1.73-1.69 (m, 7H). MS obsd. (ESI$^+$) [M+H]$^+$: 479.2.

Example 68

5-Methyl-N-[rac-(1S)-3,3-dimethyl-1-[[[rac-(2R)-2-chloro-2-fluoro-acetyl]-[[rac-(3S)-2-axopyrrolidin-3-yl]methyl]amino]carbamoyl]butyl]isoxazole-3-carboxamide

68

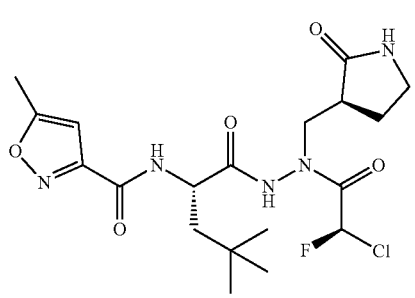

Step 1: Preparation of (2S)-4,4-dimethyl-2-[(5-methylisoxazole-3-carbonyl)amino]pentanoic acid

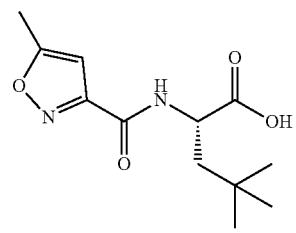

68a

Compound 68a was prepared in analogy to Example 65, step 1 by using 5-methylisoxazole-3-carbonyl chloride instead of 1H-benzimidazole-2-carbonyl chloride. (2S)-4,4-dimethyl-2-[(5-methylisoxazole-3-carbonyl)amino]pentanoic acid (3 g, compound 68a) was obtained as a white solid. MS obsd. (ESI$^+$) [M+H]$^+$: 255.2

Step 2: Preparation of tert-butyl N-[[(2S)-4,4-dimethyl-2-[(5-methylisoxazole-3-carbonyl)amino]pentanoyl]amino]-N-[[(3S)-2-axopyrrolidin-3-yl]methyl]carbamate

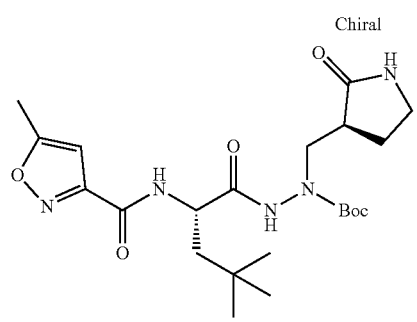

68b

Compound 68b was prepared in analogy to Example 65, step 2 by using (2S)-4,4-dimethyl-2-[(5-methylisoxazole-3-carbonyl)amino]pentanoic acid (3 g, compound 68a) and tert-butyl(S)-1-((2-axopyrrolidin-3-yl)methyl)hydrazine-1-carboxylate (2.71 g, intermediate AF) instead of (S)-2-(1H-benzo[d]imidazole-2-carboxamido)-4,4-dimethylpentanoic acid (120.0 mg, compound 65b) and tert-butyl 1-(3-amino-3-oxopropyl)hydrazine-1-carboxylate. tert-Butyl N-[[(2S)-4,4-dimethyl-2-[(5-methylisoxazole-3-carbonyl)amino]pentanoyl]amino]-N-[[(3S)-2-axopyrrolidin-3-yl]methyl] carbamate (3.3 g, compound 68c) was obtained as a white solid.

MS obsd. (ESI$^+$) [(M+H)$^+$]: 466.2

Step 4: Preparation of N—((S)-4,4-dimethyl-1-oxo-1-(2-(((S)-2-axopyrrolidin-3-yl)methyl)hydrazineyl)pentan-2-yl)-5-methylisoxazole-3-carboxamide

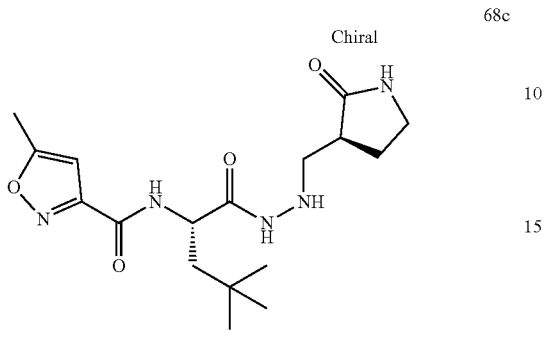

68c

Compound 68c was prepared in analogy to Example 65, step 3 by using tert-butyl N-[[(2S)-4,4-dimethyl-2-[(5-methylisoxazole-3-carbonyl)amino]pentanoyl]amino]-N-[[(3S)-2-axopyrrolidin-3-yl]methyl]carbamate (compound 68c) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (compound 65c). N—((S)-4,4-dimethyl-1-oxo-1-(2-(((S)-2-axopyrrolidin-3-yl)methyl)hydrazineyl)pentan-2-yl)-5-methylisoxazole-3-carboxamide, hydrochloride (2.2 g, 68d) was obtained as a white solid. MS obsd. (ESI⁺) [(M+H)⁺]: 366.2

Step 5: Preparation of N—((S)-1-(2-((R)-2-chloro-2-fluoroacetyl)-2-(((S)-2-axopyrrolidin-3-yl)methyl)hydrazineyl)-4,4-dimethyl-1-oxopentan-2-yl)-5-methylisoxazole-3-carboxamide

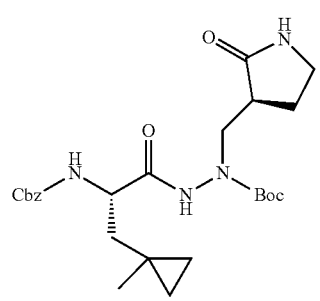

68

The title compound was prepared in analogy to Example 65, step 4 by using N—((S)-4,4-dimethyl-1-oxo-1-(2-(((S)-2-axopyrrolidin-3-yl)methyl)hydrazineyl)pentan-2-yl)-5-methylisoxazole-3-carboxamide, hydrochloride (2.2 g, 68d) and (R)-2-chloro-2-fluoroacetyl chloride instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d) and 2-chloro-2-fluoroacetic acid. N—((S)-1-(2-((R)-2-Chloro-2-fluoroacetyl)-2-(((S)-2-axopyrrolidin-3-yl)methyl)hydrazineyl)-4,4-dimethyl-1-oxopentan-2-yl)-5-methylisoxazole-3-carboxamide (1637 mg, compound 68) was obtained as a white solid. ¹H NMR (400 MHz, DMSO-d₆) δ ppm: 11.12-10.30 (m, 1H), 9.16-8.83 (m, 1H), 7.78-7.70 (m, 1H), 7.04-6.59 (m, 2H), 4.58-4.32 (m, 1H), 3.98-3.81 (m, 1H), 3.30-3.10 (m, 3H), 2.52-2.50 (m, 1H), 2.49 (s, 3H), 2.28-2.09 (m, 1H), 1.90-1.64 (m, 3H), 0.93 (s, 9H). MS obsd. (ESI⁺) [M+H]⁺: 460.1.

Example 70

N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-methyl-isoxazole-3-carboxamide

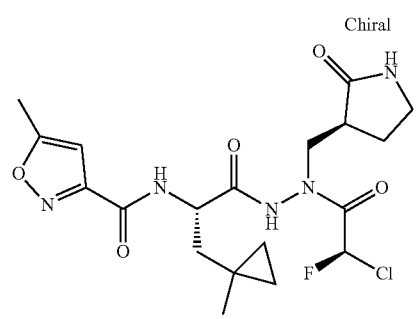

70

Step 1: Preparation of tert-butyl 2-((S)-2-(((benzyloxy)carbonyl)amino)-3-(1-methylcyclopropyl)propanoyl)-1-(((S)-2-axopyrrolidin-3-yl)methyl)hydrazine-1-carboxylate 70a Compound 70a was prepared in analogy to Example 65, step 2 by using (S)-2-(((benzyloxy)carbonyl)amino)-3-(1-methylcyclopropyl)propanoic acid and (Intermediate AD) and tert-butyl(S)-1-((2-axopyrrolidin-3-yl)methyl)hydrazine-1-carboxylate (2.96 g, Intermediate AF) instead of (S)-2-(1H-benzo[d]imidazole-2-carboxamido)-4,4-dimethylpentanoic acid (120.0 mg, compound 65b) and tert-butyl 1-(3-amino-3-oxopropyl)hydrazine-1-carboxylate. tert-Butyl 2-((S)-2-(((benzyloxy)carbonyl)amino)-3-(1-methylcyclopropyl)propanoyl)-1-(((S)-2-axopyrrolidin-3-yl)methyl)hydrazine-1-carboxylate (5.76 g, compound 70a) was obtained as a white solid. ¹H NMR (400 MHz, CDCl₃) δ ppm: 9.20-8.95 (m, 1H), 7.43-7.29 (m, 5H), 6.29 (br. s, 1H), 5.42 (d, J=5.6 Hz, 1H), 5.21-5.07 (m, 2H), 4.38 (br. s, 1H), 3.96-3.29 (m, 5H), 2.81-2.68 (m, 1H), 2.34-2.20 (m, 1H), 2.00-1.82 (m, 2H), 1.41 (s, 9H), 1.08 (s, 3H), 0.41-0.23 (m, 4H). MS obsd. (ESI⁺) [(M+H)⁺]: 489.3

Step 2: Preparation of tert-butyl 2-((S)-2-amino-3-(1-methylcyclopropyl)propanoyl)-1-(((S)-2-axopyrrolidin-3-yl)methyl)hydrazine-1-carboxylate

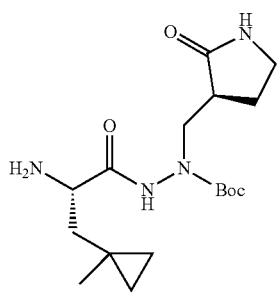

70b

To a solution of tert-butyl 2-((S)-2-(((benzyloxy)carbonyl)amino)-3-(1-methylcyclopropyl)propanoyl)-1-(((S)-2-axopyrrolidin-3-yl)methyl)hydrazine-1-carboxylate (5.76 g, compound 70a) in ethanol (100 mL) was added Pd/C (1.0 g, 10% purity on charcoal, wet). The mixture was degassed under vacuum and purged three times. After stirred at 20° C. for 1.5 hrs under H$_2$ balloon, the mixture was filtered and the filtrate was concentrated in vacuo to afford tert-butyl 2-((S)-2-amino-3-(1-methylcyclopropyl)propanoyl)-1-(((S)-2-axopyrrolidin-3-yl)methyl)hydrazine-1-carboxylate (4.0 g, compound 70b) as an off-white solid. $^1$H NMR (400 MHz, CDCl$_3$) δ ppm: 9.60-9.32 (m, 1H), 5.92 (br. s, 1H), 3.98-3.33 (m, 5H), 2.75-2.67 (m, 1H), 2.43-1.97 (m, 6H), 1.52-1.37 (m, 9H), 1.11 (s, 3H), 0.37-0.25 (m, 4H).

Step 3: Preparation of tert-butyl 2-((S)-3-(1-methylcyclopropyl)-2-(5-methylisoxazole-3-carboxamido)propanoyl)-1-(((S)-2-axopyrrolidin-3-yl)methyl)hydrazine-1-carboxylate

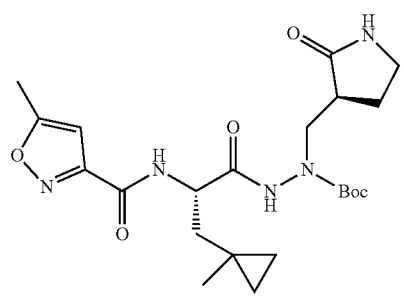

70c

To a solution of tert-butyl 2-((S)-2-amino-3-(1-methylcyclopropyl)propanoyl)-1-(((S)-2-axopyrrolidin-3-yl)methyl)hydrazine-1-carboxylate (3.5 g, compound 70b) and DIEA (5.1 g) in THF (70 mL) was added 5-methylisoxazole-3-carbonyl chloride (2.16 g) at 0° C. After stirred at 0° C. for 30 minutes, the reaction mixture was quenched by sat.aq. solution of NaHCO$_3$ (20 mL) and acidified with HCl (1M) until pH=2~3, and extracted with EtOAc (100 mL) three times. The combined organic layers were dried over anhydrous Na$_2$SO$_4$, filtered and the filtrate was concentrated in vacuo. The residue was purified by reversed-phase flash (MeCN in water (0.1% TFA)=0~ 70%) to afford tert-butyl 2-((S)-3-(1-methylcyclopropyl)-2-(5-methylisoxazole-3-carboxamido)propanoyl)-1-(((S)-2-axopyrrolidin-3-yl)methyl)hydrazine-1-carboxylate (3.47 g, compound 70c) as a light yellow oil. MS obsd. (ESI$^+$) [(M+H)$^+$]: 464.2.

Step 4: Preparation of 5-methyl-N—((S)-3-(1-methylcyclopropyl)-1-oxo-1-(2-(((S)-2-axopyrrolidin-3-yl)methyl)hydrazineyl)propan-2-yl)isoxazole-3-carboxamide

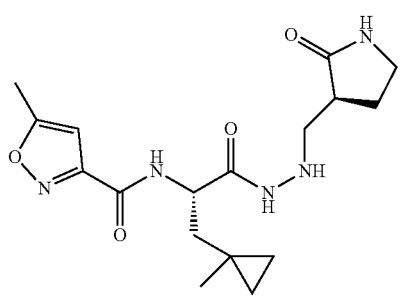

70d

Compound 70d was prepared in analogy to Example 65, step 3 by using tert-butyl 2-((S)-3-(1-methylcyclopropyl)-2-(5-methylisoxazole-3-carboxamido)propanoyl)-1-(((S)-2-axopyrrolidin-3-yl)methyl)hydrazine-1-carboxylate (3.47 g, compound 70c) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (compound 65c). 5-Methyl-N—((S)-3-(1-methylcyclopropyl)-1-oxo-1-(2-(((S)-2-axopyrrolidin-3-yl)methyl)hydrazineyl)propan-2-yl)isoxazole-3-carboxamide (2.21 g, compound 70d) was obtained as a white solid. $^1$H NMR (400 MHz, CD$_3$OD) δ ppm: 6.48 (s, 1H), 4.81-4.69 (m, 1H), 3.54-3.35 (m, 4H), 2.94-2.92 (m, 1H), 2.49 (d, J=0.8 Hz, 3H), 2.45-2.33 (m, 1H), 2.02-1.88 (m, 2H), 1.79-1.73 (m, 1H), 1.13 (s, 3H), 0.53-0.44 (m, 1H), 0.37-0.26 (m, 3H). MS obsd. (ESI$^+$) [M+H]$^+$: 364.3.

Step 5: Preparation of N—((S)-1-(2-((R)-2-chloro-2-fluoroacetyl)-2-(((S)-2-axopyrrolidin-3-yl)methyl)hydrazineyl)-3-(1-methylcyclopropyl)-1-oxopropan-2-yl)-5-methylisoxazole-3-carboxamide

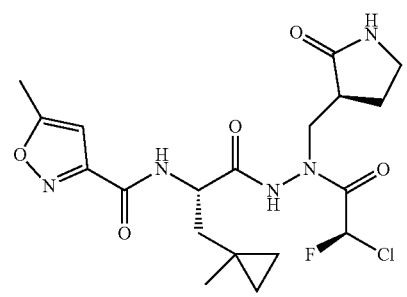

70

The title compound was prepared in analogy to Example 65, step 4 by using 5-Methyl-N—((S)-3-(1-methylcyclopropyl)-1-oxo-1-(2-(((S)-2-axopyrrolidin-3-yl)methyl)hydrazineyl)propan-2-yl)isoxazole-3-carboxamide (2.21 g, compound 70d) and (R)-2-chloro-2-fluoroacetyl chloride instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (compound 65d) and 2-chloro-2-fluoroacetic acid.

N—((S)-1-(2-((R)-2-chloro-2-fluoroacetyl)-2-(((S)-2-axopyrrolidin-3-yl)methyl)hydrazineyl)-3-(1-methylcyclopropyl)-1-oxopropan-2-yl)-5-methylisoxazole-3-carboxamide (905.1 mg, Example 70) was obtained as a white solid. ¹H NMR (400 MHz, CDCl₃) δ ppm: 10.03 (br. s, 1H), 7.33-7.29 (m, 1H), 6.49 (d, J=50.8 Hz, 1H), 6.45 (d, J=0.4 Hz, 1H), 5.65 (br. s, 1H), 4.62-4.59 (m, 1H), 4.50-4.36 (m, 1H), 3.43-3.39 (m, 2H), 2.92-2.79 (m, 2H), 2.50 (s, 3H), 2.45-2.32 (m, 1H), 2.14-2.00 (m, 1H), 1.90-1.75 (m, 1H), 1.59-1.54 (m, 1H), 1.13 (s, 3H), 0.49-0.41 (m, 2H), 0.38-0.29 (m, 2H). MS obsd. (ESI⁺) [M+H]⁺: 458.2

Example 71

N-[(1S)-1-(1-bicyclo[1.1.1]pentanylmethyl)-2-[2-[(2R)-2-chloro-2-fluoro-acetyl]-2-[[(3S)-2-axopyrrolidin-3-yl]methyl]hydrazino]-2-axo-ethyl]-5-methyl-isoxazole-3-carboxamide

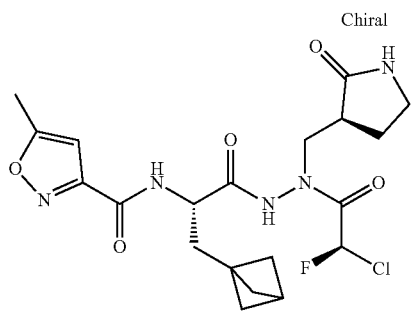

Step 1: Preparation of methyl(S)-3-(bicyclo[1.1.1]pentan-1-yl)-2-(5-methylisoxazole-3-carboxamido)propanoate

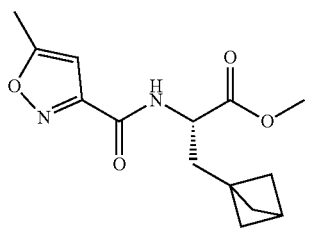

To a solution of methyl(S)-2-amino-3-(bicyclo[1.1.1]pentan-1-yl)propanoate (HCl salt) (1.6 g, Intermediate AG) and Na₂CO₃ (2.47 g) in THF (20 mL) and water (15 mL) was added 5-methylisoxazole-3-carbonyl chloride (1.13 g) at 0° C. After stirred at 20° C. for 12 hrs, the reaction mixture was poured into HCl (1M, 60 mL) and extracted with EtOAc (30 mL) three times. The combined organic layer was concentrated in vacuo. The residue was purified by silica gel column (eluted with ethyl acetate in petroleum ether=0~30%) to afford methyl(S)-3-(bicyclo[1.1.1]pentan-1-yl)-2-(5-methylisoxazole-3-carboxamido)propanoate (1.6 g, 71a) as a yellow oil. MS obsd. (ESI⁺) [M+H]⁺: 279.1.

Step 2: Preparation of (S)-3-(bicyclo[1.1.1]pentan-1-yl)-2-(5-methylisoxazole-3-carboxamido)propanoic acid

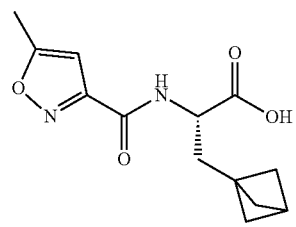

To a solution of methyl(S)-3-(bicyclo[1.1.1]pentan-1-yl)-2-(5-methylisoxazole-3-carboxamido)propanoate (1.6 g, compound 71a) in THF (15 mL) and water (15 mL) was added LiOH H₂O (482.47 mg). After stirred at 20° C. for 1 hour, the mixture was poured into HCl (1 M, 30 mL) and extracted with EtOAc (40 mL) three times. The combined organic phase was dried over anhydrous Na₂SO₄, concentrated in vacuo to afford (S)-3-(bicyclo[1.1.1]pentan-1-yl)-2-(5-methylisoxazole-3-carboxamido)propanoic acid (400 mg, compound 71b) as a white solid. MS obsd. (ESI⁺) [M+H]⁺: 265.2.

Step 3: Preparation of tert-butyl 2-((S)-3-(bicyclo[1.1.1]pentan-1-yl)-2-(5-methylisoxazole-3-carboxamido)propanoyl)-1-((2-axopyrrolidin-3-yl)methyl)hydrazine-1-carboxylate

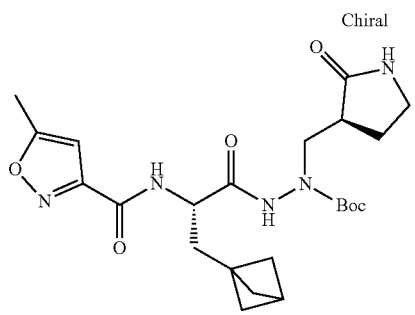

Compound 71c was prepared in analogy to Example 65, step 2 by using (S)-3-(bicyclo[1.1.1]pentan-1-yl)-2-(5-methylisoxazole-3-carboxamido)propanoic acid (400 mg, compound 71b) and tert-butyl(S)-1-((2-axopyrrolidin-3-yl)methyl)hydrazine-1-carboxylate (500 mg, Intermediate AF) instead of (S)-2-(1H-benzo[d]imidazole-2-carboxamido)-4,4-dimethylpentanoic acid (compound 65b) and tert-butyl 1-(3-amino-3-oxopropyl)hydrazine-1-carboxylate. tert-Butyl 2-((S)-3-(bicyclo[1.1.1]pentan-1-yl)-2-(5-methylisoxazole-3-carboxamido)propanoyl)-1-((2-axopyrrolidin-3-yl)methyl)hydrazine-1-carboxylate (1.7 g, compound 71c) was obtained as a white solid. MS obsd. (ESI⁺) [Ms+H]⁺: 476.2.

Step 4: Preparation of N-[(1S)-1-(1-bicyclo[1.1.1]pentanylmethyl)-2-oxo-2-[2-[[(3S)-2-axopyrrolidin-3-yl]methyl]hydrazino]ethyl]-5-methyl-isoxazole-3-carboxamide

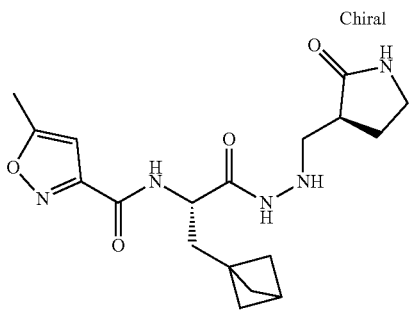

71d

Compound 71d was prepared in analogy to Example 65, Step 3 by using tert-butyl 2-((S)-3-(bicyclo[1.1.1]pentan-1-yl)-2-(5-methylisoxazole-3-carboxamido)propanoyl)-1-((2-axopyrrolidin-3-yl)methyl)hydrazine-1-carboxylate (1.7 g, compound 71c) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (compound 65c). N-[(1S)-1-(1-Bicyclo[1.1.1]pentanylmethyl)-2-oxo-2-[2-[[(3S)-2-axopyrrolidin-3-yl]methyl]hydrazino]ethyl]-5-methyl-isoxazole-3-carboxamide (1.3 g, compound 71d) was obtained as a white solid. MS obsd. (ESI+) [M+H]+: 376.2.

Step 5: Preparation of N-[(1S)-1-(1-bicyclo[1.1.1]pentanylmethyl)-2-[2-[(2R)-2-chloro-2-fluoro-acetyl]-2-[[(3S)-2-axopyrrolidin-3-yl]methyl]hydrazino]-2-axo-ethyl]-5-methyl-isoxazole-3-carboxamide

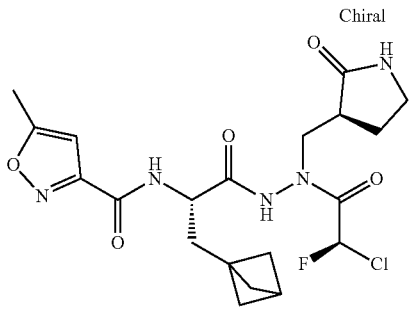

71

The title compound was prepared in analogy to Example 65, step 4 by using N-((2S)-3-(bicyclo[1.1.1]pentan-1-yl)-1-oxo-1-(2-((2-axopyrrolidin-3-yl)methyl)hydrazineyl)propan-2-yl)-5-methylisoxazole-3-carboxamide (1.3 g, compound 71d) and (R)-2-chloro-2-fluoroacetyl chloride instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d) and 2-chloro-2-fluoroacetic acid. N-[(1S)-1-(1-bicyclo[1.1.1]pentanylmethyl)-2-[2-[(2R)-2-chloro-2-fluoro-acetyl]-2-[[(3S)-2-axopyrrolidin-3-yl]methyl]hydrazino]-2-axo-ethyl]-5-methyl-isoxazole-3-carboxamide (139.66 mg, Example 71) was obtained as a white solid. 1H NMR (400 MHz, DMSO-$d_6$) δ ppm: 10.99-10.41 (m, 1H), 8.99-8.88 (m, 1H), 7.83-7.72 (m, 1H), 6.95-6.58 (m, 2H), 4.38-4.30 (m, 1H), 3.95-3.79 (m, 1H), 3.31-3.21 (m, 1H), 3.19-3.05 (m, 2H), 2.55-2.53 (m, 1H), 2.49-2.46 (m, 3H), 2.38-2.35 (m, 1H), 2.15-2.05 (m, 1H), 2.04-1.90 (m, 2H), 1.73-1.61 (m, 7H). MS obsd. (ESI+) [(M+H)+]: 470.1. SFC: RT=1.843 min, ee %=100%.

Example 74

5-Methyl-N-[rac-(1S)-2-[2-(3-amino-3-oxo-propyl)-2-(2-chloro-2-fluoro-acetyl)hydrazino]-1-(cyclohexylmethyl)-2-axo-ethyl]isoxazole-3-carboxamide

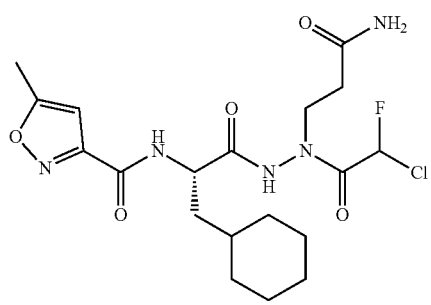

74

The title compound was prepared in analogy to Example 53, Step 3 by using 5-methylisoxazole-3-carboxylic acid and 3-(2-((S)-2-amino-3-cyclohexylpropanoyl)-1-(2-chloro-2-fluoroacetyl)hydrazinyl)propanamide (compound 56b) instead of 4-chloro-1H-indole-2-carboxylic acid and 3-[[[(2S)-2-amino-4-methyl-pentanoyl]amino]-(2-chloro-2-fluoro-acetyl)amino]propanamide (53b). 5-Methyl-N-[rac-(1S)-2-[2-(3-amino-3-oxo-propyl)-2-(2-chloro-2-fluoro-acetyl)hydrazino]-1-(cyclohexylmethyl)-2-axo-ethyl] isoxazole-3-carboxamide (21.3 mg, Example 74) was obtained as a white solid. 1H NMR (400 MHz, CD3OD) δ ppm: 6.76-6.43 (m, 1H), 6.49 (s, 1H), 4.58-4.54 (m, 1H), 4.02-3.86 (m, 1H), 3.75-3.55 (m, 1H), 2.56-2.51 (m, 2H), 2.49 (s, 3H), 1.86-1.69 (m, 7H), 1.50-1.49 (m, 1H), 1.38-1.20 (m, 3H), 1.10-0.95 (m, 2H). MS obsd. (ESI+) [(M+H)+]: 460.3

Example 75

5-Methyl-N-[rac-(1S)-2-[2-(3-amino-3-oxo-propyl)-2-(2-chloro-2-fluoro-acetyl)hydrazino]-1-(cyclopropylmethyl)-2-axo-ethyl]isoxazole-3-carboxamide

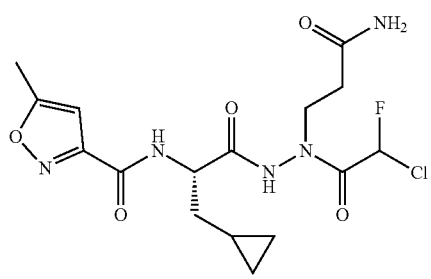

75

The title compound was prepared in analogy to Example 53, Step 3 by using 5-methylisoxazole-3-carboxylic acid and 3-(2-((S)-2-amino-3-cyclopropylpropanoyl)-1-(2-chloro-2-fluoroacetyl)hydrazineyl)propanamide (TFA salt) (40.0 mg, compound 62e) instead of 4-chloro-1H-indole-2-carboxylic acid and 3-[[[(2S)-2-amino-4-methyl-pentanoyl]amino]-(2-chloro-2-fluoro-acetyl)amino]propanamide (74.61 mg, 53b). 5-Methyl-N-[rac-(1S)-2-[2-(3-amino-3-oxo-propyl)-2-(2-chloro-2-fluoro-acetyl)hydrazino]-1-(cyclopropylmethyl)-2-axo-ethyl]isoxazole-3-carboxamide (3.2 mg, Example 77) was obtained as a white solid. $^1$H NMR (400 MHz, CD$_3$OD) δ ppm: 6.84-6.38 (m, 2H), 4.57-4.42 (m, 1H), 4.03-3.59 (m, 2H), 2.59-2.49 (m, 5H), 1.95-1.68 (m, 2H), 0.92-0.82 (m, 1H), 0.59-0.51 (m, 2H), 0.25-0.18 (m, 2H). MS obsd. (ESI$^+$) [(M+H)$^+$]: 418.3.

Example 78

N-[rac-(1S)-1-[[(3-amino-3-oxo-propyl)-(2-chloro-2-fluoro-acetyl)amino]carbamoyl]-3,3-dimethyl-butyl]pyrazine-2-carboxamide

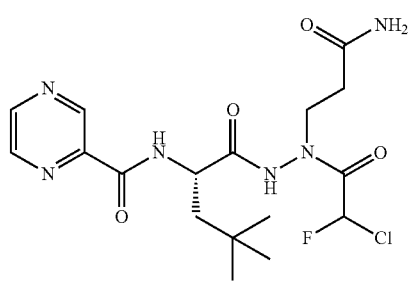

Step 1: Preparation of tert-butyl(S)-1-(3-amino-3-oxopropyl)-2-(4,4-dimethyl-2-(pyrazine-2-carboxamido)pentanoyl)hydrazine-1-carboxylate

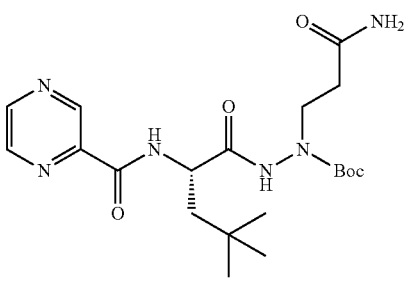

Compound 78a was prepared in analogy to Example 65, step 2 by using (S)-4,4-dimethyl-2-(pyrazine-2-carboxamido)pentanoic acid (1.3 g, compound 77c) instead of (S)-2-(1H-benzo[d]imidazole-2-carboxamido)-4,4-dimethylpentanoic acid (120.0 mg, compound 65b). tert-butyl(S)-1-(3-amino-3-oxopropyl)-2-(4,4-dimethyl-2-(pyrazine-2-carboxamido)pentanoyl)hydrazine-1-carboxylate (700 mg, compound 78a) was obtained as a yellow solid. MS obsd. (ESI$^+$) [(M+H)$^+$]: 437.2.

Step 2: Preparation of (S)—N-(1-(2-(3-amino-3-oxopropyl)hydrazineyl)-4,4-dimethyl-1-oxopentan-2-yl)pyrazine-2-carboxamide

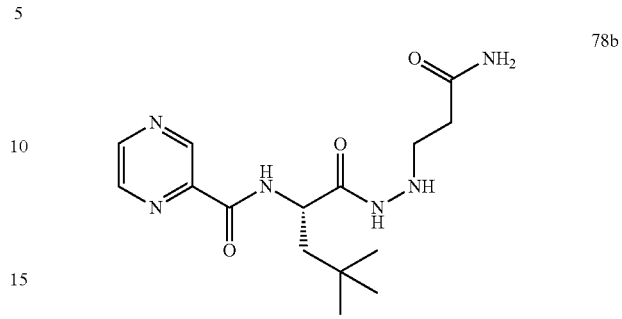

Compound 78b was prepared in analogy to Example 65, step 3 by using tert-butyl(S)-1-(3-amino-3-oxopropyl)-2-(4,4-dimethyl-2-(pyrazine-2-carboxamido)pentanoyl)hydrazine-1-carboxylate (700 mg, compound 78a) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (100.0 mg, compound 65c). (S)—N-(1-(2-(3-amino-3-oxopropyl)hydrazineyl)-4,4-dimethyl-1-oxopentan-2-yl)pyrazine-2-carboxamide (400 mg, compound 78b) was obtained as a yellow solid.

MS obsd. (ESI$^+$) [(M+H)$^+$]: 337.1.

Step 3: Preparation of N-((2S)-1-(2-(3-amino-3-oxopropyl)-2-(2-chloro-2-fluoroacetyl) hydrazineyl)-4,4-dimethyl-1-oxopentan-2-yl)pyrazine-2-carboxamide

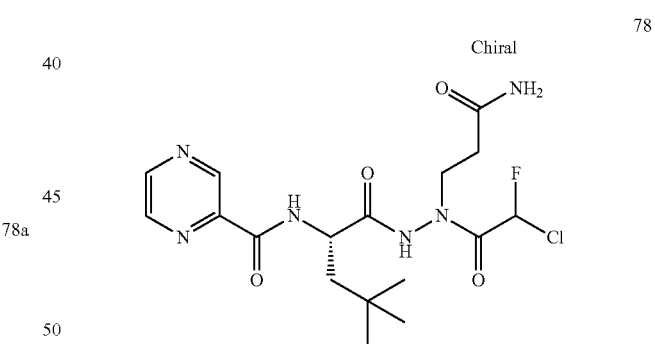

The title compound was prepared in analogy to Example 65, step 4 by using (S)—N-(1-(2-(3-amino-3-oxopropyl)hydrazineyl)-4,4-dimethyl-1-oxopentan-2-yl)pyrazine-2-carboxamide (400 mg, compound 78b) instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d). N-((2S)-1-(2-(3-amino-3-oxopropyl)-2-(2-chloro-2-fluoroacetyl)hydrazineyl)-4,4-dimethyl-1-oxopentan-2-yl)pyrazine-2-carboxamide (114.6 mg, compound 78) was obtained as a white solid. $^1$H NMR (400 MHz, CDCl$_3$) δ ppm: 9.38 (d, J=6.0 Hz, 1H), 8.81 (d, J=2.0 Hz, 1H), 8.60 (s, 1H), 8.15 (d, J=5.6 Hz, 1H), 6.56-6.05 (m, 3H), 4.67-4.56 (m, 1H), 3.82-3.60 (m, 3H), 2.71-2.55 (m, 2H), 2.05-1.95 (m, 1H), 1.83-1.71 (m, 1H), 1.03 (s, 9H). MS obsd. (ESI$^+$) [(M+H)$^+$]: 431.1.

Example 79

N-[rac-(1S)-2-[2-(3-amino-3-oxo-propyl)-2-(2-chloro-2-fluoro-acetyl)hydrazino]-1-(cyclobutylmethyl)-2-axo-ethyl]pyrazine-2-carboxamide

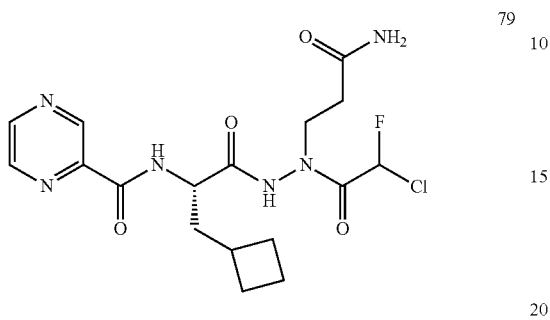

79

Step 1: Preparation of methyl(S)-2-amino-3-cyclobutylpropanoate

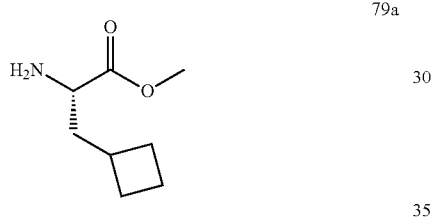

79a

To a solution of methyl(S)-2-((tert-butoxycarbonyl)amino)-3-cyclobutylpropanoate (350.0 mg) in DCM (4.0 mL) was added TFA (4.0 mL). After stirred at 25° C. for 1 hr, the mixture was concentrated in vacuo to afford methyl (S)-2-amino-3-cyclobutylpropanoate (TFA salt) (210 mg, compound 79a) as a colorless oil.

Step 2: Preparation of methyl(S)-3-cyclobutyl-2-(pyrazine-2-carboxamido)propanoate

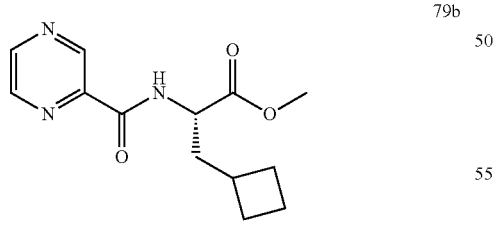

79b

To a solution of methyl(S)-2-amino-3-cyclobutylpropanoate (TFA salt) (210.0 mg, compound 79a), pyrazine-2-carboxylic acid (165.77 mg) and DIEA (1.0 g) in DCM (5 mL) was added and T₃P (1.3 g, 2 mmol, 50% in EtOAc). After stirred at 25° C. for 12 hrs, the reaction mixture was diluted with ethyl acetate (100 mL) and washed with brine (30 mL). The organic phase was dried over Na₂SO₄. The residue was purified by silica gel column, eluted with MeOH in DCM=0~10% to afford methyl(S)-3-cyclobutyl-2-(pyrazine-2-carboxamido)propanoate (330 mg, compound 79b) as a colorless oil. MS obsd. (ESI⁺) [(M+H)⁺]: 264.2.

Step 3: Preparation of (S)-3-cyclobutyl-2-(pyrazine-2-carboxamido)propanoic acid

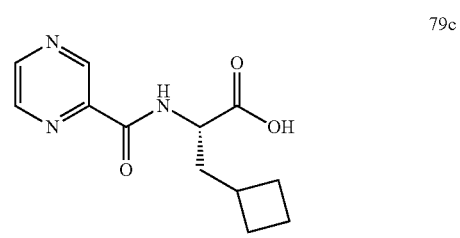 [SMILES: O=C(N[C@@H](CC1CCC1)C(=O)O)c1cnccn1]

79c

To a solution of methyl(S)-3-cyclobutyl-2-(pyrazine-2-carboxamido)propanoate (330.0 mg, compound 79b) in THF (4 mL) was added LiOH H₂O (110.57 mg) in water (4 mL) at 0° C. After stirred at 0° C. for 2 hrs, the reaction mixture was diluted with EtOAc (100 mL), washed with HCl solution (1 M 30 mL) and brine (30 mL) in turns. The organic phase was dried over anhydrous Na₂SO₄. After filtration and concentration, (S)-3-cyclobutyl-2-(pyrazine-2-carboxamido)propanoic acid (300 mg, compound 79c) was obtained as a white solid. MS obsd. (ESI⁺) [(M+H)⁺]: 250.2

Step 4: Preparation of tert-butyl(S)-1-(3-amino-3-oxopropyl)-2-(3-cyclobutyl-2-(pyrazine-2-carboxamido)propanoyl)hydrazine-1-carboxylate

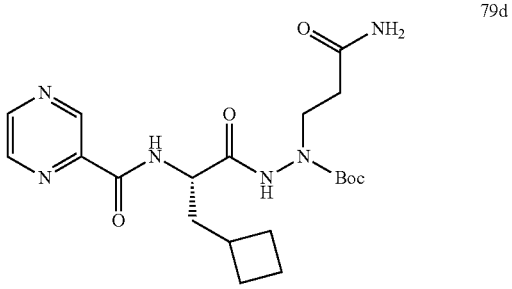 [SMILES: CC(C)(C)OC(=O)N(CCC(N)=O)NC(=O)[C@H](CC1CCC1)NC(=O)c1cnccn1]

79d

Compound 79b was prepared in analogy to Example 65, step 2 by using (S)-3-cyclobutyl-2-(pyrazine-2-carboxamido)propanoic acid (300 mg, compound 79c) instead of (2S)-2-(1H-benzimidazole-2-carbonylamino)-4,4-dimethylpentanoic acid (compound 65b). tert-Butyl(S)-1-(3-amino-3-oxopropyl)-2-(3-cyclobutyl-2-(pyrazine-2-carboxamido)propanoyl)hydrazine-1-carboxylate (400 mg, compound 79d) was obtained as a white solid. MS obsd. (ESI⁺) [(M−Boc+H)⁺]: 355.3.

145

Step 5: Preparation of (S)—N-(1-(2-(3-amino-3-oxopropyl)hydrazineyl)-3-cyclobutyl-1-oxopropan-2-yl)pyrazine-2-carboxamide

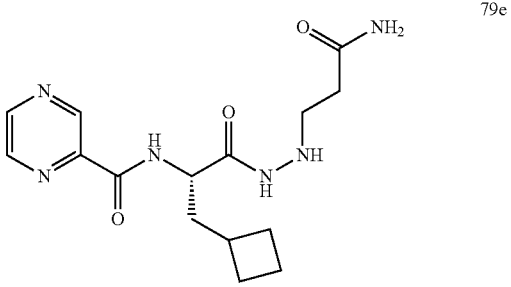 [SMILES: NC(=O)CCNNC(=O)[C@H](CC1CCC1)NC(=O)c1cnccn1]

79e

Compound 79e was prepared in analogy to Example 65, step 3 by using tert-butyl(S)-1-(3-amino-3-oxopropyl)-2-(3-cyclobutyl-2-(pyrazine-2-carboxamido)propanoyl)hydrazine-1-carboxylate (400 mg, compound 79d) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (100.0 mg, compound 65c). (S)—N-(1-(2-(3-amino-3-oxopropyl)hydrazineyl)-3-cyclobutyl-1-oxopropan-2-yl)pyrazine-2-carboxamide (TFA salt) (160 mg, compound 79e) was obtained as a yellow oil. MS obsd. (ESI$^+$) [(M+H)$^+$]: 355.3.

Step 6: Preparation of N-((2S)-1-(2-(3-amino-3-oxopropyl)-2-(2-chloro-2-fluoroacetyl)hydrazinyl)-3-cyclobutyl-1-oxopropan-2-yl)pyrazine-2-carboxamide

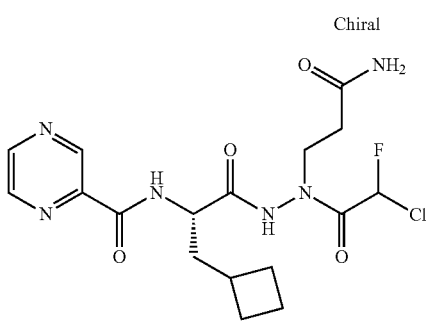

79

The title compound was prepared in analogy to Example 65, step 4 by using (S)—N-(1-(2-(3-amino-3-oxopropyl)hydrazineyl)-3-cyclobutyl-1-oxopropan-2-yl)pyrazine-2-carboxamide (TFA salt) (160 mg, compound 79e) instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d). N-((2S)-1-(2-(3-Amino-3-oxopropyl)-2-(2-chloro-2-fluoroacetyl)hydrazineyl)-3-cyclbutyl-1-oxopropan-2-yl)pyrazine-2-carboxamide (56.9 mg, Example 79) was obtained as a white solid. $^1$H NMR (400 MHz, CD$_3$OD) δ ppm: 9.26-9.24 (m, 1H), 8.82 (t, J=2.4 Hz, 1H), 8.72 (d, J=1.2 Hz, 1H), 6.84-6.49 (m, 1H), 4.53-4.33 (m, 1H), 4.13-3.85 (m, 1H), 3.72-3.61 (m, 1H), 2.58-2.46 (m, 3H), 2.16-2.02 (m, 4H), 1.94-1.75 (m, 4H). MS obsd. (ESI$^+$) [(M+H)$^+$]:429.3.

146

Example 82

N-[rac-(1S)-2-[2-(3-amino-3-oxo-propyl)-2-(2-chloro-2-fluoro-acetyl)hydrazino]-1-(cyclohexylmethyl)-2-axo-ethyl]imidazo[1,2-a]pyridine-2-carboxamide

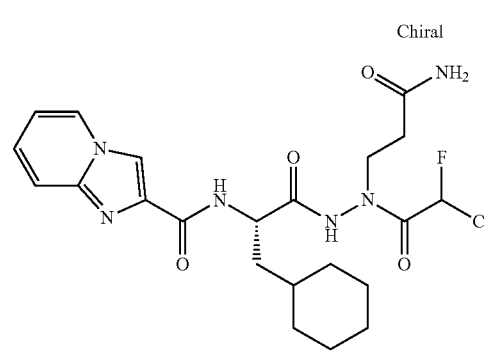

82

The title compound was prepared in analogy to Example 53, Step 3 by using imidazo[1,2-a]pyridine-2-carboxylic acid and 3-(2-((S)-2-amino-3-cyclohexylpropanoyl)-1-(2-chloro-2-fluoroacetyl)hydrazinyl)propanamide (compound 56b) instead of 4-chloro-1H-indole-2-carboxylic acid and 3-[[[(2S)-2-amino-4-methyl-pentanoyl]amino]-(2-chloro-2-fluoro-acetyl)amino]propanamide (compound 53b). N-((2S)-1-(2-(3-amino-3-oxopropyl)-2-(2-chloro-2-fluoroacetyl)hydrazinyl)-3-cyclohexyl-1-oxopropan-2-yl)imidazo[1,2-a]pyridine-2-carboxamide (2.02 mg, Example) was obtained as a white solid $^1$H NMR (400 MHz, CD$_3$OD) δ ppm: 8.60-8.63 (m, 1H), 8.49 (d, J=8.4 Hz, 1H), 7.71-7.73 (m, 1H), 7.60-7.66 (m, 1H), 7.14-25 (m, 1H), 6.72a-6.85 (m, 1H), 4.41-4.43 (m, 0.5H), 3.88-4.05 (m, 1H), 3.61-3.71 (m, 1H), 2.46-2.64 (m, 2H), 1.69-1.86 (m, 7H), 1.49-1.59 (m, 1H), 1.23-1.34 (m, 3H), 0.98-1.09 (m, 2H). MS obsd. (ESI$^+$) [(M+H)$^+$]: 495.0.

Example 83

3-[[[(2R)-2-chloro-2-fluoro-acetyl]-[[(2S)-2-[[2-(3-methoxyanilino)acetyl]amino]-4-methyl-pentanoyl]amino]amino]propanamide and 3-[[[(2S)-2-chloro-2-fluoro-acetyl]-[[(2S)-2-[[2-(3-methoxyanilino)acetyl]amino]-4-methyl-pentanoyl]amino]amino]propanamide

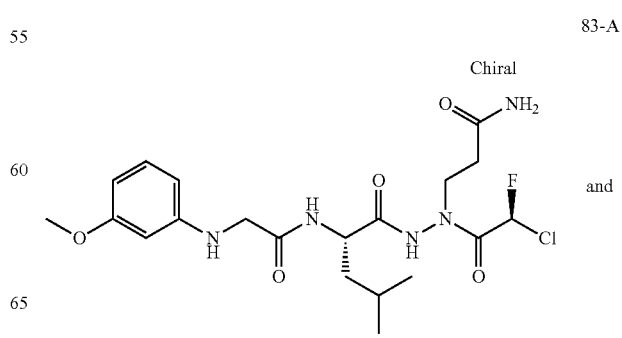

83-A and

147

-continued

Step 3: Preparation of 3-(1-(2-chloro-2-fluoro-acetyl)-2-((S)-2-(2-((3-methoxyphenyl)amino)acetamido)-4-methylpentanoyl)hydrazinyl)propanamide

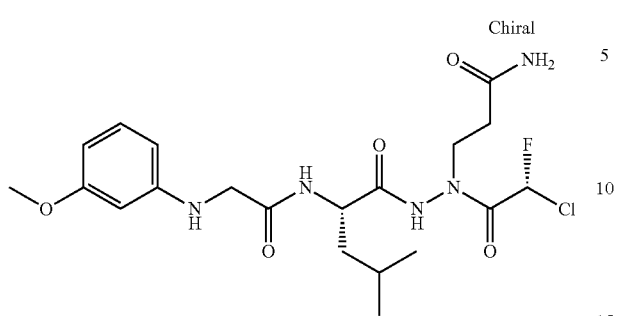
83-B

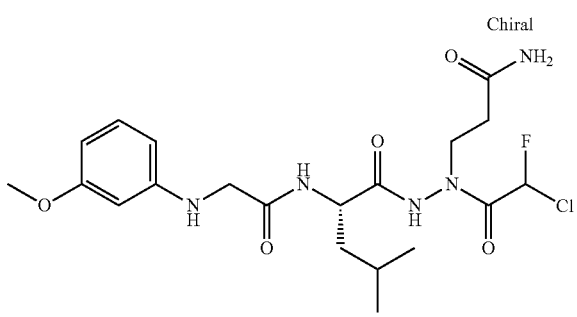 [SMILES: COc1cccc(NCC(=O)N[C@@H](CC(C)C)C(=O)NN(CCC(N)=O)C(=O)C(F)Cl)c1]

The title compound was prepared in analogy to Example 53, Step 3 by using 2-((3-methoxyphenyl)amino)acetic acid instead of 4-chloro-1H-indole-2-carboxylic acid. 3-(1-(2-chloro-2-fluoroacetyl)-2-((S)-2-(2-((3-methoxyphenyl)amino)acetamido)-4-methylpentanoyl)hydrazinyl)propanamide (20 mg, Example 83) was obtained as a white solid.

Separation of compound 83 by chiral SFC afforded Example 83-A (faster eluting, 2.18 mg) and Example 83-B (slower eluting, 3.65 mg) with Neu-ETOH; B %: 30-30%; FlowRate (ml/min): 60) on DAICEL CHIRALPAK AD-H column Example 83-A: $^1$H NMR (400 MHz, CD$_3$OD) δ8.09-8.12 (m, 1H), 7.03 (t, J=8.0 Hz, 1H), 6.47-6.80 (m, 1H), 6.15-6.33 (m, 3H), 4.20-4.46 (m, 1H), 3.82-4.02 (m, 2H), 3.49-3.77 (m, 5H), 2.35-2.49 (m, 2H), 1.48-1.75 (m, 3H), 0.91 (d, J=6.0 Hz, 3H), 0.87 (d, J=5.6 Hz, 3H). MS obsd. (ESI$^+$) [(M+H)$^+$]: 474.3. SFC: RT=4.058 min, ee %=100%.

Example 83-B: $^1$H NMR (400 MHz, CD3OD) δ 7.03 (t, J=8.0 Hz, 1H), 6.34-6.90 (m, 1H), 6.20-6.32 (m, 3H), 4.37-4.41 (m, 1H), 3.83-3.90 (m, 2H), 3.58-3.79 (m, 5H), 2.41-2.60 (m, 2H), 1.47-1.69 (m, 3H), 0.87-0.96 (m, 6H). MS obsd. (ESI$^+$) [(M+H)$^+$]: 474.3. SFC: RT=4.420 min, ee %=91.9%.

Step 1: Preparation of ethyl 2-((3-methoxyphenyl)amino)acetate

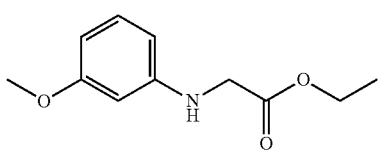
83a

To a solution of m-aminoanisole (1.0 g) and ethyl bromoacetate (1.36 g) in ethanol (20 mL) was added CH$_3$COONa (667.0 mg). After stirred at 90° C. for 12 hrs, the reaction mixture was concentrated in vacuo. The residue was purified by silica gel column, eluted with petroleum ether:EtOAc=10:1~ 3:1 to afford ethyl 2-((3-methoxyphenyl)amino)acetate (1.5 g, compound 83a) as a yellow oil. MS obsd. (ESI$^+$) [(M+H)$^+$]: 210.0

Step 2: Preparation of 2-((3-methoxyphenyl)amino)acetic acid

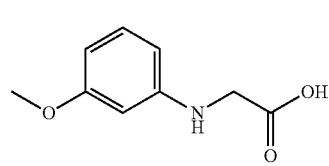
83b

To a solution of ethyl 2-(3-methoxyanilino)acetate (1.5 g, 83a) in THF (10 mL) was added NaOH (574.0 mg) in water (10 mL) at 0° C. After stirred at 20° C. for 2 hrs, the mixture was poured into HCl (1M, 15 mL) and extracted with EtOAc (30 mL) three times. The combined organic layer was washed with brine (40 mL), dried over anhydrous Na$_2$SO$_4$ and concentrated in vacuo to afford 2-((3-methoxyphenyl)amino)acetic acid (1.1 g, compound 83b) as a yellow oil. MS obsd. (ESI$^+$) [(M+H)$^+$]: 181.8.

Example 84

3-[[2-chloro-2-fluoro-acetyl)-[[rac-(2S)-2-(benzylsulfonylamino)-3-cyclohexyl-propanoyl]amino]amino]propanamide

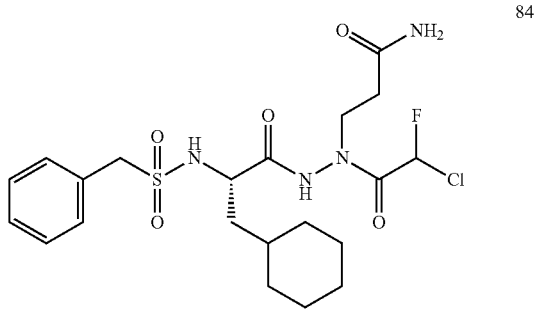 [SMILES: NC(=O)CCN(NC(=O)[C@H](CC1CCCCC1)NS(=O)(=O)Cc1ccccc1)C(=O)C(F)Cl]
84

The title compound was prepared in analogy to Example 53, Step 3 by using alpha-toluenesulfonyl chloride and 3-(2-((S)-2-amino-3-cyclohexylpropanoyl)-1-(2-chloro-2- fluoroacetyl)hydrazinyl)propanamide (compound 56b) instead of 4-chloro-1H-indole-2-carboxylic acid and 3-[[[(2S)-2-amino-4-methyl-pentanoyl]amino]-(2-chloro-2-fluoro-acetyl)amino]propanamide (compound 53b). 3-(1-(2-Chloro-2-fluoroacetyl)-2-((S)-3-cyclohexyl-2-(phenylmethylsulfonamido)propanoyl)hydrazinyl)propanamide (33.18 mg, Example 84) was obtained as a white solid. $^1$H NMR (400 MHz, CD$_3$OD) δ ppm: 7.45-7.47 (m, 2H), 7.38-7.22 (m, 3H), 6.39-6.74 (m, 1H), 4.33-4.40 (m, 2H), 3.55-4.03 (m, 3H), 2.39-2.64 (m, 2H), 1.44-1.79 (m, 7H), 1.15-1.48 (m, 4H), 0.84-0.98 (m, 2H). MS obsd. (ESI$^+$) [(M+H)$^+$]: 505.2.

Example 85

3-[(2-chloro-2-fluoro-acetyl)-[[rac-(2S)-2-(benzylsulfonylamino)-3-cyclopropyl-propanoyl]amino]amino]propanamide

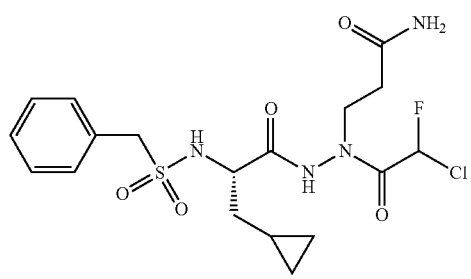

The title compound was prepared in analogy to Example 53, Step 3 by using alpha-toluenesulfonyl chloride and 3-(2-((S)-2-amino-3-cyclopropylpropanoyl)-1-(2-chloro-2-fluoroacetyl)hydrazineyl)propanamide (TFA salt) (40.0 mg, compound 62e) instead of 4-chloro-1H-indole-2-carboxylic acid and 3-[[[(2S)-2-amino-4-methyl-pentanoyl]amino]-(2-chloro-2-fluoro-acetyl)amino]propanamide (74.61 mg, compound 53b). 3-[[[(2S)-2-(Benzylsulfonylamino)-3-cyclopropyl-propanoyl]amino]-(2-chloro-2-fluoro-acetyl)amino]propanamide (2.71 mg, Example 85) was obtained as a white solid. $^1$H NMR (400 MHz, DMSO-d$_6$) δ ppm: 9.91 (br. s, 1H), 7.38-7.49 (m, 5H), 6.27-6.34 (m, 3H), 4.33 (s, 1H), 3.55-4.11 (m, 3H), 2.40-2.58 (m, 2H), 1.57-1.64 (m, 2H), 0.69-0.75 (m, 1H), 0.32-0.50 (m, 2H), 0.02-0.21 (m, 2H). MS obsd. (ESI$^+$) [M+H]$^+$: 463.1.

Example 86-A and 86-B

3-[[(2R)-2-chloro-2-fluoro-acetyl]-[[(2S)-4-methyl-2-[[(E)-3-phenylprop-2-enoyl]amino]pentanoyl]amino]amino]propanamide and 3-[[(2S)-2-chloro-2-fluoro-acetyl]-[[(2S)-4-methyl-2-[[(E)-3-phenylprop-2-enoyl]amino]pentanoyl]amino]amino]propanamide

86-A

Chiral

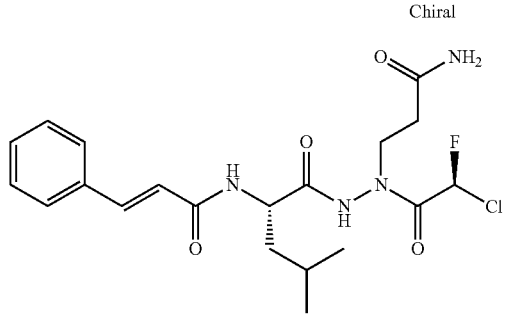

and

86-B

Chiral

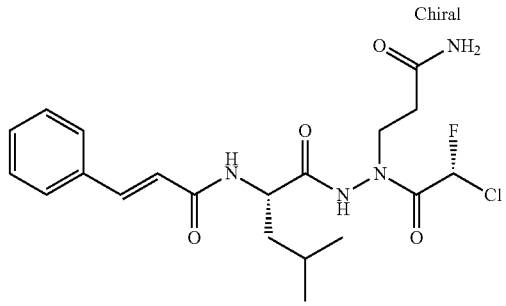

The title compound was prepared in analogy to Example 53, Step 3 by using (E)-3-phenylprop-2-enoic acid instead of 4-chloro-1H-indole-2-carboxylic acid 3-[(2-chloro-2-fluoro-acetyl)-[[(2S)-4-methyl-2-[[(E)-3-phenylprop-2-enoyl]amino]pentanoyl]amino]amino]propanamide (compound 86) was obtained as a yellow solid.

Separation of compound 86 by chiral SFC afforded Example 86-A (faster eluting, 8.13 mg) and Example 86-B (slower eluting, 11.9 mg) with Neu-ETOH; B %: 30-30%; flow rate 60 ml/min) on DAICEL CHIRALPAK AD-H column Example 86-A: $^1$H NMR (400 MHz, CD3OD) δ ppm: 7.55-7.64 (m, 3H), 7.36-7.44 (m, 3H), 6.68-6.82 (m, 2H), 4.31-4.50 (m, 1H), 3.87-4.02 (m, 1H), 3.53-3.77 (m, 1H), 2.39-2.68 (m, 2H), 1.71-1.97 (m, 2H), 1.55-1.68 (m, 1H), 1.04 (d, J=6.8 Hz, 3H), 1.00 (d, J=6.8 Hz, 3H). MS obsd. (ESI$^+$) [(M+H)$^+$]: 441.3. SFC: RT=2.225 min, ee %=99.34%

Example 86-B: $^1$H NMR (400 MHz, CD$_3$OD) δ ppm: 7.56-7.62 (m, 3H), 7.36-7.42 (m, 3H), 6.45-6.95 (m, 2H), 4.44-4.47 (m, 1H), 3.85-4.10 (m, 1H), 3.52-3.76 (m, 1H), 2.45-2.68 (m, 2H), 1.63-1.86 (m, 3H), 1.04 (d, J=6.0 Hz, 3H), 1.00 (d, J=6.0 Hz, 3H). MS obsd. (ESI$^+$) [(M+H)$^+$]: 441.3. SFC: RT=2.503 min, ee %=97.734%

Example 88-A and 88-B

N-[(1S)-1-[[(3-amino-3-oxo-propyl)-[(2R)-2-chloro-2-fluoro-acetyl]amino]carbamoyl]-3-methyl-butyl]-1H-pyrrolo[2,3-c]pyridine-2-carboxamide and N-[(1S)-1-[[(3-amino-3-oxo-propyl)-[(2S)-2-chloro-2-fluoro-acetyl]amino]carbamoyl]-3-methyl-butyl]-1H-pyrrolo[2,3-c]pyridine-2-carboxamide

88-A

Chiral

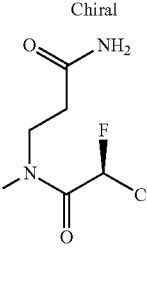

and

-continued

88-B
Chiral

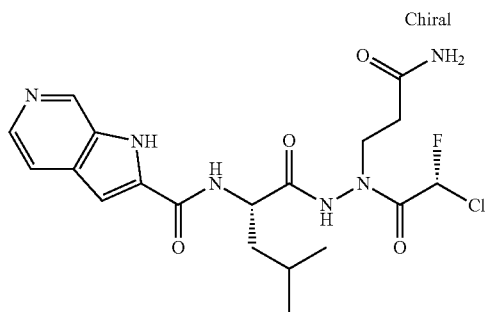

The title compound was prepared in analogy to Example 53, Step 3 by using 1H-pyrrolo[2,3-c]pyridine-2-carboxylic acid instead of 4-chloro-1H-indole-2-carboxylic acid. N-[(1S)-2-[2-(3-amino-3-oxo-propyl)-2-(2-chloro-2-fluoro-acetyl)hydrazino]-1-(cyclohexylmethyl)-2-axo-ethyl]-1H-indole-2-carboxamide (compound 88) was obtained as a yellow solid.

Separation of compound 88 by chiral SFC afforded Example 88-A (faster eluting, 5.0 mg) and Example 88-B (slower eluting, 6.6 mg) with Neu-ETOH; B %: 30-30%; flow rate 60 ml/min on DAICEL CHIRALPAK AD-H column Example 88-A: $^1$H NMR (400 MHz, CD$_3$OD) δ ppm: 8.86 (s, 1H), 8.16 (d, J=5.6 Hz, 1H), 7.83 (d, J=5.6 Hz, 1H), 7.36 (s, 1H), 6.89 (d, J=50 Hz, 1H), 4.47-4.65 (m, 1H), 3.93-4.19 (m, 1H), 3.65-3.73 (m, 1H), 2.44-2.60 (m, 2H), 1.80-1.93 (m, 2H), 1.65-1.72 (m, 1H), 1.07 (d, J=6.4 Hz, 3H), 1.02 (d, J=6.4 Hz, 3H). MS obsd. (ESI$^+$), (M+H)$^+$: 455.1. SFC: RT=0.715 min, ee %=81.2%

Example 88-B: $^1$H NMR (400 MHz, CD$_3$OD) δ ppm: 9.01 (s, 1H), 8.23-8.27 (m, 1H), 8.80-8.94 (m, 1H), 7.52 (s, 1H), 6.47-6.89 (m, 1H), 4.59-4.62 (m, 1H), 3.95-4.22 (m, 1H), 3.65-3.75 (m, 1H), 2.44-2.60 (m, 2H), 1.76-1.93 (m, 3H), 1.07 (d, J=6.4 Hz, 3H), 1.02 (d, J=6.4 Hz, 3H). MS obsd. (ESI$^+$). (M+H)$^+$: 455.1. SFC: RT=1.413 min, ee %=63%

Example 89

5-methoxy-N-[rac-(1S)-1-[[(3-amino-3-axo-propyl)-(2-chloro-2-fluoro-acetyl)amino]carbamoyl]-3-methyl-butyl]-1H-pyrrolo[2,3-c]pyridine-2-carboxamide

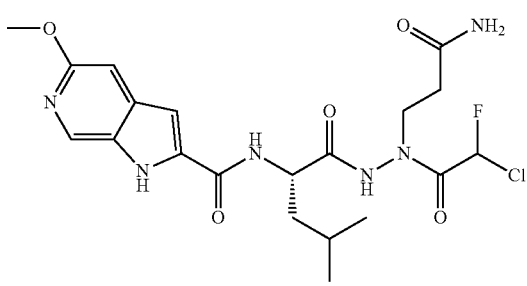 [SMILES: COc1cc2cc(C(=O)N[C@@H](CC(C)C)C(=O)NN(CCC(N)=O)C(=O)C(F)Cl)[nH]c2cn1]

The title compound was prepared in analogy to Example 53, Step 3 by using 5-methoxy-1H-pyrrolo[2,3-c]pyridine-2-carboxylic acid instead of 4-chloro-1H-indole-2-carboxylic acid and. 5-Methoxy-N-[rac-(1S)-1-[[(3-amino-3-oxo-propyl)-(2-chloro-2-fluoro-acetyl)amino]carbamoyl]-3-methyl-butyl]-1H-pyrrolo[2,3-c]pyridine-2-carboxamide (11.1 mg, Example 89) was obtained as a yellow solid.

$^1$H NMR (400 MHz, CD$_3$OD) δ ppm: 8.56 (d, J=2.8 Hz, 1H), 7.45 (s, 1H), 7.34 (s, 1H), 6.45-6.88 (m, 1H), 4.45-4.62 (m, 1H), 4.08 (s, 3H), 3.94-4.05 (m, 1H), 3.57-3.76 (m, 1H), 2.48-2.60 (m, 2H), 1.71-1.92 (m, 3H), 1.02-1.08 (m, 6H). MS obsd. (ESI$^+$) [(M+H)$^+$]: 485.1.

Example 90-A and Example 90-B

N-[rac-(1S)-1-[[(3-amino-3-oxo-propyl)-[rac-(2R)-2-chloro-2-fluoro-acetyl]amino]carbamoyl]-3-methyl-butyl]pyrazolo[1,5-a]pyridine-2-carboxamide and
N-[rac-(1S)-1-[[(3-amino-3-oxo-propyl)-[rac-(2S)-2-chloro-2-fluoro-acetyl]amino]carbamoyl]-3-methyl-butyl]pyrazolo[1,5-a]pyridine-2-carboxamide

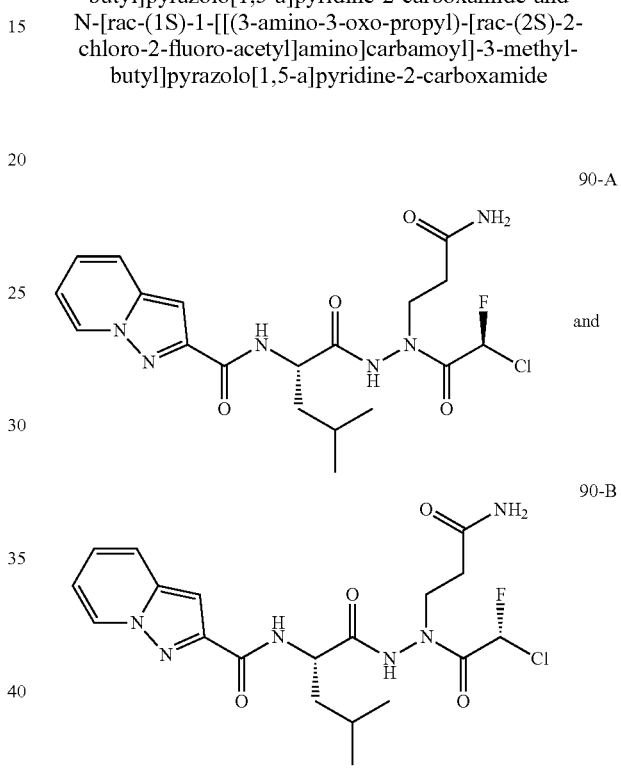

The title compound was prepared in analogy to Example 53, Step 3 by using pyrazolo[1,5-a]pyridine-2-carboxylic acid instead of 4-chloro-1H-indole-2-carboxylic acid. N,N-[rac-(1S)-1-[[(3-amino-3-oxo-propyl)-(2-chloro-2-fluoro-acetyl)amino]carbamoyl]-3-methyl-butyl]pyrazolo[1,5-a]pyridine-2-carboxamide (mg, Example 90) was obtained as a yellow solid.

Separation of compound 90 by chiral SFC afforded Example 90-A (faster eluting, 5.0 mg) and Example 90-B (slower eluting, 6.6 mg) with Neu-IPA B: 50 Gradient Time (min): 4.2; 30 FlowRate (ml/min): 70 on DAICEL CHIRALPAK IC column Example 90-A: $^1$H NMR (400 MHz, CD$_3$OD) δ ppm: 8.61 (d, J=6.4 Hz, 1H), 7.72 (d, J=9.2 Hz, 1H), 7.25-7.29 (m, 1H), 7.08 (s, 1H), 6.99-7.03 (m, 1H), 6.46-6.60 (m, 1H), 4.63-4.70 (m, 1H), 3.92-4.01 (m, 1H), 3.65-3.75 (m, 1H), 2.45-2.59 (m, 2H), 1.74-1.90 (m, 3H), 1.05 (d, J=6.4 Hz, 3H), 1.02 (d, J=6.4 Hz, 3H). MS obsd. (ESI) [(M+H)$^+$]: 455.3. SFC: RT=1.909 min, ee %=96.9%.

Example 90-B: 1H NMR (400 MHz, CD$_3$OD) δ ppm: 8.61 (d, J=6.4 Hz, 1H), 7.72 (d, J=8.8 Hz, 1H), 7.25-7.29 (m, 1H), 7.08 (s, 1H), 7.01-7.07 (m, 1H), 6.82 (d, J=50.0 Hz, 1H), 4.54-4.58 (m, 1H), 3.93-3.97 (m, 1H), 3.66-3.70 (m, 1H), 2.46-2.61 (m, 2H), 1.70-1.90 (m, 3H), 1.06 (d, J=6.0 Hz, 3H), 1.03 (d, J=6.4 Hz, 3H). MS obsd. (ESI+) [(M+H)+]: 455.3. SFC: RT=2.104 min, ee %=96.5%

Example 91-A and 91-B

N-[(1S)-1-[[(3-amino-3-oxo-propyl)-[(2R)-2-chloro-2-fluoro-acetyl]amino]carbamoyl]-3-methyl-butyl]-1H-pyrrolo[3,2-b]pyridine-2-carboxamide and
N-[(1S)-1-[[(3-amino-3-oxo-propyl)-[(2R)-2-chloro-2-fluoro-acetyl]amino]carbamoyl]-3-methyl-butyl]-1H-pyrrolo[3,2-b]pyridine-2-carboxamide

91-A

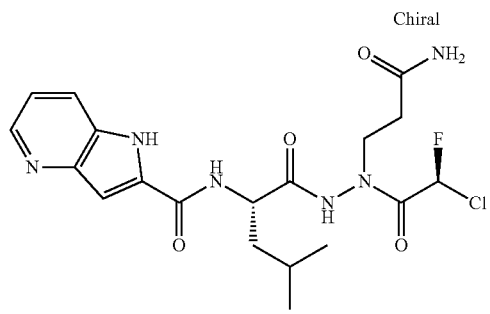

and

91-B

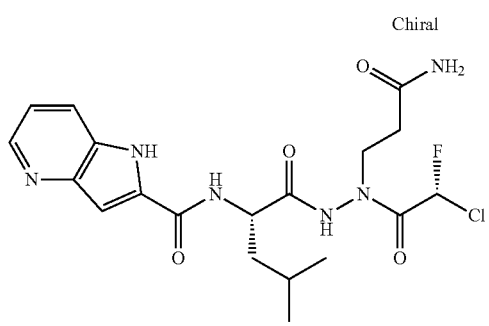

The title compound was prepared in analogy to Example 53, Step 3 by using 1H-pyrrolo[3,2-b]pyridine-2-carboxylic acid instead of 4-chloro-1H-indole-2-carboxylic acid. N-[(1S)-1-[[(3-amino-3-oxo-propyl)-(2-chloro-2-fluoro-acetyl)amino]carbamoyl]-3-methyl-butyl]-1H-pyrrolo[3,2-b]pyridine-2-carboxamide (mg, Example 91) was obtained as a yellow solid.

Separation of compound 90 by chiral SFC afforded Example 90-A (faster eluting, 5.0 mg) and Example 90-B (slower eluting, 6.6 mg) with 45% MeOH (Neu) in Supercritical CO2 flow rate 70 g/min Cycle Time: 3.0 min, total time: 50 min Single injetion volume: 2.0 ml Back Pressure: 100 bar to keep the CO2 in Supercritical flow on DAICEL CHIRALPAK IG column Example 91-A: 1H NMR (400 MHz, CD3OD) δ ppm: 8.45-8.51 (m, 1H), 8.05 (d, J=8.0 Hz, 1H), 7.36-7.50 (m, 2H), 6.50-7.09 (m, 1H), 4.59-4.62 (m, 1H), 3.89-4.07 (m, 1H), 3.65-3.80 (m, 1H), 2.47-2.60 (m, 2H), 1.76-2.00 (m, 3H), 1.09 (d, J=6.4 Hz, 3H), 1.04 (d, J=6.4 Hz, 3H). MS obsd. (ESI+) [(M+H)+]: 455.1. SFC: RT=2.066 min, ee %=97.93%

Example 91-B: 1H NMR (400 MHz, CD3OD) δ ppm: 8.02-8.04 (m, 1H), 7.36-7.50 (m, 2H), 6.89 (d, J=50.4 Hz, 1H), 4.45-4.62 (m, 1H), 3.90-4.12 (m, 1H), 3.62-3.77 (m, 1H), 2.47-2.60 (m, 2H), 1.82-1.98 (m, 2H), 1.65-1.80 (m, 1H), 1.07 (d, J=6.0 Hz, 3H), 1.03 (d, J=6.0 Hz, 3H). MS obsd. (ESI+) [(M+H)+]: 455.1. SFC: RT=2.304 min, ee %=97.93%

Example 95

N-[rac-(1S)-1-[[(3-amino-3-oxo-propyl)-[rac-(2R)-2-chloro-2-fluoro-acetyl]amino]carbamoyl]-3-methyl-butyl]imidazo[1,2-a]pyridine-2-carboxamide and
N-[rac-(1S)-1-[[(3-amino-3-oxo-propyl)-[rac-(2S)-2-chloro-2-fluoro-acetyl]amino]carbamoyl]-3-methyl-butyl]imidazo[1,2-a]pyridine-2-carboxamide

95-A

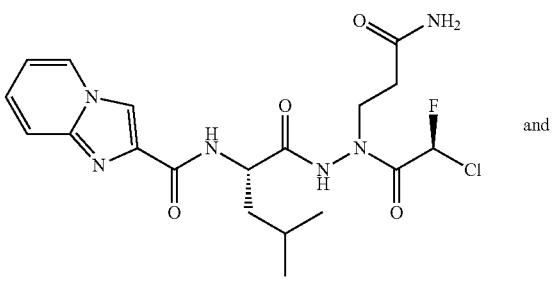

and

95-B

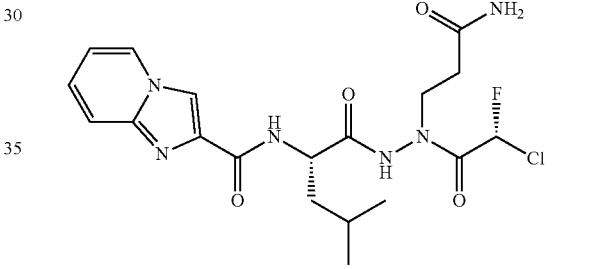

The title compound was prepared in analogy to Example 53, Step 3 by using imidazo[1,2-a]pyridine-2-carboxylic acid (Wuxi catalog, CAS number: 64951-08-2) instead of 4-chloro-1H-indole-2-carboxylic acid and N-[rac-(1S)-1-[[(3-amino-3-oxo-propyl)-(2-chloro-2-fluoro-acetyl)amino]carbamoyl]-3-methyl-butyl]imidazo[1,2-a]pyridine-2-carboxamide (compound 95) was obtained as a yellow solid.

Separation of compound 95 by chiral SFC afforded Example 95-A (faster eluting, 5.0 mg) and Example 95-B (slower eluting, 6.6 mg) with Neu-IPA; B %: 50-50%; FlowRate (ml/min): 70) on DAICEL CHIRALPAK IC column.

Example 95-A: 1H NMR (400 MHz, CD3OD) δ ppm: 8.53 (d, J=6.8 Hz, 1H), 8.41 (s, 1H), 7.65 (d, J=9.2 Hz, 1H), 7.46-7.49 (m, 1H), 7.05 (t, J=6.8 Hz, 1H), 6.53 (d, J=50.4 Hz, 1H), 4.51-4.60 (m, 1H), 3.89-4.05 (m, 1H), 3.59-3.76 (m, 1H), 2.45-2.65 (m, 2H), 1.75-1.90 (m, 3H), 1.06 (d, J=6.0 Hz, 3H), 1.02 (d, J=5.6 Hz, 3H). MS obsd. (ESI+) [(M+H)+]: 455.3. SFC: RT=1.370 min, ee %=98.4%

Example 95-B: 1H NMR (400 MHz, CD3OD) δ ppm: 8.55 (d, J=6.0 Hz, 1H), 8.47 (s, 1H), 7.64-7.76 (m, 1H), 7.47-7.57 (m, 1H), 7.06-7.09 (m, 1H), 6.61-6.79 (m, 1H), 4.55-4.60 (m, 1H), 3.79-4.05 (m, 1H), 3.58-3.76 (m, 1H), 2.48-2.58 (m, 2H), 1.76-1.89 (m, 3H), 1.06 (d, J=6.4 Hz, 3H), 1.02 (d, J=6.0 Hz, 3H). MS obsd. (ESI+) [(M+H)+]: 455.1. SFC: RT=2.148 min, ee %=96.6%

Example 96

N-[rac-(1S)-1-[[(3-amino-3-oxo-propyl)-(2-chloro-2-fluoro-acetyl)amino]carbamoyl]-3-methyl-butyl]-1H-imidazole-2-carboxamide

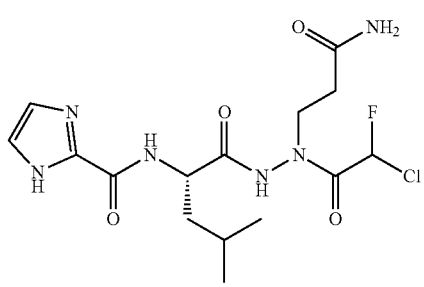

96

The title compound was prepared in analogy to Example 53, Step 3 by using 1H-imidazole-2-carboxylic acid instead of 4-chloro-1H-indole-2-carboxylic acid. N-[rac-(1S)-1-[[(3-amino-3-oxo-propyl)-(2-chloro-2-fluoro-acetyl)amino]carbamoyl]-3-methyl-butyl]-1H-imidazole-2-carboxamide (2 mg, compound 96) was obtained as a yellow solid. $^1$H NMR (400 MHz, CD$_3$OD) δ ppm: 7.14-7.28 (m, 2H), 6.47-6.88 (m, 1H), 4.39-4.89 (m, 1H), 3.71-4.05 (m, 2H), 2.41-2.60 (m, 2H), 1.72-1.95 (m, 3H), 0.99-1.05 (m, 6H). MS obsd. (ESI$^+$) [(M+H)$^+$]: 405.1.

Example 97

5-methyl-N-[rac-(1S)-1-[[(3-amino-3-oxo-propyl)-[rac-(2S)-2-chloro-2-fluoro-acetyl]amino]carbamoyl]-3-methyl-butyl]isoxazole-3-carboxamide and 5-methyl-N-[rac-(1S)-1-[[(3-amino-3-oxo-propyl)-[rac-(2R)-2-chloro-2-fluoro-acetyl]amino]carbamoyl]-3-methyl-butyl]isoxazole-3-carboxamide

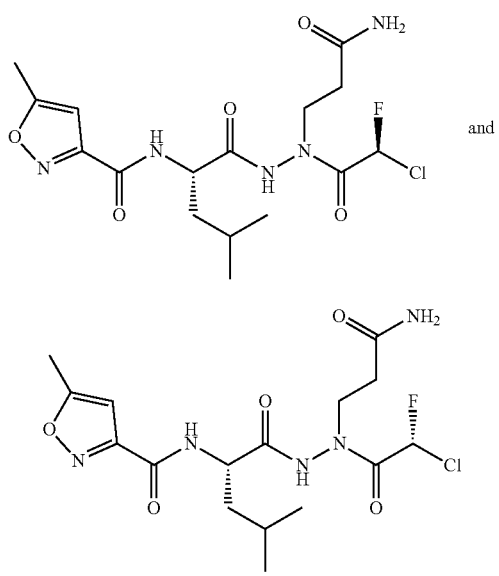

97-A and

97-B

The title compound was prepared in analogy to Example 53, Step 3 by using 5-methylisoxazole-3-carboxylic acid instead of 4-chloro-1H-indole-2-carboxylic acid. 5-Methyl-N-[rac-(1S)-1-[[(3-amino-3-oxo-propyl)-(2-chloro-2-fluoro-acetyl)amino]carbamoyl]-3-methyl-butyl]isoxazole-3-carboxamide (20 mg, compound 97) was obtained as a yellow solid.

Separation of compound 97 by chiral SFC afforded Example 97-A (faster eluting, 5.0 mg) and Example 97-B (slower eluting, 6.6 mg) with Neu-IPA; B %: 50-50%; flow rate 70 ml/min on DAICEL CHIRALPAK IC column.

Example 97-A: $^1$H NMR (400 MHz, CD$_3$OD) δ ppm: 6.50-7.02 (m, 2H), 4.51-4.56 (m, 1H), 3.50-4.09 (m, 2H), 2.50-2.60 (m, 2H), 2.49 (s, 3H), 1.64-1.92 (m, 3H), 1.03 (d, J=6.0 Hz, 3H), 0.99 (d, J=6.0 Hz, 3H). MS obsd. (ESI$^+$) [(M+H)$^+$]: 420.3. SFC: RT=1.032 min, ee %=97.82%.

Example 97-B: $^1$H NMR (400 MHz, CD$_3$OD) δ ppm: 6.76 (d, J=50.4 Hz, 1H), 6.49 (s, 1H), 4.51-4.36 (m, 1H), 3.85-4.06 (m, 1H), 3.51-3.76 (m, 1H), 2.51-2.60 (m, 2H), 2.49 (s, 3H), 1.74-1.88 (m, 2H), 1.61-1.73 (m, 1H), 1.03 (d, J=6.4 Hz, 3H), 1.00 (d, J=6.4 Hz, 3H). MS obsd. (ESI$^+$) [(M+H)$^+$]: 420.3. SFC: RT=1.116 min, ee %=83.25%

Example 98

N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-(trifluoromethyl)isoxazole-3-carboxamide

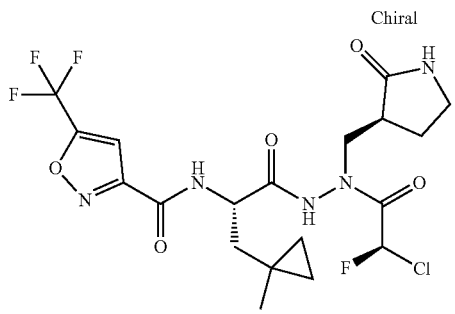

98
Chiral

Step 1: Preparation of ethyl 5-(trifluoromethyl)isoxazole-3-carboxylate

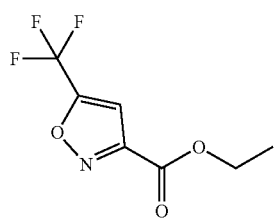

98a

To a solution of ethyl (Z)-2-chloro-2-(hydroxyimino) acetate (3.0 g) in ethyl acetate (50 mL) was added 2-bromo-3,3,3-trifluoroprop-1-ene (10.39 g, Shanghai Haohong, CAS Number: 1514-82-5) and NaHCO$_3$ (5.49 g). After stirred at 20° C. for 12 hrs, the reaction mixture was concentrated in vacuo at 30° C. to afford ethyl 5-(trifluoromethyl)isoxazole-3-carboxylate (3.75 g, compound 98a) as a yellow oil. ¹H NMR (400 MHz, DMSO-d₆) δ ppm: 7.93 (s, 1H), 4.44-4.39 (m, 2H), 1.34 (t, J=7.2 Hz, 3H)

Step 2: Preparation of 5-(trifluoromethyl)isoxazole-3-carboxylic acid

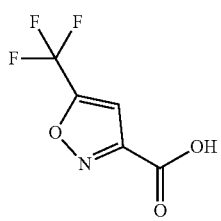

98b

To a solution of ethyl 5-(trifluoromethyl)isoxazole-3-carboxylate (3.75 g, compound 98a) in methanol (40 mL) was added the solution of NaOH (1.58 g) in water (40 mL) at 0° C. After stirred at 20° C. for 1 hr, the reaction mixture was concentrated in vacuo. The residue was dissolved with EtOAc (80 mL) and washed with HCl (1 M, 40 mL). The aqueous phase was extracted with EtOAc (80 mL) six times. The combined organic phase was dried with anhydrous Na₂SO₄ and concentrated in vacuo. The residue was purified by silica gel column, eluted with EtOAc in petroleum ether=30~50% to afford 5-(trifluoromethyl)isoxazole-3-carboxylic acid (2.3 g, compound 98b) as a white solid. ¹H NMR (400 MHz, CDCl₃) δ ppm: 7.39 (br. s, 1H), 7.18 (s, 1H).

Step 3: Preparation of 5-(trifluoromethyl)isoxazole-3-carbonyl chloride

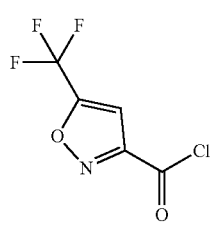

98c

To a solution of 5-(trifluoromethyl)isoxazole-3-carboxylic acid (700.0 mg, compound 98b) in DCM (10 mL) was added DMF (0.05 mL) and oxalyl chloride (588.84 mg) dropwise at 0° C. After stirred at 20° C. for 1 hr, the reaction mixture was concentrated in vacuo at 20° C. to afford 5-(trifluoromethyl)isoxazole-3-carbonyl chloride (771 mg, compound 98c) as a yellow oil.

Step 4: Preparation of tert-butyl 2-((S)-3-(1-methyl-cyclopropyl)-2-(5-(trifluoromethyl)isoxazole-3-car-boxamido)propanoyl)-1-(((S)-2-axopyrrolidin-3-yl) methyl)hydrazine-1-carboxylate

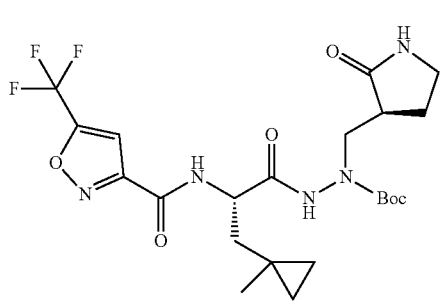

98d

To a solution of tert-butyl 2-((S)-2-amino-3-(1-methylcyclopropyl)propanoyl)-1-(((S)-2-axopyrrolidin-3-yl)methyl) hydrazine-1-carboxylate (680.0 mg, compound 70b) and DIEA (1487.7 mg) in THF (25 mL) was added 5-(trifluoromethyl)isoxazole-3-carbonyl chloride (765.57 mg, compound 98c) at 0° C. After stirred at 0° C. for 1 hr, the reaction mixture was extracted with EtOAc (30 mL) three times. The combined organic layers were dried over anhydrous Na₂SO₄, and concentrated in vacuo. The residue was purified by reversed-phase flash, eluted with MeCN in water (0.1% TFA)=0~70% to afford tert-butyl 2-((S)-3-(1-methyl-cyclopropyl)-2-(5-(trifluoromethyl)isoxazole-3-carbox-amido)propanoyl)-1-(((S)-2-axopyrrolidin-3-yl)methyl)hy-drazine-1-carboxylate (516 mg, compound 98d) as a white solid. MS obsd. (ESI⁺) [(M+H)⁺]: 518.2.

Step 5: Preparation of N—((S)-3-(1-methylcyclo-propyl)-1-oxo-1-(2-(((S)-2-axopyrrolidin-3-yl) methyl)hydrazineyl)propan-2-yl)-5-(trifluoromethyl) isoxazole-3-carboxamide

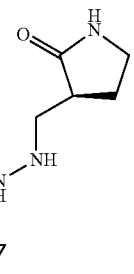

98e

Compound 98e was prepared in analogy to Example 65, step 3 by using tert-butyl 2-((S)-3-(1-methylcyclopropyl)-2-(5-(trifluoromethyl)isoxazole-3-carboxamido)propanoyl)-1-(((S)-2-axopyrrolidin-3-yl)methyl)hydrazine-1-carboxy-late (516 mg, compound 98d) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (100.0 mg, compound 65c). N—((S)-3-(1-Methylcyclopropyl)-1-oxo-1-(2-(((S)-2-axopyrrolidin-3-yl) methyl)hydrazineyl)propan-2-yl)-5-(trifluoromethyl)

isoxazole-3-carboxamide (88 mg, compound 98e) was obtained as a white solid. MS obsd. (ESI⁺) [(M+H)⁺]: 418.0.

Step 6: Preparation of N—((S)-1-(2-((R)-2-chloro-2-fluoroacetyl)-2-(((S)-2-axopyrrolidin-3-yl)methyl)hydrazineyl)-3-(1-methylcyclopropyl)-1-oxopropan-2-yl)-5-(trifluoromethyl) isoxazole-3-carboxamide

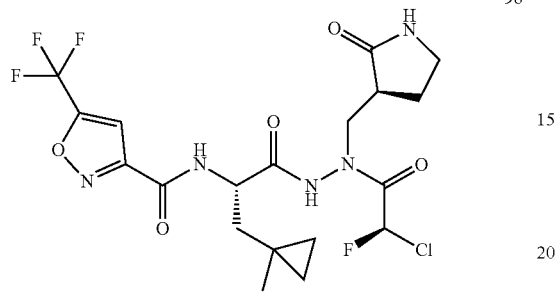

98

The title compound was prepared in analogy to Example 65, step 4 by using N—((S)-3-(1-methylcyclopropyl)-1-oxo-1-(2-(((S)-2-axopyrrolidin-3-yl)methyl)hydrazineyl)propan-2-yl)-5-(trifluoromethyl)isoxazole-3-carboxamide (88 mg, compound 98e) and (R)-2-chloro-2-fluoroacetyl chloride instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d) and 2-chloro-2-fluoroacetic acid. N—((S)-1-(2-((R)-2-Chloro-2-fluoroacetyl)-2-(((S)-2-axopyrrolidin-3-yl)methyl)hydrazineyl)-3-(1-methylcyclopropyl)-1-oxopropan-2-yl)-5-(trifluoromethyl)isoxazole-3-carboxamide (36.3 mg, Example 98) was obtained as a white solid.

¹H NMR (400 MHz, CDCl₃) δ ppm: 10.08 (br. s, 1H), 7.40-7.39 (m, 1H), 7.17 (s, 1H), 6.53 (d, J=50 Hz, 1H), 5.72 (d, J=3.2 Hz, 1H), 4.65-4.59 (m, 1H), 4.46-4.44 (m, 1H), 3.43 (dd, J₁=4.4 Hz, J₂=9.2 Hz, 2H), 2.88-2.84 (m, 2H), 2.42-2.38 (m, 1H), 2.18-2.04 (m, 1H), 1.89-1.73 (m, 1H), 1.62-1.52 (m, 1H), 1.13 (s, 3H), 0.53-0.43 (m, 2H), 0.41-0.34 (m, 2H).

MS obsd. (ESI⁺) [M+H]⁺: 512.0.

Example 99

N-[(1S)-1-(1-bicyclo[1.1.1]pentanylmethyl)-2-[2-[(2R)-2-chloro-2-fluoro-acetyl]-2-[[(3S)-2-axopyrrolidin-3-yl]methyl]hydrazino]-2-axo-ethyl]-5-(trifluoromethyl)isoxazole-3-carboxamide

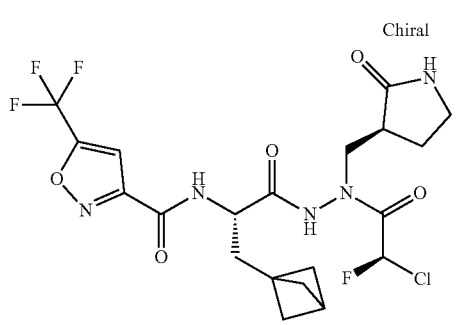

99
Chiral

Step 1: Preparation of methyl(S)-3-(bicyclo[1.1.1]pentan-1-yl)-2-(5-(trifluoromethyl)isoxazole-3-carboxamido)propanoate

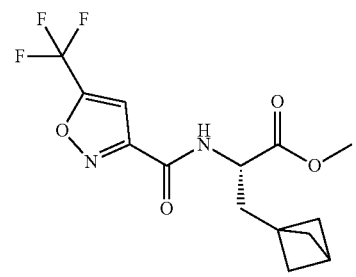

99a

Compound 99a was prepared in analogy to Example 71, step 1 by using 5-(trifluoromethyl)isoxazole-3-carbonyl chloride instead of 5-methylisoxazole-3-carbonyl chloride. Methyl(S)-3-(bicyclo[1.1.1]pentan-1-yl)-2-(5-(trifluoromethyl)isoxazole-3-carboxamido) propanoate (940 mg, compound 99a) was obtained as a colorless oil. MS obsd. (ESI⁺) [(M+H)⁺]: 333.0.

Step 2: Preparation of (S)-3-(bicyclo[1.1.1]pentan-1-yl)-2-(5-(trifluoromethyl)isoxazole-3-carboxamido)propanoic acid

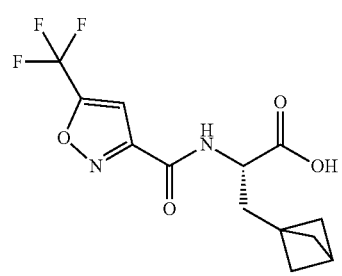

99b

Compound 99b was prepared in analogy to Example 71, step 2 by using methyl(S)-3-(bicyclo[1.1.1]pentan-1-yl)-2-(5-(trifluoromethyl)isoxazole-3-carboxamido) propanoate (890.0 mg, compound 99b) instead of methyl(S)-3-(bicyclo[1.1.1]pentan-1-yl)-2-(5-methylisoxazole-3-carboxamido) propanoate (compound 71a). (S)-3-(Bicyclo[1.1.1]pentan-1-yl)-2-(5-(trifluoromethyl)isoxazole-3-carboxamido) propanoic acid (850 mg, compound 99b) was obtained as a white solid. MS obsd. (ESI⁺) [(M+H)⁺]: 319.0

Step 3: Preparation of tert-butyl 2-((S)-3-(bicyclo[1.1.1]pentan-1-yl)-2-(5-(trifluoromethyl)isoxazole-3-carboxamido)propanoyl)-1-(((S)-2-axopyrrolidin-3-yl)methyl)hydrazine-1-carboxylate

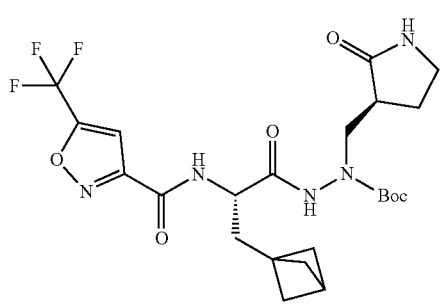

99c

Compound 99c was prepared in analogy to Example 65, step 2 by using (S)-3-(bicyclo[1.1.1]pentan-1-yl)-2-(5-(trifluoromethyl)isoxazole-3-carboxamido)propanoic acid (850 mg, compound 99b) and tert-butyl(S)-1-((2-axopyrrolidin-3-yl)methyl)hydrazine-1-carboxylate (1.0 g, Intermediate AF) instead of (S)-2-(1H-benzo[d]imidazole-2-carboxamido)-4,4-dimethylpentanoic acid (120.0 mg, compound 65b) and tert-butyl 1-(3-amino-3-oxopropyl)hydrazine-1-carboxylate. tert-Butyl 2-((S)-3-(bicyclo[1.1.1]pentan-1-yl)-2-(5-(trifluoromethyl)isoxazole-3-carboxamido)propanoyl)-1-(((S)-2-axopyrrolidin-3-yl)methyl)hydrazine-1-carboxylate (580 mg, compound 99c) was obtained as a yellow solid.

MS obsd. (ESI$^+$) [(M+H)$^+$]: 530.2.

Step 4: Preparation of N—((S)-3-(bicyclo[1.1.1]pentan-1-yl)-1-oxo-1-(2-(((S)-2-axopyrrolidin-3-yl)methyl)hydrazineyl)propan-2-yl)-5-(trifluoromethyl)isoxazole-3-carboxamide

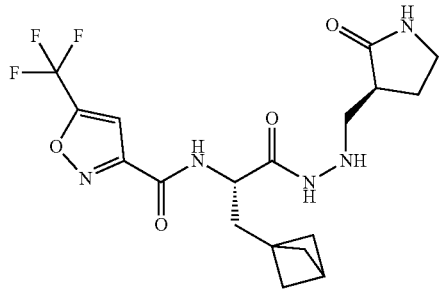

99d

Compound 99d was prepared in analogy to Example 65, step 3 by using tert-butyl 2-((S)-3-(bicyclo[1.1.1]pentan-1-yl)-2-(5-(trifluoromethyl)isoxazole-3-carboxamido)propanoyl)-1-(((S)-2-axopyrrolidin-3-yl)methyl)hydrazine-1-carboxylate (580 mg, compound 99c) instead of tert-butyl (S)-2-(2-(1H-benzo[d]imidazole-2-carboxamido)-4,4-dimethylpentanoyl)-1-(3-amino-3-oxopropyl)hydrazine-1-carboxylate (100.0 mg, compound 65c). N—((S)-3-(bicyclo[1.1.1]pentan-1-yl)-1-oxo-1-(2-(((S)-2-axopyrrolidin-3-yl)methyl)hydrazineyl) propan-2-yl)-5-(trifluoromethyl) isoxazole-3-carboxamide (400 mg, compound 99d) was obtained as a yellow solid. MS obsd. (ESI$^+$) [(M+H)$^+$]: 430.2.

Step 8: Preparation of N—((S)-3-(bicyclo[1.1.1]pentan-1-yl)-1-(2-((R)-2-chloro-2-fluoroacetyl)-2-(((S)-2-axopyrrolidin-3-yl)methyl)hydrazineyl)-1-oxopropan-2-yl)-5-(trifluoromethyl)isoxazole-3-carboxamide

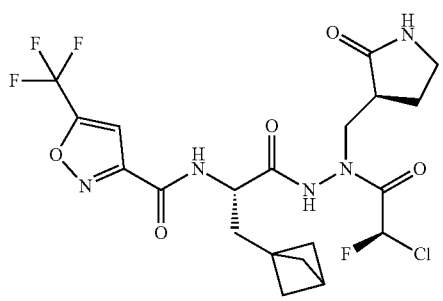

99

The title compound was prepared in analogy to Example 65, step 4 by using afford N—((S)-3-(bicyclo[1.1.1]pentan-1-yl)-1-oxo-1-(2-(((S)-2-axopyrrolidin-3-yl)methyl)hydrazineyl) propan-2-yl)-5-(trifluoromethyl)isoxazole-3-carboxamide (400 mg, compound 99d) and (R)-2-chloro-2-fluoroacetyl chloride instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d) and 2-chloro-2-fluoroacetic acid. N—((S)-3-(Bicyclo[1.1.1]pentan-1-yl)-1-(2-((R)-2-chloro-2-fluoroacetyl)-2-(((S)-2-axopyrrolidin-3-yl)methyl)hydrazineyl)-1-oxopropan-2-yl)-5-(trifluoromethyl) isoxazole-3-carboxamide (162.2 mg, Example 99) was obtained as a yellow solid. $^1$H NMR (400 MHz, CD$_3$OD) δ ppm: 7.46 (s, 1H), 6.80-6.55 (m, 1H), 4.57-4.40 (m, 1H), 4.06 (dd, J$_1$=8.4 Hz, J$_2$=13.6 Hz, 1H), 3.44 (dd, J$_1$=5.2 Hz, J$_2$=13.6 Hz, 1H), 3.40-3.32 (m, 2H), 2.78-2.64 (m, 1H), 2.46 (s, 1H), 2.36-2.22 (m, 1H), 2.09-2.03 (m, 2H), 2.00-1.90 (m, 1H), 1.87-1.72 (m, 6H). MS obsd. (ESI$^+$) [(M+H)$^+$]: 524.1.

Example 100

N-[(1S)-2-[2-[(2R)-2-chloro-2-fluoro-acetyl]-2-[[(3S)-2-axopyrrolidin-3-yl]methyl]hydrazino]-1-[(1-methylcyclopropyl)methyl]-2-axo-ethyl]-5-(difluoromethyl)isoxazole-3-carboxamide

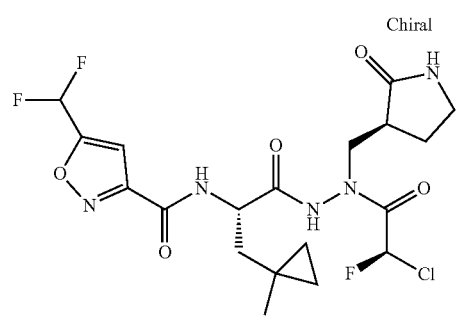

100
Chiral

Step 1: Preparation of ethyl 5-formylisoxazole-3-carboxylate

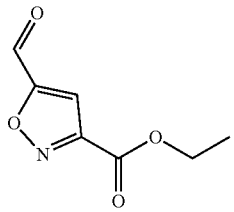

100a

To a solution of ethyl 5-(hydroxymethyl)isoxazole-3-carboxylate (7.0 g, Bidepharm, CAS number: 123770-62-7), TEA (13.04 g) and DMSO (15.98 g) in DCM (110 mL) was added pyridine-SO₃ complex (39.06 g, 245.4 mmol) at 0° C. under N₂ protection. After stirred at 20° C. for 12 hrs, the reaction mixture was concentrated in vacuo. The residue was diluted with EtOAc (200 mL) and washed with H₂O (100 mL). The aqueous phase was extracted with EtOAc (100 mL) two times. The combined organic phase was washed with brine (50 mL) three times, dried over anhydrous Na₂SO₄ and concentrated in vacuo. The residue was purified by silica gel column, eluted with EtOAc in petroleum ether=0~20% to afford ethyl 5-formylisoxazole-3-carboxylate (4 g, compound 100a) as a yellow oil. $^1$H NMR (400 MHz, CDCl₃) δ ppm: 10.03 (s, 1H), 7.37 (s, 1H), 4.49 (q, J=6.8 Hz, 2H), 1.45 (t, J=6.8 Hz, 3H).

Step 2: Preparation of ethyl 5-(difluoromethyl)isoxazole-3-carboxylate

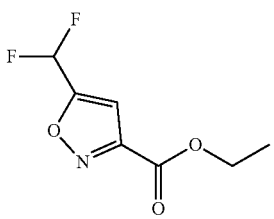

100b

To a solution of ethyl 5-formylisoxazole-3-carboxylate (4.0 g, 23.65 mmol, compound 100a) in DCM (60 mL) was added DAST (11.44 g) at −40° C. under N₂ protection. After stirred at 20° C. for 16 hrs, the reaction mixture was poured into ice water (60 mL) and basified with sat. aq. solution of NaHCO₃ until pH=9. The resulting mixture was extracted with DCM (60 mL) three times. The combined organic phase was dried over anhydrous Na₂SO₄, and concentrated in vacuo. The residue was purified by column (eluted with EtOAc in petroleum ether=10~20%) to afford ethyl 5-(difluoromethyl)isoxazole-3-carboxylate (2.5 g, compound 100b) as a yellow oil. $^1$H NMR (400 MHz, DMSO-d₆) δ ppm: 7.53-7.27 (m, 2H), 4.39 (q, J=7.2 Hz, 2H), 1.33 (t, J=7.2 Hz, 3H)

Step 3: Preparation of 5-(difluoromethyl)isoxazole-3-carboxylic acid

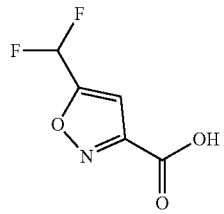

100c

To a solution of ethyl 5-(difluoromethyl)isoxazole-3-carboxylate (2.5 g, 13.08 mmol, compound 100b) in methanol (30 mL) was added NaOH (1.15 g) in water (30 mL) at 0° C. After stirred at 0° C. for 1 hr, the reaction mixture was concentrated in vacuo to remove MeOH. The residue was dissolved with EtOAc (50 mL) and washed with HCl (1 M, 30 mL). The aqueous phase was extracted with EtOAc (50 mL) six times. The combined organic phase was dried over anhydrous Na₂SO₄, and concentrated in vacuo. The residue was purified by silica gel column, eluted with EtOAc in petroleum ether=10~35% to afford 5-(difluoromethyl)isoxazole-3-carboxylic acid (1.6 g, 9.81 mmol, compound 100c) as a white solid. $^1$H NMR (400 MHz, CDCl₃) δ ppm: 7.05 (s, 1H), 6.83 (t, J=53.2 Hz, 1H).

Step 4: Preparation of 5-(difluoromethyl)isoxazole-3-carbonyl chloride

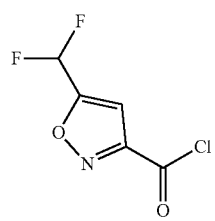

100d

To a solution of 5-(difluoromethyl)isoxazole-3-carboxylic acid (4.23 g, compound 100c) in DCM (50 mL) was added DMF (0.2 mL) and oxalyl chloride (3.98 g, 31.37 mmol) dropwise at 0° C. After stirred at 20° C. for 1 hr, the reaction mixture was concentrated in vacuo below 20° C. to afford 5-(difluoromethyl)isoxazole-3-carbonyl chloride (4.6 g, compound 100d) as a yellow oil.

Step 5: Preparation of tert-butyl 2-((S)-2-(5-(difluoromethyl)isoxazole-3-carboxamido)-3-(1-methylcyclopropyl)propanoyl)-1-(((S)-2-axopyrrolidin-3-yl)methyl)hydrazine-1-carboxylate

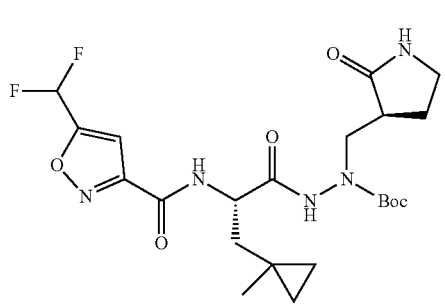

100e

Compound 100e was prepared in analogy to Example 65, step 2 by using 5-(difluoromethyl)isoxazole-3-carbonyl chloride (4.6 g, compound 100d) and tert-butyl(S)-1-((2-axopyrrolidin-3-yl)methyl)hydrazine-1-carboxylate (2.71 g, Intermediate AF) instead of (S)-2-(1H-benzo[d]imidazole-2-carboxamido)-4,4-dimethylpentanoic acid (120.0 mg, compound 65b) and tert-butyl 1-(3-amino-3-oxopropyl)hydrazine-1-carboxylate. tert-Butyl 2-((S)-2-(5-(difluoromethyl)isoxazole-3-carboxamido)-3-(1-methylcyclopropyl)propanoyl)-1-(((S)-2-axopyrrolidin-3-yl)methyl)hydrazine-1-carboxylate (3.9 g, 7.81 mmol, compound 100e) was obtained as a yellow solid. MS obsd. (ESI⁺) [(M+H)⁺]: 500.2.

Step 6: Preparation of 5-(difluoromethyl)-N—((S)-3-(1-methylcyclopropyl)-1-oxo-1-(2-(((S)-2-axopyrrolidin-3-yl)methyl)hydrazineyl)propan-2-yl)isoxazole-3-carboxamide

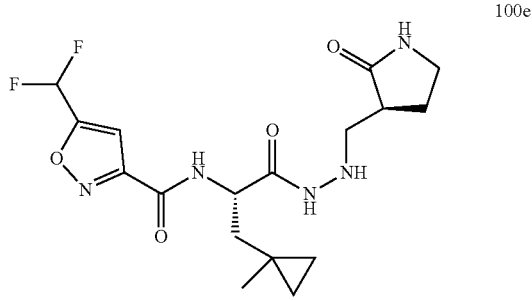 [SMILES: CC1(C[C@H](NC(=O)c2cc(C(F)F)on2)C(=O)NNC[C@@H]2CCNC2=O)CC1]

100e

Compound 100e was prepared in analogy to Example 65, step 3 by using tert-butyl 2-((S)-2-(5-(difluoromethyl)isoxazole-3-carboxamido)-3-(1-methylcyclopropyl)propanoyl)-1-(((S)-2-axopyrrolidin-3-yl)methyl)hydrazine-1-carboxylate (3.9 g, compound 100d) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (100.0 mg, compound 65c). 5-(Difluoromethyl)-N—((S)-3-(1-methylcyclopropyl)-1-oxo-1-(2-(((S)-2-axopyrrolidin-3-yl)methyl)hydrazineyl)propan-2-yl)isoxazole-3-carboxamide (2.8 g, compound 100e) was obtained as a white solid. MS obsd. (ESI⁺) [(M+H)⁺]: 400.1.

Step 7: Preparation of N—((S)-1-(2-((R)-2-chloro-2-fluoroacetyl)-2-(((S)-2-axopyrrolidin-3-yl)methyl)hydrazineyl)-3-(1-methylcyclopropyl)-1-axopropan-2-yl)-5-(difluoromethyl) isoxazole-3-carboxamide

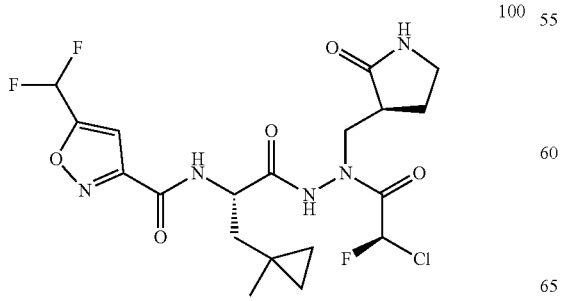

100

The title compound was prepared in analogy to Example 65, step 4 by using 5-(difluoromethyl)-N—((S)-3-(1-methylcyclopropyl)-1-oxo-1-(2-(((S)-2-axopyrrolidin-3-yl)methyl)hydrazineyl)propan-2-yl)isoxazole-3-carboxamide (2.8 g, compound 100e) and (R)-2-chloro-2-fluoroacetyl chloride instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d) and 2-chloro-2-fluoroacetic acid. N—((S)-1-(2-((R)-2-Chloro-2-fluoroacetyl)-2-(((S)-2-axopyrrolidin-3-yl)methyl)hydrazineyl)-3-(1-methylcyclopropyl)-1-oxopropan-2-yl)-5-(difluoromethyl)isoxazole-3-carboxamide (1941 mg, Example 100) was obtained as a white solid. ¹H NMR (400 MHz, CDCl₃) δ ppm: 10.16 (br. s, 1H), 7.47 (d, J=3.6 Hz, 1H), 7.04 (s, 1H), 6.80 (t, J=53.6 Hz, 1H), 6.57-6.36 (m, 1H), 5.94 (s, 1H), 4.75-4.63 (m, 1H), 4.43 (d, J=9.6 Hz, 1H), 3.43-3.39 (m, 2H), 2.99-2.76 (m, 2H), 2.41-2.36 (m, 1H), 2.12-2.09 (m, 1H), 1.92-1.79 (m, 1H), 1.59-1.53 (m, 1H), 1.13 (s, 3H), 0.50-0.42 (m, 2H), 0.39-0.33 (m, 2H).

MS obsd. (ESI⁺) [(M+H)⁺]: 494.1.

Example 101

N-[(1S)-1-[[[(2R)-2-chloro-2-fluoro-acetyl]-[[(3S)-2-axopyrrolidin-3-yl]methyl]amino]carbamoyl]-4-methyl-pentyl]-5-methyl-isoxazole-3-carboxamide

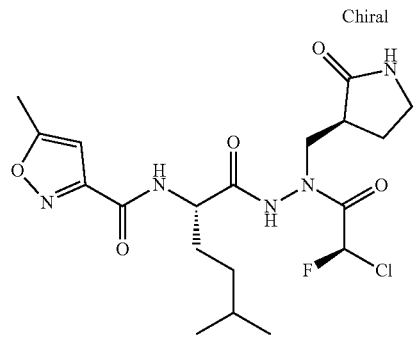

101
Chiral

Step 1: Preparation of (S)-5-methyl-2-(5-methyl-isoxazole-3-carboxamido)hexanoic acid

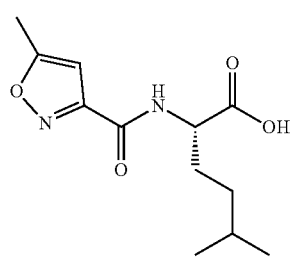

101a

Compound 101a was prepared in analogy to Example 65, step 1 by using (2S)-2-amino-5-methyl-hexanoic acid (Energy chemical, CAS number: 31872-98-7) and 5-methyl-isoxazole-3-carbonyl chloride and instead of (S)-2-amino- 4,4-dimethylpentanoic acid (TFA salt) (compound 65a) and 1H-benzimidazole-2-carbonyl chloride. (S)-5-methyl-2-(5-methylisoxazole-3-carboxamido)hexanoic acid (800 mg, compound 101a) was obtained as a white solid. MS obsd. (ESI⁺) [M+H]⁺: 254.8.

Step 2: Preparation of tert-butyl 2-((S)-5-methyl-2-(5-methylisoxazole-3-carboxamido)hexanoyl)-1-(((S)-2-axopyrrolidin-3-yl)methyl)hydrazine-1-carboxylate Compound 101b was prepared in analogy to Example 65, step 2 by using (S)-5-methyl-2-(5-methylisoxazole-3-carboxamido)hexanoic acid (800 mg, compound 101a) and tert-butyl(S)-1-((2-axopyrrolidin-3-yl)methyl)hydrazine-1-carboxylate (2.71 g, Intermediate AF) instead of (S)-2-(1H-benzo[d]imidazole-2-carboxamido)-4,4-dimethylpentanoic acid (120.0 mg, compound 65b) and tert-butyl 1-(3-amino-3-oxopropyl)hydrazine-1-carboxylate. tert-Butyl 2-((S)-5-methyl-2-(5-methylisoxazole-3-carboxamido)hexanoyl)-1-(((S)-2-axopyrrolidin-3-yl)methyl)hydrazine-1-carboxylate (800 mg, compound 101b) was obtained as a yellow solid. MS obsd. (ESI⁺) [M+H]⁺: 466.2.

Step 3: Preparation of 5-methyl-N—((S)-5-methyl-1-oxo-1-(2-(((S)-2-axopyrrolidin-3-yl)methyl)hydrazineyl)hexan-2-yl)isoxazole-3-carboxamide Compound 101c was prepared in analogy to Example 65, step 3 by using tert-butyl 2-((S)-5-methyl-2-(5-methylisoxazole-3-carboxamido)hexanoyl)-1-(((S)-2-axopyrrolidin-3-yl)methyl)hydrazine-1-carboxylate (800 mg, compound 101b) instead of tert-butyl(S)-2-(2-(1H-benzo[d]imidazole-2-carboxamido)-4,4-dimethylpentanoyl)-1-(3-amino-3-oxopropyl)hydrazine-1-carboxylate (compound 65c). 5-Methyl-N—((S)-5-methyl-1-oxo-1-(2-(((S)-2-axopyrrolidin-3-yl)methyl)hydrazineyl)hexan-2-yl)isoxazole-3-carboxamide (620 mg, compound 101c) was obtained as a white solid. MS obsd. (ESI⁺) [M+H]: 366.3.

Step 4: Preparation of N—((S)-1-(2-((R)-2-chloro-2-fluoroacetyl)-2-(((S)-2-axopyrrolidin-3-yl)methyl)hydrazineyl)-5-methyl-1-oxohexan-2-yl)-5-methyl-isoxazole-3-carboxamide The title compound was prepared in analogy to Example 65, step 4 by using 5-methyl-N—((S)-5-methyl-1-oxo-1-(2-(((S)-2-axopyrrolidin-3-yl)methyl)hydrazineyl)hexan-2-yl)isoxazole-3-carboxamide (620 mg, compound 101c) and (R)-2-chloro-2-fluoroacetyl chloride instead of (S)—N-(1-(2-(3-amino-3-oxopropyl)hydrazineyl)-4,4-dimethyl-1-oxopentan-2-yl)-1H-benzo[d]imidazole-2-carboxamide (TFA salt) (75.0 mg, compound 65d) and 2-chloro-2-fluoroacetic acid. N—((S)-1-(2-((R)-2-Chloro-2-fluoroacetyl)-2-(((S)-2-axopyrrolidin-3-yl)methyl)hydrazineyl)-5-methyl-1-oxohexan-2-yl)-5-methylisoxazole-3-carboxamide (479.2 mg, Example 101) was obtained as a white solid. ¹H NMR (400 MHz, CD₃OD) δ ppm: 6.80 (d, J=50.4 Hz, 1H), 6.50 (s, 1H), 4.45-4.24 (m, 1H), 4.15-4.09 (m, 1H), 3.43-3.33 (m, 3H), 2.83-2.64 (m, 1H), 2.49 (s, 3H), 2.40-2.24 (m, 1H), 2.08-1.80 (m, 3H), 1.65-1.59 (m, 1H), 1.43-1.38 (m, 1H), 1.34-1.23 (m, 1H), 0.95 (d, J=6.4 Hz, 6H). MS obsd. (ESI⁺) [M+H]⁺: 460.1.

BIOLOGICAL EXAMPLES

Example 102

SARS-CoV-2 3CL$^{pro}$ Inhibition Assay

The full-length gene encoding SARS-CoV-2 3CL$^{pro}$ was optimized and synthesized for *Escherichia coli* (*E. coli*) BL21 (DE3) expression, with the protein sequence of

SGFRKMAFPSGKVEGCMVQVTCGTTTLNGLWLDDVVYCPRHVICTSEDM

LNPNYEDLLIRKSNHNFLVQAGNVQLRVIGHSMQNCVLKLKVDTANPKT

PKYKFVRIQPGQTFSVLACYNGSPSGVYQCAMRPNFTIKGSFLNGSCGS

VGFNIDYDCVSFCYMHHMELPTGVHAGTDLEGNFYGPFVDRQTAQAAGT

DTTITVNVLAWLYAAVINGDRWFLNRFTTTLNDFNLVAMKYNYEPLTQD

HVDILGPLSAQTGIAVLDMCASLKELLQNGMNGRTILGSALLEDEFTPF

DVVRQCSGVTFQ (according to SEQ ID NO: 1).

The method of cloning and producing authentic SARS-CoV-2 3CL$^{pro}$ was followed by the protocol published for SARS-CoV 3CL$^{pro}$ previously (Grum-Tokars V. et al. "Evaluating the 3C-like protease activity of SARS-Coronavirus: Recommendations for standardized assays for drug discovery." Virus Res. 2008 April; 133(1):63-73).

For the SARS-CoV-2 3CL$^{pro}$ assay, 2 μL of 0.02 μM recombinant SARS-CoV-2 3CL protease were mixed with serial dilutions of each compound in 4 μL assay buffer containing 40 mM HEPES, pH=8.0, 1 mM CHAPS, 150 mM NaCl, 1 mM EDTA, 1 mM TCEP in a well of a 384-well plate and pre-incubated at rt for 1 hr. The custom-synthesized fluorogenic 3CL$^{pro}$ peptide substrate used in the assay is as follows: FAM-KTSAVLQSGFRKMEK-TAMRA (peptide sequence according to SEQ ID NO: 3). This FRET-based substrate contains a FAM fluorophore attached at the N-terminus of a canonical 3CL$^{Pro}$ peptide substrate. The fluorophore is internally quenched by the TAMRA. The reaction was initiated by the addition of 10 μL of the substrate with a final concentration of 15 μM and each well was incubated at RT for 30 mins. The final concentration of the protease used at the assay was 25 nM and each compound was at a final concentration range of 100-0.0016 μM. The IC$_{50}$ value which is the value causing 50% inhibition of the catalytic activity of the SARS-CoV 3CL$^{Pro}$ was calculated by four parameters equation analysis.

Example 103

SARS-CoV 3CL$^{pro}$ inhibition assay

The SARS-CoV 3CL$^{pro}$ was expressed in *E. coli* BL21 (DE3) with the protein sequence of

SGFRKMAFPSGKVEGCMVQVTCGTTTLNGLWLDDTVYCPRHVICTAEDM

LNPNYEDLLIRKSNHSFLVQAGNVQLRVIGHSMQNCLLRLKVDTSNPKT

PKYKFVRIQPGQTFSVLACYNGSPSGVYQCAMRPNHTIKGSFLNGSCGS

VGFNIDYDCVSFCYMHHMELPTGVHAGTDLEGKFYGPFVDRQTAQAAGT

DTTITLNVLAWLYAAVINGDRWFLNRFTTTLNDFNLVAMKYNYEPLTQD

HVDILGPLSAQTGIAVLDMCAALKELLQNGMNGRTILGSTILEDEFTPF

DVVRQCSGVTFQ (according to SEQ ID NO: 2).

For the SARS-CoV 3CL$^{pro}$ assay, 2 μL of 0.02 μM recombinant SARS-CoV 3CL protease were mixed with serial dilutions of each compound in 4 μL assay buffer containing 40 mM HEPES, pH=8.0, 1 mM CHAPS, 150 mM NaCl, 1 mM EDTA, 1 mM TCEP in a well of a 384-well plate and pre-incubated at rt for 1 hr. The custom-synthesized fluorogenic 3CL$^{pro}$ peptide substrate used in the assay is as follows: FAM-KTSAVLQSGFRKMEK-TAMRA (peptide sequence according to SEQ ID NO: 3). This FRET-based substrate contains a FAM fluorophore attached at the N-terminus of a canonical 3CL$^{pro}$ peptide substrate. The fluorophore is internally quenched by the TAMRA. The reaction was initiated by the addition of 10 μL of the substrate with a final concentration of 15 μM and each well was incubated at RT for 30 mins. The final concentration of the protease used at the assay was 25 nM and each compound was at a final concentration range of 100-0.0016 μM. The IC$_{50}$ value which is the value causing 50% inhibition of the catalytic activity of the SARS-CoV 3CL$^{pro}$ was calculated by four parameters equation analysis.

Example 104

MERS-CoV 3CL$^{pro}$ inhibition assay

The MERS-CoV 3CL$^{pro}$ was expressed in *E. coli* BL21 (DE3) with the protein sequence of

SGLVKMSHPSGDVEACMVQVTCGSMTLNGLWLDNTVWCPRHVMCPADQL

SDPNYDALLISMTNHSFSVQKHIGAPANLRVVGHAMQGTLLKLTVDVAN

PSTPAYTFTTVKPGAAFSVLACYNGRPTGTFTVVMRPNYTIKGSFLCGS

CGSVGYTKEGSVINFCYMHQMELANGTHTGSAFDGTMYGAFMDKQVHQV

QLTDKYCSVNVVAWLYAAILNGCAWFVKPNRTSVVSFNEWALANQFTEF

VGTQSVDMLAVKTGVAIEQLLYAIQQLYTGFQGKQILGSTMLEDEFTPE

DVNMQIMGVVMQ (according to SEQ ID NO: 4)

For the MERS-CoV 3CL$^{pro}$ assay, 2 μL of 0.02 μM recombinant MERS-CoV 3CL protease were mixed with serial dilutions of each compound in 4 μL assay buffer containing 40 mM HEPES, pH=8.0, 1 mM CHAPS, 150 mM NaCl, 1 mM EDTA, 1 mM TCEP in a well of a 384-well plate and pre-incubated at rt for 1 hr. The custom-synthesized fluorogenic 3CL$^{pro}$ peptide substrate used in the assay is as follows: FAM-KTSAVLQSGFRKMEK-TAMRA (peptide sequence according to SEQ ID NO: 3). This FRET-based substrate contains a FAM fluorophore attached at the N-terminus of a canonical 3CL$^{pro}$ peptide substrate. The fluorophore is internally quenched by the TAMRA. The reaction was initiated by the addition of 10 μL of the substrate with a final concentration of 15 μM and each well was incubated at RT for 30 mins. The final concentration of the protease used at the assay was 25 nM and each compound was at a final concentration range of 100-0.0016 μM. The IC$_{50}$ value which is the value causing 50% inhibition of the catalytic activity of the MERS-CoV 3CL$^{pro}$ was calculated by four parameters equation analysis.

Example 105

HCoV-229E 3CL$^{pro}$ inhibition assay

The HCoV-229E 3CL$^{pro}$ was expressed in *E. coli* BL21 (DE3) with the protein sequence of

AGLRKMAQPSGFVEKCVVRVCYGNTVLNGLWLGDIVYCPRHVIASNTTS

AIDYDHEYSIMRLHNFSIISGTAFLGVVGATMHGVTLKIKVSQTNMHTP

RHSFRTLKSGEGFNILACYDGCAQGVFGVNMRTNWTIRGSFINGACGSP

GYNLKNGEVEFVYMHQIELGSGSHVGSSFDGVMYGGFEDQPNLQVESAN

QMLTVNVVAFLYAAILNGCTWWLKGEKLFVEHYNEWAQANGFTAMNGED

AFSILAAKTGVCVERLLHAIQVLNNGFGGKQILGYSSLNDEFSINEVVK

QMFGVNLQ (according to SEQ ID NO: 5)

For the HCoV-229E 3CL$^{pro}$ assay, 2 μL of 0.02 μM recombinant HCoV-229E 3CL protease were mixed with serial dilutions of each compound in 4 μL assay buffer containing 40 mM HEPES, pH=8.0, 1 mM CHAPS, 150 mM NaCl, 1 mM EDTA, 1 mM TCEP in a well of a 384-well plate and pre-incubated at rt for 1 hr. The custom-synthesized fluorogenic 3CL$^{pro}$ peptide substrate used in the assay is as follows: FAM-KTSAVLQSGFRKMEK-TAMRA (peptide sequence according to SEQ ID NO: 3). This FRET-based substrate contains a FAM fluorophore attached at the N-terminus of a canonical 3CL$^{pro}$ peptide substrate. The fluorophore is internally quenched by the TAMRA. The reaction was initiated by the addition of 10 μL of the substrate with a final concentration of 15 μM and each well was incubated at RT for 30 mins. The final concentration of the protease used at the assay was 25 nM and each compound was at a final concentration range of 100-0.0016 μM. The IC$_{50}$ value which is the value causing 50% inhibition of the catalytic activity of the HCoV-229E 3CL$^{pro}$ was calculated by four parameters equation analysis.

Example 106

HCoV-OC43 3CL$^{pro}$ Inhibition Assay

The HCoV-OC43 3CL$^{pro}$ was expressed in *E. coli* BL21 (DE3) with the protein sequence of

```
SGIVKMVNPTSKVEPCVVSVTYHNMTLNGLWLDDKVYCPRHVICSASDM

TNPDYTNLLCVTSSDFTVLFDRLSLTVMSYQMRGCMLVLTVTLQNSRTP

KYTFGVVKPGETFTVLAAYNGKPQGAFHVTMRSSYTIKGSFLCGSCGSV

GYVIMGDCVKFVYMHQLELSTGCHTGTDFNGDFYGPYKDAQVVOLPIQD

YIQSVNFLAWLYAAILNNCNWFIQSDKCSVEDFNVMALSNGFSQVKSDL

VIDALASMTGVSLETLLAAIKRLKNGFQGRQIMGSCSFEDELTPSDVYQ

QLAGIKLQ (according to SEQ ID NO: 6)
```

For the HCoV-OC43 3CL$^{pro}$ assay, 2 μL of 0.02 μM recombinant HCoV-OC43 3CL protease were mixed with serial dilutions of each compound in 4 μL assay buffer containing 40 mM HEPES, pH=8.0, 1 mM CHAPS, 150 mM NaCl, 1 mM EDTA, 1 mM TCEP in a well of a 384-well plate and pre-incubated at rt for 1 hr. The custom-synthesized fluorogenic 3CL$^{pro}$ peptide substrate used in the assay is as follows: FAM-KTSAVLQSGFRKMEK-TAMRA (peptide sequence according to SEQ ID NO: 3). This FRET-based substrate contains a FAM fluorophore attached at the N-terminus of a canonical 3CL$^{pro}$ peptide substrate. The fluorophore is internally quenched by the TAMRA. The reaction was initiated by the addition of 10 μL of the substrate with a final concentration of 15 μM and each well was incubated at RT for 30 mins. The final concentration of the protease used at the assay was 25 nM and each compound was at a final concentration range of 100-0.0016 μM. The IC$_{50}$ value which is the value causing 50% inhibition of the catalytic activity of the HCoV-OC43 3CL$^{pro}$ was calculated by four parameters equation analysis.

TABLE 1

Activity of Examples and Compounds of present invention in SARS-CoV-2 3CL$^{Pro}$ assay

| Example | IC50 (μM) |
|---|---|
| Example 1 | 4.590 |
| Example 2 | 0.017 |
| Example 3 | 0.890 |
| Example 4 | 0.330 |
| Example 5 | 1.76 |
| Example 7 | 0.540 |
| Example 8 | 0.008 |
| Example 10 | 0.006 |
| Example 11 | 0.023 |
| Example 15 | 1.2 |
| Example 16 | 0.009 |
| Example 16-A | 0.053 |
| Example 16-B | 0.002 |
| Example 17 | 0.09 |
| Example 17-A | 1.63 |
| Example 17-B | 0.077 |
| Example 18 | 0.017 |
| Example 20 | 0.0046 |
| Example 21 | 0.39 |
| Example 23 | 0.034 |
| Example 24 | 0.087 |
| Example 26 | 0.67 |
| Example 27 | 0.006 |
| Example 28 | 0.007 |
| Example 29 | 0.034 |
| Example 30 | 0.16 |
| Example 31 | 0.65 |
| Example 32 | 0.002 |
| Example 33 | 0.002 |
| Example 34 | 0.005 |
| Example 35 | 0.002 |
| Example 36 | 0.14 |
| Example 37 | 0.038 |
| Example 38 | 0.29 |
| Example 38-A | 0.074 |
| Example 38-B | 3.16 |
| Example 39 | 0.002 |
| Example 40 | 0.007 |
| Example 41 | N/A |
| Example 41-A | 0.005 |
| Example 41-B | 0.034 |
| Example 42 | 0.005 |
| Example 43 | 0.036 |
| Example 44 | 0.017 |
| Example 45 | 0.046 |
| Example 46 | 0.07 |
| Example 47 | 0.014 |
| Example 48 | 0.004 |
| Example 49 | 0.015 |
| Example 50 | 0.074 |
| Example 51 | 0.004 |
| Example 51-A | 0.004 |
| Example 51-A | 0.0027 |
| Example 52 | 0.014 |
| Example 53-A | 0.014 |
| Example 53-B | 0.025 |
| Example 54-A | 0.004 |
| Example 54-B | 0.017 |
| Example 56-A | 0.008 |
| Example 56-B | 0.003 |
| Example 57-A | 0.067 |
| Example 57-B | 0.01 |
| Example 58-A | 0.032 |
| Example 58-B | 0.007 |
| Example 59-A | 0.023 |
| Example 59-B | 0.005 |
| Example 60-A | 0.008 |
| Example 60-B | 0.052 |
| Example 61 | 0.056 |
| Example 62 | 0.017 |
| Example 63-A | 0.043 |
| Example 63-B | 0.007 |
| Example 65-A | 0.18 |
| Example 65-B | 0.013 |
| Example 66 | 0.034 |
| Example 67 | 0.023 |
| Example 70 | 0.059 |
| Example 71 | 0.11 |
| Example 72 | 0.09 |
| Example 74 | 0.028 |
| Example 75 | 0.32 |
| Example 78 | 0.25 |
| Example 79 | 0.15 |
| Example 82 | 0.043 |
| Example 83-A | 0.9 |
| Example 83-B | 0.06 |
| Example 84-A | 0.028 |

TABLE 1-continued

Activity of Examples and Compounds of present invention in SARS-CoV-2 3CL$^{Pro}$ assay

| Example | IC50 (μM) |
|---|---|
| Example 84-B | 0.86 |
| Example 86-A | 0.75 |
| Example 86-B | 0.023 |
| Example 88 | 0.013 |
| Example 89 | 0.019 |
| Example 90 | 0.073 |
| Example 91 | 0.038 |
| Example 95 | 0.65 |
| Example 96 | 0.66 |
| Example 97 | 0.91 |
| Example 98 | 0.017 |
| Example 99 | 0.071 |
| Example 100 | 0.024 |
| Example 101 | 0.09 |

TABLE 2

Activity of Examples and Compounds of present invention in different coronaviruses

| | 229E | MERS | OC43 | SARS |
|---|---|---|---|---|
| Example 28 | 0.013 | 0.05 | 0.017 | 0.016 |
| Example 51-A | 0.017 | 0.060 | 0.019 | 0.015 |
| Example 70 | 0.024 | 0.054 | 0.015 | 0.094 |
| Example 71 | 0.025 | 0.16 | 0.011 | 0.18 |
| Example 72 | 0.033 | 0.17 | 0.013 | 0.62 |
| Example 73 | 0.041 | 0.22 | 0.041 | 0.41 |
| Example 99 | 0.024 | 0.23 | 0.021 | 0.093 |
| Example 100 | 0.028 | 0.094 | 0.017 | 0.031 |
| Example 101 | 0.074 | 0.32 | 0.023 | 0.16 |

The invention claimed is:
1. A compound of formula (II),

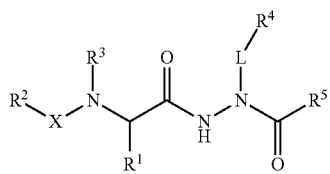

(II)

wherein
X is carbonyl or SO$_2$;
R$^1$ is H, C$_{1-6}$alkyl, C$_{3-7}$cycloalkylC$_{1-6}$alkyl, or (C$_{1-6}$alkyl)$_3$Si—C$_{1-6}$alkyl, wherein said C$_{3-7}$cycloalkyl is optionally substituted with one to two substituents independently selected from halogen and C$_{1-6}$alkyl;

R$^2$ is C$_{1-6}$alkoxy, phenylC$_{2-6}$alkenyl, benzyloxy, oxazolyl, isoxazolyl, 1H-pyrrolo[2,3-b]pyridinyl, 1H-pyrrolo[3,2-c]pyridinyl, 6H-pyrrolo[2,3-c]pyridinyl, 1H-indolyl, 1H-benzimidazolyl, benzyl, imidazolyl, pyrazinyl, thiazolyl, imidazo[1,2-a]pyridine, pyrazolo[1,5-a]pyridine, phenyl-NH—C$_{1-6}$alkyl; wherein each of said phenylC$_{2-6}$alkenyl, phenyl-NH—C$_{1-6}$alkyl, oxazolyl, isoxazolyl, thiazolyl, benzimidazolyl, 6H-pyrrolo[2,3-c]pyridinyl, and 1H-indolyl is unsubstituted or substituted with one to two substituents independently selected from halogen, C$_{1-6}$alkyl, halo-C$_{1-6}$alkyl, and C$_{1-6}$alkoxy;

R$^3$ is H or C$_{1-6}$alkyl;

R⁴ is H, carbamoyl, axopyrrolidinyl, oxopiperidinyl, 1H-pyrazolyl, 1H-imidazolyl, or ($C_{1-6}$ alkylamino)carbonyl;
R⁵ is $C_{1-6}$alkyl substituted twice with halogen;
L is —$C_xH_{2x}$—, wherein x is 1, 2, 3, 4, 5, or 6;
or a pharmaceutically acceptable salt thereof.

2. The compound of formula (II) according to claim 1, or a pharmaceutically acceptable salt thereof, wherein the compound of formula (II) is a compound of formula (IIa),

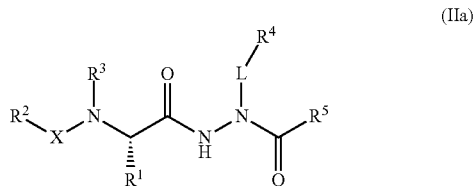

wherein X, L, R¹, R², R³, R⁴, and R⁵ are as defined in claim 1.

3. The compound of formula (II) according to claim 1, or a pharmaceutically acceptable salt thereof, wherein the compound of formula (II) is a compound of formula (I),

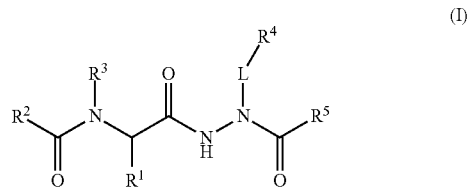

wherein L, R¹, R², R³, R⁴, and R⁵ are as defined in claim 1.

4. The compound of formula (II) according to claim 1, or a pharmaceutically acceptable salt thereof, wherein R¹ is $C_{1-6}$alkyl, ($C_{1-6}$alkyl)$_3$Si—$C_{1-6}$alkyl, or $C_{3-7}$cycloalkyl $C_{1-6}$alkyl, wherein said $C_{3-7}$ cycloalkyl is optionally substituted with one $C_{1-6}$alkyl substituent.

5. The compound of formula (II) according to claim 4, or a pharmaceutically acceptable salt thereof, wherein R¹ is isobutyl, isopentyl, 2,2, dimethylpropyl, trimethylsilylmethyl, cyclopropylmethyl, (1-methylcyclopropyl)methyl, 1-bicyclo[1.1.1]pentanylmethyl, or cyclohexylmethyl.

6. The compound of formula (II) according to claim 1, or a pharmaceutically acceptable salt thereof, wherein R² is benzyloxy, 1H-indolyl, benzimidazolyl, or isoxazolyl, wherein each of said 1H-indolyl, benzimidazolyl, and isoxazolyl is unsubstituted or substituted with one substituent selected from halogen, $C_{1-6}$ alkyl, halo-$C_{1-6}$alkyl, and $C_{1-6}$alkoxy.

7. The compound of formula (II) according to claim 6, or a pharmaceutically acceptable salt thereof, wherein R² is benzyloxy, 1H-indolyl, benzimidazolyl, 5-methylisoxazolyl, 5-(difluoromethyl)isoxazolyl, 5-(trifluoromethyl)isoxazolyl, 5-chloro-1H-benzimidazolyl, 5-chloro-1H-indolyl, or 4-methoxy-1H-indolyl.

8. The compound of formula (II) according to claim 1, or a pharmaceutically acceptable salt thereof, wherein R³ is H.

9. The compound of formula (II) according to claim 1, or a pharmaceutically acceptable salt thereof, wherein R⁴ is carbamoyl or axopyrrolidinyl.

10. The compound of formula (II) according to claim 1, or a pharmaceutically acceptable salt thereof, wherein L is —$CH_2$— or —$CH_2$—$CH_2$—.

11. The compound of formula (II) according to claim 1, or a pharmaceutically acceptable salt thereof, wherein R⁵ is chlorofluoromethyl.

12. The compound of formula (II) according to claim 1, or a pharmaceutically acceptable salt thereof, wherein
R¹ is $C_{1-6}$alkyl, ($C_{1-6}$alkyl)$_3$Si—$C_{1-6}$alkyl, or $C_{3-7}$cycloalkyl$C_{1-6}$alkyl, wherein said $C_{3-7}$cycloalkyl is optionally substituted with one $C_{1-6}$alkyl substituent;
R² is benzyloxy, 1H-indolyl, benzimidazolyl, or isoxazolyl, wherein each of said 1H-indolyl, benzimidazolyl, and isoxazolyl is unsubstituted or substituted with one substituent selected from halogen, $C_{1-6}$alkyl, halo-$C_{1-6}$alkyl, and $C_{1-6}$alkoxy;
R³ is H;
R⁴ is carbamoyl or axopyrrolidinyl;
R⁵ is $C_{1-6}$alkyl substituted twice with halogen; and
L is —$CH_2$— or —$CH_2$—$CH_2$—.

13. The compound of formula (II) according to claim 12, or a pharmaceutically acceptable salt thereof, wherein
R¹ is isobutyl, isopentyl, 2,2, dimethylpropyl, trimethylsilylmethyl, cyclopropylmethyl, (1-methylcyclopropyl)methyl, 1-bicyclo[1.1.1]pentanylmethyl, or cyclohexylmethyl;
R² is benzyloxy, 1H-indolyl, benzimidazolyl, 5-methylisoxazolyl, 5-(difluoromethyl)isoxazolyl, 5-(trifluoromethyl)isoxazolyl, 5-chloro-1H-benzimidazolyl, 5-chloro-1H-indolyl, or 4-methoxy-1H-indolyl;
R³ is H;
R⁴ is carbamoyl or axopyrrolidinyl;
R⁵ is chlorofluoromethyl; and
L is —$CH_2$— or —$CH_2$—$CH_2$—.

14. A pharmaceutical composition comprising a compound of formula (II) according to claim 1, or pharmaceutically acceptable salt thereof, and a therapeutically inert carrier.

15. A compound selected from:

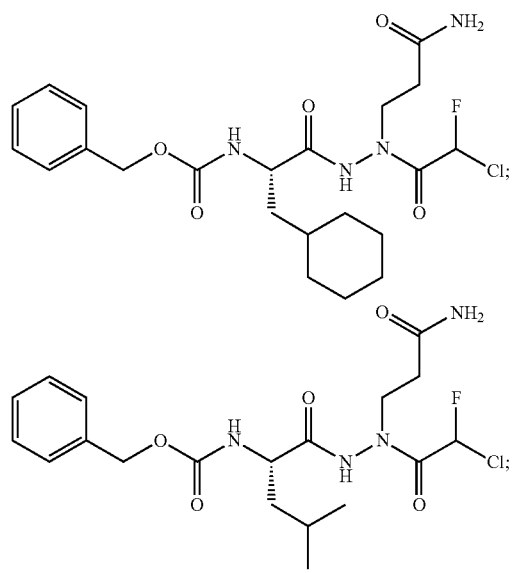

-continued
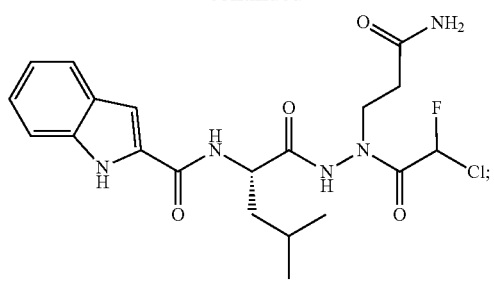
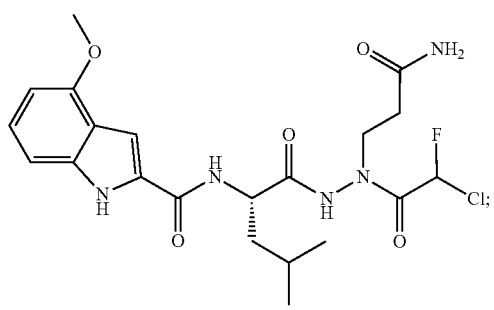
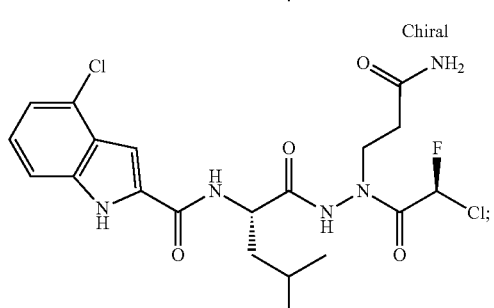
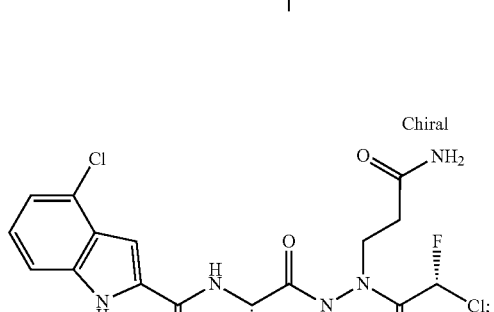
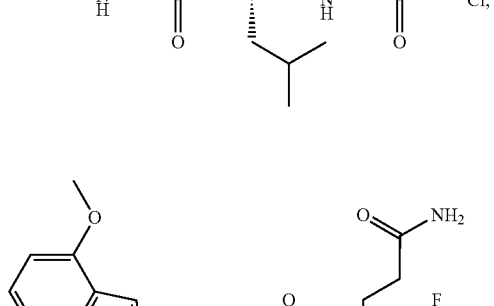
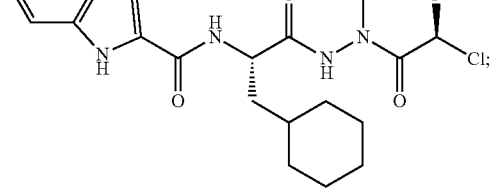
-continued
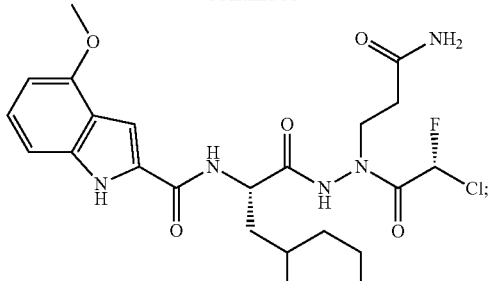
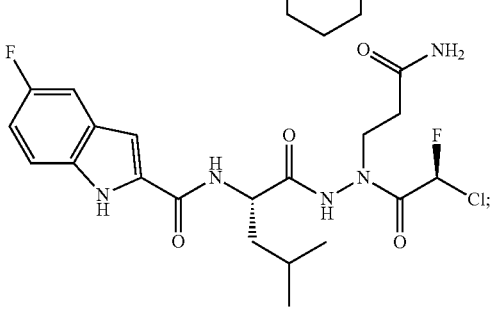
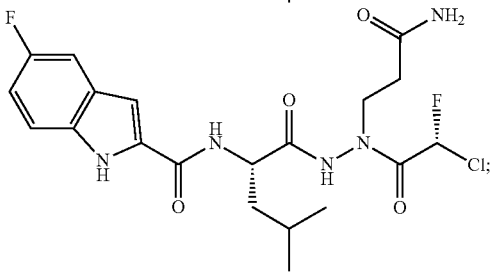
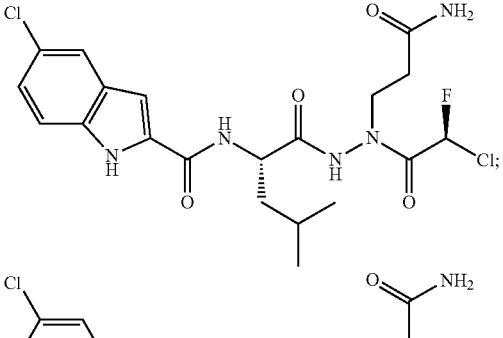
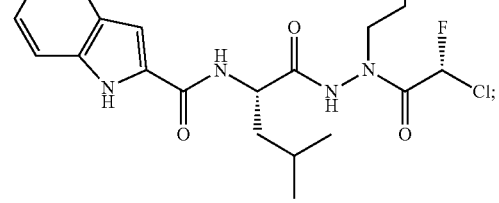
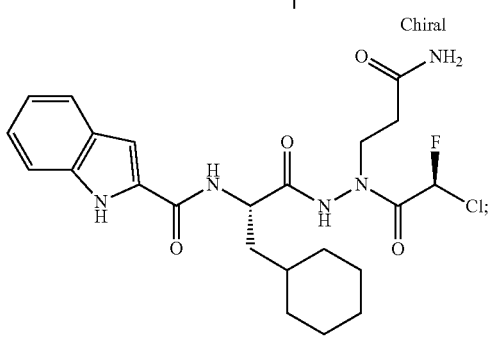

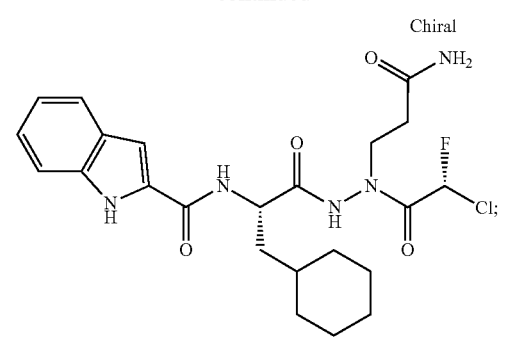
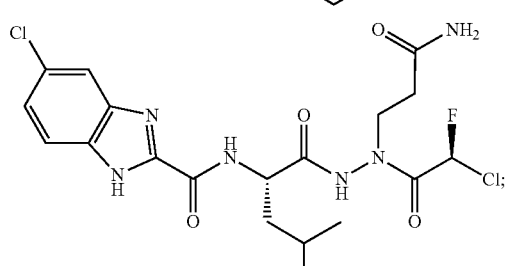
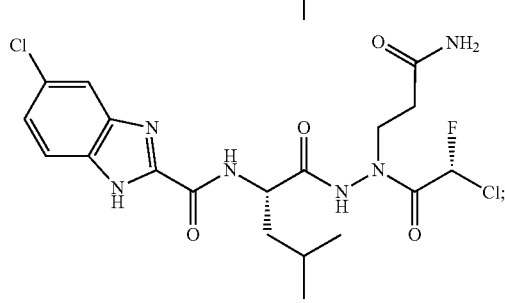
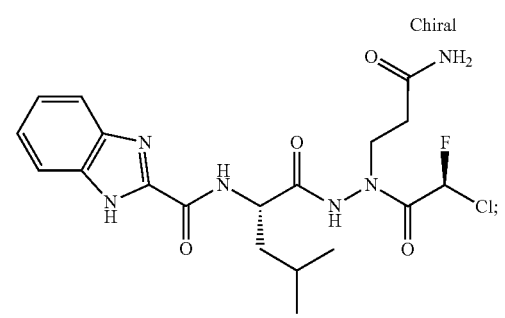
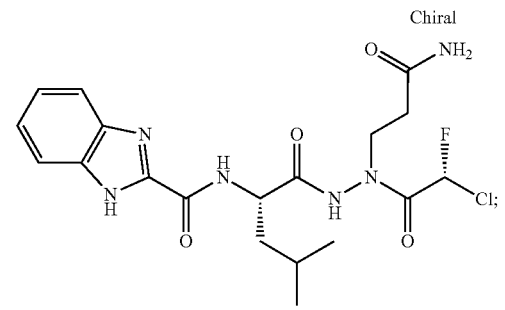
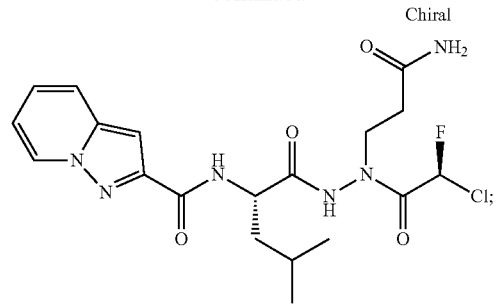
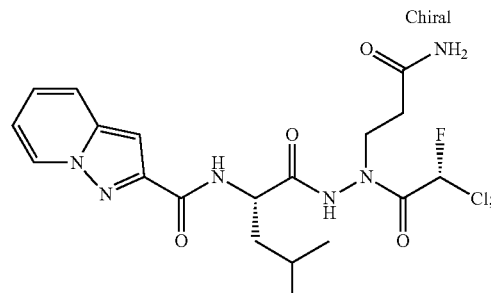
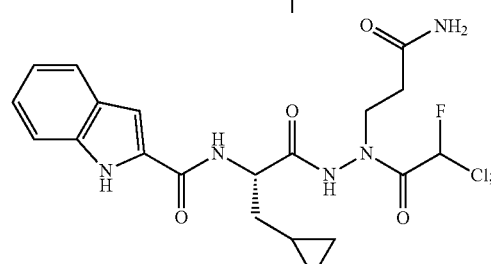
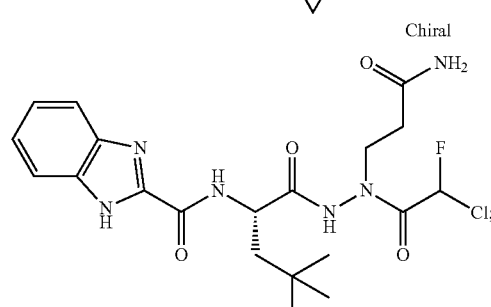
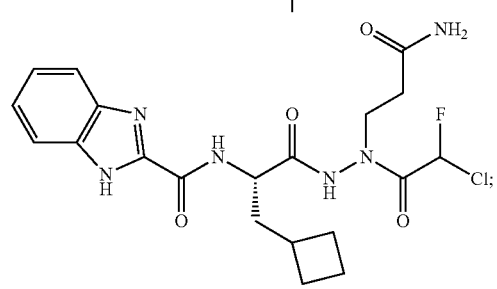
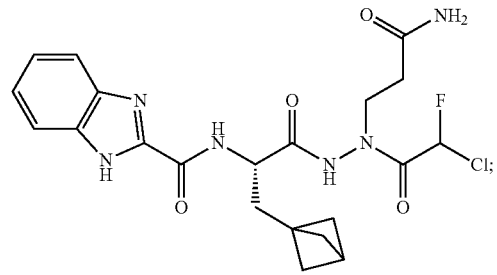

189
-continued
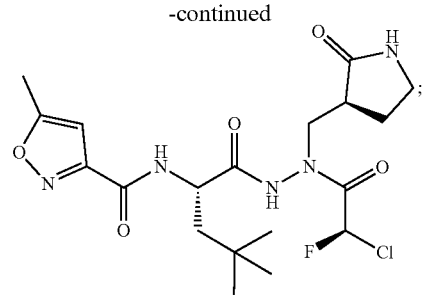
Chiral
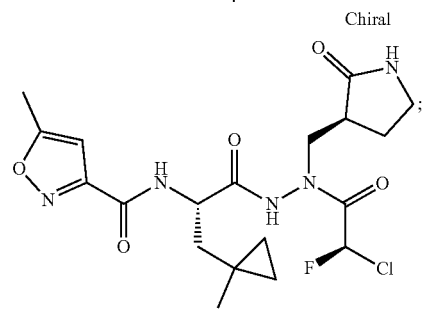
Chiral
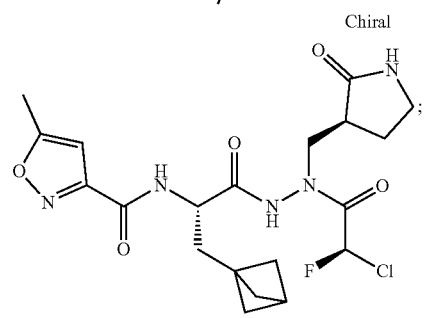
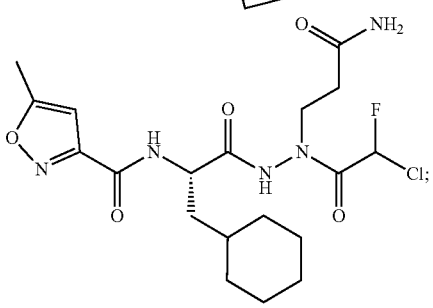
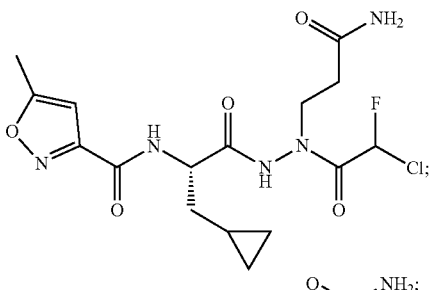
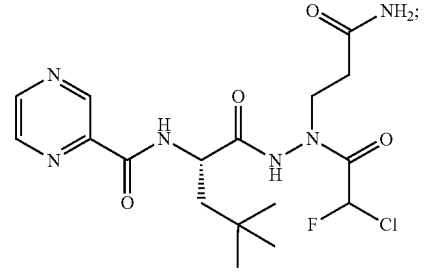
190
-continued
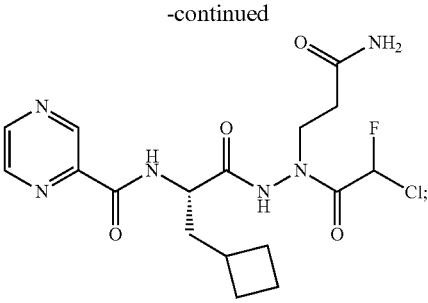
Chiral
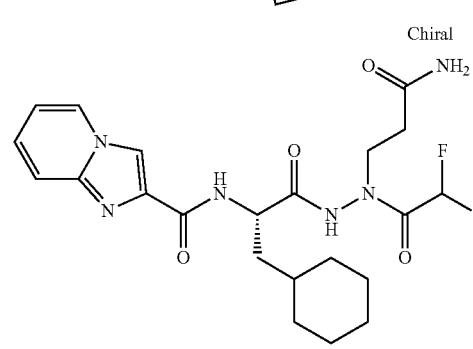
Chiral
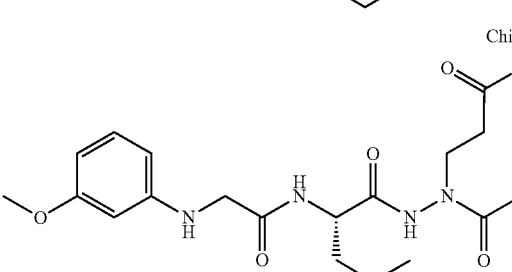
Chiral
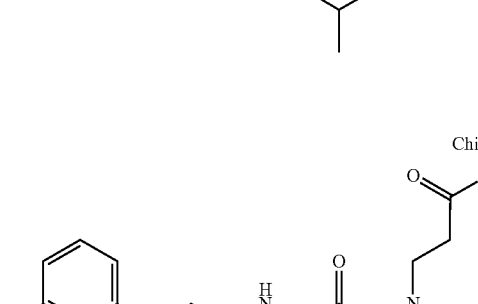
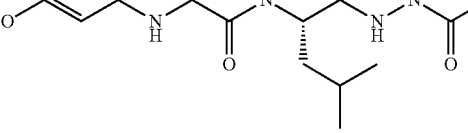
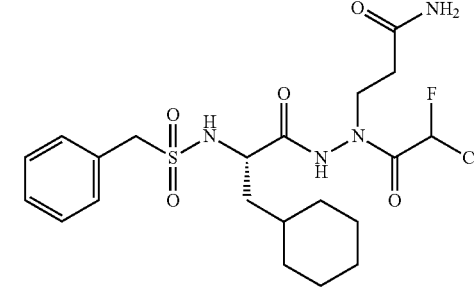

191
-continued
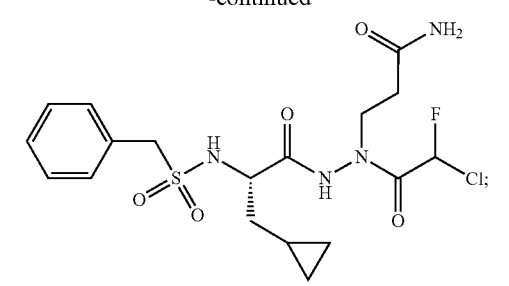
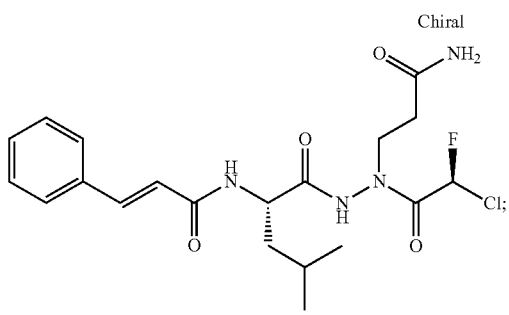
Chiral
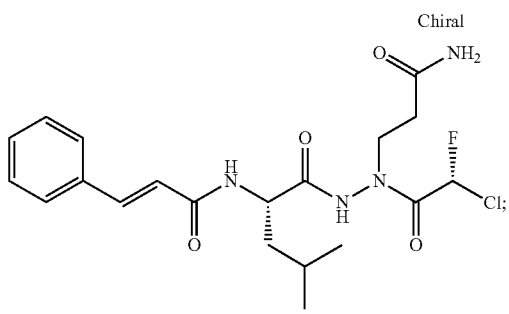
Chiral
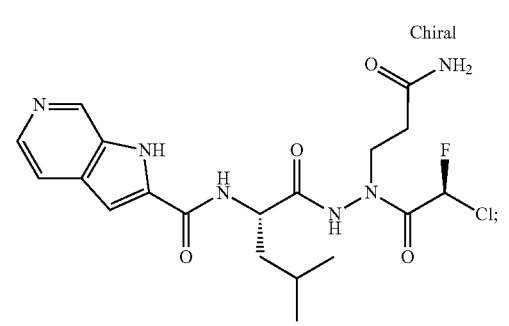
Chiral
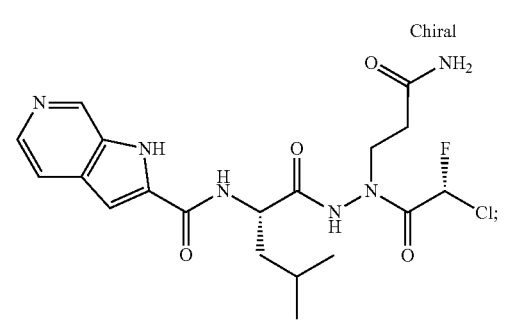
Chiral
192
-continued
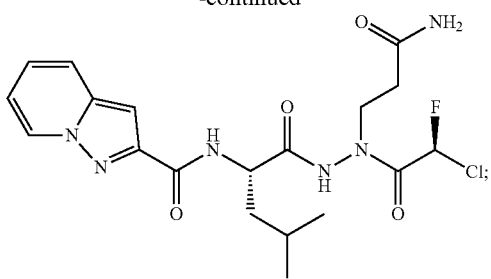
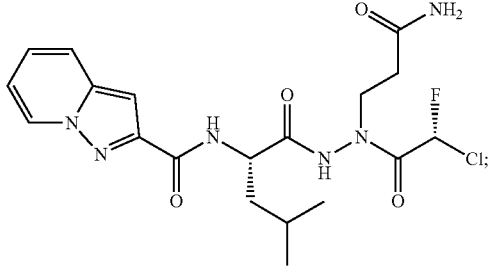
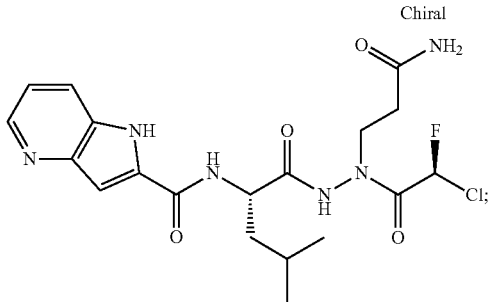
Chiral
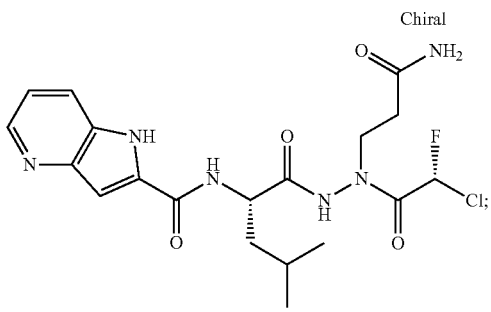
Chiral
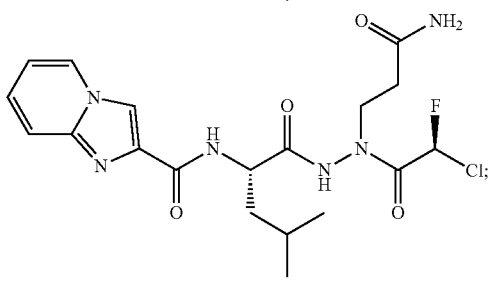
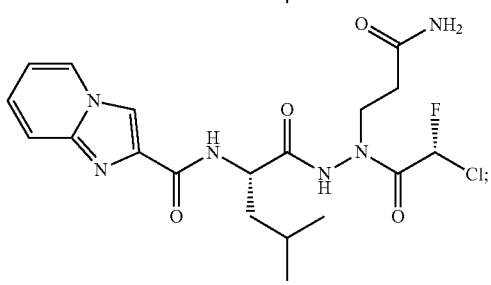

193
-continued
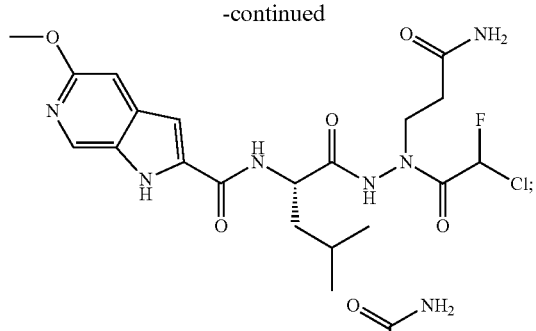
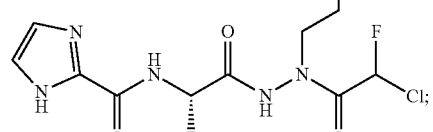
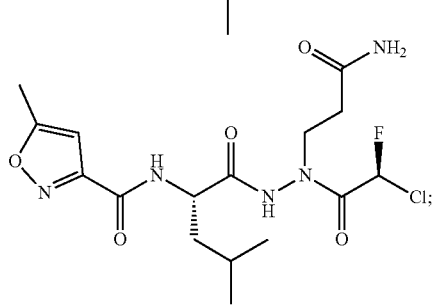
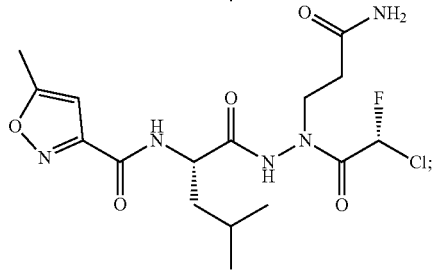
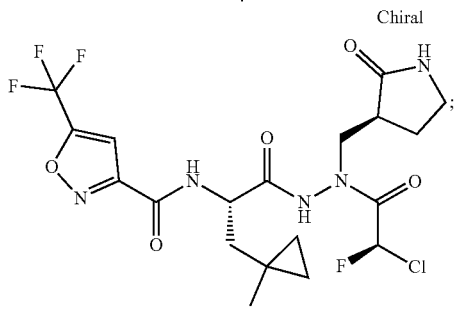
194
-continued
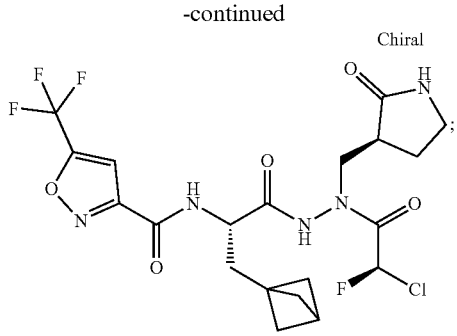
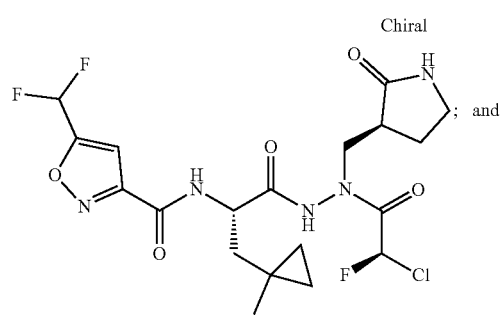
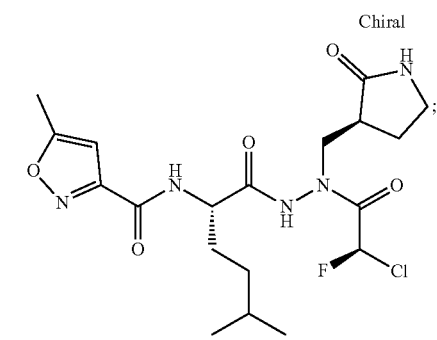
or a stereoisomer or a pharmaceutically acceptable salt thereof.
* * * * *